United States Patent
Beisel et al.

(10) Patent No.: US 11,439,712 B2
(45) Date of Patent: Sep. 13, 2022

(54) METHODS AND COMPOSITIONS FOR RNA-DIRECTED REPRESSION OF TRANSCRIPTION USING CRISPR-ASSOCIATED GENES

(71) Applicant: North Carolina State University, Raleigh, NC (US)

(72) Inventors: Chase Beisel, Raleigh, NC (US); Michelle Luo, Cary, NC (US)

(73) Assignee: North Carolina State University, Raleigh, NC (US)

(*) Notice: Subject to any disclaimer, the term of this patent is extended or adjusted under 35 U.S.C. 154(b) by 0 days.

(21) Appl. No.: 15/302,655

(22) PCT Filed: Apr. 7, 2015

(86) PCT No.: PCT/IB2015/052515
§ 371 (c)(1),
(2) Date: Oct. 7, 2016

(87) PCT Pub. No.: WO2015/155686
PCT Pub. Date: Oct. 15, 2015

(65) Prior Publication Data
US 2017/0028083 A1 Feb. 2, 2017

Related U.S. Application Data

(60) Provisional application No. 62/058,365, filed on Oct. 1, 2014, provisional application No. 61/976,883, filed on Apr. 8, 2014.

(51) Int. Cl.
| *A61K 48/00* | (2006.01) |
| *C12N 15/72* | (2006.01) |
| *C12N 9/22* | (2006.01) |
| *C12N 15/63* | (2006.01) |
| *C12N 15/10* | (2006.01) |
| *C12N 15/11* | (2006.01) |

(52) U.S. Cl.
CPC .............. *A61K 48/005* (2013.01); *C12N 9/22* (2013.01); *C12N 15/102* (2013.01); *C12N 15/111* (2013.01); *C12N 15/63* (2013.01); *C12N 15/72* (2013.01); *C12N 2310/20* (2017.05); *C12N 2320/30* (2013.01)

(58) Field of Classification Search
CPC .... C12N 2310/20; C12N 9/22; C12N 15/113; C12N 2800/80
See application file for complete search history.

(56) References Cited

U.S. PATENT DOCUMENTS

| 8,697,359 | B1 | 4/2014 | Zhang |
| 9,023,649 | B2 | 5/2015 | Mali et al. |
| 9,260,723 | B2 | 2/2016 | Mali et al. |
| 2006/0199190 | A1 | 9/2006 | Russell et al. |
| 2009/0007301 | A1 | 1/2009 | Wintz et al. |
| 2013/0288251 | A1 | 10/2013 | Horvath et al. |
| 2014/0068797 | A1 | 3/2014 | Doudna et al. |
| 2014/0113376 | A1* | 4/2014 | Sorek .................... C12N 15/113 435/471 |
| 2014/0186958 | A1* | 7/2014 | Zhang ...................... C12N 9/22 435/462 |
| 2014/0273233 | A1 | 9/2014 | Chen et al. |
| 2014/0315985 | A1* | 10/2014 | May ..................... A61K 38/465 514/44 R |
| 2014/0356867 | A1 | 12/2014 | Peter et al. |
| 2014/0356956 | A1 | 12/2014 | Church et al. |
| 2015/0050699 | A1 | 2/2015 | Siksnys et al. |
| 2015/0056628 | A1 | 2/2015 | Russell et al. |
| 2015/0064138 | A1 | 3/2015 | Lu et al. |
| 2015/0093473 | A1 | 4/2015 | Barrangou et al. |
| 2015/0098954 | A1 | 4/2015 | Hyde et al. |
| 2015/0132263 | A1 | 5/2015 | Liu et al. |
| 2015/0291961 | A1 | 10/2015 | Siksnys et al. |
| 2015/0315576 | A1 | 11/2015 | Caliando et al. |
| 2015/0353901 | A1 | 12/2015 | Liu et al. |
| 2016/0017366 | A1 | 1/2016 | Chen et al. |
| 2016/0024510 | A1 | 1/2016 | Bikard et al. |
| 2016/0186152 | A1 | 6/2016 | Brouns et al. |

(Continued)

FOREIGN PATENT DOCUMENTS

| EP | 2860267 | 4/2015 |
| WO | 2006/113709 | 10/2006 |

(Continued)

OTHER PUBLICATIONS

Qi et al., Repurposing CRISPR as an RNA-Guided Platform for Sequence-Specific Control of Gene Expression; Cell, vol. 152, pp. 1173-1183, 2013.*
Beloglazova et al., Structure and activity of the Cas3 HD nuclease MJ0384, an effector enzyme of the CRISPR interference; EMBO Journal, vol. 30, pp. 4616-4627, 2011 (Year: 2011).*
Luo, Michelle Lynn Understanding and exploiting the properties of Type I CRISPR-Cas systems. 2016. Dissertation submitted to the Graduate Faculty of North Carolina State University in partial fulfillment of the requirements for the degree of Doctor of Philosophy. 167 pages. (Year: 2016).*
Lou et al. The CRISPR RNA-guided surveillance complex in *Escherichia coli* accommodates extended RNA spacers. Published online May 12, 2016. Nucleic Acids Research. vol. 44, No. 15, pp. 7385-7394. (Year: 2016).*

(Continued)

*Primary Examiner* — Antonio Galisteo Gonzalez
(74) *Attorney, Agent, or Firm* — Myers Bigel, P.A.

(57) ABSTRACT

The present invention is directed to methods and compositions for targeted gene silencing that provide the ability to not only repress expression but to modulate the repression of expression of one or more target genes. In one aspect, a recombinant nucleic acid molecule is provided comprising a nucleotide sequence encoding a subset of CRISPR-cas polypeptides, or functional fragments thereof, from a type-I CRISPR-cas system. In some aspects, a recombinant nucleic acid of the invention comprises a nucleotide sequence encoding three or more Type I Cascade polypeptides having substantial identity to a type I Cascade polypeptide.

17 Claims, 12 Drawing Sheets

Specification includes a Sequence Listing.

(56) References Cited

U.S. PATENT DOCUMENTS

| | | | |
|---|---|---|---|
| 2016/0186213 A1 | 6/2016 | Zhang et al. | |
| 2016/0186214 A1* | 6/2016 | Brouns | C12N 15/66 435/91.5 |
| 2016/0289700 A1 | 10/2016 | Barrangou et al. | |
| 2016/0333348 A1 | 11/2016 | Clube et al. | |
| 2016/0345578 A1 | 12/2016 | Barrangou et al. | |
| 2017/0002339 A1 | 1/2017 | Barrangou et al. | |
| 2017/0196225 A1 | 7/2017 | Clube et al. | |
| 2017/0246221 A1 | 8/2017 | Clube et al. | |
| 2017/0275648 A1 | 9/2017 | Barrangou et al. | |
| 2018/0064114 A1 | 3/2018 | Clube | |
| 2018/0064115 A1 | 3/2018 | Clube et al. | |
| 2018/0070594 A1 | 3/2018 | Clube et al. | |
| 2018/0084785 A1 | 3/2018 | Clube | |
| 2018/0084786 A1 | 3/2018 | Clube | |
| 2018/0146681 A1 | 5/2018 | Clube | |
| 2018/0155729 A1 | 6/2018 | Beisel et al. | |
| 2018/0200387 A1 | 7/2018 | Porteus | |
| 2018/0258411 A1 | 9/2018 | Kadiyala et al. | |
| 2018/0273937 A1 | 9/2018 | Beisel et al. | |

FOREIGN PATENT DOCUMENTS

| | | | |
|---|---|---|---|
| WO | WO 2010/054154 | 5/2010 | |
| WO | 2010/075424 | 7/2010 | |
| WO | WO 2010/075424 | 7/2010 | |
| WO | WO 2013/098244 | 7/2013 | |
| WO | 2013/141680 | 9/2013 | |
| WO | WO 2013176772 | 11/2013 | |
| WO | WO 2013/188638 | 12/2013 | |
| WO | WO 2013188522 | 12/2013 | |
| WO | WO 2014/022702 | 2/2014 | |
| WO | WO 2014/071235 | 5/2014 | |
| WO | WO 2014065596 | 5/2014 | |
| WO | WO-2014093479 A1 * | 6/2014 | C12N 15/63 |
| WO | WO 2014110006 | 7/2014 | |
| WO | WO 2014113493 | 7/2014 | |
| WO | WO 2014/124226 | 8/2014 | |
| WO | WO 2014144155 | 9/2014 | |
| WO | WO 2014144592 | 9/2014 | |
| WO | WO 2014150624 | 9/2014 | |
| WO | WO 2014186686 | 11/2014 | |
| WO | 2014/204727 | 12/2014 | |
| WO | WO 2014191128 | 12/2014 | |
| WO | WO 2014191518 | 12/2014 | |
| WO | WO 2014201015 | 12/2014 | |
| WO | WO 20142014727 | 12/2014 | |
| WO | WO 2015021353 | 2/2015 | |
| WO | WO 2015026886 | 2/2015 | |
| WO | WO 2015/034872 | 3/2015 | |
| WO | WO 2015035139 | 3/2015 | |
| WO | WO 2015040402 | 3/2015 | |
| WO | WO 2015/053995 | 4/2015 | |
| WO | WO 2015/070193 | 5/2015 | |
| WO | WO 2015077290 | 5/2015 | |
| WO | 2015/089486 | 6/2015 | |
| WO | WO 2015089277 | 6/2015 | |
| WO | WO 2015089406 | 6/2015 | |
| WO | 2015112896 A2 | 7/2015 | |
| WO | WO 2015116686 | 8/2015 | |
| WO | WO 2015119941 | 8/2015 | |
| WO | WO 2015 139139 | 9/2015 | |
| WO | 2015/159068 | 10/2015 | |
| WO | WO 2015/148680 | 10/2015 | |
| WO | WO 2015/155686 | 10/2015 | |
| WO | WO 2015/159086 | 10/2015 | |
| WO | WO 2015/159087 | 10/2015 | |
| WO | WO 2015153791 | 10/2015 | |
| WO | WO 2015153889 | 10/2015 | |
| WO | WO 2015153940 | 10/2015 | |
| WO | WO 2015155686 | 10/2015 | |
| WO | WO 2015160683 | 10/2015 | |
| WO | WO 2015189693 | 12/2015 | |
| WO | WO 2015200555 | 12/2015 | |
| WO | 2016/084088 | 6/2016 | |
| WO | WO 2016/084088 | 6/2016 | |
| WO | 2016/177682 | 11/2016 | |
| WO | 2018/196361 | 12/2016 | |
| WO | 2017/027423 | 2/2017 | |
| WO | 2017/066497 | 4/2017 | |
| WO | 2017112620 | 6/2017 | |
| WO | 2017/147507 | 8/2017 | |
| WO | 2018217981 | 11/2018 | |

OTHER PUBLICATIONS

Barrangou R. "CRISPR-Cas systems and RNA-guided interference", *Wiley interdisciplinary reviews, RNA* (2013) 4: pp. 267-278.

Barrangou R., et al. "CRISPR: new horizons in phage resistance and strain identification" *Annu Rev Food Sci Technol* (2012) 3, pp. 143-162.

Barrangou R., et al. "CRISPR-Cas systems: prokaryotes upgrade to adaptive immunity", *Mol Cell* (2014) 54(2): pp. 234-244.

Barrangou, R. "Diversity of CRISPR-Cas immune systems and molecular machines", *Genome Biology* (2015) 16:247, 11 pages.

Barrangou, R., et al. "CRISPR provides acquired resistance against viruses in prokaryotes", *Science* (2007) 315(5819): pp. 1709-1712.

Bhaya et al. "CRISPR-Cas Systems in Bacteria and Archaea: Versatile Small RNAs for Adaptive Defense and Regulation", *Annu. Rev. Genet.* (2011) 45: pp. 273-297.

Bikard D. et al. "Programmable repression and activation of bacterial gene expression using an engineered CRISPR-Cas system" *Nucleic Acids Res* (2013) 41(15): pp. 7429-7437.

Bikard D., et al. "CRISPR interference can prevent natural transformation and virulence acquisition during in vivo bacterial infection", *Cell Host & Microbe* (2012), 10 pages.

Bikard D., et al. "Exploiting CRISPR-Cas nucleases to produce sequence-specific antimicrobial", *Nature Biotechnology* 2014, 6 pages.

Briner et al. "Guide RNA Functional Modules Direct Cas9 Activity and Orthogonality", *Molecular Cell.* (2014) 56(2): pp. 333-339.

Briner AE, Barrangou R. "*Lactobacillus buchneri* Genotyping on the Basis of Clustered Regularly Interspaced Short Palindromic Repeat (CRISPR) Locus Diversity", *Appl Environ Microbiol.* 80:994-1001, (2014).

Brouns SJJ, et al. "Small CRISPR RNAs guide antiviral defense in prokaryotes", *Science* (2008) 321:5891, pp. 960-964.

Carte et al. "The three major types of CRISPR-Cas systems function independently in CRISPR RNA biogenesis in *Streptococcus thermophilus*", *Molecular Microbiology*, 93(1), pp. 98-112 (2014).

Chylinski at al. "The tracrRNA and Cas9 families of type II CRISPR-Cas immunity systems", *RNA Biology*, 10:5 (2013) pp. 726-737.

Chylinski et al. "Classification and evolution of type II CRISPR-Cas Systems", *Nucleic Acids Research*, (2014) 15 pages.

Citorik R., et al. "Sequence-specific antimicrobials using efficiently delivered RNA-guided nucleases", *Nature Biotechnology* 2014, 7 pages.

Cong et al. "Multiplex Genome Engineering Using CRISPR/Cas Systems" *Science* (2013) vol. 339 (6121): pp. 819-823.

Darmon E, Leach DF "Bacterial Genome Instability", *Microbiol. Mol. Biol.* Rev. (2014) vol. 78, pp. 1-39.

Deltcheva, E. et al. "CRISPR Rna maturation by trans-encoded small RNA and host factor RNase III", *Nature*, vol. 471, (Mar. 2011) pp. 602-607.

Doench et al. "Rational design of highly active sgRNAs for CRISPR-Cas9-mediated gene inactivation", *Nature Biotechnology*, 32:12 (2014) 8 pages.

Edgar R., et al. "The *Escherichia call* CRISPR System Protects from Lysogenization, Lysogens, and Prophage Induction", *Journal of Bacteriology* (2010), vol. 192, No. 23, pp. 6292-6294.

Estvelt et al. "Orthogonal Cas9 proteins for RNA-guided gene regulation and editing", *Nature Methods*, 10:11 (2013) pp. 1116-1121.

Fonfara, I. et al. "Phylogeny of Cas9 determines functional exchangeability of dual-RNA and Cas9 among orthologous type II CRISPR-Cas systems", *Nucleic Acids Res* (2013) 14 pages.

(56) References Cited

OTHER PUBLICATIONS

Fu et al. "Improving CRISPR-Cas nuclease specificity using truncated guide RNAs", *Nature Biotechnology*, 32:3 (2013) 9 pages.
Garneau Je, et al. "The CRISPR/Cas bacterial immune system cleaves bacteriophage and plasmid DNA" *Nature* (2010) 468(7320): pp. 67-71.
Gasiunas et al. "Cas9-crRNA ribonucleoprotein complex mediates specific DNA cleavage for adaptive immunity in bacteria", *Proc. Natl. Acad. Sci.* (2012), 109:E2579-E2586.
Gilbert, L. A. et al. "CRISPR-Mediated Modular RNA-Guided Regulation of Transcription in Eukaryotes", *Cell* 154 (2013) pp. 442-451.
Gilbert et al. "Genome-Scale CRISPR-Mediated Control of Gene Repression and Activation", *Cell*, 159 (2014) pp. 647-661.
Gomaa AA, et al. "Programmable Removal of Bacterial Strains by Use of Genome-Targeting CRISPR-Cas Systems", *mBio* (2014), 5(1):e00928-13.
Haurwitz et al. "Sequence- and Structure-Specific RNA Processing by a CRISPR Endonuclease", *Science* (2010) 329: pp. 1355-1358.
Horvath and Barrangou "CRISPR/Cas, the Immune System of Bacteria and Archaea", *Science* (2010) 327, pp. 167-170.
Horvath, P. et al. "Diversity, Activity, and Evolution of CRISPR Loci in *Streptococcus thermophilus*", *J Bacteriol.* 190 (2008) pp. 1401-1412.
Hsu et al. "DNA targeting specificity of RNA-guided Cas9 nucleases", *Nature Biotechnology*, 31:9 (2013) pp. 827-834.
Jiang, W. et al. "Dealing with the Evolutionary Downside of CRISPR Immunity: Bacteria and Beneficial Plasmids", *PLOS Genetics* (2013) vol. 9, issue 9, 13 pages.
Jiang, W. et al. "RNA-guided editing of bacterial genomes using CRISPR-Cas systems", *Nat. Biotechnol.* (2013) vol. 31, pp. 233-239.
Jinek et al. "A Programmable Dual-RNA-Guided DNA Endonuclease in Adaptive Bacterial Immunity", *Science* (2012) vol. 337, pp. 816-821.
Jinek, M. et al.,"Structures of Cas9 endonucleases reveal RNA-mediated conformational activation", *Science* (2014) vol. 343, 6176, 28 pages.
Karvelis et al. "crRNA and tracrRNA guide Cas9-mediated DNA interference in *Streptococcus thermophilus*", *RNA Biol.* (2013) vol. 10: pp. 841-851.
Kobayashi K, et al. "Essential *Bacillus subtilis* genes", *Proc. Natl. Acad. Sci. U.S.A.* (2003) vol. 100, pp. 4678-4683.
Labrie SJ et al. "Bacteriophage resistance mechanisms" *Nat. Rev. Microbiol* (2010) vol. 8, pp. 317-327.
Luo, M. et al., "Repurposing endogenous type I CRISPR-Cas systems for programmable gene repression", *Nucleic Acid Research* (2014) 8 pages.
Magadan et al. "Cleavage of Phage DNA by the *Streptococcus thermophilus* CRISPR3-Cas System", *PLoS One* (2012) 7:e40913, 8 pages.
Mahillon J. et al. "Insertion sequences", *Microbiol Mol Biol Rev* (1998) vol. 62(3): pp. 725-774.
Makarova and Koonin "Annotation and Classification of CRISPR-Cas Systems", *Methods Mol Biol.* (2015), 1311: pp. 47-75.
Makarova et al. "An updated evolutionary classification of CRISPR-Cas systems", *Nat Rev Microbiol.* 13:722-736 (2015), 15 pages.
Makarova et al. "Unification of Cas protein families and a simple scenario for the origin and evolution of CRISPRCas systems", *Biol Direct.* (2011) vol. 6:38, 27 pages.
Makarova, K. S. et al. "Evolution and classification of the CRISPR-Cas systems", *Nat Rev Microbiol* (2011) vol. 9, pp. 467-477.
Marraffini and Sontheimer "CRISPR Interference Limits Horizontal Gene Transfer in *Staphylococci* by Targeting DNA", *Science* (2008) vol. 322: pp. 1843-1845.
Mojica, F. et al. "Short motif sequences determine the targets of the prokaryotic CRISPR defence system", *Microbiology* (2009) vol. 155, 8 pages.
Nishimasu, H., et al. "Crystal Structure of Cas9 in Complex with Guide RNA and Target DNA", *Cell* (2014) vol. 156, pp. 935-949.

Oh JH and van Pijkeren JP "CRISPR-Cas9-assisted recombineering in *Lactobacillus reuteri*", *Nucleic Acids Res* (2014) vol. 10.1093/nar/gku623.
Qi, L. S. et al. "Repurposing CRISPR as an RNA-Guided Platform for Sequence-Specific Control of Gene Expression", *Cell* 152, 1173-1183 (2013), 11 pages.
Sander JD, and Joung JK. "CRISPR-Cas systems for editing, regulating and targeting genomes", *Nat. Biotechnol.* (2014) vol. 32, pp. 347-355.
Sapranauskas et al. "The *Streptococcus thermophilus* CRISPR/Cas system provides immunity in *Escherichia coli*", *Nucleic Acid Res.* (2011) vol. 39: pp. 9275-9282.
Selle K, Barrangou R. "Harnessing CRISPR-Cas systems for bacterial genome editing", *Cell Press: Trends Microbiol.* (2015) vol. 23(4): pp. 225-232.
Selle, K. et al. "CRISPR-based screening of genomic island excision events in bacteria", *Proc Natl Acad Sci USA;* (2015); 112(26): pp. 8076-8081.
Selle, K. et al., "CRISPR-Based Technologies and the Future of Food Science", *Journal of Food Science* (2015) vol. 80, 6 pages.
Semenova et al. "Interference by clustered regularly interspaced short palindromic repeat (CRISPR) RNA is governed by a seed sequence", *PNAS,* 108:25 (2011) 6 pages.
Sinkuna, T. et al. "In vitro reconstitution of Cascade-mediated CRISPR immunity in *Streptococcus thermophilus*", *The EMBO Journal* (2013) vol. 32, pp. 385-394.
Stern, A. et al., "Self-targeting by CRISPR: gene regulation of autoimmunity", *Cell Press: Trends in Genetics,* (2010) vol. 26, No. 8, 6 pages.
Sternberg et al. "DNA interrogation by the CRISPR RNA-guided endonuclease Cas9", *Nature,* vol. 507, (2014) 17 pages.
Terns and Terns "CRISPR-based adaptive immune systems", *Curr. Opin. Microbiol.* (2011) vol. 14: pp. 321-327.
Vercoe RB, et al. "Cytotoxic chromosomal targeting by CRISPR/Cas systems can reshape bacterial genomes and expel or remodel pathogenicity islands", *PLoS Genet* (2013) vol. 9(4):e1003454.
Westra et al. "The CRISPRs, They Are A-Changin': How Prokaryotes Generate Adaptive Immunity", *Annu. Rev. Genet.* (2012) vol. 46: pp. 311-339.
Notification of Transmittal of the International Search Report and the Written Opinion of the International Searching Authority, or the Declaration, PCT/US2016/034812, dated Sep. 15, 2016, 9 pages.
Notification of International Preliminary Report on Patentability corresponding to International Application No. PCT/IB2015/052515; dated Oct. 12, 2016, 7 pages.
Notification and Transmittal of International Search Report and Written Opinion of the International Searching Authority for International Application No. PCT/IB2015/052515; dated Oct. 10, 2015; 12 pages.
Beisel CL et al. A CRISPR design for next-generation antimicrobials. Genome Biology. 2014; 15: 516, 4 pages.
Citorik RJ et al. "Sequence-specific antimicrobials using efficiently delivered RNA-gulding nucleases Supplemental Material." Nature Biotechnology. Sep. 21, 2014; 32(11): 1141-1145. DOI:10.1038/nbt.3011, 14 pages.
Liu S et al. Complete genome sequence of Lactobacillus buchneri NRRL B-30929, a novel strain from a commercial ethanol plant. Journal of Bacteriology. Aug. 2011: 193(15): 4019-4020.
Liu S et al. NCBI (2011) CRISPR-associated protein, Csn1 family [Lactobacillus buchneri], pp. 1-3.
Final Office Action, U.S. Appl. No. 15/113,656, dated Jul. 30, 2018, 8 pages.
Ajdic et al. "hypothetical protein SMU_1405c [*Streptococcus mutans* UA159]", Proc. Natl. Acad. Sci. U.S.A. 99 (22), 14434-14439 (2002) URL: https://www.ncbi.nlm.nih.gov/protein/NP_721764.1/, retrieved Jul. 20, 2018.
Cochrane Kyla et al., "Complete genome sequences and analysis of the Fusobacterium nucleatum subspecies animalis 7-1 bacteriophage PHIFunu1 and PHIFunu2", Anaerobe, 38:125-129 (2016).
Dupuis Me et al., "CRISPR-Cas and restriction-modification systems are compatible and increase phage resistance", Nat Commun., vol. 4, p. 2087 (2013).

(56) References Cited

OTHER PUBLICATIONS

Heinl, Stefan et al. "Insights into the completely annotated genome of Lactobacillus buchneri CD034, a strain isolated from stable grass silage", Journal of Biotechnology, 161:153-166 (2012).
International Search Report and Written Opinion for PCT/US2015/047136 dated Nov. 26, 2015, 10 pages.
Karvelis, Tautvydas et al., "crRNA and tracerRNK guide Cas9-mediated DNA interference in *Streptococcus thermophilus*," RNA Biology, 2013, vol. 10, Issue 5, pp. 841-851.
Karvelis, Tautvydas et al., "Programmable DNA cleavage in vitro by Cas9," Biochem. Soc. Trans. 2013, vol. 41, part 6, pp. 1401-1406.
Marcotte, H. et al. "Proteomes—Lactobacillus gasseri DSM 14869", NCBI Reference Sequence CP006803, (2013) URL: https://www.uniprot.org/proteomes/UP000217220, retrieved Jul. 20, 2018.
Nale Janet Y. et al., "Diverse temperate bacteriophage carriage in Clostridium difficile 027 strains", PLoS One, 7(5) 1-9 (2012).
Notificaton and Transmittal of International Search Report and Written Opinion of the International Searching Authority for International Application No. PCT/IB2015/052516; dated Oct. 10, 2016; 12 pages.
Novagen "pCDF-1b Vector" Sep. 10, 2003, Retrieved from the Internet on Sep. 1, 2015, at http://www.helmholtz-muenchen.de/fieadmin/PEPF/pCDF_vectors/pCDF-1b_map.pdf, 2 pages.
Ramakrishna Suresh et al. "Gene disruption by cell-penetrating peptide-mediated delivery of Cas9 protein and guide RNA", Genome Research, 24:1020-1027 (2014).
Seed Kimberley D. et al., "A bacteriophage encodes its own CRISPR/Cas adaptive response to evade host innate immunity", Nature, 494:7438, pp. 469-491 (2013).
Uchiyama Jumpei et al., "Charactenzation of Helicobacter pylori bacteriophage KHP30", Applied and environmental mioroblology, 79(10):3176-3184 (2013).
Wiedenheft et al. "RNA-guided complex from a bacterial immune system enhances target recognition through seed sequence interactions", PNAS, 108:36 (2011) 7 pages.
Written Opinion and International Search Report corresponding to International Application No. PCT/US2016/037493, dated Sep. 15, 2016, 8 pages.
Written Opinion of the Intemnational Search Report regarding International Application No. PCT/US2016/067657, dated Mar. 6, 2017, 9 pages.
Milani C et al. Genomic encyclopedia of type strains of the genus *Bifidobacterium*. Applied and Environmental Microbiology. Oct. 2014; 80(20): 6290-6302.
Database GenBank [online]. NBI, U.S. National Library of Medicine. Aug. 6, 2014. "CRISPER-associated protein, Csn1 family[Bifidobacterium bombi DSM 19703]." XP002785852, retrieved from NCBI accession No. GenBank: KFF31259. Database accession No. KFF31259. 1 page.
International Search Report and Written Opinion, PCT/US2018/034322, dated Sep. 13, 2018, 7 pages.
Final Office Action, U.S. Appl. No. 16/153,052, dated Dec. 26, 2018, 14 pages.
Office Action, U.S. Appl. No. 15/032,985, dated Feb. 5, 2019, 11 pages.
Rath D et al. The CRISPR-Cas immune system: Biology, mechanisms and applications. Biochimie. 2015;117: 119-128.
Spath K et al. Lactobacillus plantarum and Lactobacillus buchneri as expression systems: Evaluation of different origins of replication for the design of suitable shuttle vectors. Mol. Biotechnol. 2012; 52: 40-48.
Grissa I et al. The CRISPRdb database and tools to display CRISPRs and to generate dictionaries of spacers and repeats. BMC Bioinformatics. 2007; 8(172): pp. 1-10.
Cong et al. Supplementary Materials for "Multiplex Genome Engineering Using CRISPR/Cas Systems" Science, 339 (6121):819-823 (2013).
Office Action, U.S. Appl. No. 15/113,656, dated Mar. 11, 2019, 22 pages.
Boudry et al. "Function of CRISPR-Cas System of the Human Pathogen Clostridium difficile" mBio, 6(5):1-15 2015.
Edgar et al. Supplemental Material "The *Escherichia coli* CRISPR System Protects from Lysogenization, Lysogens, and Prophage Induction" Journal of Bacteriology, 192(23): 6292-6294 2010.
Shinkai "Structure and Function of CRISPR-Cas System" Seibutsu Butsuri, 54(5):247-252 (2014) Abstract Only.
Extended European Search Report regarding European Application No. EP19196063, dated Jun. 26, 2020 12 pages.
Third Party Observations corresponding to European Patent Application No. 16804164.8, dated Jul. 24, 2019 60 pages.
Third Party Observations corresponding to European Patent Application No. 16812275.2, dated May 15, 2020 108 pages.
International Preliminary Report on Patentability Notification, PCT/US2018/034322, dated Dec. 5, 2019, 7 pages.
International Search Report and Written Opinion corresponding to PCT/US2019/52883, dated Dec. 23, 2019, 9 pages.
Internatianal Search Report and Written Opinion corresponding to PCT/US2019/52878, dated Dec. 27, 2019, 14 pages.
International Search Report and Written Opinion corresponding to PCT/US2019/52864, dated Dec. 17, 2019, 15 pages.
International Search Report and Written Opinion corresponding to PCT/US2019/52861, dated Feb. 12, 2020, 18 pages.
GenBank Accession No. FN692037.1, "Lactobacillus crispatus ST1 complete genome, strain ST1" Feb. 27, 2015.
Ojala et al. "Comparative genomics of Lactobacillus crispatus suggests novel mechanisms for the competitive exclusion of Garnerella vaginalis" BNC Genomics, 15:1070 (2014).
Gasiunas et al. "Molecular mechanisms of CRISPR-mediated microbial immunity" Cellular and Molecular Life Sciences, 71:449-465 (2014).
Jackson et al. "Crystal structure of the CRISPR RNA-guided surveillance complex from *Escherichia coli*" Science, 345(6203):1473-1479 (2014).
Westra et al., "CRISPR Immunity Relies on the Consecutive Binding and Degradation of Negatively Supercoiled Invader DNA by Cascade and Cas3" Molecular Cell, 46:595-605 (2012).
Hidalgo-Cantabrana et al. "Genome editing using the endogenous type I CRISPR-Cas system in Lactobacillus crispatus" PNAS, 116)32):15774-15783 (2019).
Yosef et al. "High-temperature protein G is essential for activity of the *Escherichia coli* clustered regularly interspaced short palindromic repeats (CRISPR)/Cas system" Proc Nat Acad Sci, 108(50):20136-20141 (2011).
Sanozky-Dawes et al. "Occurrence and activity of a type II CRISPR-Cas system in Lactobacillus gasseri" Microbiology, 161:1752-1761 2015.
Anderson et al. "Lactobacillus gasseri CRISPR-Cas9 characterization In Vitro reveals a flexible mode of protospacer-adjacent motif recognition" PLOS ONE, 13(2) 14 pages 2018.
Gutierrez et al. "Predicting CRISPR-Cas9 activity in *E. coli*" bioRxviv, https://doi.org/10.1101/308148, pp. 1-22 2018.
Hochstrassera et al. "CasA mediates Cas3-catalyzed target degradation during CRISPR RNA-guided interference" PNAS, 111(18):6618-23 2014.
Nizet et al. "Bacterial sepsis and meningitis" Remington and Klein's Infectious diseases of the fetus and newborn infant, 8th Edition, pp. 217-271 2011.
Verco et al. "Cytotoxic Chromosomal Targeting by CRISPR/Cas Systems Can Reshape Bacterial Genomes and Expel or Remodel Pathogenicity Islands" PLOS Genetics, 9(4):1-13 2013.
Brouns et al. "Small CRISPR RNAs Guide Antiviral Defense in Prokaryotes" Science, 321 (5891):960-964 2008.
Cady et al. "The CRISPR/Cas Adaptive Immune System of Pseudomonas aeruginosa Mediates Resistance to Naturally Occurring and Engineered Phages" J. Bacteriol., 194(21):5728-5738 2012.
Erdmann et al., "Selective and hyperactive uptake of foreign DNA by adaptive immune systems of an archaeon via two distinct mechanisms" Mol Microbiol, 85(6):1044-1056 2012.
Gleditzsch et al. "Modulating the Cascade architecture of a minimal Type I-F CRISPR-Cas system" Nucleic Acids Res., 44(12):5872-5882 2016.

(56) References Cited

OTHER PUBLICATIONS

Grissa et al. "The CRISPRdb database and tools to display CRISPRs and to generate dictionaries of spacers and repeats" BMC Informatics, 8(172) 10 pages 2007.
Kuznedelov et al. "Altered stoichiometry *Escherichia coli* Cascade complexes with shortened CRISPR RNA spacers are capable of interference and primed adaptation" Nucleic Acids Res., 44(22):10849-10861 2016.
Maier et al. "Essential requirements for the detection and degradation of invaders by the Haloferax volcanii CRISPR/Cas system I-B" RNA Biology, 10(5):865-874 2013.
Marakova et al. "Evolution and classification of the CRISPR-Cas systems" Nat. Rev. Microbiol., 9(6):467-477 2011.
Nam et al. "Cas5d protein processes pre-crRNA and assembles into a Cascade-like interference complex in Subtype I-C/Dvulg CRISPR-Cas system" Structure, 20(9):1574-1584 2012.
Scholz et al. "CRISPR-Cas Systems in the *Cyanobacterium synechocystis* sp. PCC6803 Exhibit Distinct Processing Pathways Involving at Least Two Cas6 and a Cmr2 Protein" PLosONE, 8(2) 15 pages 2013.
Chauthaiwale, V. M. et al. "Bacteriophage Lamda as a Cloning Vector" Microbiological Reviews, 56(4):577-591 (1992).
Dang, Y. et al. "Optimizing sgRNA structure to improve CRISPR-Cas9 knockout efficiency" Genome Biology, 16(280):1-10 (2015).
Edgar, R. et al. "Reversing Bacterial Resistance to Antibiotics by Phage-Mediated Delivery of Dominant Sensitive Genes" Applied and Environmental Microbiology, 78(3):744-751 (2011).
Extended European Search Report corresponding to European Patent Application No. 18806333.3 (8 pages) (dated Feb. 9, 2021).
Third Party Observation filed in European Patent Application No. 16804164.8 dated Feb. 19, 2021, 15 pages.
Third Party Observation filed in European Patent Application No. 16812275.2 dated Feb. 19, 2021, 38 pages.
Yosef, I. et al. "Temperate and lytic bacteriophages programmed to sensitize and kill antibiotic-resistant bacteria" PNAS, 112(23):7267-7272 (2015).
Sashital et al. "Mechanism of foreign DNA selection in a bacterial adaptive immune system" Mol Cell., 46 (5):6061-615 2012.
Third Party Observations corresponding to U.S. Appl. No. 15/735,028, dated Aug. 30, 2019 17 pages.

* cited by examiner

METHODS AND COMPOSITIONS FOR RNA-DIRECTED REPRESSION OF TRANSCRIPTION USING CRISPR-ASSOCIATED GENES

STATEMENT OF PRIORITY

This application is a 35 U.S.C. § 371 national phase application of International Application Serial No. PCT/IB2015/052515, filed Apr. 7, 2015, which claims the benefit, under 35 U.S.C. § 119 (a) of U.S. Provisional Patent Application No. 61/976,883, filed Apr. 8, 2014, and U.S. Provisional Patent Application No. 62/058,365, filed Oct. 1, 2014, the entire contents of each of which are incorporated by reference herein.

SEQUENCE LISTING STATEMENT

A Sequence Listing in ASCII text format, submitted under 37 C.F.R. § 1.821, entitled 5051-861_ST25.txt, 60,109,388 bytes in size, generated on Nov. 29, 2020 and filed via EFS-Web, is provided in lieu of a paper copy. The Sequence Listing is incorporated herein by reference into the specification for its disclosures.

FIELD OF THE INVENTION

The invention relates to a synthetic CRISPR-Cas system and methods of use thereof for repression and modulation of gene expression.

BACKGROUND OF THE INVENTION

Clustered Regularly Interspaced Short Palindromic Repeats (CRISPR), in combination with CRISPR-associated genes (cas) constitute the CRISPR-Cas system, which confers adaptive immunity in many bacteria and most archaea. CRISPR-mediated immunization occurs through the integration of DNA from invasive genetic elements such as plasmids and phages that can be used to thwart future infections by invaders containing the same sequence.

CRISPR-Cas systems consist of CRISPR arrays of short DNA "repeats" interspaced by hypervariable "spacer" sequences and a set of flanking cas genes. The system acts by providing adaptive immunity against invasive genetic elements such as phage and plasmids through the sequence-specific targeting and interference of foreign nucleic acids (Barrangou et al. 2007. *Science.* 315:1709-1712; Brouns et al. 2008. *Science* 321:960-4; Horvath and Barrangou. 2010. *Science.* 327:167-70; Marraffini and Sontheimer. 2008. *Science.* 322:1843-1845; Bhaya et al. 2011. *Annu. Rev. Genet.* 45:273-297; Terns and Terns. 2011. *Curr. Opin. Microbiol.* 14:321-327; Westra et al. 2012. *Annu. Rev. Genet.* 46:311-339; Barrangou R. 2013. *RNA.* 4:267-278). Typically, invasive DNA sequences are acquired as novel "spacers" (Barrangou et al. 2007. *Science.* 315:1709-1712), each paired with a CRISPR repeat and inserted as a novel repeat-spacer unit in the CRISPR locus. The "spacers" are acquired by the Cas1 and Cas2 proteins universal to all CRISPR-Cas systems (Makarova et al. 2011. *Nature Rev. Microbiol.* 9:467-477; Yosef et al. 2012. *Nucleic Adds Res.* 40:5569-5576), with involvement by the Cas4 protein in some systems (Plagens et al. 2012. *J. Bact.* 194: 2491-2500; Zhang et al. 2012. *PLoS One* 7:e47232). The resulting repeat-spacer array is transcribed as a long pre-CRISPR RNA (pre-crRNA) (Brouns et al. 2008. *Science* 321:960-4), which is processed into CRISPR RNAs (crRNAs) that drive sequence-specific recognition of DNA or RNA. Specifically, crRNAs guide nucleases towards complementary targets for sequence-specific nucleic acid cleavage mediated by Cas endonucleases (Gameau et al. 2010. *Nature.* 468:67-71; Haurwitz et al. 2010. *Science.* 329:1355-1358; Sapranauskas et al. 2011. *Nucleic Acid Res.* 39:9275-9282; Jinek et al. 2012. *Science.* 337:816-821; Gasiunas et al. 2012. *Proc. Natl. Acad. Sci.* 109:E2579-E2586; Magadan et al. 2012. *PLoS One.* 7:e40913; Karvelis et al. 2013. *RNA Biol.* 10:841-851).

These widespread systems occur in nearly half of bacteria (~46%) and the large majority of archaea (~90%). They are classified into three main types (Makarova et al. 2011. *Nature Rev. Microbiol.* 9:467-477; Makarova et al. 2013. *Nucleic Acid Res.* 41:4360-4377) based on the cas gene content, organization and variation in the biochemical processes that drive crRNA biogenesis, and Cas protein complexes that mediate target recognition and cleavage. The type I systems are the most prevalent in bacteria and in archaea (Makarova et al. 2011. *Nature Rev. Microbiol.* 9:467-477) and target DNA (Brouns et al. 2008. *Science* 321:960-4). A complex of 3-8 Cas proteins called the CRISPR associated complex for antiviral defense (Cascade) process the pre-crRNAs (Brouns et al. 2008. *Science* 321: 960-4), retaining the crRNA to recognize DNA sequences called "protospacers" that are complementary to the spacer portion of the crRNA. Aside from complementarity between the crRNA spacer and the protospacer, targeting requires a protospacer-adjacent motif (PAM) located at the 5' end of the protospacer (Mojica et al. 2009. *Microbiology* 155:733-740; Sorek et al. 2013. *Ann. Rev. Biochem.* 82:237-266). For type I systems, the PAM is directly recognized by Cascade (Sashital et al. 2012. *Mol. Cell* 46:606-615; Westra et al. 2012. *Mol. Cell* 46:595-605). The exact PAM sequence that is required can vary between different type I systems and can be identified through established bioinformatics and experimental procedures (Esvelt et al. 2013. *Nat. Methods* 10:1116-11121; Jiang et al. 2013. *Nat. Biotechnol.* 31:233-239; Mojica et al. 2009. *Microbiology* 155:733-740). Once a protospacer is recognized, Cascade generally recruits the endonuclease Cas3, which cleaves and degrades the target DNA (Sinkunas et al. 2011. *EMBO J.* 30:1335-1342; Sinkunas et al. 2013. *EMBO J.* 32:385-394).

Interference requires that all of the Cas proteins comprising the complex, the Cas3 protein, and the CRISPR array be expressed. In most organisms, these proteins appear to be constitutively expressed, although, in a few examples, some of these proteins are inducibly expressed. For instance, in *Escherichia coli*, the genes encoding the complex are encoded in a single operon that is repressed under normal growth conditions. However, repression of the operon can be eliminated through deletion of the repressor H-NS (Pul et al. 2010. *Mol. Microbiol.* 75:1495-1512; Westra et al. 2010. *Mol. Microbiol.* 77:1380-1393).

The present disclosure provides methods and compositions for targeted gene silencing that provide the ability to not only repress expression but to modulate the repression of expression of one or more target genes.

SUMMARY OF THE INVENTION

In one aspect, a recombinant nucleic acid molecule is provided comprising a nucleotide sequence encoding a subset of CRISPR-cas polypeptides, or functional fragments thereof, from a type-I CRISPR-cas system. In some aspects, a recombinant nucleic acid of the invention comprises a nucleotide sequence encoding three or more Type I Cascade polypeptides having substantial identity to a type I Cascade polypeptide. In still other aspects, the three or more type-I Cascade polypeptides, or functional fragments thereof, can be fused to form a single polypeptide.

In another aspect, a recombinant nucleic acid molecule is provided comprising a nucleotide sequence having substantial similarity to: (a) a nucleotide sequence encoding a Cas6b polypeptide, a nucleotide sequence encoding a Cas8b (Csh1) polypeptide, a nucleotide sequence encoding a Cas7 (Csh2) polypeptide and a nucleotide sequence encoding a Cas5 polypeptide (type I-B); (b) a nucleotide sequence encoding a Cas5d polypeptide, a nucleotide sequence encoding a Cas8c (Csd1) polypeptide, and a nucleotide sequence encoding a Cas7 (Csd2) polypeptide (type I-C); (c) a nucleotide sequence encoding a Cse1 (CasA) polypeptide, a nucleotide sequence encoding a Cse2 (CasB) polypeptide, a nucleotide sequence encoding a Cas7 (CasC) polypeptide, a nucleotide sequence encoding a Cas5 (CasD) polypeptide and a nucleotide sequence encoding a Cas6e (CasE) polypeptide (type I-E); (d) a nucleotide sequence encoding a Cys1 polypeptide, a nucleotide sequence encoding a Cys2 polypeptide, a nucleotide sequence encoding a Cas7 (Cys3) polypeptide and a nucleotide sequence encoding a Cas6f polypeptide (type I-F); (e) a nucleotide sequence encoding a Cas7 (Csa2) polypeptide, a nucleotide sequence encoding a Cas8a1 (Csx13) polypeptide or a Cas8a2 (Csx9) polypeptide, a nucleotide sequence encoding a Cas5 polypeptide, a nucleotide sequence encoding a Csa5 polypeptide, a nucleotide sequence encoding a Csa5 polypeptide, a nucleotide sequence encoding a Cas6a polypeptide, a nucleotide sequence encoding a Cas3' polypeptide, and a nucleotide sequence encoding a Cas3" polypeptide having no nuclease activity (type I-A); and/or (f) a nucleotide sequence encoding a Cas10d (Csc3) polypeptide, a nucleotide sequence encoding a Csc2 polypeptide, a nucleotide sequence encoding a Csc1 polypeptide, a nucleotide sequence encoding a Cas6d polypeptide (type I-D).

A further aspect of the invention provides a recombinant Clustered Regularly Interspaced Short Palindromic Repeats (CRISPR) RNA comprising at least one spacer nucleotide sequence linked at its 3' end to a repeat nucleotide sequence, wherein said at least one spacer nucleotide sequence optionally comprises at its 5' end at least one additional nucleotide.

An additional aspect of the invention provides a recombinant CRISPR array comprising two or more repeat nucleotide sequences and one or more spacer nucleotide sequence(s), wherein each spacer nucleotide sequence in said CRISPR array linked at its 5' end and at its 3' end to a repeat nucleotide sequence.

Another aspect of the invention provides a method for repressing the expression (e.g., reducing transcription) of a target nucleotide sequence, comprising: introducing into an organism a recombinant nucleic acid molecule of this invention and at least one recombinant CRISPR array of this invention, thereby repressing the expression of said target nucleotide sequence in said organism. A further aspect provides a method for modulating (increasing/decreasing) the repression of a target gene, wherein the at least one recombinant CRISPR array introduced into the organism comprises at least two spacer nucleotide sequences each comprising a nucleotide sequence that is complementary to a different target nucleotide sequence from a single target gene, thereby modulating the repression of said target gene. A still further aspect provides a method for repressing the expression of at least two genes in an organism, wherein the at least one recombinant CRISPR array comprises at least two spacer nucleotide sequences each comprising a nucleotide sequence that is complementary to a different target nucleotide sequence from a different target gene, thereby repressing the expression of at least two genes in said organism.

A further aspect of the invention comprises a method of repressing the expression (reducing transcription) of a bacterium or archaeon target nucleotide sequence, comprising: disrupting an endogenous cas3 nucleotide sequence in a bacterium or archaeon, wherein the disrupted endogenous cas3 nucleotide sequence is not present, or is present but not expressed and/or is expressed but non-functional; and introducing into said bacterium or archaeon at least one expression cassette comprising the recombinant CRISPR array of this invention, thereby repressing the expression of said bacterium or target nucleotide sequence. In some embodiments, the method further comprises modulating (increasing/decreasing) the repression (e.g., the reduction in transcription) of the target gene, wherein at least one recombinant CRISPR array comprises at least two spacer nucleotide sequences each comprising a nucleotide sequence that is complementary to a different target nucleotide sequence from a single target gene, thereby modulating the repression of said bacterium or archaeon target gene. A still further aspect comprises repressing the expression of at least two target genes in a bacterium or archaeon, wherein at least one recombinant CRISPR array comprises at least two spacer nucleotide sequences each comprising a nucleotide sequence that is complementary to a different target nucleotide sequence from a different target gene and the bacterium or archaeon comprises a disrupted endogenous cas3 nucleotide sequence, thereby repressing the expression of at least two target genes of said bacterium or archaeon.

Further provided herein are expression cassettes, cells, and kits comprising the recombinant nucleic acid molecules, CRISPR arrays, and/or nucleotide sequences of the invention.

These and other aspects of the invention are set forth in more detail in the description of the invention below.

BRIEF DESCRIPTION OF THE DRAWINGS

FIG. 4A provides the genetic locus of the Type I-E system. The cas3 gene is located upstream of the casABCDE operon encoding the Cascade protein complex. The two downstream genes cas1 and cas2 are involved in spacer acquisition. The native spacer array is composed of identical repeats (white ovals) and intervening spacers (dotted and hatched ovals). FIG. 4B shows the mechanism of DNA destruction based on previous work (Sorek et al. (2013) Annu. Rev. Biochem., 82, 237-266; Barrangou et al. (2007) Science, 315, 1709-17122). The transcribed array is processed into individual crRNAs by Cascade. The spacer portion of the array is then used to identify complementary DNA sequences flanked by a PAM (white circle). DNA binding leads to recruitment of Cas3, which cleaves and degrades the target DNA.

FIG. 5A shows conversion of the Type I-E CRISPR-Cas system into a programmable repressor. The deletion of cas3 and insertion of a constitutive promoter upstream of the Cascade operon allows crRNA-directed DNA binding without cleavage. FIG. 5B shows a putative mechanism of crRNA-directed gene repression. Cascade processes the transcribed CRISPR array into individual crRNAs. The Cascade-crRNA complex then binds target DNA sequences (dotted line) flanked by a PAM (white circle), leading to transcriptional repression.

FIG. 7A shows targeted silencing of plasmid-based GFP expression. The gfp gene is under the control of the lacZ promoter in the low-copy plasmid pUA66-lacZ. Each spacer sequence (medium gray lines) and PAM (black circle) matches the closest strand of the protospacer. RBS, ribosome-binding site. FIG. 7B shows location-dependent and strand-dependent repression of GFP expression. BW25113 Δcas3::cat harboring the medium-copy pUA66-lacZ and the indicated single-spacer plasmid were subjected to flow cytometry analysis following induction with IPTG and L-arabinose. The non-targeting mviM spacer serves as a negative control. Repression is calculated as the ratio of the autofluorescence-subtracted fluorescence for the inducible no-spacer plasmid (pcrRNA.ind) and each single-spacer plasmid. FIG. 7C shows the reversibility of gene silencing. BW25113 Δcas3::cat cells harboring pUA66-lacZ and either the no-spacer plasmid (pcrRNA.ind, white circles) or the T2 single-spacer plasmid (T2, hashmark circles) were pre-induced with only IPTG and switched to both IPTG and L-arabinose (left) or were pre-induced with both IPTG and L-arabinose and switched to only IPTG (right). Following the inducer switch at t=0, the autofluorescence-subtracted fluorescence for individual cells and the turbidity of the culture were followed over time. GFP fluorescence was about 10-fold lower for cells with the targeting plasmid versus the spacer-free plasmid, which was attribute to leaky expression from the $P_{araB}$ promoter under these growth conditions (Afroz et al. (2014) TACS Synth. Biol., 10.1021/sb400162z). Values represent geometric mean and S.E.M. from independent experiments starting with three separate colonies. Error bars in C are smaller than the symbols.

FIG. 8A shows GFP fluorescence of BW25113 (top) or BW25113 ΔCRISPR-Cas (bottom) harboring pUA66-lacZ and the indicated plasmid. Cells were grown for ~3-4 hours in M9 minimal medium containing 0.2% casamino acids, 0.4% glycerol, 0.2% L-arabinose, and 0.1 mM IPTG to $ABS_{600}$~0.2 prior to flow cytometry analysis. The reported values are the absolute fluorescence minus autofluorescence from cells lacking GFP. FIG. 8B shows transformation efficiencies in the presence or absence of cas3. BW25113 Δcas3::cat or NM500 cas3' cells harboring pUA66-lacZ were transformed with 50 ng of the indicated plasmid and plated on LB agar with ampicillin, kanamycin, IPTG, and L-arabinose, and the number of colonies was counted. The differences in transformation efficiencies between strains were attributed to switching cuvette manufacturers. FIG. 8C shows GFP repression following excision of the resistance cassette or in the presence of cas3. BW25113 Δcas3 or NM500 cas3$_+$ cells harboring pUA66-lacZ and pCRISPR.ind, pCRISPR.ind-T2 (T2), pCRISPR.ind-NT2 (NT2), or pCRISPR.ind-mviM (mviM) were grown as indicated for FIG. 8A. Repression is calculated as the ratio of the autofluorescence-subtracted fluorescence for pcrRNA.ind and each single-spacer plasmid. See FIGS. 7A-7C for more information. Values represent the geometric mean and S.E.M. from independent experiments with three colonies.

FIG. 10, panel A shows targeting operons responsible for sugar catabolism. Spacers were designed to target the promoter of each catabolic operon required for growth on its cognate sugar. FIG. 10, panel B shows repression of promoter activity. Repression is calculated as the ratio of the autofluorescence-subtracted fluorescence for the constitutive no-spacer plasmid (pcrRNA.con) and each single-spacer or multi-spacer plasmid. Values represent geometric mean and S.E.M. from independent experiments with three colonies. FIG. 10, panel C shows repression of endogenous genes. MG1655 Δcas3::cat cells harboring the indicated single-spacer plasmid were harvested for total RNA following induction with the cognate sugar and subjected to qRT-PCR analysis. Repression is calculated as the ratio of the relative mRNA levels from the no-spacer plasmid (pcrRNA.con) and the indicated single-spacer plasmid. Values represent the geometric mean and S.E.M. for quadruple technical replicates. FIG. 10, panel D shows targeted suppression of growth. MG1655 Δcas3::cat cells harboring the indicated single-spacer or mufti-spacer plasmid were grown on each sugar as the sole carbon source turbidity was measured after 24 hours of growth. Values represent the geometric mean of the measured $ABS_{600}$ values from independent experiments starting with three separate colonies.

FIG. 11A shows individual $ABS_{600}$ values for the growth assays. The data represent those shown in FIG. 10, panel D with the exception of the last column showing growth in media containing four sugars. Dots represent individual measurements from independent cultures. FIG. 11B provides doubling times of MG1655 Δcas3 cells harboring the constitutive pcrRNA.con plasmid grown in minimal medium with the indicated sugar as the sole carbon source. Values represent the geometric mean and S.E.M. from independent experiments with three colonies.

FIG. 12A shows the construct and the location of the protospacer. See FIG. 7A for more information. FIG. 12B shows that repression is increased by increasing the length of spacer and decreased by decreasing the spacer length.

FIG. 20A shows the *B. halodurans* Type I-C Cascade operon (above) and the CRISPR guiding the Cascade complex to silence GFP expression by targeting the lac promoter (below); FIG. 20B shows fluorescence measurements of cultures by flow cytometry analysis.

DETAILED DESCRIPTION

Figure 1:
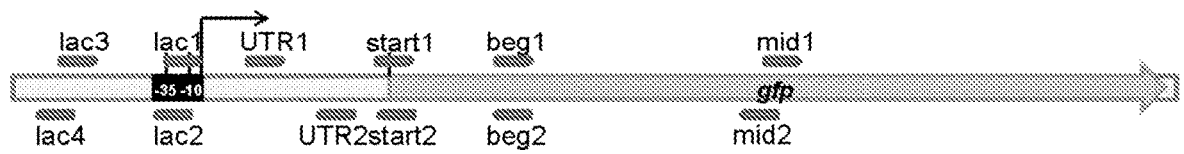
FIG. 1 shows the region of interest in the plasmid pUA66lacZ that encodes fluorescent GFP polypeptide under control of the LacZ promoter. The long arrow indicates the coding region of gfp. The thin black arrow indicates the start of transcription with the −35 and −10 elements of the promoter outlined in black. Each spacer on the top matches the top strand or the coding strand (and therefore, binds the bottom strand or non-coding strand). Similarly each spacer on the bottom matches the bottom strand or the non-coding strand (and therefore, binds the top strand). The established PAM AAG or AGG is located at the 5' end of each protospacer.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," 'an' and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative (or).

The term "about," as used herein when referring to a measurable value such as a dosage or time period and the like refers to variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, "chimeric" refers to a nucleic acid molecule or a polypeptide in which at least two components are derived from different sources (e.g., different organisms, different coding regions).

"Complement" as used herein can mean 100% complementarity or identity with the comparator nucleotide sequence or it can mean less than 100% complementarity (e.g., about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

The terms "complementary" or "complementarity," as used herein, refer to the natural binding of polynucleotides under permissive salt and temperature conditions by base-pairing. For example, the sequence "5'-A-G-T-3'" binds to the complementary sequence "5'-T-C-A-3'." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, "contact," contacting," "contacted," and grammatical variations thereof, refers to placing the components of a desired reaction together under conditions suitable for carrying out the desired reaction (e.g., integration, transformation, site-specific cleavage (nicking, cleaving), amplifying, site specific targeting of a polypeptide of interest and the like). The methods and conditions for carrying out such reactions are well known in the art (See, e.g., Gasiunas et al. (2012) *Proc. Natl. Acad. Sci.* 109: E2579-E2586; M. R. Green and J. Sambrook (2012) Molecular Cloning: A Laboratory Manual. 4th Ed., Cold Spring Harbor Laboratory Press, Cold Spring Harbor, N.Y.).

As used herein, type I Clustered Regularly Interspaced Short Palindromic Repeats (CRISPR)-associated complex for antiviral defense (Cascade) refers to a complex of polypeptides involved in processing of pre-crRNAs and subsequent binding to the target DNA in type I CRISPR-Cas systems. These polypeptides include, but are not limited to, the Cascade polypeptides of type I subtypes I-A, I-B, I-C, 1-D, I-E and I-F. Non-limiting examples of type I-A polypeptides include Cas7 (Csa2), Cas8a1 (Csx13), Cas8a2 (Csx9), Cas5, Csa5, Cas6a, Cas3' and/or a Cas3". Non-limiting examples of type I-B polypeptides include Cas6b, Cas8b (Csh1), Cas7 (Csh2) and/or Cas5. Non-limiting examples of type-IC polypeptides include Cas5d, Cas8c (Csd1), and/or Cas7 (Csd2). Non-limiting examples of type-ID polypeptides include Cas10d (Csc3), Csc2, Csc1, and/or Cas6d. Non-limiting examples of type I-E polypeptides include Cse1 (CasA), Cse2 (CasB), Cas7 (CasC), Cas5 (CasD) and/or Cas6e (CasE). Non-limiting examples of type I-F polypeptides include Cys1, Cys2, Cas7 (Cys3) and/or Cas6f (Csy4). Thus, in some embodiments of this invention, a recombinant nucleic acid comprises, consists essentially of, consists of a nucleotide sequence encoding a subset of type-I Cascade polypeptides that function to process a CRISPR array and subsequently bind to a target DNA using the spacer of the processed CRISPR RNA as a guide.

A"fragment" or "portion" of a nucleotide sequence will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent. In some embodiments, a fragment of a polynucleotide can be a fragment that encodes a polypeptide that retains its function (e.g., encodes a fragment of a Type-1 Cascade polypeptide that is reduce in length as compared to the wild type polypeptide but which retains at least one function of a Type-1 Cascade protein (e.g., process CRISPR RNAs, bind DNA and/or form a complex).

As used herein, the term "gene" refers to a nucleic acid molecule capable of being used to produce mRNA, tRNA, rRNA, miRNA, anti-microRNA, regulatory RNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A"hairpin sequence" as used herein, is a nucleotide sequence comprising hairpins. A hairpin (e.g., stem-loop, fold-back) refers to a nucleic acid molecule having a secondary structure that includes a region of nucleotides that form a single strand that are further flanked on either side by a double stranded-region. Such structures are well known in the art. As known in the art, the double stranded region can comprise some mismatches in base pairing or can be perfectly complementary. In some embodiments, a repeat nucleotide sequence comprises, consists essentially of, consists of a hairpin sequence that is located within said repeat nucleotide sequence (i.e., at least one nucleotide (e.g., one, two, three, four, five, six, seven, eight, nine, ten, or more) of the repeat nucleotide sequence is present on either side of the hairpin that is within said repeat nucleotide sequence).

A"heterologous" or a "recombinant" nucleotide sequence is a nucleotide sequence not naturally associated with a host cell into which it is introduced, including non-naturally occurring multiple copies of a naturally occurring nucleotide sequence.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used herein, hybridization, hybridize, hybridizing, and grammatical variations thereof, refer to the binding of two complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500%, 750%, 1000%, 2500%, 5000%, 10,000%, 20,000% or more as compared to a control (e.g., a CRISPR array targeting a particular gene having, for example, more spacer nucleotide sequences targeting different regions of that gene and therefore having increased repression of that gene as compared to a CRISPR array targeting the same gene but having, for example, fewer spacer nucleotide sequences targeting different regions of that gene).

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is a mRNA that is naturally occurring in or endogenous to the organism. A "homologous" nucleic acid sequence is a nucleotide sequence naturally associated with a host cell into which it is introduced.

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

A "synthetic" nucleic acid or nucleotide sequence, as used herein, refers to a nucleic acid or nucleotide sequence that is not found in nature but is constructed by the hand of man and as a consequence is not a product of nature.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Except as otherwise indicated, nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end. Thus, for example, an element in the 3' region of a polynucleotide can be located anywhere from the first nucleotide located at the 3' end of the polynucleotide to the nucleotide located halfway through the polynucleotide.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

A "target nucleotide sequence" refers to the portion of the target gene that is complementary to the spacer sequence of the recombinant CRISPR array.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction results in no or essentially no (i.e., an insignificant amount, e.g., less than about 10% or even less than about 5%) detectable activity or amount. Thus, in some embodiments, a mutation in a Cas3 nuclease can reduce the nuclease activity of the Cas3 by at least about 90%, 95%, 97%, 98%, 99%, or 100% as compared to a control (e.g., wild-type Cas3).

In other embodiments, as used herein, modulating repression can result in a decrease in repression as compared to a control (e.g., a CRISPR array targeting a particular gene having, for example, fewer spacer nucleotide sequences targeting different regions of that gene and therefore having decreased repression of that gene as compared to a CRISPR array targeting the same gene but having, for example, more spacer nucleotide sequences targeting different regions of that gene; or a CRISPR array targeting a particular gene having, for example, a spacer nucleotide sequence with less complementarity for a target sequence having decreased repression of that gene as compared to a CRISPR array, for example, targeting the same sequence with greater complementarity for the target sequence. In further embodiments, a control can also comprise a CRISPR array that does not target any gene, a CRISPR array that targets an entirely unrelated gene or no CRISPR array at all. Thus, in some embodiments, reduced repression as compared to a control can be reduced by about 5% to about 100% (e.g., about 5%, 10%, 15%, 20%, 25%, 35%, 50%, 75%, 80%, 85%, 90%, 95%, 97%, 98%, 99%, or 100%, or any range or value therein). In other embodiments, reduced repression as compared to a control can be reduced by about 1.1 fold to about 10,000 fold (e.g., about 1.1, 1.5, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 750, 1000, 1500, 2000, 2500, 3000, 3500, 4000, 4500, 5000, 5500, 6000, 6500, 7000, 7500, 8000, 8500, 9000, 9500, 10,000 fold and the like, and any range or value therein). Thus, in some embodiments, reduced repression as compared to a control can be greater than 1 fold. In other embodiments, reduced repression as compared to a control can be about 2 fold to about 100 fold, about 10 fold to about 100 fold, about 20 fold to about 100 fold, about 20 fold to about 1000 fold, about 50 fold to about 1000 fold, about 100 fold to about 1000 fold, about 500 fold to about 2000 fold, about 500 fold to about 5000 fold, about 2500 fold to about 7500 fold, about 5000 fold to about 10,000 fold, and the like, or any value or range therein.

A "repeat nucleotide sequence" as used herein refers to any known repeat sequence of any wild-type CRISPR Type I loci or can be a synthetic repeat sequence having a different nucleotide sequence than those known in the art but sharing similar structure to that of the wild-type repeat nucleotide sequences of a hairpin structure with a loop region. Thus, in some embodiments, a repeat nucleotide sequence can be identical to or substantially identical to a repeat sequence from a wild-type CRISPR Type I loci. In some embodiments, a repeat nucleotide sequence can comprise a portion of a wild type repeat nucleotide sequence (e.g., 1, 2, 3, 4, 5, 6, 7, 8, 9, 10, 11, 12, 13, 14, 15 or more contiguous nucleotides of a wild type repeat nucleotide sequence). In some embodiments, a repeat sequence comprises, consists essentially of, or consists of at least one nucleotide (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, or more nucleotides, or any range therein). In other embodiments, a repeat sequence comprises, consists essentially of, or consists of at least about one to about 150 nucleotides. In still other embodiments, a repeat sequence comprises, consists essentially of, or consists of at least about one nucleotide to about 100 nucleotides, or any range or value therein. In further embodiments, a repeat sequence can comprise, consist essentially of, or consist of about 3 nucleotides to about 100 nucleotides, about 10 nucleotides to about 100 nucleotides, about 15 nucleotides to about 100 nucleotides, about 20 to about 50 nucleotides, about 20 to about 40 nucleotides, about 20 to about 30 nucleotides, about 30 to about 40 nucleotides, about 25 to about 40 nucleotides, about 25 to about 45 nucleotides, and/or about 25 to about 50 nucleotides, or any range or value therein. In representative embodiments, a repeat sequence can comprise, consist essentially of, or consist of about 25 nucleotides to about 38 nucleotides, or any range or value therein. In still further embodiments, a repeat sequence can comprise, consist essentially of, or consist of about 29 nucleotides. In yet further embodiments, the repeat sequence can comprise, consist essentially of, or consist of a hairpin only having at least about 20 to 30 nucleotides in length. In still other embodiments, a repeat sequence comprises, consists essentially of, or consists of at least about at least three nucleotides. When more than one spacer nucleotide sequence is present in a CRISPR array, each spacer nucleotide sequence is separated from another by "repeat nucleotide sequences." Thus, in some representative embodiments, a repeat nucleotide sequence linked to the 5' end of a spacer nucleotide sequence can be about three nucleotides in length (e.g., 3, 4, 5, 6, 7, 8, 9, 10 nucleotides or more) and have at least 90% identity (e.g., at least 90%, 91%, 92%, 93%, 94%, 95%, 96%, 97%, 98%, 99%, or more) to the same region (e.g., 5' end) of a wild type repeat nucleotide sequence. In other embodiments, the portion of a repeat sequence linked to the 3' end of a spacer sequence can have three or more nucleotides having at least about 50% or more identity to a wild type repeat nucleotide sequence. In yet further embodiments, a repeat sequence can comprise, consist essentially of, or consist of a hairpin only having at least about 20 to 30 nucleotides in length.

A "CRISPR array" as used herein means a nucleic acid molecule that comprises at least two repeat nucleotide sequence, or a portion thereof, and at least one spacer sequence, wherein one of the two repeat nucleotide sequences, or a portion thereof, is linked to the 5' end of the spacer nucleotide sequence and the other of the two repeat nucleotide sequences, or portion thereof, is linked to the 3' end of the spacer nucleotide sequence. In a recombinant CRISPR array, the combination of repeat nucleotide sequences and spacer nucleotide sequences is synthetic, made by man and not found in nature.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

A "spacer nucleotide sequence" as used herein is a nucleotide sequence that is complementary to a target nucleotide sequence on a target gene. In some embodiments, a spacer nucleotide sequence of this invention can be about 15 nucleotides to about 150 nucleotides in length. In other embodiments, a spacer nucleotide sequence of this invention can be about 15 nucleotides to about 100 nucleotides in length (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides or more). In some particular embodiments, a spacer nucleotide sequence can be a length of about 8 to about 150 nucleotides, about 8 to about 100 nucleotides, about 8 to about 50 nucleotides, about 8 to about 40 nucleotides, about 8 to about 30 nucleotides, about 8 to about 25 nucleotides, about 8 to about 20 nucleotides, about 10 to about 50 nucleotides, about 10 to about 40, about 10 to about 30, about 10 to about 25, about 10 to about 20, about 15 to about 50, at least about 8, at least about 10, at least about 15, at least about 20, at least about 25, at least about 30, at least about 35, at least about 40, at least about 50, at least about 60, at least about 70, at least about 80, at least about 90, at least about 100, at least about 110, at least about 120, at least about 130, at least about 140, at least about 150 nucleotides in length, or more, and any value or range therein.

In further embodiments a spacer sequence can be complementary to (fully (100%) complementary) or substantially complementary (substantially complementary) (e.g., at least 50% identical (e.g., 50%, 51%, 52%, 53%, 54%, 55%, 56%, 57%, 58%, 59%, 60%, 61%, 62%, 63%, 64%, 65%, 66%, 67%, 68%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleotide sequence of a target gene. Thus, in some embodiments, the spacer nucleotide sequence can have one, two, three, four, or five mismatches that can be contiguous or noncontiguous. In representative embodiments, the spacer nucleotide sequence can have 50% complementarity to a target nucleotide sequence of a target gene. In further embodiments, the spacer nucleotide sequence can have 70% complementarity to a target nucleotide sequence of a target gene. In still further embodiments, the spacer nucleotide sequence can have 80% complementarity to a target nucleotide sequence of a target gene. In other embodiments, the spacer nucleotide sequence can have 85% complementarity, 90% complementarity, 95%, 96%, 97%, 98%, 99% complementarity, and the like, to a target nucleotide sequence of a target gene. In particular embodiments, the spacer nucleotide sequence can be 100% complementary to a target nucleotide sequence of a target gene. In particular embodiments, a spacer sequence has complete complementarity or substantial complementarity over a region of a target nucleotide sequence that is at least about 8 nucleotides to about 150 nucleotides in length. In some embodiments, the 5' region of a spacer nucleotide sequence can be complementary to a target nucleotide sequence while the 3' region of said spacer can be substantially complementary to the said target nucleotide sequence. Accordingly, in some embodiments, the 5' region of a spacer nucleotide sequence (e.g., the first 8 nucleotides at the 5' end, the first 10 nucleotides at the 5' end, the first 15 nucleotides at the 5' end, the first 20 nucleotides at the 5' end) has about 75% identity or more (75% to about 100% identity) to a target nucleotide sequence, while the remainder of the spacer nucleotide sequence can have about 50% or more complementarity to the target nucleotide sequence. Thus, for example, the first 8 nucleotides at the 5' end of a spacer nucleotide sequence can be 100% complementary to the target nucleotide sequence or it can have one or two mutations and therefore can be about 88% identical or about 75% complementary to a target nucleotide sequence, respectively, while the remainder of the spacer nucleotide sequence can be at least about 50% or more complementary to the target nucleotide sequence.

As used herein, the phrase "substantially identical," or "substantial identity" in the context of two nucleic acid molecules, nucleotide sequences or protein sequences, refers to two or more sequences or subsequences that have at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In particular embodiments, substantial identity can refer to two or more sequences or subsequences that have at least about 70%, at least about 75%, at least about 80%, at least about 85%, at least about 90%, at least about 95, 96, 96, 97, 98, or 99% identity.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 SM NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

In some aspects, a target nucleotide sequence is located adjacent to or flanked by a PAM (protospacer adjacent motif). While PAMs are often specific to the particular CRISPR-Cas system, a PAM sequence can be determined by those skilled in the art through established experimental and computational approaches. Thus, for example, experimental approaches include targeting a sequence flanked by all possible nucleotides sequences and identifying sequence members that do not undergo targeting, such as through in vitro cleavage of target DNA (Patanayak et al. 2013. *Nat. Biotechnol.* 31:839-843) or the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

Any nucleotide sequence and/or recombinant nucleic acid molecule of this invention can be codon optimized for expression in any species of interest. Codon optimization is well known in the art and involves modification of a nucleotide sequence for codon usage bias using species-specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., 50%, 60%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original nucleotide sequence. Thus, in representative embodiments of the invention, the nucleotide sequence and/or recombinant nucleic acid molecule of this invention can be codon optimized for expression in the particular organism/species of interest.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, nucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the recombinant nucleic acid molecules, nucleotide sequences and their encoded polypeptides are "isolated" in that, by the hand of man, they exist apart from their native environment and therefore are not products of nature, however, in some embodiments, they can be introduced into and exist in a recombinant host cell.

In any of the embodiments described herein, the recombinant CRISPR arrays, nucleotide sequences, and/or nucleic acid molecules of the invention can be operatively associated with a variety of promoters, terminators and other regulatory elements for expression in various organisms or cells. Thus, in representative embodiments, at least one promoter and/or terminator can be operably linked to a recombinant nucleic acid molecule and/or a recombinant CRISPR array of the invention. Any promoter useful with this invention can be used and includes, for example, promoters functional with the organism of interest as well as constitutive, inducible, developmentally regulated, tissue-specific/preferred-promoters, and the like, as described herein. A regulatory element as used herein can be endogenous or heterologous. In some embodiments, an endogenous regulatory element derived from the subject organism can be inserted into a genetic context in which it does not naturally occur (e.g., a different position in the genome than as found in nature), thereby producing a recombinant or non-native nucleic acid.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence, means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase and directs the initiation of transcription. In general, promoters are found 5', or upstream, relative to the start of the coding region of the corresponding coding sequence. The promoter region may comprise other elements that act as regulators of gene expression. These include, but are not limited to, a −35 element consensus sequence and a −10 consensus sequence (Simpson. 1979. *Proc. Natl. Acad. Sci. U.S.A.* 76:3233-3237). In mammalian cells, this includes a TATA box consensus sequence, and often a CAAT box consensus sequence (Breathnach and Chambon. 1981. *Annu. Rev. Biochem.* 50:349). In plants, the CAAT box may be substituted by the AGGA box (Messing et al. 1983. in Genetic Engineering of Plants, T. Kosuge, C. Meredith and A. Hollaender (eds.), Plenum Press, pp. 211-227).

Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." These various types of promoters are known in the art.

Thus, in some embodiments, repression can be made constitutive, inducible, temporally regulated, developmentally regulated, chemically regulated, tissue-preferred and/or tissue-specific promoters using the recombinant nucleic acid constructs of the invention operatively linked to the appropriate promoter functional in an organism of interest. In representative embodiments, repression can be made reversible using the recombinant nucleic acid constructs of the invention operatively linked to, for example, an inducible promoter functional in an organism of interest.

The choice of promoter will vary depending on the quantitative, temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

Exemplary promoters include, but are not limited to, promoters functional in eukaryotes and prokaryotes including but not limited to, plants, bacteria, fungi, archaea, animals, and mammals. For example, promoters useful with archaea include, but are not limited to, *Haloferax volcanii* tRNA(Lys) promoter (Palmer et al. *J. Bacteriol.* 1995. 177(7):1844-1849), *Pyrococcus furiosus* gdh promoter (Waege et al. 2010. *Appl. Environ. Microbiol.* 76:3308-3313), *Sulfolobus sulfataricus* 16S/23S rRNA gene core promoter (DeYoung et al. 2011. *FEMS Microbiol. Lett.* 321:92-99).

Exemplary promoters useful with yeast can include a promoter from phosphoglycerate kinase (PGK), glyceraldehyde-3-phosphate dehydrogenase (GAP), triose phosphate isomerase (TPI), galactose-regulon (GAL1, GAL10), alcohol dehydrogenase (ADH1, ADH2), phosphatase (PHO5), copper-activated metallothionine (CUP1), MFα1, PGK/α2 operator, TPI/α2 operator, GAP/GAL, PGK/GAL, GAP/ADH2, GAP/PHO5, iso-1-cytochrome c/glucocorticoid response element (CYC/GRE), phosphoglycerate kinase/angrogen response element (PGK/ARE), transcription elongation factor EF-1α (TEF1), triose phosphate dehydrogenase (TDH3), phosphoglycerate kinase 1 (PGK1), pyruvate kinase 1 (PYK1), and/or hexose transporter (HXT7) (See, Romanos et al. *Yeast* 8:423-488 (1992); and Partow et al. *Yeast* 27:955-964 (2010)).

In additional embodiments, a promoter useful with bacteria can include, but is not limited to, L-arabinose inducible (araBAD, $P_{BAD}$) promoter, any lac promoter, L-rhamnose inducible (rhaP$_{BAD}$) promoter, T7 RNA polymerase promoter, trc promoter, tac promoter, lambda phage promoter ($p_L$, $p_L$-9G-50), anhydrotetracycline-inducible (tetA) promoter, trp, lpp, phoA, recA, proU, cst-1, cadA, nar, lpp-lac, cspA, T7-lac operator, T3lac operator, T4 gene 32, T5-lac operator, nprM-lac operator, Vhb, Protein A, corynebacterial-*E. coli* like promoters, thr, hom, diphtheria toxin promoter, sig A, sig B, nusG, SoxS, katb, α-amylase (Pamy), Ptms, P43 (comprised of two overlapping RNA polymerase a factor recognition sites, σA, σB), Ptms, P43, rplK-rplA, ferredoxin promoter, and/or xylose promoter. (See, K. Terpe *Appl. Microbiol, Biotechnol.* 72:211-222 (2006); Hannig et al. Trends in Biotechnology 16:54-60 (1998); and Srivastava Protein Expr Purif 40:221-229 (2005)).

Non-limiting examples of a promoter functional in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Non-limiting examples of tissue-specific promoters include those associated with genes encoding the seed storage proteins (such as s-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) Seed Sci. Res. 1:209-219; as well as EP Patent No. 255378). Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459, 252), the lectin promoter (Lindstrom et al. (1990) Der. Genet. 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), and/or S-adenosyl-L-methionine synthetase (SAMS) (Vander Mijnsbrugge et al. (1996) *Plant and Cell Physiology*, 37(8): 1108-1115).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the RNAs and/or the polypeptides of the invention to be synthesized only when, for example, a crop of plants are treated with the inducing chemicals. Depending upon the objective, the promoter may be a chemical-inducible promoter, where application of a chemical induces gene expression, or a chemical-repressible promoter, where application of the chemical represses gene expression. In some aspects, a promoter can also include a light-inducible promoter, where application of specific wavelengths of light induce gene expression (Levskaya at al. 2005. *Nature* 438:441-442). In other aspects, a promoter can include a light-repressible promoter, where application of specific wavelengths of light repress gene expression (Ye et al. 2011. *Science* 332:1565-1568).

Chemical inducible promoters useful with plants are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid (e.g., the PR1a system), steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz at al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

In some particular embodiments, promoters useful with algae include, but are not limited to, the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)), the promoter of the $\sigma^{70}$-type plastid rRNA gene (Prm), the promoter of the psbA gene (encoding the photosystem-II reaction center protein D1) (PpsbA), the promoter of the psbD gene (encoding the photosystem-II reaction center protein D2) (PpsbD), the promoter of the psaA gene (encoding an apoprotein of photosystem 1) (PpsaA), the promoter of the ATPase alpha subunit gene (PatpA), and promoter of the RuBisCo large subunit gene (PrbcL), and any combination thereof (See, e.g., De Cosa et al. *Nat. Biotechnol.* 19:71-74 (2001); Daniell et al. *BMC Biotechnol.* 9:33 (2009); Muto et al. *BMC Biotechnol.* 9:26 (2009); Surzycki et al. *Biologicals* 37:133-138 (2009)).

In further embodiments, a promoter useful with this invention can include, but is not limited to, pol III promoters such as the human U6 small nuclear promoter (U6) and the human H1 promoter (H1) (Mäkinen et al. *J Gene Med.* 8(4):433-41 (2006)), and pol II promoters such as the CMV (Cytomegalovirus) promoter (Barrow et al. *Methods in Mol. Biol.* 329:283-294 (2006)), the SV40 (Simian Virus 40)-derived initial promoter, the EF-1α (Elongation Factor-1α) promoter, the Ubc (Human Ubiquitin C) promoter, the PGK (Murine Phosphoglycerate Kinase-1) promoter and/or constitutive protein gene promoters such as the β-actin gene promoter, the tRNA promoter and the like.

Moreover, tissue-specific regulated nucleic acids and/or promoters as well as tumor-specific regulated nucleic acids and/or promoters have been reported. Thus, in some embodiments, tissue-specific or tumor-specific promoters can be used. Some reported tissue-specific nucleic acids include, without limitation, B29 (B cells), CD14 (monocytic cells), CD43 (leukocytes and platelets), CD45 (hematopoietic cells), CD68 (macrophages), desmin (muscle), elastase-1 (pancreatic acinar cells), endoglin (endothelial cells), fibronectin (differentiating cells and healing tissues), FLT-1 (endothelial cells), GFAP (astrocytes), GPIIb (megakaryocytes), ICAM-2 (endothelial cells), INF-β (hematopoietic cells), Mb (muscle), NPHSI (podocytes), OG-2 (osteoblasts, SP-B (lungs), SYN1 (neurons), and WASP (hematopoietic cells). Some reported tumor-specific nucleic acids and promoters include, without limitation, AFP (hepatocellular carcinoma), CCKAR (pancreatic cancer), CEA (epithelial cancer), c-erbB2 (breast and pancreatic cancer), COX-2, CXCR4, E2F-1, HE4, LP, MUC1 (carcinoma), PRC1 (breast cancer), PSA (prostate cancer), RRM2 (breast cancer), survivin, TRP1 (melanoma), and TYR (melanoma).

In some embodiments, inducible promoters can be used in mammalian cells. Examples of inducible promoters include, but are not limited to, tetracycline repressor system promoters, Lac repressor system promoters, copper-inducible system promoters, salicylate-inducible system promoters (e.g., the PR1a system), glucocorticoid-inducible promoters, and ecdysone-inducible system promoters.

In some embodiments, a nucleic acid construct of the invention can be an "expression cassette" or can be comprised within an expression cassette. As used herein, "expression cassette" means a recombinant nucleic acid molecule comprising a nucleotide sequence of interest (e.g., the recombinant nucleic acid molecules and CRISPR arrays of the invention), wherein said nucleotide sequence is operably associated with at least a control sequence (e.g., a promoter). Thus, some aspects of the invention provide expression cassettes designed to express the nucleotides sequences of the invention (e.g., the recombinant nucleic acid molecules and/or the recombinant CRISPR arrays).

An expression cassette comprising a nucleotide sequence of interest may be chimeric, meaning that at least one of its components is heterologous with respect to at least one of its other components. An expression cassette may also be one that is naturally occurring but has been obtained in a recombinant form useful for heterologous expression.

An expression cassette also can optionally include a transcriptional and/or translational termination region (i.e., termination region) that is functional in the selected host cell. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof). In some embodiments of this invention, terminators can be operably linked to the recombinant nucleic acid molecule and CRISPR array of the invention.

An expression cassette also can include a nucleotide sequence for a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Of course, many examples of suitable selectable markers are known in the art and can be used in the expression cassettes described herein.

In addition to expression cassettes, the nucleic acid molecules and nucleotide sequences described herein can be used in connection with vectors. The term "vector" refers to a composition for transferring, delivering or introducing a nucleic acid (or nucleic acids) into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the nucleic acid molecules of this invention (e.g., the recombinant nucleic acid molecules and/or the recombinant CRISPR arrays) and/or expression cassettes comprising the nucleic acid molecules of this invention can be comprised in vectors as described herein and as known in the art.

As used herein, the terms "contacting," "introducing," "delivering," and "administering" refer to a process by which the recombinant nucleic acid molecules and/or recombinant CRISPR arrays of the present invention are delivered to a cell or a subject, in order to repress expression or modify the repression of expression of one or more target genes in the cell or subject. The recombinant nucleic acid molecules and/or recombinant CRISPR arrays may be administered in a number of ways, including, but not limited to, direct introduction into a cell (i.e., intracellularty) and/or extracellular introduction into a cavity, interstitial space, regional circulation feeding a particular organ or tissue, or into a tissue or structure (e.g., a tumor).

"Introducing," "introduce," "introduced" (and grammatical variations thereof) in the context of a polynucleotide of interest means presenting the nucleotide sequence of interest to the host organism or cell of said organism (e.g., host cell) in such a manner that the nucleotide sequence gains access to the interior of a cell and includes such terms as transformation," "transfection," and/or "transduction." Where more than one nucleotide sequence is to be introduced these nucleotide sequences can be assembled as part of a single polynucleotide or nucleic acid construct, or as separate polynucleotide or nucleic acid constructs, and can be located on the same or different expression constructs or transformation vectors. Accordingly, these polynucleotides can be introduced into cells in a single transformation event, in separate transformation events, or, for example, they can be incorporated into an organism by conventional breeding protocols. Thus, in some aspects of the present invention one or more nucleic acid constructs of this invention (e.g., a recombinant nucleic acid molecule, a recombinant CRISPR array, and the like) can be introduced into a host organism or a cell of said host organism.

The terms "transformation," "transfection," and "transduction" as used herein refer to the introduction of a heterologous nucleic acid into a cell. Such introduction into a cell may be stable or transient. Thus, in some embodiments, a host cell or host organism is stably transformed with a nucleic acid molecule of the invention. In other embodiments, a host cell or host organism is transiently transformed with a recombinant nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear, the plasmid and the plastid genome, and therefore includes integration of the nucleic acid construct into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant, a mammal, an insect, an archaea, a bacterium, and the like). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, the nucleotide sequences, constructs, expression cassettes can be expressed transiently and/or they can be stably incorporated into the genome of the host organism.

A recombinant nucleic acid molecule and/or CRISPR array of the invention can be introduced into a cell by any method known to those of skill in the art. Exemplary methods of transformation or transfection include biological methods using viruses and bacteria (e.g., *Agrobacterium*), physicochemical methods such as electroporation, floral dip methods, particle or ballistic bombardment, microinjection, whiskers technology, pollen tube transformation, calcium-phosphate-mediated transformation, nanoparticle-mediated transformation, polymer-mediated transformation including cyclodextrin-mediated and polyethyleneglycol-mediated transformation, sonication, infiltration, as well as any other electrical, chemical, physical (mechanical) and/or biological mechanism that results in the introduction of nucleic acid into a cell, including any combination thereof.

In some embodiments of the invention, transformation of a cell comprises nuclear transformation. In other embodiments, transformation of a cell comprises plastid transformation (e.g., chloroplast transformation). In still further embodiments, the recombinant nucleic acid molecule or CRISPR array of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013))

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, or in separate transformation events, or, alternatively, where relevant, a nucleotide sequence can be incorporated into a plant, as part of a breeding protocol.

The present invention is directed to compositions and methods for targeted gene silencing or more particularly for repressing expression and/or modulating the repression of expression in an organism of interest or cell thereof or in a cell free system.

Accordingly, in one aspect of the invention, a recombinant nucleic acid molecule is provided that comprises a nucleotide sequence encoding a subset of type I CRISPR-Cas polypeptides involved in the CRISPR associated complex for antiviral defense (Cascade) process. The type-I Cascade polypeptides that are useful with this invention process CRISPR arrays to produce a processed RNA that is then used to bind the complex to a DNA that is complementary to a spacer in the processed RNA. In some embodiments, the Cascade polypeptides that are involved in acquisition are not comprised in a nucleic acid molecule of the invention (e.g., Cas1, Cas2). Any such subset of Cascade polypeptides from a type I CRISPR-cas system known in the art or those later discovered can be comprised in a recombinant nucleic acid molecule of this invention. Such polypeptides can be identified, for example, via BLAST searching.

Thus, in some aspects of the invention, a recombinant nucleic acid molecule is provided comprising, consisting essentially of, or consisting of a nucleotide sequence encoding a subset of CRISPR-Cas polypeptides from a type I CRISPR-Cas system. In particular embodiments, a recombinant nucleic acid of the invention comprises, consists essentially of, consists of a nucleotide sequence encoding three or more type I Cascade polypeptides having substantial identity to a wild type I Cascade polypeptide (e.g., at least 80%; about 80%, 85%, 90%, 95%, 96%, 97%, 98%, 99%, 100%, and any range or value therein). In some embodiments, a recombinant nucleic acid of the invention comprises, consists essentially of, or consists of a nucleotide sequence encoding functional fragments of said three or more type-I Cascade polypeptides. As used herein, a functional fragment of a type I Cascade polypeptide means a polypeptide reduced in length as compared to the wild type polypeptide but which can still function as a type I Cascade protein (e.g., process CRISPR RNAs, bind DNA and/or form a complex). In further embodiments, a recombinant nucleic acid of the invention can comprise, consist essentially of, or consist of a nucleotide sequence encoding a fusion of two or more type I Cascade polypeptides, or functional fragments thereof, or any combination thereof.

In a representative embodiment, a recombinant nucleic acid molecule is provided comprising, consisting essentially of, or consisting of a nucleotide sequence having substantial identity to: (a) a nucleotide sequence encoding a Cas6b polypeptide, a nucleotide sequence encoding a Cas8b (Csh1) polypeptide, a nucleotide sequence encoding a Cas7 (Csh2) polypeptide and a nucleotide sequence encoding a Cas5 polypeptide (Type I-B); (b) a nucleotide sequence encoding a Cas5d polypeptide, a nucleotide sequence encoding a Cas8c (Csd1) polypeptide, and a nucleotide sequence encoding a Cas7 (Csd2) polypeptide (Type I-C); (c) a nucleotide sequence encoding a Cse1 (CasA) polypeptide, a nucleotide sequence encoding a Cse2 (CasB) polypeptide, a nucleotide sequence encoding a Cas7 (CasC) polypeptide, a nucleotide sequence encoding a Cas5 (CasD) polypeptide and a nucleotide sequence encoding a Cas6e (CasE) polypeptide (Type I-E); (d) a nucleotide sequence encoding a Cys1 polypeptide, a nucleotide sequence encoding a Cys2 polypeptide, a nucleotide sequence encoding a Cas7 (Cys3) polypeptide and a nucleotide sequence encoding a Cas6f polypeptide (Type I-F); (e) a nucleotide sequence encoding a Cas7 (Csa2) polypeptide, a nucleotide sequence encoding a Cas8a1 (Csx13) polypeptide or a Cas8a2 (Csx9) polypeptide, a nucleotide sequence encoding a Cas5 polypeptide, a nucleotide sequence encoding a Csa5 polypeptide, a nucleotide sequence encoding a Cas6a polypeptide, a nucleotide sequence encoding a Cas3' polypeptide, and a nucleotide sequence encoding a Cas3" polypeptide having no nuclease activity (Type I-A); and/or (f) a nucleotide sequence encoding a Cas10d (Csc3) polypeptide, a nucleotide sequence encoding a Csc2 polypeptide, a nucleotide sequence encoding a Csc1 polypeptide, a nucleotide sequence encoding a Cas6d polypeptide (Type I-D).

In representative embodiments of the invention, a nucleotide sequence encoding a Cas6b polypeptide includes, but is not limited to, a nucleotide sequence encoding the amino acid sequence of SEQ ID NO:18, SEQ ID NO:19 and/or SEQ ID NO:20; a nucleotide sequence encoding a Cas8b (Csh1) polypeptide includes, but is not limited to, a nucleotide sequence encoding the amino acid sequence of SEQ ID NO:21 and/or SEQ ID NO:22; a nucleotide sequence encoding a Cas7 (Csh2) polypeptide includes, but is not limited to, a nucleotide sequence encoding the amino acid sequence of SEQ ID NO:23 and/or SEQ ID NO:24; a nucleotide sequence encoding a Cas5 polypeptide includes, but is not limited to, a nucleotide sequence encoding the amino acid sequence of SEQ ID NO:25 and/or SEQ ID NO:26; a nucleotide sequence encoding a Cas5d polypeptide includes, but is not limited to, a nucleotide sequence encoding the amino acid sequence of SEQ ID NO:27 and/or SEQ ID NO:28; a nucleotide sequence encoding a Cas8c (Csd1) polypeptide includes, but is not limited to, a nucleotide sequence encoding the amino acid sequence of SEQ ID NO:29 and/or SEQ ID NO:30; a nucleotide sequence encoding a Cas7 (Csd2) polypeptide includes, but is not limited to, a nucleotide sequence encoding the amino acid sequence of SEQ ID NO:31 and/or SEQ ID NO:32; a nucleotide sequence encoding a Cse1 (CasA) polypeptide includes, but is not limited to, a nucleotide sequence encoding the amino acid sequence of SEQ ID NO:41 and/or SEQ ID NO:42; a nucleotide sequence encoding a Cse2 (CasB) polypeptide includes, but is not limited to, a nucleotide sequence encoding the amino acid sequence of SEQ ID NO:43 and/or SEQ ID NO:44; a nucleotide sequence encoding a Cas7 (CasC) includes, but is not limited to, a nucleotide sequence encoding the amino acid sequence of SEQ ID NO:45 and/or SEQ ID NO:46; a nucleotide sequence encoding a Cas5 (CasD) polypeptide includes, but is not limited to, a nucleotide sequence encoding the amino acid sequence of SEQ ID NO:47 and/or SEQ ID NO:48; a nucleotide sequence encoding a Cas6e (CasE) polypeptide includes, but is not limited to, a nucleotide sequence encoding the amino acid sequence of SEQ ID NO:49 and/or SEQ ID NO:50; a nucleotide sequence encoding a Cys1 polypeptide includes, but is not limited to, a nucleotide sequence encoding the amino acid sequence of SEQ ID NO:51 and/or SEQ ID NO:52; a nucleotide sequence encoding a Cys2 polypeptide includes, but is not limited to, a nucleotide sequence encoding the amino acid sequence of SEQ ID NO:53 and/or SEQ ID NO:54; a nucleotide sequence encoding a Cas7 (Cys3) polypeptide includes, but is not limited to, a nucleotide sequence encoding the amino acid sequence of SEQ ID NO:55 and/or SEQ ID NO:56; a nucleotide sequence encoding a Cas6f polypeptide includes, but is not limited to, a nucleotide sequence encoding the amino acid sequence of SEQ ID NO:57 and/or SEQ ID NO:58; a nucleotide sequence encoding a Cas7 (Csa2) polypeptide includes, but is not limited to, a nucleotide sequence encoding the amino acid sequence of SEQ ID NO:1, SEQ ID NO:2 and/or SEQ ID NO:3; a nucleotide sequence encoding a Cas8a1 (Csx13) polypeptide includes, but is not limited to, a nucleotide sequence encoding the amino acid sequence of SEQ ID NO:4; a nucleotide sequence encoding a Cas8a2 (Csx9) polypeptide includes, but is not limited to, a nucleotide sequence encoding the amino acid sequence of SEQ ID NO: 5, and/or SEQ ID NO: 6; a nucleotide sequence encoding a Cas5 polypeptide includes, but is not limited to, a nucleotide sequence encoding the amino acid sequence of SEQ ID NO:7, SEQ ID NO:8 and/or SEQ ID NO:9; a nucleotide sequence encoding a Cas6a polypeptide includes, but is not limited to, a nucleotide sequence encoding the amino acid sequence of SEQ ID NO:10 and/or SEQ ID NO:11; a nucleotide sequence encoding a Cas3' polypeptide includes, but is not limited to, a nucleotide sequence encoding the amino acid sequence of SEQ ID NO:12, SEQ ID NO:13 and/or SEQ ID NO:14; a nucleotide sequence encoding a Cas3" polypeptide includes, but is not limited to, a nucleotide sequence encoding the amino acid sequence of SEQ ID NO:15, SEQ ID NO:16 and/or SEQ ID NO:17; a nucleotide sequence encoding a Cas10d (Csc3) polypeptide includes, but is not limited to, a nucleotide sequence encoding the amino acid sequence of SEQ ID NO:33 and/or SEQ ID NO:34; a nucleotide sequence encoding a Csc2 polypeptide includes, but is not limited to, a nucleotide sequence encoding the amino acid sequence of SEQ ID NO:35 and/or SEQ ID NO:36; a nucleotide sequence encoding a Csc1 polypeptide includes, but is not limited to, a nucleotide sequence encoding the amino acid sequence of SEQ ID NO:37 and/or SEQ ID NO:38; and/or a nucleotide sequence encoding a Cas6d polypeptide includes, but is not limited to, a nucleotide sequence encoding the amino acid sequence of SEQ ID NO:39 and/or SEQ ID NO:40.

Additional amino acid and nucleotide sequences encoding type I Cascade polypeptides can be identified by the skilled artisan using methods routine in the art for identifying homologues, as for example, screening the NCBI GenBank database using the amino acid sequence, gene name, or protein family of a known Cascade polypeptide. Accordingly, further non-limiting examples of a Type I polypeptides include the following as identified by their GenBank accession numbers.

Thus, for example, Type I-A cas7/csa2 polypeptides include, but are not limited to, GenBank accession number ACP34796.1, ACV25240.1, ADC69851.1, ADX81774.1, ADX84848.1, BAB84980.2, Q97Y91.1, YP_002831441.1, YP_003128740.1, YP_003458587.1, YP_005844988.1, and/or YP_005848062.

In other embodiments, Type I-A cas8a1/csx13 polypeptides include, but are not limited to, GenBank accession number as set forth in Table 6.

TABLE 6

Type I-A cas8a1/csx13 polypeptide accession numbers
(the sequence identifier for each accession number, in the order provided in
Table 6, is SEQ ID NOs: 341-640).

AAL95378.1, AAZ69290.1, ABG85850.1, ABP67977.1, ABQ90254.1, ABR48349.1, ABS22299.1,
ABU59349.1, ABX07704.1, ABY36145.1, ACD66304.1, ACD89534.1, ACI19672.1, ACI21434.1,
ACK40458.1, ACL23511.1, ACM54569.1, ACM59280.1, ACN98336.1, ACO02971.1, ACS24737.1,
ACV38707.1, ACV61808.1, ADC88653.1, ADG13584.1, ADG71319.1, ADH59814.1, ADI02112.1,
ADI26429.1, ADL41486.1, ADP74262.1, ADQ08188.1, ADQ41858.1, ADU97573.1, ADY55689.1,
AEA46792.1, AEE48384.1, AEF19060.1, AEF93612.1, AEH24640.1, AEH47542.1, AEH91548.1,
AEN78299.1, AEO02602.1, AEO38050.1, AEV69187.1, AFA49668.1, AFL94587.1, AFS77693.1,
AGF58568.1, AGG14993.1, AGG15485.1, AGI39652.1, AGI39866.1, AGR03384.1, AGR15961.1,
AGR27586.1, CBL20527.1, CBY03036.1, CBY48110.1, CCY59072.1, CDB20969.1, CDC03261.1,
CDC19289.1, CDC79971.1, CDC92385.1, CDC93207.1, CDE55652.1, CDI49498.1, CDI64710.1,

TABLE 6-continued

Type I-A cas8a1/csx13 polypeptide accession numbers
(the sequence identifier for each accession number, in the order provided in
Table 6, is SEQ ID NOs: 341-640).

EAY25594.1, EDK88416.1, EDO58922.1, EDR97019.1, EDS77895.1, EDT23081.1, EDU38639.1,
EEG35956.1, EEG37130.1, EEO38468.1, EEP60017.1, EES51331.1, EEW20706.1, EEW67155.1,
EEX23204.1, EFD25239.1, EFE87452.1, EFG27734.1, EFG95262.1, EFH05799.1, EFH17183.1,
EFH93278.1, EFI68562.1, EFK93763.1, EFL54064.1, EFM38861.1, EFR88687.1, EFR88692.1,
EFS01187.1, EFS20741.1, EFS21645.1, EFS24401.1, EFS28319.1, EFV16756.1, EGG91964.1,
EGL83969.1, EGY80091.1, EHJ36418.1, EHL19483.1, EHN61774.1, EHR79718.1, EIJ72305.1,
EJP23274.1, EJU08078.1, EJU19990.1, EKA92426.1, EKU43637.1, EMS70152.1, ERI07860.1,
ERI93854.1, ERM91451.1, ERT47389.1, EUJ23986.1, EUJ39372.1, EUJ57885.1, NP_604079.1,
WP_002187923.1, WP_002702613.1, WP_002835744.1, WP_002838037.1, WP_002840042.1,
WP_003019330.1, WP_003364961.1, WP_003374705.1, WP_003488957.1, WP_003693852.1,
WP_003721305.1, WP_003731260.1, WP_003733577.1, WP_003745650.1, WP_003770616.1,
WP_004066403.1, WP_004228702.1, WP_004456286.1, WP_004628964.1, WP_004820498.1,
WP_005345375.1, WP_005366755.1, WP_005896414.1, WP_005903146.1, WP_005917190.1,
WP_005957249.1, WP_005969637.1, WP_005971576.1, WP_006806657.1, WP_007502704.1,
WP_007547872.1, WP_008118711.1, WP_008401177.1, WP_008794388.1, WP_008800820.1,
WP_008801714.1, WP_008821022.1, WP_009005906.1, WP_009081463.1, WP_009200361.1,
WP_009220010.1, WP_009264828.1, WP_009371070.1, WP_009423366.1, WP_009528186.1,
WP_009528502.1, WP_009531670.1, WP_009643660.1, WP_009926150.1, WP_009926261.1,
WP_010248767.1, WP_010479701.1, WP_010528951.1, WP_010680292.1, WP_010885339.1,
WP_011012263.1, WP_011016968.1, WP_011249418.1, WP_011591962.1, WP_011917899.1,
WP_011956601.1, WP_012063325.1, WP_012094492.1, WP_012121773.1, WP_012192593.1,
WP_012258798.1, WP_012459381.1, WP_012465415.1, WP_012546150.1, WP_012548304.1,
WP_012574443.1, WP_012581885.1, WP_012615877.1, WP_012673661.1, WP_012675210.1,
WP_012984910.1, WP_012991060.1, WP_013100330.1, WP_013144989.1, WP_013149500.1,
WP_013175514.1, WP_013289493.1, WP_013400575.1, WP_013404326.1, WP_013433573.1,
WP_013538358.1, WP_013624559.1, WP_013683464.1, WP_013749292.1, WP_013876765.1,
WP_013905697.1, WP_014073500.1, WP_014091943.1, WP_014255749.1, WP_014357265.1,
WP_014601720.1, WP_014788228.1, WP_014835335.1, WP_014966830.1, WP_015394877.1,
WP_015526375.1, WP_015756524.1, WP_015769055.1, WP_015864171.1, WP_015906759.1,
WP_019416834.1, WP_021623245.1, WP_021654356.1, WP_022172991.1, WP_022302635.1,
WP_022304353.1, WP_022588389.1, WP_023438295.1, YP_001181168.1, YP_001276204.1,
YP_001320008.1, YP_001375294.1, YP_001433367.1, YP_001547832.1, YP_001636534.1,
YP_001930858.1, YP_001942513.1, YP_002249829.1, YP_002249954.1, YP_002351072.1,
YP_002461947.1, YP_002570895.1, YP_002572053.1, YP_002728803.1, YP_002731103.1,
YP_002950003.1, YP_003163698.1, YP_003190431.1, YP_003472780.1, YP_003616548.1,
YP_003633518.1, YP_003671006.1, YP_003675825.1, YP_003702677.1, YP_003839472.1,
YP_003988873.1, YP_003993557.1, YP_004027471.1, YP_004152214.1, YP_004265690.1,
YP_004341507.1, YP_004445257.1, YP_004496524.1, YP_004587623.1, YP_004603183.1,
YP_004623912.1, YP_004832235.1, YP_005047111.1, YP_005270557.1, YP_005946606.1,
YP_005964502.1, YP_005970332.1, YP_006424381.1, YP_006680968.1, YP_006692468.1,
YP_006787540.1, YP_007457822.1, YP_007500036.1, YP_007500528.1, YP_007679670.1,
YP_007679884.1, YP_007784190.1, YP_008273810.1, YP_008282081.1, YP_008299753.1,
YP_008428017.1, YP_008773535.1, YP_303870.1, and/or YP_698243.1

In some embodiments, type I-A cas8a2/csx9 polypeptides include, but are not limited to, GenBank accession number as set forth in Table 7.

TABLE 7

Type I-A cas8a2/csx9 polypeptide accession numbers
(the sequence identifier for each accession number, in the order provided in
Table 7, is SEQ ID NOs: 641-666).

ACS33798.1, ACV25238.1, ADC69853.1, ADV65298.1, AEH24649.1,
AFK22399.1, AFL66344.1, EHR79726.1, Q57830.1, WP_004066420.1,
WP_010479713.1, WP_010868141.1, WP_010885009.1,
WP_011249406.1, WP_012980762.1, WP_013905706.1,

TABLE 7-continued

Type I-A cas8a2/csx9 polypeptide accession numbers
(the sequence identifier for each accession number, in the order provided in
Table 7, is SEQ ID NOs: 641-666).

WP_014733925.1, WP_015791971.1, YP_002959662.1,
YP_003128738.1, YP_003458589.1, YP_004176780.1,
YP_004623921.1, YP_006354474.1, YP_006401919.1,
and/or YP_008428007.1

In some embodiments, type I-A cas5 polypeptides include, but are not limited to, GenBank accession number as set forth in Table 8.

TABLE 8

Type I-A cas5 polypeptide accession numbers
(the sequence identifier for each accession number, in the order provided in
Table 8, is SEQ ID NOs: 667-871).

AAB89384.1, AAB98378.1, AAK41635.1, AAK41674.1, AAK42188.1, AAL62628.1, AAL80765.1,
ABG65171.1, ABM80500.1, ABN69435.1, ABP50706.1, ABP95303.1, ABU82316.1, ACB07186.1,
ACH62180.1, ACL11102.1, ACP34797.1, ACP37659.1, ACP37697.1, ACP45051.1, ACP49135.1,
ACP54855.1, ACP54893.1, ACR41523.1, ACS33795.1, ACV25239.1, ACX92458.1, ADB86650.1,
ADC66006.1, ADC69852.1, ADG91075.1, ADM27731.1, ADN51066.1, ADT83453.1, ADX81773.1,
ADX84849.1, ADY01599.1, AEB95257.1, AEC52734.1, AEE94621.1, AEM38302.1, AET32402.1,

TABLE 8-continued

Type I-A cas5 polypeptide accession numbers
(the sequence identifier for each accession number, in the order provided in
Table 8, is SEQ ID NOs: 667-871).

AFA39173.1, AFH42056.1, AFK51440.1, AFL66341.1, AFL66901.1, AFN03430.1, AFU57333.1,
AFU57334.1, AGJ61863.1, AHC52233.1, BAA30015.1, BAA80223.2, BAB64981.1, BAB67760.1,
BAD84641.1, BAJ48045.1, BAJ48055.1, BAJ50845.1, BAN89822.1, CAB49935.1, CAT72675.1,
CCC81887.1, CCE70433.1, EDX76563.1, EFL34103.1, EGK04694.1, EHP69910.1, EWG06386.1,
G4RJZ2.1, NP_070697.1, NP_126704.1, NP_142843.2, NP_147810.2, NP_247356.1, NP_342845.1,
NP_342884.1, NP_343398.1, NP_375872.1, NP_378651.1, NP_558446.1, NP_578370.1, Q57827.1,
Q97WW2.1, Q97Y92.1, Q97YC6.1, WP_002364198.1, WP_003992208.1, WP_006100291.1,
WP_006844672.1, WP_009070154.1, WP_009988394.1, WP_009991627.1, WP_010479711.1,
WP_010729831.1, WP_010866247.1, WP_010868142.1, WP_010869881.1, WP_010879365.1,
WP_010885010.1, WP_010923406.1, WP_010977963.1, WP_010980734.1, WP_011007100.1,
WP_011011761.1, WP_011249407.1, WP_011583112.1, WP_011821818.1, WP_011838626.1,
WP_011900613.1, WP_012021090.1, WP_012123280.1, WP_012309083.1, WP_012608443.1,
WP_012710927.1, WP_012710964.1, WP_012717742.1, WP_012718680.1, WP_012966345.1,
WP_012980761.1, WP_013129668.1, WP_013303381.1, WP_013336791.1, WP_013466751.1,
WP_013604761.1, WP_013737755.1, WP_013749284.1, WP_013776536.1, WP_014025979.1,
WP_014127142.1, WP_014288230.1, WP_014346690.1, WP_014511987.1, WP_014513745.1,
WP_014557205.1, WP_014737690.1, WP_014767242.1, WP_014777797.1, WP_015580743.1,
WP_015791972.1, WP_015858907.1, WP_016730681.1, WP_016731906.1, WP_016732169.1,
WP_016732175.1, WP_018033623.1, WP_018192944.1, WP_018193690.1, WP_020265384.1,
WP_020511164.1, WP_020864070.1, WP_021968299.1, WP_022071463.1, WP_022541099.1,
WP_024084610.1, WP_024265300.1, YP_001012845.1, YP_001040343.1, YP_001153358.1,
YP_001191227.1, YP_001435723.1, YP_001736869.1, YP_002225090.1, YP_002428469.1,
YP_002828957.1, YP_002828995.1, YP_002831442.1, YP_002836973.1, YP_002841057.1,
YP_002842900.1, YP_002842938.1, YP_002914191.1, YP_002959659.1, YP_003128739.1,
YP_003419020.1, YP_003436281.1, YP_003458588.1, YP_003650027.1, YP_003859611.1,
YP_003902117.1, YP_004070676.1, YP_004245101.1, YP_004409741.1, YP_004424738.1,
YP_004458919.1, YP_004780554.1, YP_004892965.1, YP_005084654.1, YP_005259780.1,
YP_005644059.1, YP_005644987.1, YP_005648063.1, YP_005841508.1, YP_006363578.1,
YP_006401916.1, YP_006402476.1, YP_006491722.1, YP_006860990.1, YP_006860991.1,
YP_007864863.1, YP_008603756.1, YP_008797475.1, YP_008948135.1, and/or YP_182865.1

In still other embodiments, type I-A csa5 polypeptides include, but are not limited to, GenBank accession number as set forth in table 9.

In some embodiments, type I-A cas6a polypeptides include, but are not limited to, GenBank accession number CCC39326.1 (SEQ ID NO:325), Q57820.1 (SEQ ID

TABLE 9

Type I-A csa5 polypeptide accession numbers
(the sequence identifier for each accession number, in the order provided in
Table 9, is SEQ ID NOs: 872-1042).

AAB89385.1, AAK41676.1, AAK42186.1, ABB24054.1, ABK78026.1, ABM80502.1, ABN69433.1,
ABP95305.1, ABR33799.1, ABU82318.1, ACB07184.1, ACI21287.1, ACL11104.1, ACP34795.1,
ACP37695.1, ACP45049.1, ACP49137.1, ACP54891.1, ACR41521.1, ACV25241.1, ADB86648.1,
ADC69850.1, ADX81775.1, ADX84847.1, AEB07988.1, AEB95255.1, AEE94623.1, AEE95241.1,
AEH24646.1, AEM38381.1, AFK22402.1, AGI51452.1, AGJ61865.1, AHC52235.1, BAA30017.1,
BAB67758.1, BAD84643.1, BAE63890.1, BAJ48057.1, BAJ50847.1, CAB49937.1, CAQ41128.1,
CAT72674.1, CBX31380.1, CCE70435.1, EEK52966.1, EEQ91179.1, EGE82524.1, EGL20033.1,
EHN78776.1, EHP69908.1, EHR79724.1, ELS34753.1, ENU25210.1, ENV11469.1, ENX58900.1,
ENX61893.1, EOR09267.1, EPD82015.1, ESU14071.1, EWG06384.1, G4RJZ0.1, NP_070695.1,
NP_126706.1, NP_142845.1, NP_342886.1, NP_343396.1, NP_378649.1, O28409.1, Q97Y90.1,
WP_000270013.1, WP_002746890.1, WP_002764565.1, WP_004066416.1, WP_004652132.1,
WP_004801272.1, WP_005202326.1, WP_005323045.1, WP_007388860.1, WP_008426480.1,
WP_009070150.1, WP_009625124.1, WP_009671504.1, WP_009990722.1, WP_009991624.1,
WP_010479707.1, WP_010868144.1, WP_010879363.1, WP_010885012.1, WP_010923408.1,
WP_010923715.1, WP_010980732.1, WP_011249409.1, WP_011357926.1, WP_011821820.1,
WP_011838624.1, WP_011968951.1, WP_012021092.1, WP_012123282.1, WP_012309081.1,
WP_012546006.1, WP_012608445.1, WP_012710962.1, WP_012713193.1, WP_012715848.1,
WP_012717744.1, WP_012718679.1, WP_012980759.1, WP_013482651.1, WP_013705101.1,
WP_013737753.1, WP_013776538.1, WP_013779675.1, WP_013905703.1, WP_014026058.1,
WP_014511989.1, WP_014513743.1, WP_014733928.1, WP_015791974.1, WP_016162949.1,
WP_016729979.1, WP_016731904.1, WP_018033625.1, WP_018192942.1, WP_018193688.1,
WP_018541940.1, WP_019324664.1, WP_020265382.1, WP_020265487.1, WP_020268818.1,
WP_020269141.1, WP_020864072.1, WP_021052469.1, WP_024084612.1, XP_001825023.2,
XP_002259861.1, XP_790100.2, YP_001012847.1, YP_001040341.1, YP_001191229.1,
YP_001308755.1, YP_001435725.1, YP_001736867.1, YP_002248920.1, YP_002428471.1,
YP_002828993.1, YP_002831440.1, YP_002836971.1, YP_002841059.1, YP_002842936.1,
YP_002914189.1, YP_003128741.1, YP_003419018.1, YP_003458586.1, YP_004369169.1,
YP_004409739.1, YP_004458921.1, YP_004462063.1, YP_004623918.1, YP_004780633.1,
YP_005644989.1, YP_005648061.1, YP_006354477.1, YP_007864865.1, YP_008428011.1,
YP_008474533.1, YP_008797477.1, YP_008948137.1, YP_182867.1, YP_375097.1, and/or
YP_876330.1

NO:326), Q97Y96.1 (SEQ ID NO:327), and/or YP_005839101.1 (SEQ ID NO:328).

In further embodiments, type I-A cas3' polypeptides include, but are not limited to, GenBank accession number NP_147808.1 (SEQ ID NO:329), NP_343399.1 (SEQ ID NO:330), and/or CCC81888.1 (SEQ ID NO:331).

In still further embodiments, type I-A cas3" polypeptides include, but are not limited to, GenBank accession number NP_147807.1 (SEQ ID NO:332), NP_343400.1 (SEQ ID NO:333), and/or CCC81889.1 (SEQ ID NO:334).

In some embodiments, type I-B cas6b polypeptides include, but are not limited to, GenBank accession number Q8U3R3.1 (SEQ ID NO:335), Q97WV8.1 (SEQ ID NO:336), Q58631.1 (SEQ ID NO:337), YP_003533663.1 (SEQ ID NO:338), YP_002534242.1 (SEQ ID NO:339), and/or YP_002534249.1 (SEQ ID NO:340).

In other embodiments, type I-B cas8b/csh1 polypeptides include, but are not limited to, GenBank accession number as set forth in Table 10.

TABLE 10

Type I-B cas8b/csh1 polypeptide accession numbers
(the sequence identifier for each accession number, in the order provided in
Table 10, is SEQ ID NOs: 1043-1158).

ACB09368.1, ACV11630.1, ACV48938.1, AEM58842.1, AFK21437.1, AFO56172.1, AFZ74575.1,
AGB03160.1, AGF96002.1, AGF96003.1, AGO61197.1, AGX43472.1, AHB67946.1, AHG05445.1,
BAL52721.1, CCK87449.1, CCK90903.1, CCK96290.1, CCK98531.1, CCQ33713.1, EAY30146.1,
EDR99204.1, EEP56084.1, EES90449.1, EFH07552.1, EFH15423.1, EHP85065.1, EID43009.1,
ELY41482.1, ELY72601.1, ELY83890.1, ELY91754.1, ELY96632.1, ELZ04987.1, ELZ16933.1,
ELZ40751.1, ELZ42764.1, ELZ59537.1, ELZ60426.1, ELZ68872.1, ELZ72052.1, ELZ72263.1,
ELZ84579.1, ELZ88967.1, ELZ93658.1, ELZ97246.1, ELZ99739.1, EMA18803.1, EMA25147.1,
EMA34109.1, EMA56841.1, EMA69343.1, EMT39606.1, ERJ06790.1, ESP86779.1, ETA67346.1,
ETI90104.1, GAC90881.1, WP_003377299.1, WP_003380931.1, WP_003413122.1, WP_004046328.1,
WP_004060812.1, WP_004064662.1, WP_004971283.1, WP_005533726.1, WP_005576677.1,
WP_006165794.1, WP_006168574.1, WP_006601038.1, WP_006648207.1, WP_006653096.1,
WP_006673617.1, WP_007188933.1, WP_007736473.1, WP_007982327.1, WP_008094396.1,
WP_008164964.1, WP_008320680.1, WP_008324580.1, WP_008444873.1, WP_008452268.1,
WP_008524855.1, WP_008572456.1, WP_008847067.1, WP_009887249.1, WP_011099685.1,
WP_011222266.1, WP_011722697.1, WP_012310881.1, WP_012660067.1, WP_014030718.1,
WP_014555903.1, WP_014863256.1, WP_015763780.1, WP_015789204.1, WP_018129134.1,
WP_018258161.1, WP_021373546.1, WP_021403257.1, WP_021412247.1, WP_022615726.1,
WP_022746620.1, WP_023396040.1, YP_001739051.1, YP_003130363.1, YP_003178645.1,
YP_004785826.1, YP_006351424.1, YP_006540248.1, YP_007179024.1, YP_007249667.1,
YP_008142098.1, YP_008377024.1, YP_008675509.1, and/or YP_008874106.1

In some embodiments, type I-B cas7/csh2 polypeptides include, but are not limited to, GenBank accession number as set forth in Table 11.

TABLE 11

Type I-B cas7/csh2 polypeptide accession numbers
(the sequence identifier for each accession number, in the order provided in
Table 11, is SEQ ID NOs: 1159-1209).

ABR54140.1, ACB09369.1, ACN13664.1, ACV11629.1, ACV48939.1,
AEK19972.1, AEM58841.1, AFK21438.1, AHB67947.1, AHD18305.1,
CCQ33714.1, ERJ06791.1, WP_004046327.1, WP_004060811.1,
WP_004082348.1, WP_004966754.1, WP_004971285.1,
WP_005533725.1, WP_006168573.1, WP_007188932.1,
WP_007982329.1, WP_008164963.1, WP_008320681.1,
WP_008324577.1, WP_008524853.1, WP_008572454.1,
WP_011032514.1, WP_011222267.1, WP_011972043.1,

TABLE 11-continued

Type I-B cas7/csh2 polypeptide accession numbers
(the sequence identifier for each accession number, in the order provided in
Table 11, is SEQ ID NOs: 1159-1209).

WP_012310882.1, WP_012660066.1, WP_012662913.1,
WP_013999402.1, WP_014030717.1, WP_015763781.1,
WP_015789203.1, WP_018258160.1, WP_020220934.1,
YP_001322752.1, YP_001739052.1, YP_002534251.1,
YP_002601828.1, YP_003130362.1, YP_003178646.1,
YP_003533665.1, YP_004742715.1, YP_004785825.1,
YP_006351425.1, YP_008377025.1, YP_008874107.1, and/or
YP_008991099.1

In some embodiments, Type I-B cas5 polypeptides include, but are not limited to, GenBank accession number as set forth in Table 12.

TABLE 12

Type I-B cas5 polypeptide accession numbers
(the sequence identifier for each accession number, in the order provided in
Table 12, is SEQ ID NOs: 1210-2372).

AAB85576.1, AAC06653.1, AAD36863.1, AAM30258.1, AAO36023.1, AAR38875.1, AAV44423.1,
ABB15084.1, ABE52050.1, ABG03245.1, ABI69104.1, ABI69807.1, ABJ60926.1, ABK14430.1,

TABLE 12-continued

Type I-B cas5 polypeptide accession numbers
(the sequence identifier for each accession number, in the order provided in
Table 12, is SEQ ID NOs: 1210-2372).

ABN54398.1, ABO35079.1, ABP65713.1, ABP65962.1, ABR30222.1, ABR54141.1, ABR56648.1,
ABS22297.1, ABS51485.1, ABV32774.1, ABX32567.1, ABY93797.1, ACB09370.1, ACI18906.1,
ACJ33146.1, ACJ75703.1, ACJ76380.1, ACK41910.1, ACL21951.1, ACL70272.1, ACM22886.1,
ACM61724.1, ACN13665.1, ACN98723.1, ACO03885.1, ACR79388.1, ACS23234.1, ACS24735.1,
ACS90540.1, ACV11628.1, ACV25245.1, ACV38705.1, ACV48940.1, ACV61810.1, ACV63756.1,
ACV64956.1, ACX52109.1, ACX77838.1, ACZ43322.1, ADB39857.1, ADC46646.1, ADC69846.1,
ADD03494.1, ADE01943.1, ADF51863.1, ADG07364.1, ADG07375.1, ADG13848.1, ADG83329.1,
ADH59812.1, ADH61863.1, ADI26431.1, ADI36186.1, ADI61856.1, ADL06864.1, ADL41488.1,
ADL43515.1, ADL70072.1, ADO35161.1, ADO45628.1, ADP74264.1, ADP76109.1, ADQ08186.1,
ADQ08235.1, ADQ14922.1, ADQ41856.1, ADQ41963.1, ADQ42006.1, ADQ47253.1, ADQ47299.1,
ADR19819.1, ADU51672.1, ADU92812.1, ADU97575.1, ADV78761.1, ADY32338.1, ADY55691.1,
AEB69537.1, AEB77226.1, AEE14450.1, AEE90320.1, AEE97376.1, AEF18280.1, AEF19062.1,
AEG14078.1, AEG14216.1, AEG46351.1, AEG61211.1, AEH25122.1, AEH47544.1, AEH49390.1,
AEH51742.1, AEH54512.1, AEI14613.1, AEJ40709.1, AEK19971.1, AEK72019.1, AEM58840.1,
AEM74922.1, AEM74971.1, AEN78297.1, AEP01119.1, AER66005.1, AEV68770.1, AEV69185.1,
AEW01076.1, AEW06746.1, AFK07935.1, AFK21439.1, AFK21704.1, AFK85421.1, AFL96011.1,
AFM22198.1, AFO56174.1, AFU57333.1, AFV12619.1, AFZ74577.1, AGA59189.1, AGB20226.1,
AGC68638.1, AGC68870.1, AGF58566.1, AGG14995.1, AGH93292.1, AGI39650.1, AGI39868.1,
AGL00110.1, AGL00360.1, AGL50734.1, AGR27754.1, AGT06852.1, AGY75623.1, AHB67948.1,
AHD18306.1, AHF79950.1, AHG05447.1, AHJ12409.1, BAA29240.1, BAI69702.1, BAI70178.1,
BAI80034.1, BAI81693.1, CAB05527.1, CAJ69873.1, CBA65392.1, CBE06412.1, CBH26573.1,
CBL06453.1, CBL20525.1, CBL28677.1, CBV37093.1, CBV37147.1, CBV37210.1, CCA14225.1,
CCC40225.1, CCK87447.1, CCK87792.1, CCK88323.1, CCK90901.1, CCK91258.1, CCK91758.1,
CCK94930.1, CCK95461.1, CCK96292.1, CCK98529.1, CCK98870.1, CCK99454.1, CCL02782.1,
CCL08295.1, CCL10367.1, CCL11550.1, CCL15413.1, CCL19412.1, CCL23335.1, CCL26733.1,
CCL30689.1, CCL34647.1, CCL35213.1, CCL38536.1, CCL39060.1, CCL43259.1, CCL47272.1,
CCL50402.1, CCL54352.1, CCL58497.1, CCL61502.1, CCL66040.1, CCL69962.1, CCL73647.1,
CCL77343.1, CCL80653.1, CCL81172.1, CCL84107.1, CCL84682.1, CCL88857.1, CCL91964.1,
CCL92530.1, CCL96800.1, CCP24803.1, CCQ33715.1, CCZ35983.1, CDC34386.1, CDG37685.1,
CDH46485.1, CDI49617.1, CDM67379.1, EAU00173.1, EDU38641.1, EEA85700.1, EEB35642.1,
EEB73082.1, EEB76591.1, EEC57350.1, EEG35954.1, EEG37132.1, EEM80237.1, EEM86545.1,
EEO34258.1, EEO38466.1, EEO39221.1, EEO43827.1, EEP56330.1, EEQ26091.1, EES49281.1,
EES63309.1, EES76423.1, EES90262.1, EES90483.1, EEU11824.1, EEU61362.1, EEV18896.1,
EEW20241.1, EEX23202.1, EFB38349.1, EFB61539.1, EFC90518.1, EFE87454.1, EFG03490.1,
EFG27736.1, EFG95260.1, EFH05801.1, EFH07554.1, EFH07717.1, EFH15421.1, EFH16150.1,
EFH17185.1, EFH93276.1, EFI68560.1, EFJ68937.1, EFK40166.1, EFK93738.1, EFL54048.1,
EFQ22711.1, EFQ45709.1, EFS01189.1, EFS20743.1, EFS21647.1, EFS24403.2, EFS26650.1,
EFS28321.1, EFV21399.1, EFW90577.1, EFX83389.1, EGC74256.1, EGC84815.1, EGJ42919.1,
EGL83971.1, EGL83996.1, EGM53068.1, EGN41570.1, EGN64312.1, EGO87701.1, EGQ22908.1,
EGQ80953.1, EGQ80954.1, EGV32623.1, EGY80083.1, EGZ43696.1, EHI55262.1, EHI57521.1,
EHI79000.1, EHJ01148.1, EHJ25274.1, EHJ27821.1, EHJ35719.1, EHJ36416.1, EHL03878.1,
EHL13042.1, EHL19481.1, EHL79449.1, EHM00796.1, EHM89754.1, EHM91459.1, EHN62646.1,
EHO09810.1, EHO40937.1, EHO68882.1, EHO77292.1, EHQ30579.1, EHQ45000.1, EHQ46727.1,
EID43007.1, EJN53432.1, EJX26016.1, EKA92428.1, EKU43639.1, ELY41480.1, ELY72599.1,
ELY73832.1, ELY83892.1, ELY91752.1, ELZ04989.1, ELZ16931.1, ELZ59539.1, ELZ60428.1,
ELZ71860.1, ELZ72261.1, ELZ89350.1, ELZ97244.1, ELZ99741.1, EMA72145.1, EMA34111.1,
EPC07705.1, EQB84124.2, EQE01732.1, EQE03339.1, EQE03948.1, EQE05304.1, EQE07512.1,
EQE08412.1, EQE15241.1, EQE18540.1, EQE21462.1, EQE26379.1, EQE32669.1, EQE38502.1,
EQE42083.1, EQE43177.1, EQE44313.1, EQE47253.1, EQE53152.1, EQE56671.1, EQE60307.1,
EQE60899.1, EQE61751.1, EQE68275.1, EQE73582.1, EQE77127.1, EQE79062.1, EQE90139.1,
EQE90276.1, EQE90964.1, EQE95151.1, EQF02571.1, EQF02867.1, EQF04763.1, EQF09813.1,
EQF13623.1, EQF18498.1, EQF25384.1, EQF30949.1, EQF36165.1, EQF38901.1, EQF44618.1,
EQF48772.1, EQF50396.1, EQF51993.1, EQF60175.1, EQF60780.1, EQF66131.1, EQF67188.1,
EQF68274.1, EQF74295.1, EQF75097.1, EQF79635.1, EQF86680.1, EQF87551.1, EQF94119.1,
EQF94458.1, EQF99415.1, EQG00993.1, EQG08939.1, EQG09378.1, EQG17676.1, EQG18642.1,
EQG22092.1, EQG27623.1, EQG31829.1, EQG32967.1, EQG33291.1, EQG39236.1, EQG43179.1,
EQG44913.1, EQG51716.1, EQG55903.1, EQG59371.1, EQG64721.1, EQG67977.1, EQG74365.1,
EQG77054.1, EQG80757.1, EQG82489.1, EQG90008.1, EQG92006.1, EQG93624.1, EQH01839.1,
EQH02774.1, EQH07310.1, EQH11134.1, EQH17403.1, EQH28778.1, EQH34061.1, EQH34296.1, EQH35981.1, EQH40011.1, EQH47226.1, EQH49250.1, EQH54011.1, EQH59206.1,
EQH60286.1, EQH63975.1, EQH67919.1, EQH69652.1, EQH74804.1, EQH79337.1, EQH81451.1,
EQH88358.1, EQH92873.1, EQH97194.1, EQH98214.1, EQH98657.1, EQI04921.1, EQI09869.1,
EQI11163.1, EQI20937.1, EQI20989.1, EQI27274.1, EQI33531.1, EQI37445.1, EQI39861.1,
EQI45210.1, EQI50521.1, EQI54642.1, EQI57315.1, EQI58425.1, EQI64544.1, EQI65626.1,
EQI72802.1, EQI77848.1, EQI78279.1, EQI78482.1, EQI85053.1, EQI90256.1, EQI94963.1,
EQI95828.1, EQI99103.1, EQJ05444.1, EQJ06157.1, EQJ09401.1, EQJ14706.1, EQJ15344.1,
EQJ16768.1, EQJ23077.1, EQJ28979.1, EQJ33651.1, EQJ34573.1, EQJ39165.1, EQJ44701.1,
EQJ45565.1, EQJ55006.1, EQJ55505.1, EQJ57779.1, EQJ66394.1, EQJ67361.1, EQJ77085.1,
EQJ77540.1, EQJ80734.1, EQJ82551.1, EQJ87869.1, EQJ89135.1, EQJ89796.1, EQJ94704.1,
EQK00393.1, EQK02221.1, EQK04295.1, EQK11853.1, EQK14515.1, EQK15563.1, EQK16873.1,
EQK21904.1, EQK26713.1, EQK27485.1, EQK30841.1, EQK33182.1, EQK32445.1, EQK37615.1,
EQK64317.1, EQK68374.1, EQK70289.1, EQK72808.1, EQK74231.1, EQK74942.1, EQK80483.1,
EQK85815.1, EQK86186.1, EQK86596.1, EQL07765.1, ERH10110.1, ERJ06792.1, ERM24612.1,
ERM26943.1, ERM33457.1, ERM34409.1, ERM35045.1, ERM45721.1, ERM46920.1, ERM47348.1,
ERT39868.1, ERT41605.1, ETZ26411.1, EUB15686.1, EUB26806.1, EUB30975.1, EUB36180.1,
EUJ23988.1, EUJ32650.1, EUJ39373.1, EUJ45451.1, NP_142172.1, NP_213256.1, NP_229597.1,

TABLE 12-continued

Type I-B cas5 polypeptide accession numbers
(the sequence identifier for each accession number, in the order provided in
Table 12, is SEQ ID NOs: 1210-2372).

NP_276215.1, NP_497019.1, NP_632586.1, NP_782086.1, NP_963314.1, WP_000372921.1,
WP_000643645.1, WP_000643646.1, WP_001276288.1, WP_002090051.1, WP_002097354.1,
WP_002187918.1, WP_002193569.1, WP_002204284.1, WP_002599337.1, WP_002656857.1,
WP_002695760.1, WP_002729366.1, WP_002736261.1, WP_002756406.1, WP_002835742.1,
WP_002838002.1, WP_002840022.1, WP_002926177.1, WP_003019326.1, WP_003253164.1,
WP_003352579.1, WP_003371725.1, WP_003377369.1, WP_003377740.1, WP_003380933.1,
WP_003383461.1, WP_003393814.1, WP_003413402.1, WP_003416594.1, WP_003422614.1,
WP_003424503.1, WP_003430916.1, WP_003439785.1, WP_003442545.1, WP_003480768.1,
WP_003488960.1, WP_003511800.1, WP_003537505.1, WP_003538011.1, WP_003646797.1,
WP_003650047.1, WP_003651915.1, WP_003693854.1, WP_003728517.1, WP_003745655.1,
WP_003868742.1, WP_003871404.1, WP_004032886.1, WP_004043128.1, WP_004046326.1,
WP_004053330.1, WP_004060810.1, WP_004064674.1, WP_004082347.1, WP_004228695.1,
WP_004399633.1, WP_004454740.1, WP_004628952.1, WP_004804177.1, WP_004814809.1,
WP_004816081.1, WP_004820504.1, WP_004839794.1, WP_004966755.1, WP_004971286.1,
WP_004972493.1, WP_005041358.1, WP_005345379.1, WP_005348718.1, WP_005533724.1,
WP_005541006.1, WP_005546401.1, WP_005557131.1, WP_005576674.1, WP_005584763.1,
WP_005659292.1, WP_005816131.1, WP_005817562.1, WP_005869135.1, WP_005903141.1,
WP_005910162.1, WP_005917186.1, WP_005937046.1, WP_005948317.1, WP_005957039.1,
WP_005969641.1, WP_005971580.1, WP_005977421.1, WP_006114886.1, WP_006165797.1,
WP_006168572.1, WP_006186929.1, WP_006258367.1, WP_006299857.1, WP_006305874.1,
WP_006320564.1, WP_006441124.1, WP_006521012.1, WP_006523429.1, WP_006565554.1,
WP_006567721.1, WP_006569796.1, WP_006648205.1, WP_006653094.1, WP_006673619.1,
WP_006782618.1, WP_006788405.1, WP_006884525.1, WP_006928014.1, WP_007039823.1,
WP_007043770.1, WP_007044908.1, WP_007188931.1, WP_007220333.1, WP_007286909.1,
WP_007305584.1, WP_007429321.1, WP_007473124.1, WP_007502661.1, WP_007502706.1,
WP_007736477.1, WP_007982330.1, WP_008094400.1, WP_008118714.1, WP_008164961.1,
WP_008194420.1, WP_008210714.1, WP_008286679.1, WP_008286997.1, WP_008320682.1,
WP_008324576.1, WP_008444868.1, WP_008452273.1, WP_008512433.1, WP_008524852.1,
WP_008538511.1, WP_008565745.1, WP_008572452.1, WP_008576913.1, WP_008694964.1,
WP_008702877.1, WP_008706837.1, WP_008791536.1, WP_008793026.1, WP_008793806.1,
WP_008800822.1, WP_008801716.1, WP_008821024.1, WP_008847069.1, WP_008908200.1,
WP_008910044.1, WP_008976788.1, WP_009005907.1, WP_009056604.1, WP_009171795.1,
WP_009186589.1, WP_009251670.1, WP_009264825.1, WP_009290820.1, WP_009361658.1,
WP_009423364.1, WP_009448529.1, WP_009524579.1, WP_009528284.1, WP_009528500.1,
WP_009531618.1, WP_009609715.1, WP_009643649.1, WP_009650627.1, WP_009890657.1,
WP_009898076.1, WP_009903199.1, WP_010297529.1, WP_010349458.1, WP_010416802.1,
WP_010478263.1, WP_010539053.1, WP_010680294.1, WP_010747304.1, WP_010876711.1,
WP_010880194.1, WP_010884280.1, WP_011032513.1, WP_011099683.1, WP_011153017.1,
WP_011222268.1, WP_011345042.1, WP_011406022.1, WP_011406529.1, WP_011460587.1,
WP_011499197.1, WP_011563263.1, WP_011591964.1, WP_011641199.1, WP_011641887.1,
WP_011695827.1, WP_011722695.1, WP_011731898.1, WP_011868533.1, WP_011876919.1,
WP_011915679.1, WP_011915922.1, WP_011972044.1, WP_011973780.1, WP_011992225.1,
WP_012002255.1, WP_012056583.1, WP_012094490.1, WP_012108278.1, WP_012209664.1,
WP_012310883.1, WP_012547538.1, WP_012574445.1, WP_012580096.1, WP_012580506.1,
WP_012582995.1, WP_012636455.1, WP_012660065.1, WP_012662914.1, WP_012674044.1,
WP_012676124.1, WP_012749051.1, WP_012876353.1, WP_012928368.1, WP_012955597.1,
WP_012963882.1, WP_012964358.1, WP_012980755.1, WP_012984912.1, WP_012996180.1,
WP_013007282.1, WP_013008930.1, WP_013035118.1, WP_013071006.1, WP_013076647.1,
WP_013076658.1, WP_013100593.1, WP_013121323.1, WP_013144991.1, WP_013149498.1,
WP_013150996.1, WP_013179914.1, WP_013274916.1, WP_013289495.1, WP_013291509.1,
WP_013299028.1, WP_013378496.1, WP_013400577.1, WP_013401699.1, WP_013404324.1,
WP_013404370.1, WP_013406000.1, WP_013431321.1, WP_013431364.1, WP_013433571.1,
WP_013433674.1, WP_013433716.1, WP_013452028.1, WP_013495975.1, WP_013522865.1,
WP_013538360.1, WP_013611556.1, WP_013624561.1, WP_013720552.1, WP_013720767.1,
WP_013756175.1, WP_013777244.1, WP_013781803.1, WP_013789006.1, WP_013821593.1,
WP_013821731.1, WP_013842963.1, WP_013860398.1, WP_013886103.1, WP_013906178.1,
WP_013932950.1, WP_013987427.1, WP_013999401.1, WP_014011704.1, WP_014030716.1,
WP_014043370.1, WP_014043409.1, WP_014097198.1, WP_014121669.1, WP_014162428.1,
WP_014220988.1, WP_014255349.1, WP_014255747.1, WP_014357263.1, WP_014255905.1,
WP_014731690.1, WP_014733230.1, WP_014757342.1, WP_014789642.1, WP_014807423.1,
WP_014863258.1, WP_014958324.1, WP_014966832.1, WP_015017880.1, WP_015051481.1,
WP_015255924.1, WP_015312651.1, WP_015359322.1, WP_015359550.1, WP_015394875.1,
WP_015411188.1, WP_015419281.1, WP_015425006.1, WP_015526373.1, WP_015556824.1,
WP_015562678.1, WP_015738986.1, WP_015756526.1, WP_015758448.1, WP_015759626.1,
WP_015763782.1, WP_015769053.1, WP_015789202.1, WP_015791978.1, WP_015849757.1,
WP_015864169.1, WP_015868054.1, WP_015908968.1, WP_015919205.1, WP_015944885.1,
WP_016357733.1, WP_016647300.1, WP_016749617.1, WP_016677943.1, WP_016777739.1,
WP_016779144.1, WP_016994003.1, WP_017189923.1, WP_017434389.1, WP_017552095.1,
WP_017554266.1, WP_017810384.1, WP_017826607.1, WP_017859611.1, WP_017873805.1,
WP_017890209.1, WP_017894954.1, WP_017950341.1, WP_017980957.1, WP_018060553.1,
WP_018130449.1, WP_018153317.1, WP_018154663.1, WP_018198202.1, WP_018206663.1,
WP_018212753.1, WP_018258159.1, WP_018336665.1, WP_018449895.1, WP_018590790.1,
WP_018621541.1, WP_018676647.1, WP_018713222.1, WP_018963747.1, WP_019117053.1,
WP_019118942.1, WP_019279291.1, WP_019416835.1, WP_019419612.1, WP_019540683.1,
WP_019555032.1, WP_019989965.1, WP_020005376.1, WP_020220935.1, WP_020253928.1,
WP_020448804.1, WP_020537507.1, WP_020597827.1, WP_020764874.1, WP_020765660.1,

TABLE 12-continued

Type I-B cas5 polypeptide accession numbers
(the sequence identifier for each accession number, in the order provided in
Table 12, is SEQ ID NOs: 1210-2372).

WP_020774541.1, WP_020807610.1, WP_021107120.1, WP_021253690.1, WP_021269704.1,
WP_021283464.1, WP_021359474.1, WP_021362775.1, WP_021363719.1, WP_021365608.1,
WP_021366837.1, WP_021370585.1, WP_021371379.1, WP_021373544.1, WP_021376075.1,
WP_021376238.1, WP_021377151.1, WP_021377511.1, WP_021385852.1, WP_021397104.1,
WP_021401513.1, WP_021408544.1, WP_021412493.1, WP_021412801.1, WP_021418533.1,
WP_021423807.1, WP_021780359.1, WP_021836910.1, WP_021875388.1, WP_021914500.1,
WP_021941129.1, WP_021988548.1, WP_022048652.1, WP_022070399.1, WP_022070968.1,
WP_022169013.1, WP_022172989.1, WP_022213074.1, WP_022228560.1, WP_022234505.1,
WP_022298983.1, WP_022302637.1, WP_022343367.1, WP_022431365.1, WP_022477154.1,
WP_022588387.1, WP_022670961.1, WP_022711582.1, WP_022745992.1, WP_022746618.1,
WP_022748671.1, WP_022819291.1, WP_022846698.1, WP_022854086.1, WP_022855920.1,
WP_022856208.1, WP_023037412.1, WP_023039491.1, WP_023039733.1, WP_023438404.1,
WP_023484747.1, WP_023844484.1, WP_023991513.1, XP_003208052.1, XP_004141494.1,
YP_001039591.1, YP_001089497.1, YP_001097294.1, YP_001111907.1, YP_001178904.1,
YP_001179153.1, YP_001305607.1, YP_001322753.1, YP_001325260.1, YP_001375292.1,
YP_001405996.1, YP_001408163.1, YP_001469838.1, YP_001568890.1, YP_001664133.1,
YP_001739053.1, YP_002250044.1, YP_002315131.1, YP_002335044.1, YP_002335721.1,
YP_002352524.1, YP_002460387.1, YP_002509267.1, YP_002534252.1, YP_002574497.1,
YP_002581621.1, YP_002601829.1, YP_002728848.1, YP_002731106.1, YP_002940392.1,
YP_002948500.1, YP_002950001.1, YP_002994889.1, YP_003128745.1, YP_003130361.1,
YP_003163696.1, YP_003178647.1, YP_003190433.1, YP_003192379.1, YP_003193579.1,
YP_003215318.1, YP_003215785.1, YP_003219292.1, YP_003238959.1, YP_003252320.1,
YP_003324144.1, YP_003388656.1, YP_003423538.1, YP_003432903.1, YP_003433379.1,
YP_003458582.1, YP_003463661.1, YP_003478056.1, YP_003495790.1, YP_003497449.1,
YP_003533666.1, YP_003584059.1, YP_003590508.1, YP_003590519.1, YP_003616812.1,
YP_003641230.1, YP_003671008.1, YP_003675823.1, YP_003677874.1, YP_003707159.1,
YP_003728008.1, YP_003824487.1, YP_003839474.1, YP_003841501.1, YP_003853156.1,
YP_003877866.1, YP_003958124.1, YP_003988875.1, YP_003990720.1, YP_003993555.1,
YP_003993604.1, YP_003995276.1, YP_004025072.1, YP_004025118.1, YP_004027469.1,
YP_004027576.1, YP_004027619.1, YP_004051982.1, YP_004102399.1, YP_004130955.1,
YP_004152216.1, YP_004185144.1, YP_004252518.1, YP_004265692.1, YP_004385355.1,
YP_004385601.1, YP_004437581.1, YP_004459627.1, YP_004464198.1, YP_004471952.1,
YP_004515879.1, YP_004516017.1, YP_004546497.1, YP_004569898.1, YP_004587625.1,
YP_004589471.1, YP_004603181.1, YP_004624394.1, YP_004660838.1, YP_004720452.1,
YP_004742714.1, YP_004761696.1, YP_004785824.1, YP_004799899.1, YP_004799948.1,
YP_004832233.1, YP_004859899.1, YP_004932102.1, YP_005010479.1, YP_005046694.1,
YP_005047109.1, YP_005258418.1, YP_005270555.1, YP_005511921.1, YP_005839932.1,
YP_006199528.1, YP_006199999.1, YP_006347178.1, YP_006351426.1, YP_006353779.1,
YP_006391020.1, YP_006425805.1, YP_006444523.1, YP_006540250.1, YP_006761819.1,
YP_006860990.1, YP_006921118.1, YP_006932081.1, YP_006950412.1, YP_007179026.1,
YP_007214187.1, YP_007270779.1, YP_007299923.1, YP_007373248.1, YP_007373480.1,
YP_007457820.1, YP_007489272.1, YP_007500038.1, YP_007647092.1, YP_007679668.1,
YP_007679886.1, YP_007784188.1, YP_007827923.1, YP_007835090.1, YP_007943786.1,
YP_007944036.1, YP_007978159.1, YP_008285600.1, YP_008377026.1, YP_008406928.1,
YP_008698879.1, YP_008773654.1, YP_008874108.1, YP_008915223.1, YP_008991100.1,
YP_134129.1, YP_360969.1, YP_398447.1, YP_519003.1, YP_519038.1, YP_565800.1, YP_643057.1,
YP_754475.1, YP_755178.1, YP_815364.1, and/or YP_878707.1

In some embodiments, Type I-C cas5d polypeptides include, but are not limited to, GenBank accession number as set forth in Table 13.

TABLE 13

Type I-C cas5d polypeptide accession numbers
(the sequence identifier for each accession number, in the order provided in
Table 13, is SEQ ID NOs: 2373-2973).

AAN47887.1, AAS71465.1, AAU93027.1, AAW74125.1, ABA05200.1, ABB24156.1, ABB28271.1,
ABB31305.1, ABC21630.1, ABD12699.1, ABE48872.1, ABF32471.1, ABF34436.1, ABF36361.1,
ABF38347.1, ABF88231.1, ABM29988.1, ABN07020.1, ABO49538.1, ABP81369.1, ABQ92672.1,
ABR74840.1, ABR74645.1, ACA16216.1, ACD60966.1, ACL75831.1, ACM21758.1, ACO79325.1,
ACR11997.1, ADD28250.1, ADK85026.1, ADP88372.1, ADX47760.1, ADY55247.1, ADY61451.1,
ADY61692.1, ADZ26350.1, AEB11036.1, AEC00930.1, AEE12857.1, AEE17592.1, AEF93427.1,
AEG01411.1, AEG34528.1, AEH55427.1, AEI38602.1, AEO47325.1, AER01367.1, AER57692.1,
AEY65499.1, AFM23519.1, AFM40489.1, AFY70023.1, AGB03721.1, AGC48888.1, AGF80046.1,
AGH38686.1, AGK13303.1, AGK17629.1, AHC14003.1, AHC19699.1, AHG83784.1, AHG86670.1,
BAE67552.1, BAF39966.1, BAF60174.1, BAG13699.1, BAL68714.1, BAM02852.1, CAI07977.1,
CAP54006.1, CBA17364.1, CCF16785.1, CCF67638.1, CCG39875.1, CCI63164.1, CCK83453.1,
CCO74227.1, CCP41950.1, CCU72640.1, CCU78371.1, CCW39407.1, CCX48117.1, CCX73938.1,
CCY00154.1, CCY02819.1, CCY33507.1, CCZ32691.1, CCZ61766.1, CCZ62159.1, CCZ84350.1,
CDA15005.1, CDA52082.1, CDA89887.1, CDB26704.1, CDB62743, CDC12997.1, CDC50441.1,
CDC62359.1, CDD04553.1, CDD57368.1, CDD59788.1, CDD98974.1, CDE11994.1, CDE46264.1,

TABLE 13-continued

Type I-C cas5d polypeptide accession numbers
(the sequence identifier for each accession number, in the order provided in
Table 13, is SEQ ID NOs: 2373-2973).

CDE57765.1, CDF15831.1, CDI43446.1, EAQ36306.1, EAT02164.1, EAW36788.1, EBA01539.1,
EDN01971.1, EDN73323.1, EDN76105.1, EDN84715.1, EDP14354.1, EDP25154.1, EDS00205.1,
EDS06800.1, EDT45690.1, EDY32905.1, EDY96625.1, EEA82743.1, EEF65984.1, EEF76899.1,
EEG30526.1, EEG33494.1, EEG56415.1, EEG71148.1, EEG75123.1, EEG96116.1, EEK17367.1,
EEN82611.1, EEO46556.1, EEO62000.1, EEP28832.1, EEP68243.1, EEQ48800.1, EEQ57500.1,
EER56004.1, EES74000.1, EET16694.2, EET44432.1, EET62042.1, EEV89051.1, EEX49287.1,
EEX75937.1, EEY11080.1, EEZ20539.1, EEZ74756.1, EEZ75907.1, EFA89364.1, EFB90880.1,
EFC51247.1, EFC87155.1, EFE11615.1, EFE27918.2, EFF66131.1, EFH21870.1, EFP59912.1,
EFR33752.1, EFR34549.1, EFR37025.1, EFR40957.1, EFR44859.1, EFT83495.1, EFV01200.1,
EFW29035.1, EGB18208.1, EGC03292.1, EGC18025.1, EGC88888.1, EGN35867.1, EGN46214.1,
EGV28562.1, EGZ49812.1, EHJ47330.1, EHQ07660.1, EHQ62726.1, EHQ90704.1, EIA28593.1,
EIA30742.1, EIC02345.1, EIG30391.1, EIG54632.1, EIJ33768.1, EIJ71548.1, EIJ72649.1, EIJ78013.1,
EIK41596.1, EIQ00066.1, EIQ82361.1, EIT84251.1, EIT88137.1, EIW20398.1, EIW25543.1,
EIW30558.1, EIW33390.1, EIW37237.1, EIY19180.1, EJF40816.1, EJG08368.1, EJL40220.1,
EJN54261.1, EJO19217.1, EJO71191.1, EJO77909.1, EJP02512.1, EJP15600.1, EJP31579.1,
EJP85726.1, EJR26612.1, EJR51643.1, EJR72343.1, EJR80197.1, EJS99959.1, EJU16729.1,
EJU25585.1, EJV73300.1, EJW17219.1, EKD25943.1, EKE30555.1, EKF43331.1, EKF36597.1,
EKM99102.1, EKN16809.1, EKN28426.1, EKN66244.1, EKN88372.1, EKN97010.1, EKO05463.1,
EKO14413.1, EKO24496.1, EKO52394.1, EKO59410.1, EKO69592.1, EKO85513.1, EKO94714.1,
EKP04538.1, EKP23618.1, EKP78025.1, EKP85221.1, EKP95534.1, EKQ39148.1, EKQ47929.1,
EKQ85360.1, EKR06490.1, EKR19532.1, EKR25214.1, EKR36497.1, EKR44692.1, EKR54130.1,
EKR74668.1, EKR81621.1, EKT63594.1, EKU24260.1, EKU70788.1, EKU87705.1, EKX89481.1,
EKX93849.1, EKX95308.1, EKY02929.1, ELK39519.1, ELQ17187.1, ELR65960.1, EMB53450.1,
EMB56302.1, EMB59747.1, EMB80077.1, EMB82084.1, EMB86593.1, EMB91875.1, EMB92064.1,
EMB98504.1, EMC28293.1, EMC29746.1, EMC55689.1, EMC60782.1, EME03979.1, EMF35391.1,
EMF42537.1, EMF73168.1, EMG11434.1, EMG19652.1, EMI28181.1, EMI63036.1, EMI71643.1,
EMJ34610.1, EMJ52878.1, EMJ58561.1, EMJ63192.1, EMJ69822.1, EMJ72472.1, EMJ80487.1,
EMJ91108.1, EMK06063.1, EMK07518.1, EMK16097.1, EMK18463.1, EMK26085.1, EMM84360.1,
EMM90741.1, EMM95783.1, EMM98819.1, EMN05664.1, EMN10273.1, EMN27475.1, EMN31752.1,
EMN36998.1, EMN40224.1, EMN50554.1, EMN52177.1, EMN64664.1, EMN64895.1, EMN71239.1,
EMN74221.1, EMN81741.1, EMN86854.1, EMN94812.1, EMN98288.1, EMO03582.1, EMO16704.1,
EMO29549.1, EMO34946.1, EMO42449.1, EMO51779.1, EMO65720.1, EMO77648.1, EMO79157.1,
EMO89088.1, EMO95187.1, EMP06745.1, EMP59158.1, EMP62865.1, EMS72177.1, EMS78533.1,
EMS83941.1, EMS85265.1, EMY05817.1, EMY23092.1, EMY55686.1, EMZ33824.1, ENO72457.1,
ENO77317.1, ENO81519.1, ENO88271.1, ENZ10232.1, ENZ16947.1, ENZ39043.1, ENZ43232.1,
ENZ45620.1, ENZ47416.1, ENZ54159.1, ENZ69350.1, EOA56068.1, EOH98199.1, EOO33053.1,
EOP18423.1, EOP32138.1, EOP44811.1, EOP55656.1, EOP60321.1, EOP87876.1, EOQ6053.1,
EOS00147.1, EOS28523.1, EOS50042.1, EOS54453.1, EOS63279.1, EOS64688.1, EOS73779.1,
EOS81387.1, EOT59712.1, EPD37767.1, EPD56031.1, EPD62541.1, EPD77060.1, EPE60577.1,
EPE83066.1, EPF25861.1, EPG50259.1, EPL64359.1, EPP16776.1, EPP17871.1, EPT71507.1,
EPT84064.1, EPU02094.1, EPU03828.1, EPU52082.1, EPU54910.1, EPU81442.1, EPU87008.1,
EPU94208.1, EPU97405.1, EPV01336.1, EPV02195.1, EPV09631.1, EPV18668.1, EPV22733.1,
EPV25619.1, EPV40784.1, EPV50545.1, EPV51910.1, EPV55807.1, EPV62103.1, EPV65175.1,
EPV98861.1, EPW00870.1, EPW07126.1, EPW16761.1, EPW44453.1, EPW59772.1, EPW65049.1,
EPW65528.1, EPW80674.1, EPW81318.1, EPW82924.1, EPW86859.1, EPX25333.1, EPX29203.1,
EPY00286.1, EPZ01875.1, EPZ27872.1, EPZ29478.1, EPZ29867.1, EPZ46610.1, EQA71137.1,
EQA92571.1, ERF77711.1, ERH28583.1, ERH28850.1, ERH97080.1, ERI04267.1, ERI61373.1,
ERI68386.1, ERJ00271.1, ERJ69593.1, ERJ89572.1, ERJ93149.1, ERK03389.1, ERK56583.1,
ERK64508.1, ERK89621.1, ERL04025.1, ERL17229.1, ERP31666.1, ERP96324.1, ERS87977.1,
ERV42109.1, ERV60145.1, ERY77980.1, ESA51291.1, ESQ15434.1, EST51947.1, ESU95723.1,
ETA80090.1, ETD20913.1, ETE90141.1, ETI70720.1, GAB60573.1, GAC40772.1, GAD39350.1,
GAE10003.1, NP_710869.1, WP_000448696.1, WP_002270820.1, WP_002284930.1,
WP_003680283.1, WP_004260232.1, WP_004448864.1, WP_004757770.1, WP_005487698.1,
WP_006966953.1, WP_007465278.1, WP_008224256.1, WP_009605936.1, WP_009729418.1,
WP_009784757.1, WP_010259997.1, WP_010543173.1, WP_011257746.1, WP_011315193.1,
WP_011388584.1, WP_011556938.1, WP_011743510.1, WP_011745279.1, WP_011787403.1,
WP_011914754.1, WP_011959009.1, WP_012033149.1, WP_012062878.1, WP_012073022.1,
WP_012222310.1, WP_012331626.1, WP_014436072.1, WP_015164989.1, WP_015286683.1,
WP_015405728.1, WP_015432824.1, WP_015487358.1, WP_015924973.1, WP_016217545.1,
WP_016229737.1, WP_016271358.1, WP_016293318.1, WP_016309858.1, WP_016313870.1,
WP_016314947.1, WP_016323949.1, WP_016439663.1, WP_016441069.1, WP_016453851.1,
WP_016478058.1, WP_016480397.1, WP_017690352.1, WP_018887427.1, WP_018916770.1,
WP_019604447.1, WP_021495565.1, WP_021615274.1, WP_021615581.1, WP_021625750.1,
WP_021631528.1, WP_021636852.1, WP_021659784.1, WP_021666376.1, WP_021685844.1,
WP_021687360.1, WP_021774882.1, WP_021932607.1, WP_022180174.1, WP_023389231.1,
WP_023411381.1, WP_023967437.1, WP_023988272.1, YP_001030287.1, YP_001174211.1,
YP_001212543.1, YP_001278622.1, YP_001319499.1, YP_001344580.1, YP_001600359.1,
YP_001768650.1, YP_001915498.1, YP_002018512.1, YP_002505811.1, YP_002538859.1,
YP_002800300.1, YP_002828.1, YP_003074489.1, YP_003377358.1, YP_003507270.1,
YP_003807620.1, YP_004236327.1, YP_004265248.1, YP_004271473.1, YP_004271714.1,
YP_004294512.1, YP_004367146.1, YP_004414389.1, YP_004440723.1, YP_004442025.1,
YP_004496339.1, YP_004513910.1, YP_004673775.1, YP_004931733.1, YP_005147304.1,
YP_005444749.1, YP_005641655.1, YP_005704010.1, YP_005987350.1, YP_006047122.1,
YP_006250657.1, YP_006720033.1, YP_007102451.1, YP_007250228.1, YP_007364572.1,
YP_007469699.1, YP_007548477.1, YP_007682877.1, YP_007894110.1, YP_007899159.1,
YP_008086287.1, YP_008911632.1, YP_088180.1, YP_113169.1, YP_199510.1, YP_318552.1,

TABLE 13-continued

Type I-C cas5d polypeptide accession numbers
(the sequence identifier for each accession number, in the order provided in
Table 13, is SEQ ID NOs: 2373-2973).

YP_375199.1, YP_379314.1, YP_425917.1, YP_434017.1, YP_449826.1, YP_482428.1, YP_525132.1,
YP_544713.1, YP_635132.1, YP_910048.1, YP_911887.1, and/or YP_961176.1

In some embodiments, Type I-C cas8c/csd1 polypeptides include, but are not limited to, GenBank accession number as set forth in Table 14.

TABLE 14

Type I-C cas8c/csd1 polypeptide accession numbers
(the sequence identifier for each accession number, in the order provided in
Table 14, is SEQ ID NOs: 2974-3847).

ABA05199.1, ABB24157.1, ABB28270.1, ABB31306.1, ABC18826.1, ABC21631.1, ABD12700.1,
ABD71602.1, ABE48873.1, ABF44540.1, ABF90712.1, ABI59275.1, ABI67812.1, ABK46006.1,
ABL65462.1, ABM29987.1, ABN07019.1, ABO49539.1, ABP37314.1, ABQ92671.1, ABR47841.1,
ABR74967.1, ACA16217.1, ACB33428.1, ACB59636.1, ACD60967.1, ACE84720.1, ACF43896.1,
ACG61922.1, ACI51408.1, ACL08916.1, ACM01819.1, ACM21757.1, ACO32176.1, ACO79324.1,
ACR12476.1, ACS96760.1, ACV55941.1, ACV64359.1, ACV76426.1, ACX95670.1, ADB10233.1,
ADB47146.1, ADD28249.1, ADD43241.1, ADE15051.1, ADE85054.1, ADG82737.1, ADH65195.1,
ADI02309.1, ADI14779.1, ADK80204.1, ADK85027.1, ADO43028.1, ADP70486.1, ADP88373.1,
ADU21656.1, ADU26220.1, ADU44692.1, ADV45013.1, ADW17643.1, ADX47761.1, ADY55248.1,
ADY61450.1, ADY61691.1, ADZ26349.1, AEB11037.1, AEC00929.1, AEE12858.1, AEE17591.1,
AEF28113.1, AEF93428.1 AEG01412.1, AEG34529.1, AEG59677.1, AEH52451.1, AEH55428.1,
AEI38601.1, AEI64170.1, AEJ20057.1, AEM41208.1, AEN97652.1, AEO47326.1, AEP00022.1,
AER57693.1, AET67442.1, AEV30965.1, AEY65500.1, AFI86060.1, AFI87838.1, AFK56997.1,
AFM23520.1, AFM40490.1, AFU17710.1, AFY70024.1, AFY93137.1, AFY97160.1, AGA59292.1,
AGB03720.1, AGB28831.1, AGC48887.1, AGF80045.1, AGG05730.1, AGH38687.1, AGH40905.1,
AGI32649.1, AGI35531.1, AGK06311.1, AGK13351.1, AGK17701.1, AGL03421.1, AGQ24918.1,
AGQ37969.1, AGQ40483.1, AGR74823.1, AGS46823.1, AHB48174.1, AHF04637.1, AHG75933.1,
AHG77943.1, AHG79312.1, AHG81512.1, AHG83783.1, AHG86052.1, AHG86671.1, AHJ19773.1,
BAG13700.1, BAK19890.1, BAK56463.1, BAK66415.1, BAK79792.1, BAK81139.1, BAL68715.1,
BAN13313.1, BAN59902.1, CBK76220.1, CBK91609.1, CBK92830.1, CBK99509.1, CBL17827.1,
CBL34516.1, CCE23846.1, CCF67637.1, CCG39876.1, CCI63163.1, CCQ74034.1, CCQ93019.1,
CCU78373.1, CCW39408.1, CCY14613.1, CCY86584.1, CCZ32692.1, CCZ61765.1, CCZ84351.1,
CDA52083.1, CDA72500.1, CDB26703.1, CDB62744.1, CDC38727.1, CDC50442.1, CDD54040.1,
CDD59789.1, CDE06406.1, CDE11995.1, CDE34088.1, CDE46265.1, CDF23237.1, CDI43445.1,
EDN01972.1, EDN76104.1, EDN84716.1, EDP25155.1, EDS00206.1, EDS06799.1, EDT45691.1,
EDY32906.1, EDY84711.1, EDY96624.1, EEA82742.1, EEF66037.1, EEF76900.1, EEG30525.1,
EEG33493.1, EEG56416.1, EEG71147.1, EEG75122.1, EEG96117.1, EEK17397.1, EEN82623.1,
EEO46555.1, EEO62001.1, EEP28831.1, EEP68242.1, EEQ48799.1, EEQ57499.1, EER55952.1,
EES74001.1, EET16693.1, EET44433.1, EET62043.1, EEV89052.1, EEX49286.1, EEX75938.1,
EEZ20540.1, EEZ75908.1, EFA89355.1, EFB90881.1, EFC51246.1, EFC87154.1, EFC91098.1,
EFE11614.1, EFE27917.1, EFE93114.1, EFF66130.1, EFH21871.1, EFI35152.1, EFR33734.1,
EFR34562.1, EFR36958.1, EFR40986.1, EFR44838.1, EFT83496.1, EFV01199.1, EFW29036.1,
EGB16323.1, EGB18207.1, EGB94719.1, EGC03294.1, EGC16024.1, EGC76280.1, EGC88882.1,
EGD49242.1, EGJ10201.1, EGN46212.1, EGO64861.1, EGQ14153.1, EGQ77215.1, EGT75761.1,
EGT79805.1, EGT80245.1, EGT82116.1, EGV28563.1, EGV37140.1, EGV37199.1, EGW49962.1,
EGW53125.1, EGX28856.1, EGX72598.1, EGY32747.1, EGY34069.1, EGY34246.1, EGY35532.1,
EGY35533.1, EGY37221.1, EGY37222.1, EGY38194.1, EGY38195.1, EGY38196.1, EGY39574.1,
EGY39515.1, EGY39871.1, EGY41443.1, EGY43833.1, EGY43834.1, EGY46702.1, EGY53774.1,
EGY61571.1, EGY70644.1, EGY70863.1, EGY70864.1, EGZ44570.1, EGZ49813.1, EHB62323.1,
EHB89139.1, EHE98230.1, EHF02460.1, EHG19004.1, EHG22081.1, EHG23346.1, EHG32769.1,
EHJ47329.1, EHK89719.1, EHM10679.1, EHM13739.1, EHM50511.1, EHM53517.1, EHO85750.1,
EHP86556.1, EHQ07661.1, EHQ90703.1, EIA21871.1, EIA23998.1, EIA23999.1, EIA26371.1,
EIA26756.1, EIA28592.1, EIA30743.1, EIC02344.1, EIC21113.1, EIG54631.1, EIJ33767.1, EIL98038.1,
EIM57402.1, EIQ00067.1, EIT88136.1, EIW20397.1, EIW25544.1, EIW30557.1, EIW33391.1,
EIW37238.1, EJG08367.1, EJL40221.1, EKD25944.1, EKD37960.1, EKD69492.1, EKD96705.1,
EKM99103.1, EKP95535.1, EKU24259.1, EKX89480.1, EKX93848.1, EKX94125.1, EKX95307.1,
EKY02930.1, ELQ17186.1, ELR65961.1, ELT53857.1, ELT54756.1, ELT58107.1, ELT59489.1,
EME03980.1, EMI28182.1, EMS72167.1, EPE60583.1, EPL64358.1, EPR34125.1, EPR43457.1,
EPT71506.1, EPU52081.1, EPU54909.1, EPU81441.1, EPU87009.1, EPU94207.1, EPU97404.1,
EPV01335.1, EPV02196.1, EPV09632.1, EPV18667.1, EPV22732.1, EPV25620.1, EPV35742.1,
EPV40783.1, EPV50546.1, EPV51909.1, EPV55808.1, EPV65176.1, EPV98862.1, EPW00871.1,
EPW07125.1, EPW16760.1, EPW44452.1, EPW59771.1, EPW65048.1, EPW65529.1, EPW80673.1,
EPW82925.1, EPW86858.1, EPX25332.1, EPX29204.1, EPY00287.1, EPZ01876.1, EPZ27871.1,
EPZ29477.1, EPZ29668.1, EQA92570.1, ERH28584.1, ERH28851.1, ERI04266.1, ERI61374.1,
ERI68076.1, ERI68387.1, ERI74757.1, ERJ00272.1, ERJ69594.1, ERJ89573.1, ERJ93148.1,
ERK56584.1, ERK64509.1, ERK89620.1, ERL04024.1, ESR08823.1, ETA80089.1, ETD02079.1,
ETD77753.1, ETD86666.1, ETE54111.1, EWS78075.1, GAF23122.1, WP_000345443.1,
WP_000345444.1, WP_002568438.1, WP_002595865.1, WP_002606245.1, WP_002703148.1,
WP_002707716.1, WP_002725660.1, WP_002773709.1, WP_002849082.1, WP_002930618.1,
WP_002989033.1, WP_003044513.1, WP_003051949.1, WP_003062221.1, WP_003465420.1,

TABLE 14-continued

Type I-C cas8c/csd1 polypeptide accession numbers
(the sequence identifier for each accession number, in the order provided in
Table 14, is SEQ ID NOs: 2974-3847).

WP_003680670.1, WP_003685597.1, WP_003708651.1, WP_003713924.1, WP_003744750.1,
WP_003746232.1, WP_003754490.1, WP_003758690.1, WP_003762755.1, WP_003777776.1,
WP_003781698.1, WP_003797746.1, WP_004040744.1, WP_004093890.1, WP_004284051.1,
WP_004285513.1, WP_004331271.1, WP_004333880.1, WP_004397038.1, WP_004513242.1,
WP_004520755.1, WP_004612294.1, WP_004617478.1, WP_004625421.1, WP_004826227.1,
WP_004853850.1, WP_005487699.1, WP_005540295.1, WP_005540298.1, WP_005540835.1,
WP_005550134.1, WP_005552081.1, WP_005552083.1, WP_005555120.1, WP_005556489.1,
WP_005557287.1, WP_005563370.1, WP_005563372.1, WP_005563373.1, WP_005565164.1,
WP_005565917.1, WP_005567427.1, WP_005578608.1, WP_005579127.1, WP_005582661.1,
WP_005586615.1, WP_005587225.1, WP_005610783.1, WP_005626995.1, WP_005635205.1,
WP_005636526.1, WP_005642817.1, WP_005646984.1, WP_005660279.1, WP_005702613.1,
WP_005703627.1, WP_005759025.1, WP_005806400.1, WP_005820512.1, WP_005846119.1,
WP_005856772.1, WP_005927103.1, WP_005955348.1, WP_006116165.1, WP_006194036.1,
WP_006248108.1, WP_006250670.1, WP_006252735.1, WP_006253508.1, WP_006269870.1,
WP_006306919.1, WP_006521533.1, WP_006599002.1, WP_006689561.1, WP_006693577.1,
WP_006695539.1, WP_006786410.1, WP_006860504.1, WP_006872858.1, WP_006903556.1,
WP_006986820.1, WP_007042344.1, WP_007363024.1, WP_007364828.1, WP_007439947.1,
WP_007439948.1, WP_007465280.1, WP_007489325.1, WP_007524562.1, WP_007708673.1,
WP_007785240.1, WP_007863415.1, WP_007892671.1, WP_007931218.1, WP_008104116.1,
WP_008387836.1, WP_008398233.1, WP_008437583.1, WP_008494662.1, WP_008519402.1,
WP_008523302.1, WP_008664695.1, WP_008687427.1, WP_008816402.1, WP_008870466.1,
WP_008974804.1, WP_008979465.1, WP_009002351.1, WP_009109519.1, WP_009117236.1,
WP_009117700.1, WP_009151516.1, WP_009164689.1, WP_009180733.1, WP_009213700.1,
WP_009245301.1, WP_009255682.1, WP_009257010.1, WP_009278655.1, WP_009303812.1,
WP_009311471.1, WP_009350456.1, WP_009427626.1, WP_009437516.1, WP_009438895.1,
WP_009441727.1, WP_009605933.1, WP_009646998.1, WP_009657051.1, WP_009658389.1,
WP_009666494.1, WP_009796705.1, WP_009856766.1, WP_009880809.1, WP_009984821.1,
WP_010245161.1, WP_010259993.1, WP_010372414.1, WP_010381903.1, WP_010543172.1,
WP_010603693.1, WP_010621278.1, WP_010626368.1, WP_010922511.1, WP_010932805.1,
WP_010959997.1, WP_011052556.1, WP_011074659.1, WP_011134781.1, WP_011174430.1,
WP_011176708.1, WP_011200164.1, WP_011257745.1, WP_011284986.1, WP_011285646.1,
WP_011315192.1, WP_011358029.1, WP_011362035.1, WP_011388585.1, WP_011392033.1,
WP_011396662.1, WP_011478970.1, WP_011528830.1, WP_011529386.1, WP_011556937.1,
WP_011634098.1, WP_011715062.1, WP_011743508.1, WP_011743509.1, WP_011745278.1,
WP_011787404.1, WP_011877368.1, WP_011890537.1, WP_011914755.1, WP_011959008.1,
WP_012062879.1, WP_012073023.1, WP_012222309.1, WP_012331627.1, WP_012346190.1,
WP_012508383.1, WP_012515198.1, WP_012553887.1, WP_012560835.1, WP_012613091.1,
WP_012678341.1, WP_012701708.1, WP_012743317.1, WP_012771280.1, WP_012817718.1,
WP_012823706.1, WP_012917358.1, WP_012938135.1, WP_013013751.1, WP_013032917.1,
WP_013067033.1, WP_013120747.1, WP_013159709.1, WP_013175711.1, WP_013178147.1,
WP_013253668.1, WP_013258480.1, WP_013300568.1, WP_013384679.1, WP_013418890.1,
WP_013448701.1, WP_013484590.1, WP_013497833.1, WP_013502809.1, WP_013548690.1,
WP_013559648.1, WP_0135962371, WP_013624119.1, WP_013630167.1, WP_013647393.1,
WP_013703092.1, WP_013759293.1, WP_013760347.1, WP_013809681.1, WP_013819641.1,
WP_013841448.1, WP_013858350.1, WP_013902815.1, WP_013903479.1, WP_013937331.1,
WP_013945609.1, WP_013969347.1, WP_014017910.1, WP_014076066.1, WP_014080658.1,
WP_014094599.1, WP_014096166.1, WP_014161866.1, WP_014184259.1, WP_014271804.1,
WP_014312879.1, WP_014323747.1, WP_014511147.1, WP_014612477.1, WP_014677805.1,
WP_014702219.1, WP_014702545.1, WP_014747986.1, WP_014826497.1, WP_015164990.1,
WP_015353140.1, WP_015405727.1, WP_015406748.1, WP_015423228.1, WP_015432825.1,
WP_015450165.1, WP_015484658.1, WP_015517329.1, WP_015558733.1, WP_015565151.1,
WP_015567095.1, WP_015572965.1, WP_015724184.1, WP_015759046.1, WP_015818588.1,
WP_015860138.1, WP_015895951.1, WP_015921089.1, WP_016480398.1, WP_016510768.1,
WP_016687509.1, WP_017113403.1, WP_017116852.1, WP_017117513.1, WP_017119023.1,
WP_017364194.1, WP_017551361.1, WP_017647433.1, WP_017907376.1, WP_018305950.1,
WP_018366929.1, WP_018465584.1, WP_018652891.1, WP_019273185.1, WP_019314884.1,
WP_019703287.1, WP_019802801.1, WP_019802802.1, WP_020880188.1, WP_020886853.1,
WP_021133647.1, WP_021615275.1, WP_021615582.1, WP_021625749.1, WP_021631529.1,
WP_021636853.1, WP_021637096.1, WP_021640899.1, WP_021666785.1, WP_021666377.1,
WP_021685845.1, WP_021687359.1, WP_021751294.1, WP_021774881.1, WP_021906521.1,
WP_022009885.1, WP_022033203.1, WP_022049339.1, WP_022108014.1, WP_022127777.1,
WP_022177038.1, WP_022202383.1, WP_022264214.1, WP_022272155.1, WP_022356883.1,
WP_022363356.1, WP_022402825.1, WP_022410982.1, WP_022427821.1, WP_022445691.1,
WP_022512574.1, WP_022654264.1, WP_022656791.1, WP_022681041.1, WP_023389232.1,
WP_023514069.1, WP_023786786.1, WP_023921140.1, WP_024105343.1, WP_024108605.1,
WP_024109517.1, YP_001112364.1, YP_001130816.1, YP_001174212.1, YP_001278621.1,
YP_001319500.1, YP_001344581.1, YP_001768651.1, YP_001790193.1, YP_001812653.1,
YP_001915499.1, YP_001956161.1, YP_001982916.1, YP_002018513.1, YP_002122935.1,
YP_002276023.1, YP_002436384.1, YP_002526320.1, YP_002538858.1, YP_002753896.1,
YP_002800299.1, YP_003006847.1, YP_003074488.1, YP_003182330.1, YP_003192982.1,
YP_003227010.1, YP_003262717.1, YP_003361057.1, YP_003398461.1, YP_003507269.1,
YP_003512334.1, YP_003527438.1, YP_003577461.1, YP_003640638.1, YP_003686703.1,
YP_003702874.1, YP_003705322.1, YP_003802798.1, YP_003807621.1, YP_003964328.1,
YP_004011585.1, YP_004090951.1, YP_004104290.1, YP_004109425.1, YP_004162599.1,
YP_004194934.1, YP_004236328.1, YP_004265249.1, YP_004271472.1, YP_004271713.1,
YP_004294511.1, YP_004367147.1, YP_004414388.1, YP_004440722.1, YP_004442026.1,

TABLE 14-continued

Type I-C cas8c/csd1 polypeptide accession numbers
(the sequence identifier for each accession number, in the order provided in
Table 14, is SEQ ID NOs: 2974-3847).

YP_004496340.1, YP_004513911.1, YP_004544963.1, YP_004567837.1, YP_004665248.1,
YP_004673774.1, YP_004698565.1, YP_004771205.1, YP_004834872.1, YP_004839584.1,
YP_004857065.1, YP_004858802.1, YP_004917438.1, YP_004931734.1, YP_004969957.1,
YP_005053777.1, YP_005063975.1, YP_005147305.1, YP_005169126.1, YP_005641656.1,
YP_005668368.1, YP_005704011.1, YP_005795204.1, YP_006047123.1, YP_006250658.1,
YP_006285892.1, YP_006287670.1, YP_006373979.1, YP_006445784.1, YP_006465822.1,
YP_006720034.1, YP_006815949.1, YP_006905221.1, YP_007096664.1, YP_007102452.1,
YP_007214290.1, YP_007250227.1, YP_007296337.1, YP_007318535.1, YP_007364571.1,
YP_007469698.1, YP_007483072.1, YP_007548478.1, YP_007593345.1, YP_007666157.1,
YP_007669039.1, YP_007773723.1, YP_007829835.1, YP_007837793.1, YP_007840045.1,
YP_007841640.1, YP_007848218.1, YP_007881808.1, YP_007894109.1, YP_007899158.1,
YP_007947097.1, YP_008086288.1, YP_008145544.1, YP_008219474.1, YP_008221969.1,
YP_008233396.1, YP_008338545.1, YP_008866150.1, YP_009171.1, YP_113168.1, YP_318551.1,
YP_375200.1, YP_379313.1, YP_425918.1, YP_429369.1, YP_525133.1, YP_544714.1, YP_603709.1,
YP_635131.1, YP_747240.1, YP_867412.1, YP_910046.1, YP_910047.1, YP_911886.1, and/or
YP_961175.1

In some embodiments, Type I-C cas7/csd2 polypeptides include, but are not limited to, GenBank accession number as set forth in Table 15.

TABLE 15

Type I-C cas7/csd2 polypeptide accession numbers
(the sequence identifier for each accession number, in the
order provided in Table 15, is SEQ ID NOs: 3848-4371).

ABA05198.1, ABB24158.1, ABB28269.1, ABB31307.1, ABC18825.1, ABC21632.1, ABD12701.1,
ABD71603.1, ABF44539.1, ABI59274.1, ABI67813.1, ABK46001.1, ABM29986.1, ABN07018.1,
ABO49540.1, ABP37315.1, ABQ92670.1, ABR47842.1, ABR74647.1, ACB33427.1, ACB59637.1,
ACD60968.1, ACE85492.1, ACG61923.1, ACI51409.1, ACL08917.1, ACL20219.1, ACM21756.1,
ACO79323.1, ACR11071.1, ACS96761.1, ACV55940.1, ACV64358.1, ACV76427.1, ACX95669.1,
ADB47147.1, ADD28248.1, ADD43240.1, ADE15052.1, ADH65194.1, ADI02308.1,
ADI14780.1, ADK80205.1, ADK85028.1, ADN01352.1, ADO43029.1, ADP88374.1, ADU21657.1,
ADU26219.1, ADU44693.1, ADV45012.1, ADW17644.1, ADX47762.1, ADY55249.1, ADY61449.1,
ADY61690.1, ADZ26348.1, AEA19527.1, AEA19528.1, AEA19529.1, AEA19530.1, AEA19531.1,
AEA19532.1, AEC00928.1, AEE12859.1, AEE17590.1, AEF93429.1, AEG01413.1, AEG59678.1,
AEH55429.1, AEI38600.1, AEJ20056.1, AEM41209.1, AEN97651.1, AEO47327.1, AEP00021.1,
AER57694.1, AET67443.1, AEV30966.1, AEW77431.1, AEY65501.1, AFI86059.1, AFI87839.1,
AFM23521.1, AFM40491.1, AFU17709.1, AFV38402.1, AFV71911.1, AFY70025.1, AFY93136.1,
AGA59293.1, AGB03719.1, AGB28832.1, AGF80044.1, AGH38688.1, AGK06312.1, AGK13352.1,
AGK17702.1, AGK70468.1, AGL03420.1, AGS46824.1, AHB48173.1, AHG79313.1, AHG81511.1,
AHG83782.1, AHG86672.1, BAG13701.1, BAK19891.1, BAK56464.1, BAK66416.1, BAL68716.1,
BAN13314.1, CBA17366.1, CBK76221.1, CBK91610.1, CBK92829.1, CBK99510.1, CBL17828.1,
CBL19923.1, CBL34517.1, CCE23038.1, CCE23845.1, CCG39877.1, CCH29339.1, CCH68439.1,
CCI63162.1, CCQ74035.1, CCQ75831.1, CCQ78091.1, CCQ93985.1, CCU72638.1, CCU78374.1,
CCW39409.1, CCW41577.1, CCX50886.1, CCY14614.1, CCY42897.1, CCZ62161.1, CDA15003.1,
CDA52084.1, CDA72501.1, CDB26702.1, CDB29308.1, CDB98427.1, CDC38734.1, CDC50443.1,
CDC67800.1, CDD54041.1, CDD59790.1, CDD98976.1, CDE06407.1, CDE11996.1, CDE34087.1,
CDE80446.1, CDF15829.1, CDF27765.1, EDY82084.1, EEG33491.1, EEL61422.1, EEL61569.1,
EEL61570.1, EEL61625.1, EEM13962.1, EEM56162.1, EEV24884.1, EEV89053.1, EFB90882.1,
EFC91099.1, EFI35153.1, EFV34597.1, EGA91855.1, EGA93920.1, EGB16324.1, EGB94720.1,
EGC76281.1, EGD26423.1, EGD49243.1, EGE48067.1, EGJ10200.1, EGJ38118.1, EGK58601.1,
EGN35864.1, EGT75762.1, EGT79804.1, EGT80243.1, EGV28564.1, EGV37198.1, EGW49963.1,
EGW53124.1, EGX28855.1, EGX72599.1, EGY31355.1, EGY32746.1, EGY34247.1, EGY35534.1,
EGY38197.1, EGY39516.1, EGY39870.1, EGY41444.1, EGY43831.1, EGY43832.1, EGY46703.1,
EGY61572.1, EGY70645.1, EGY70862.1, EGZ49814.1, EHB62324.1, EHF02461.1, EHG19005.1,
EHG23345.1, EHK89720.1, EHK89932.1, EHM10678.1, EHM13738.1, EHO85751.1, EHP86557.1,
EHQ07662.1, EHQ90702.1, EIA23997.1, EIA26370.1, EIA26757.1, EIA28591.1, EIA30744.1,
EIC02343.1, EIC21112.1, EIG54630.1, EIJ33766.1, EIL98037.1, EIM57403.1, EIQ00068.1, EIT84253.1,
EIW20396.1, EIW25545.1, EIW30556.1, EIW33392.1, EIW37239.1, EJG08366.1, EJL40222.1,
EJS99961.1, EJW17221.1, EKD37966.1, EKE30553.1, EKF36591.1, EKM99104.1, EKP95536.1,
EKT63592.1, ELK39521.1, ELQ17185.1, ELR65962.1, ELT58108.1, ELT59490.1, EMB14047.1,
EME03981.1, EMI28183.1, EMI57443.1, EMS72154.1, ENO77319.1, EPE60578.1, EPR34124.1,
EPR43458.1, EPY00288.1, ERK89619.1, ETD02080.1, ETD77754.1, ETD86665.1, ETE54112.1,
ETE90143.1, ETE90144.1, GAE10005.1, GAF06946.1, WP_000462625.1, WP_000467673.1,
WP_001167480.1, WP_002063064.1, WP_002063097.1, WP_002063098.1, WP_002166872.1,
WP_002182191.1, WP_002183179.1, WP_002725662.1, WP_003345765.1, WP_003465419.1,
WP_003504657.1, WP_004260238.1, WP_004625408.1, WP_005487700.1, WP_005540837.1,
WP_005563374.1, WP_005565165.1, WP_005567428.1, WP_005582660.1, WP_005635207.1,
WP_005660281.1, WP_005758893.1, WP_005876727.1, WP_005966189.1, WP_006116164.1,
WP_006475674.1, WP_006903557.1, WP_007042345.1, WP_007294885.1, WP_007427673.1,
WP_007439946.1, WP_007465282.1, WP_007524600.1, WP_007931217.1, WP_008224253.1,

TABLE 15-continued

Type I-C cas7/csd2 polypeptide accession numbers
(the sequence identifier for each accession number, in the
order provided in Table 15, is SEQ ID NOs: 3848-4371).

WP_008387837.1, WP_008494663.1, WP_008664697.1, WP_008675255.1, WP_008709260.1,
WP_008910923.1, WP_009151515.1, WP_009796706.1, WP_010357662.1, WP_010543171.1,
WP_010621279.1, WP_011194447.1, WP_011237670.1, WP_011315191.1, WP_011362034.1,
WP_011388586.1, WP_011418637.1, WP_011466166.1, WP_011529385.1, WP_011715063.1,
WP_011959007.1, WP_012033147.1, WP_012073024.1, WP_012222308.1, WP_012488051.1,
WP_012553888.1, WP_012648484.1, WP_012817719.1, WP_013013750.1, WP_013067034.1,
WP_013071005.1, WP_013159708.1, WP_013175710.1, WP_013384680.1, WP_013502810.1,
WP_013624120.1, WP_013759292.1, WP_013945608.1, WP_013987428.1, WP_014076067.1,
WP_014147834.1, WP_014148633.1, WP_014167735.1, WP_014481879.1, WP_014481880.1,
WP_014481881.1, WP_014808677.1, WP_014840104.1, WP_015099452.1, WP_015164991.1,
WP_015405726.1, WP_015423229.1, WP_015432826.1, WP_015487356.1, WP_015517330.1,
WP_015525790.1, WP_015558734.1, WP_015565152.1, WP_015567096.1, WP_015572966.1,
WP_015604457.1, WP_015817183.1, WP_016480399.1, WP_016502589.1, WP_016566412.1,
WP_018276375.1, WP_018289542.1, WP_018465585.1, WP_019271084.1, WP_019403925.1,
WP_019604445.1, WP_020880189.1, WP_020886852.1, WP_021133648.1, WP_021906522.1,
WP_021932605.1, WP_022033513.1, WP_022074734.1, WP_022108015.1, WP_022127778.1,
WP_022177037.1, WP_022180176.1, WP_022228954.1, WP_022272156.1, WP_022272615.1,
WP_022287597.1, WP_022356884.1, WP_022363357.1, WP_022400170.1, WP_022402826.1,
WP_022410983.1, WP_022427820.1, WP_022475428.1, WP_022506622.1, WP_022513469.1,
WP_022659417.1, WP_022681040.1, WP_023514068.1, WP_023786785.1, WP_023921138.1,
WP_023967440.1, YP_001112365.1, YP_001130817.1, YP_001278620.1, YP_001319501.1,
YP_001344582.1, YP_001790192.1, YP_001812654.1, YP_001915500.1, YP_001956162.1,
YP_001982915.1, YP_002122936.1, YP_002276024.1, YP_002436385.1, YP_002458655.1,
YP_002538857.1, YP_002800298.1, YP_003006848.1, YP_003074487.1, YP_003182329.1,
YP_003192981.1, YP_003227011.1, YP_003262716.1, YP_003377360.1, YP_003398462.1,
YP_003507268.1, YP_003512333.1, YP_003527439.1, YP_003640637.1, YP_003686702.1,
YP_003702873.1, YP_003705323.1, YP_003802799.1, YP_003807622.1, YP_003873625.1,
YP_003964329.1, YP_004090950.1, YP_004104291.1, YP_004109426.1, YP_004162598.1,
YP_004194935.1, YP_004236329.1, YP_004265250.1, YP_004271471.1, YP_004271712.1,
YP_004294510.1, YP_004414387.1, YP_004440721.1, YP_004442027.1, YP_004496341.1,
YP_004513912.1, YP_004544964.1, YP_004621357.1, YP_004673773.1, YP_004698564.1,
YP_004771206.1, YP_004834873.1, YP_004839583.1, YP_004858801.1, YP_004916632.1,
YP_004917437.1, YP_004931735.1, YP_004949175.1, YP_004969958.1, YP_005053778.1,
YP_005063976.1, YP_005147306.1, YP_005169127.1, YP_005569631.1, YP_005569632.1,
YP_005569633.1, YP_005569634.1, YP_005569635.1, YP_005569636.1, YP_005704012.1,
YP_005795205.1, YP_006047124.1, YP_006250659.1, YP_006285891.1, YP_006287671.1,
YP_006445785.1, YP_006465823.1, YP_006720035.1, YP_006815948.1, YP_006905220.1,
YP_006933355.1, YP_006950855.1, YP_007036212.1, YP_007096663.1, YP_007102453.1,
YP_007214291.1, YP_007250226.1, YP_007296338.1, YP_007469697.1, YP_007548479.1,
YP_007682875.1, YP_007773724.1, YP_007783586.1, YP_007829836.1, YP_007837794.1,
YP_007840046.1, YP_007841639.1, YP_007848219.1, YP_007881809.1, YP_007894108.1,
YP_007899157.1, YP_007922620.1, YP_007947096.1, YP_008086289.1, YP_008117179.1,
YP_008866149.1, YP_425919.1, YP_603708.1, YP_747239.1, YP_867413.1, and/or YP_961174.1

In other embodiments, Type I-D cas10d/csc3 polypeptides include, but are not limited to, GenBank accession number as set forth in Table 16.

TABLE 16

Type I-D cas10d/csc3 polypeptide accession numbers
(the sequence identifier for each accession number, in the
order provided in Table 16, is SEQ ID NOs: 4372-4678).

AAT42592.1, AAY81179.1, ABA23770.1, ABD41580.1, ABK15325.1, ABL78722.1, ABX04869.1,
ACB00885.1, ACC81235.1, ACK64599.1, ACK70149.1, ACK85929.1, ACL15520.1, ACL44816.1,
ACM59081.1, ACR73139.1, ACS42755.1, ACU99472.1, ACX52862.1, ACX71879.1, ADB86684.1,
ADE15986.1, ADL12353.1, ADN17498.1, ADX82113.1, AEF95767.1, AEH06114.1, AEJ60972.1,
AEM74230.1, AEN04685.1, AFV12097.1, AFW97300.1, AFY31720.1, AFY33388.1, AFY42101.1,
AFY46832.1, AFY52834.1, AFY78761.1, AFY84408.1, AFY85315.1, AFZ00744.1, AFZ09738.1,
AFZ11796.1, AFZ33068.1, AFZ37989.1, AFZ42915.1, AFZ57017.1, AGE71797.1, AGE74069.1,
AGF53569.1, AGJ62073.1, AGY58207.1, AHE60848.1, AHE97755.1, AHF03469.1, BAB77928.1,
BAD01914.1, BAG02893.1, BAM01333.1, CAI49724.1, CAO91121.1, CBK91863.1, CBN54050.1,
CCC39328.1, CCH94174.1, CCH99027.1, CCI01087.1, CCI08755.1, CCI14109.1, CCI18602.1,
CCI20994.1, CCI26602.1, CCI35031.1, CDF59229.1, CDL45977.1, EAW34720.1, EDX77067.1,
EFA70017.1, EFA71317.1, EFA72475.1, EFH90018.1, EFK07866.1, EFO81885.1, EGZ43965.1,
EHC10665.1, EIJ32870.1, EKV02087.1, ELR97242.1, ELS48634.1, ELW63880.1, ELY96080.1,
ELY97118.1, ELZ94462.1, ELZ96024.1, EMA56573.1, EPF21994.1, EPZ17369.1, ERT08778.1,
ERT67946.1, ESA33790.1, GAD53621.1, GAF34918.1, NP_485602.1, NP_942300.1, WP_000498810.1,
WP_000498811.1, WP_000498823.1, WP_000498826.1, WP_000498833.1, WP_001313298.1,
WP_001343599.1, WP_001351044.1, WP_001369667.1, WP_001372648.1, WP_001379189.1,
WP_001380057.1, WP_001382434.1, WP_001409955.1, WP_001410894.1, WP_001413967.1,
WP_001419560.1, WP_001424845.1, WP_001433649.1, WP_001544092.1, WP_002706834.1,

TABLE 16-continued

Type I-D cas10d/csc3 polypeptide accession numbers
(the sequence identifier for each accession number, in the
order provided in Table 16, is SEQ ID NOs: 4372-4678).

WP_002742885.1, WP_002755924.1, WP_002762263.1, WP_002766201.1, WP_002778662.1,
WP_002784663.1, WP_002788625.1, WP_002791884.1, WP_002797933.1, WP_002800251.1,
WP_005371068.1, WP_006099180.1, WP_006111345.1, WP_006275556.1, WP_006277053.1,
WP_006423429.1, WP_006516472.1, WP_006529931.1, WP_006560838.1, WP_006600197.1,
WP_006647394.1, WP_006651365.1, WP_006788289.1, WP_007274330.1, WP_007353277.1,
WP_007736985.1, WP_007907034.1, WP_009343568.1, WP_009458810.1, WP_009555193.1,
WP_009786737.1, WP_010995731.1, WP_011153681.1, WP_011176808.1, WP_011278681.1,
WP_011320852.1, WP_011323345.1, WP_011448844.1, WP_011696704.1, WP_011752987.1,
WP_012189772.1, WP_012266046.1, WP_012308500.1, WP_012409229.1, WP_012593876.1,
WP_012599092.1, WP_012616839.1, WP_012627889.1, WP_012660273.1, WP_012744509.1,
WP_012819425.1, WP_012952622.1, WP_013033838.1, WP_013277799.1, WP_013334248.1,
WP_013798376.1, WP_013866300.1, WP_014042852.1, WP_014050466.1, WP_014101101.1,
WP_014434559.1, WP_014512278.1, WP_014555212.1, WP_014624350.1, WP_015050974.1,
WP_015081721.1, WP_015112327.1, WP_015116412.1, WP_015127542.1, WP_015129198.1,
WP_015137288.1, WP_015145060.1, WP_015151025.1, WP_015151920.1, WP_015178944.1,
WP_015190935.1, WP_015197391.1, WP_015201918.1, WP_015211902.1, WP_015213666.1,
WP_015224793.1, WP_015580875.1, WP_015739739.1, WP_015783165.1, WP_015857614.1,
WP_015952816.1, WP_016515572.1, WP_016863180.1, WP_016865349.1, WP_016949545.1,
WP_017306101.1, WP_017311493.1, WP_017323373.1, WP_017326894.1, WP_017652462.1,
WP_017659640.1, WP_017662195.1, WP_017662202.1, WP_017714173.1, WP_017720463.1,
WP_017740219.1, WP_017750003.1, WP_018034883.1, WP_018084460.1, WP_018398405.1,
WP_018399542.1, WP_018632664.1, WP_018666493.1, WP_019490247.1, WP_019503800.1,
WP_020200336.1, WP_020221133.1, WP_020505200.1, WP_020560715.1, WP_021247655.1,
WP_021547740.1, WP_021572945.1, WP_022738936.1, WP_023051696.1, WP_023065124.1,
WP_023075355.1, WP_023173331.1, WP_024191264.1, WP_024261066.1, YP_001544997.1,
YP_001658085.1, YP_001736140.1, YP_001866178.1, YP_002370755.1, YP_002377017.1,
YP_002423857.1, YP_002465243.1, YP_002483177.1, YP_002567678.1, YP_002939660.1,
YP_002966032.1, YP_003136308.1, YP_003239712.1, YP_003246361.1, YP_003419054.1,
YP_003528373.1, YP_003827418.1, YP_003899564.1, YP_004483832.1, YP_004575892.1,
YP_004799207.1, YP_004807058.1, YP_004863880.1, YP_005443230.1, YP_005645327.1,
YP_005839103.1, YP_006044689.1, YP_006920596.1, YP_006998407.1, YP_007049251.1,
YP_007053381.1, YP_007064554.1, YP_007066222.1, YP_007074429.1, YP_007082318.1,
YP_007088328.1, YP_007089235.1, YP_007118154.1, YP_007130228.1, YP_007136716.1,
YP_007141306.1, YP_007151360.1, YP_007155927.1, YP_007167129.1, YP_007434945.1,
YP_007437217.1, YP_007452953.1, YP_007773977.1, YP_007865076.1, YP_008711914.1,
YP_022785.1, YP_256472.1, YP_324663.1, YP_327280.1, YP_503299.1, YP_843965.1, and/or
YP_920725.1

In some embodiments, Type I-D csc2 polypeptides include, but are not limited to, GenBank accession number as set forth in Table 17.

TABLE 17

Type I-D csc2 polypeptide accession numbers
(the sequence identifier for each accession number, in the
order provided in Table 17, is SEQ ID NOs: 4679-4985).

AAT42592.1, AAY81179.1, ABA23770.1, ABD41580.1, ABK15325.1, ABL78722.1, ABX04869.1,
ACB00885.1, ACC81235.1, ACK64599.1, ACK70149.1, ACK85929.1, ACL15520.1, ACL44816.1,
ACM59081.1, ACR73139.1, ACS42755.1, ACU99472.1, ACX52862.1, ACX71879.1, ADB86684.1,
ADE15986.1, ADL12353.1, ADN17498.1, ADX82113.1, AEF95767.1, AEH06114.1, AEJ60972.1,
AEM74230.1, AEN04685.1, AFV12097.1, AFW97300.1, AFY31720.1, AFY33388.1, AFY42101.1,
AFY46832.1, AFY52834.1, AFY78761.1, AFY84408.1, AFY85315.1, AFZ00744.1, AFZ09738.1,
AFZ11796.1, AFZ33068.1, AFZ37989.1, AFZ42915.1, AFZ57017.1, AGE71797.1, AGE74069.1,
AGF53569.1, AGJ62073.1, AGY58207.1, AHE60848.1, AHE97755.1, AHF03469.1, BAB77928.1,
BAD01914.1, BAG02893.1, BAM01333.1, CAI49724.1, CAO91121.1, CBK91863.1, CBN54050.1,
CCC39328.1, CCH94174.1, CCH99027.1, CCI01087.1, CCI08755.1, CCI14109.1, CCI18602.1,
CCI20994.1, CCI26602.1, CCI35031.1, CDF59229.1, CDL45977.1, EAW34720.1, EDX77067.1,
EFA70017.1, EFA71317.1, EFA72475.1, EFH90018.1, EFK07866.1, EFO81885.1, EGZ43965.1,
EHC10665.1, EIJ32870.1, EKV02087.1, ELR97242.1, ELS48634.1, ELW63880.1, ELY96080.1,
ELY97118.1, ELZ94462.1, ELZ96024.1, EMA56573.1, EPF21994.1, EPZ17369.1, ERT08778.1,
ERT67946.1, ESA33790.1, GAD53621.1, GAF34918.1, NP_485602.1, NP_942300.1 WP_000498810.1,
WP_000498811.1, WP_000498823.1, WP_000498826.1, WP_000498833.1, WP_001313298.1,
WP_001343599.1, WP_001351044.1, WP_001369667.1, WP_001372648.1, WP_001379189.1,
WP_001380057.1, WP_001382434.1, WP_001409955.1, WP_001410894.1, WP_001413967.1,
WP_001419560.1, WP_001424845.1, WP_001433649.1, WP_001544092.1, WP_002706834.1,
WP_002742885.1, WP_002755924.1, WP_002762263.1, WP_002766201.1, WP_002778662.1,
WP_002784663.1, WP_002788625.1, WP_002791884.1, WP_002797933.1, WP_002800251.1,
WP_005371068.1, WP_006099180.1, WP_006111345.1, WP_006275556.1, WP_006277053.1,
WP_006423429.1, WP_006516472.1, WP_006529931.1, WP_006560838.1, WP_006600197.1,
WP_006647394.1, WP_006651365.1, WP_006788289.1, WP_007274330.1, WP_007353277.1,
WP_007736985.1, WP_007907034.1, WP_009343568.1, WP_009458810.1, WP_009555193.1,

TABLE 17-continued

Type I-D csc2 polypeptide accession numbers
(the sequence identifier for each accession number, in the
order provided in Table 17, is SEQ ID NOs: 4679-4985).

WP_009786737.1, WP_010995731.1, WP_011153681.1, WP_011176808.1, WP_011278681.1,
WP_011320852.1, WP_011323345.1, WP_011448844.1, WP_011696704.1, WP_011752987.1,
WP_012189772.1, WP_012266046.1, WP_012308500.1, WP_012409229.1, WP_012593876.1,
WP_012599092.1, WP_012616839.1, WP_012627889.1, WP_012660273.1, WP_012744509.1,
WP_012819425.1, WP_012952622.1, WP_013033838.1, WP_013277799.1, WP_013334248.1,
WP_013798376.1, WP_013866300.1, WP_014042852.1, WP_014050466.1, WP_014101101.1,
WP_014434559.1, WP_014512278.1, WP_014555212.1, WP_014624350.1, WP_015050974.1,
WP_015081721.1, WP_015112327.1, WP_015116412.1, WP_015127542.1, WP_015129198.1,
WP_015137288.1, WP_015145060.1, WP_015151025.1, WP_015151920.1, WP_015178944.1,
WP_015190935.1, WP_015197391.1, WP_015201918.1, WP_015211902.1, WP_015213666.1,
WP_015224793.1, WP_015580875.1, WP_015739739.1, WP_015783165.1, WP_015857614.1,
WP_015952816.1, WP_016515572.1, WP_016863180.1, WP_016865349.1, WP_016949545.1,
WP_017306101.1, WP_017311493.1, WP_017323373.1, WP_017326894.1, WP_017652462.1,
WP_017659640.1, WP_017662195.1, WP_017662202.1, WP_017714173.1, WP_017720463.1,
WP_017740219.1, WP_017750003.1, WP_018034883.1, WP_018084460.1, WP_018398405.1,
WP_018399542.1, WP_018632664.1, WP_018666493.1, WP_019490247.1, WP_019503800.1,
WP_020200336.1, WP_020221133.1, WP_020505200.1, WP_020560715.1, WP_021247655.1,
WP_021547740.1, WP_021572945.1, WP_022738936.1, WP_023051696.1, WP_023065124.1,
WP_023075355.1, WP_023173331.1, WP_024191264.1, WP_024261066.1, YP_001544997.1,
YP_001658085.1, YP_001736140.1, YP_001866178.1, YP_002370755.1, YP_002377017.1,
YP_002423857.1, YP_002465243.1, YP_002483177.1, YP_002567678.1, YP_002939660.1,
YP_002966032.1, YP_003136308.1, YP_003239712.1, YP_003246361.1, YP_003419054.1,
YP_003528373.1, YP_003827418.1, YP_003899564.1, YP_044483832.1, YP_004575892.1,
YP_004799207.1, YP_004807058.1, YP_004863880.1, YP_005443230.1, YP_005645327.1,
YP_005839103.1, YP_006044689.1, YP_006920596.1, YP_006984407.1, YP_007049251.1,
YP_007053381.1, YP_007064554.1, YP_007066222.1, YP_007074429.1, YP_007082318.1,
YP_007088328.1, YP_007089235.1, YP_007118154.1, YP_007130228.1, YP_007136716.1,
YP_007141306.1, YP_007151360.1, YP_007155927.1, YP_007167129.1, YP_007434945.1,
YP_007437217.1, YP_007452953.1, YP_007773977.1, YP_007865076.1, YP_008711914.1,
YP_022785.1, YP_256472.1, YP_324665.1, YP_327280.1, YP_503299.1, YP_843965.1, and/or
YP_920725.1

In some embodiments, Type I-D csc1 polypeptides include, but are not limited to, GenBank accession number as set forth in Table 18.

TABLE 18

Type I-D csc1 polypeptide accession numbers
(the sequence identifier for each accession number, in the
order provided in Table 18, is SEQ ID NOs: 4986-5234).

AAT42591.1, AAY81178.1, ABA23771.1, ABD41579.1, ABK15326.1, ABL78721.1, ABX04870.1,
ACB00884.1, ACC81234.1, ACK64598.1, ACK70150.1, ACL15521.1, ACL44817.1, ACM59082.1,
ACU99471.1, ACX71878.1, ADB86683.1, ADL12354.1, ADN17497.1, ADX82112.1, AEF95768.1,
AEH06113.1, AEM74229.1, AEN04684.1, AFW97299.1, AFY31719.1, AFY33387.1, AFY42100.1,
AFY46831.1, AFY52835.1, AFY78762.1, AFY84407.1, AFY85316.1, AFZ00745.1, AFZ09739.1,
AFZ11797.1, AFZ19098.1, AFZ27301.1, AFZ33069.1, AFZ37988.1, AFZ42914.1, AFZ57016.1,
AGD98072.1, AGE71796.1, AGE74068.1, AGF53570.1, AGJ62072.1, AGY58208.1, BAB77929.1,
BAD01915.1, BAG02894.1, CAI49725.1, CAO91122.1, CBN54051.1, CCC39329.1, CCH94173.1,
CCH99028.1, CCI01088.1, CCI08756.1, CCI14108.1, CCI18601.1, CCI20996.1, CCI26604.1,
CCI35030.1, CDF59228.1, EAW34719.1, EDX73941.1, EDX77236.1, EFA70018.1, EFA71316.1,
EFA72474.1, EFH90017.1, EFO81886.1, EGG83583.1, EHC10666.1, EKQ70618.1, EKV02088.1,
ELR97241.1, ELS48633.1, ELY96081.1, ELY97117.1, ELZ94461.1, ELZ96025.1, EMA56572.1,
EPF21993.1, ERT08676.1, ESA33791.1, GAD53620.1, NP_485603.1, NP_942301.1, WP_002742884.1,
WP_002755922.1, WP_002762264.1, WP_002766203.1, WP_002784661.1, WP_002788624.1,
WP_002791885.1, WP_003447113.1, WP_006099350.1, WP_006102703.1, WP_006111344.1,
WP_006275555.1, WP_006277054.1, WP_006516473.1, WP_006529930.1, WP_006560839.1,
WP_006600196.1, WP_006651366.1, WP_007274331.1, WP_007353278.1, WP_007736984.1,
WP_007907033.1, WP_009343567.1, WP_009458811.1, WP_009555192.1, WP_009757367.1,
WP_009786736.1, WP_010219108.1, WP_010656181.1, WP_010995732.1, WP_011153682.1,
WP_011176807.1, WP_011278680.1, WP_011320853.1, WP_011323346.1, WP_011448843.1,
WP_011696705.1, WP_011752986.1, WP_012189773.1, WP_012266047.1, WP_012308499.1,
WP_012409228.1, WP_012593875.1, WP_012599093.1, WP_012616840.1, WP_012627890.1,
WP_012660274.1, WP_012819424.1, WP_012952621.1, WP_013277800.1, WP_013334247.1,
WP_013798377.1, WP_013866299.1, WP_014042851.1, WP_014050465.1, WP_014512277.1,
WP_014555213.1, WP_014326326.1, WP_015081720.1, WP_015112327.1, WP_015116413.1, WP_015127541.1,
WP_015129197.1, WP_015137287.1, WP_015145061.1, WP_015151024.1, WP_015151921.1,
WP_015178945.1, WP_015183241.1, WP_015190936.1, WP_015197392.1, WP_015201919.1,
WP_015210536.1, WP_015211901.1, WP_015213665.1, WP_015224792.1, WP_015370562.1,
WP_015580874.1, WP_015783164.1, WP_016515571.1, WP_016863181.1, WP_016865350.1,
WP_016872951.1, WP_016949544.1, WP_017306100.1, WP_017311494.1, WP_017323374.1,
WP_017326893.1, WP_017652461.1, WP_017659641.1, WP_017662197.1, WP_017662203.1,

TABLE 18-continued

Type I-D csc1 polypeptide accession numbers
(the sequence identifier for each accession number, in the
order provided in Table 18, is SEQ ID NOs: 4986-5234).

WP_017714174.1, WP_017720462.1, WP_017740218.1, WP_017750004.1, WP_018034884.1,
WP_018084461.1, WP_018398406.1, WP_018399543.1, WP_018666491.1, WP_019490248.1,
WP_019503801.1, WP_020200335.1, WP_020221134.1, WP_022738938.1, WP_023065022.1,
WP_023075356.1, WP_023173332.1, YP_001544998.1, YP_001658086.1, YP_001736139.1,
YP_001866177.1, YP_002370754.1, YP_002377018.1, YP_002465244.1, YP_002483178.1,
YP_002567679.1, YP_003136307.1, YP_003246360.1, YP_003419053.1, YP_003827419.1,
YP_003899563.1, YP_004483833.1, YP_004575891.1, YP_004799206.1, YP_004807057.1,
YP_005645326.1, YP_005839104.1, YP_006998406.1, YP_007049250.1, YP_007053382.1,
YP_007064553.1, YP_007066221.1, YP_007074428.1, YP_007082319.1, YP_007088327.1,
YP_007089236.1, YP_007118155.1, YP_007122504.1, YP_007130229.1, YP_007136717.1,
YP_007141307.1, YP_007149981.1, YP_007151359.1, YP_007155926.1, YP_007167128.1,
YP_007391825.1, YP_007434944.1, YP_007437216.1, YP_007452954.1, YP_007865075.1,
YP_008711915.1, YP_022784.1, YP_256471.1, YP_324666.1, YP_327281.1, YP_503298.1,
YP_843966.1, YP_920724.1

In some embodiments, type 1-D cas6d polypeptides include, but are not limited to, GenBank accession number YP_503301.1 (SEQ ID NOs:39), and/or YP_327278.1 (SEQ ID NOs:40).

In other embodiments, Type I-E cse1/casA polypeptides include, but are not limited to, GenBank accession number as set forth in Table 19.

TABLE 19

Type I-E cse1/casA polypeptide accession numbers
(the sequence identifier for each accession number, in the
order provided in Table 19, is SEQ ID NOs: 5235-6111).

AAC75802.1, AAR34761.1, ABA88210.1, ACL06607.1, ADB13717.1, ADI84212.1, ADP38753.1,
ADR37700.1, ADY27677.1, AEB06539.1, AEB11721.1, AEB71776.1, AEC02347.1, AEJ53445.1,
AFH39942.1, AFL72519.1, AFM27182.1, AFR99214.1, AFV75987.1, AGB27118.1, AGQ58154.1,
AGQ66822.1, AGQ74241.1, AGQ78969.1, AGQ87241.1, AGS64000.1, AGW09894.1, AGX11571.1,
AGX34769.1, AHB45480.1, AHB94781.1, CCK86079.1, CCX87057.1, EDN80091.1, EDP20981.1,
EEB22224.1, EEB34860.1, EEH65617.1, EEI14200.1, EEI27966.1, EEI78888.1, EEI86603.1,
EEP20787.1, EET77376.1, EEW16905.1, EEW42244.1, EEW53942.1, EEX47611.1, EEZ61815.1,
EFA23032.1, EFB87472.1, EFB90862.1, EFD84089.1, EFD93805.1, EFE06764.1, EFF79646.1,
EFH10702.1, EFI89986.1, EFJ64185.1, EFJ75314.1, EFJ78692.1, EFJ85026.1, EFJ97185.1,
EFK01968.1, EFK08613.1, EFK13801.1, EFK21927.1, EFK32764.1, EFK39592.1, EFK47880.1,
EFK52819.1, EFK65277.1, EFK74802.1, EFL93068.1, EFM24727.1, EFM43106.1, EFO58465.1,
EFO71177.1, EFQ06779.1, EFQ22973.1, EFQ47738.1, EFQ49137.1, EFQ52099.1, EFS88256.1,
EFT11292.1, EFT25766.1, EFT64288.1, EFT66652.1, EFU34517.1, EFU63288.1, EFU77566.1,
EFX55034.1, EGB85502.1, EGC81877.1, EGE70488.1, EGF23574.1, EGF57391.1, EGF60537.1,
EGG33817.1, EGG50904.1, EGJ06274.1, EGL13335.1, EGL36663.1, EHI77348.1, EHO49963.1,
EHQ05138.1, EIC19435.1, EIC29373.1, EID50558.1, EIE98892.1, EIG78874.1, EIH03922.1,
EIH21856.1, EIH33564.1, EIH43625.1, EIH53908.1, EIH65188.1, EIH76837.1, EIH89440.1, EII01915.1,
EII11996.1, EII24897.1, EII34511.1, EII46454.1, EII55459.1, EIJ03929.1, EIJ14858.1, EIM64765.1,
EIN19700.1, EIN21473.1, EIN21900.1, EIN36944.1, EIN38077.1, EIN40216.1, EIN52181.1, EIN55483.1,
EIN58777.1, EIN69733.1, EIN73954.1, EIN74349.1, EIN86510.1, EIN93695.1, EIN95421.1, EIN98712.1,
EIO11891.1, EIO12436.1, EIO15244.1, EIO26602.1, EIO35235.1, EIO35910.1, EIO36499.1,
EIO48182.1, EIO55978.1, EIO56220.1, EIO62659.1, EIO70811.1, EIO73008.1, EIO81517.1,
EIO90647.1, EIO93918.1, EIO95550.1, EIP08618.1, EIP08964.1, EIP13149.1, EIP22622.1, EIP26482.1,
EIP31367.1, EIP38412.1, EIP43370.1, EIP51977.1, EIP54293.1, EIP58464.1, EIP66206.1, EIP76257.1,
EIP77689.1, EIV92934.1, EJN52394.1, EJU32173.1, EKG98245.1, EKH00137.1, EKH03277.1,
EKH12298.1, EKH15516.1, EKH23467.1, EKH29555.1, EKH35394.1, EKH39836.1, EKH45833.1,
EKH51234.1, EKH56934.1, EKH66297.1, EKH68815.1, EKH74466.1, EKH82251.1, EKH86929.1,
EKH90629.1, EKH99479.1, EKI05873.1, EKI08568.1, EKI36919.1, EKI40772.1, EKI49588.1,
EKI60112.1, EKI64089.1, EKI68328.1, EKI75986.1, EKI79310.1, EKI85620.1, EKI93279.1, EKI96030.1,
EKJ04229.1, EKJ08783.1, EKJ13733.1, EKJ23816.1, EKJ24259.1, EKJ33912.1, EKJ39701.1,
EKJ41438.1, EKJ50521.1, EKJ56867.1, EKJ59593.1, EKK25398.1, EKK25683.1, EKK26848.1,
EKK43173.1, EKK53359.1, EKK55962.1, EKK65125.1, EKK69921.1, EKK73971.1, EKK84922.1,
EKO32513.1, EKO79131.1, EKP14571.1, EKQ92399.1, EKQ99848.1, EKR63516.1, EKR75188.1,
EKR90048.1, EKS02017.1, EKS09390.1, EKS99224.1, EKT00177.1, EKT12809.1, EKT14274.1,
EKT17197.1, EKT27020.1, EKT27533.1, EKT32171.1, EKT39313.1, EKT44823.1, EKV73580.1,
EKV75706.1, EKV77180.1, EKV89037.1, EKV91802.1, EKV95653.1, EKW07860.1, EKW08455.1,
EKW11945.1, EKW25815.1, EKW26225.1, EKW29160.1, EKW39951.1, EKW42672.1, EKW46451.1,
EKW54141.1, EKW60787.1, EKW62693.1, EKW73537.1, EKW76255.1, EKW80485.1, EKW88428.1,
EKW89455.1, EKY37317.1, EKY39009.1, ELV17238.1, ELV18608.1, ELV25663.1, ELV34236.1,
ELV34682.1, ELV39485.1, ELV48633.1, ELV51980.1, ELV54637.1, ELV67264.1, ELV67562.1,
ELV69368.1, ELV79850.1, ELV80618.1, ELV88789.1, ELV96183.1, ELV97125.1, ELW02419.1,
ELW10617.1, ELW13578.1, ELW17524.1, ELW26217.1, ELW31305.1, ELW35270.1, ELW40989.1,
EMF80096.1, EMF90493.1, EMH94948.1, EMI67337.1, EMI69736.1, EMJ47430.1, EMJ65147.1,
EMJ83278.1, EMK10454.1, EMK25488.1, EMM72287.1, EMM76994.1, EMM88578.1, EMN02660.1,
EMN23237.1, EMN46415.1, EMN58221.1, EMN90211.1, EMO14863.1, EMO23363.1, EMO33334.1,
EMO39045.1, EMO44218.1, EMO48220.1, EMO56134.1, EMO69676.1, EMO83287.1, EMO88887.1,
EMO99953.1, EMP03176.1, EMP69813.1, EMP80123.1, EMQ01915.1, EMR53802.1, EMS84265.1,

TABLE 19-continued

Type I-E cse1/casA polypeptide accession numbers
(the sequence identifier for each accession number, in the
order provided in Table 19, is SEQ ID NOs: 5235-6111).

EMS89950.1, EMU77117.1, EMU79863.1, EMU81925.1, EMU92000.1, EMU93518.1, EMU96753.1,
EMV05447.1, EMV10183.1, EMV20685.1, EMV20944.1, EMV31572.1, EMV37851.1, EMV40012.1,
EMV45281.1, EMV56148.1, EMV56284.1, EMV56703.1, EMV69991.1, EMV70936.1, EMV74436.1,
EMV84047.1, EMV88768.1, EMV92182.1, EMW01026.1, EMW01243.1, EMW07010.1, EMW17418.1,
EMW22260.1, EMW30606.1, EMW40792.1, EMW48039.1, EMW49825.1, EMW56697.1, EMW59913.1,
EMW66837.1, EMW73499.1, EMW77338.1, EMW78912.1, EMW94558.1, EMW98876.1, EMX07968.1,
EMX14130.1, EMX19224.1, EMX22618.1, EMX29304.1, EMX37758.1, EMX48579.1, EMX50486.1,
EMX52607.1, EMX61623.1, EMX68505.1, EMX68784.1, EMX74575.1, EMX87159.1, EMX92277.1,
EMZ62959.1, EMZ66591.1, EMZ68494.1, EMZ77563.1, EMZ83215.1, EMZ91186.1, EMZ95757.1,
ENA02804.1, ENA04452.1, ENA13951.1, ENA19514.1, ENA26189.1, ENA30282.1, ENA50834.1,
ENA63244.1, ENA67183.1, ENA77978.1, ENA79440.1, ENA81200.1, ENA92105.1, ENA94513.1,
ENA97212.1, ENB05958.1, ENB14774.1, ENB26894.1, ENB33400.1, ENB36542.1, ENB46916.1,
ENB50303.1, ENB54275.1, ENB68369.1, ENB69286.1, ENB70953.1, ENB74215.1, ENB86956.1,
ENB90833.1, ENB91040.1, ENB93839.1, ENB98051.1, ENC02948.1, ENC09611.1, ENC15003.1,
ENC16395.1, ENC23716.1, ENC30744.1, ENC31435.1, ENC39393.1, ENC45913.1, ENC53604.1,
ENC54573.1, ENC60390.1, ENC69953.1, ENC70105.1, ENC77975.1, ENC82714.1, ENC97848.1,
END01584.1, END09660.1, END13721.1, END21437.1, END25413.1, END31629.1, END39636.1,
END41653.1, END42391.1, END51642.1, END57071.1, END59213.1, END67056.1, END78179.1,
END78712.1, END81375.1, END91687.1, END97699.1, ENE06567.1, ENE08935.1, ENE21067.1,
ENE21659.1, ENE28700.1, ENE35155.1, ENE40418.1, ENE44978.1, ENE50645.1, ENE55965.1,
ENE62926.1, ENE64645.1, ENE70429.1, ENE76512.1, ENE80411.1, ENE85871.1, ENE92893.1,
ENE99559.1, ENF00392.1, ENF08349.1, ENF11291.1, ENF18240.1, ENF22923.1, ENF29687.1,
ENF33363.1, ENF39390.1, ENF45673.1, ENF50088.1, ENF50716.1, ENF61280.1, ENF67276.1,
ENF70641.1, ENF74816.1, ENF82094.1, ENF84651.1, ENF89282.1, ENF95862.1, ENG01924.1,
ENG03189.1, ENG11232.1, ENG15734.1, ENG15816.1, ENG24890.1, ENG29467.1, ENG32953.1,
ENG41297.1, ENG41796.1, ENG50476.1, ENG54481.1, ENG60849.1, ENG64006.1, ENG70197.1,
ENG76593.1, ENG81862.1, ENG94881.1, ENH01461.1, ENH01622.1, ENH16164.1, ENH17549.1,
ENH19105.1, ENH31379.1, ENH31607.1, ENH39003.1, ENH44707.1, ENH50513.1, ENH55857.1,
ENO64180.1, EPA89712.1, EPE82172.1, EPG58686.1, EPG75171.1, EPG81677.1, EPI42420.1,
EPI44037.1, EPI53337.1, EPI53372.1, EPI56336.1, EPI57192.1, EPI61099.1, EPI61158.1, EPI62386.1,
EPI66851.1, EPI68834.1, EPI71023.1, EPI82121.1, EPI84755.1, EPI87542.1, EPI96745.1, EPJ01395.1,
EPJ03484.1, EPJ11332.1, EPO19661.1, EPO86951.1, EQA24787.1, EQA60395.1, ERA58832.1,
ERB70896.1, ERB72237.1, ERB73419.1, ERB82599.1, ERB89436.1, ERB96681.1, ERB96885.1,
ERC04536.1, ERC12232.1, ERC16335.1, ERC19176.1, ERC27445.1, ERC33293.1, ERC38070.1,
ERC42733.1, ERC50095.1, ERC55908.1, ERC58904.1, ERC64561.1, ERC68390.1, ERC77314.1,
ERC81429.1, ERC84026.1, ERC93630.1, ERC97461.1, ERC97908.1, ERD08682.1, ERD13172.1,
ERD13495.1, ERD25528.1, ERD27720.1, ERD31330.1, ERD40007.1, ERD43427.1, ERD48231.1,
ERD57532.1, ERD59790.1, ERD62130.1, ERD70741.1, ERD75930.1, ERD79098.1, ERD86415.1,
ERD91415.1, ERE02668.1, ERE03502.1, ERE13280.1, ERE16916.1, ERE25907.1, ERE27664.1,
ERE32314.1, ERE40209.1, ERF87381.1, ERF89307.1, ERF94194.1, ERF98324.1, ERH14165.1,
ERH14495.1, ERH20067.1, ERH20459.1, ERH21168.1, ERH32724.1, ERH36678.1, ERJ75893.1,
ERJ83444.1, ERJ96446.1, ERN66754.1, ERN72164.1, ERN77269.1, ERN80222.1, ERN86671.1,
ERN89327.1, ERN90341.1, ERN96205.1, ERO01325.1, ERO03092.1, ERO11234.1, ERO19088.1,
ERO20372.1, ERO26621.1, ERO30440.1, ESA60137.1, ESA65714.1, ESA72996.1, ESA77456.1,
ESA86349.1, ESA88077.1, ESD00140.1, ESD09712.1, ESD21951.1, ESD26436.1, ESD31842.1,
ESD51509.1, ESD61895.1, ESD64308.1, ESD64392.1, ESD71331.1, ESD80284.1, ESD81866.1,
ESD83158.1, ESE11368.1, ESK58508.1, ESV51433.1, ETA02741.1, ETA89353.1, ETB86383.1,
ETC51273.1, ETC70942.1, ETD45571.1, ETD59789.1, ETE24479.1, ETE43683.1, ETI74543.1,
ETI79260.1, ETJ60188.1, ETJ80202.1, ETX32972.1, EUB32589.1, EWM59168.1, EYD84416.1,
EYR72872.1, NP_417240.1, Q46901.1, Q53VY1.1, WP_000086035.1, WP_000086036.1,
WP_000086037.1, WP_000086038.1, WP_000283634.1, WP_000312544.1, WP_000348836.1,
WP_000368576.1, WP_000368577.1, WP_000368578.1, WP_000368579.1, WP_000368581.1,
WP_000368582.1, WP_000368583.1, WP_000368584.1, WP_000368585.1, WP_000368586.1,
WP_000368587.1, WP_000368588.1, WP_000368589.1, WP_000484004.1, WP_000535130.1,
WP_000834842.1, WP_001084074.1, WP_001084076.1, WP_001084077.1, WP_001084078.1,
WP_001084079.1, WP_001084080.1, WP_001084081.1, WP_001084082.1, WP_001084083.1,
WP_001084084.1, WP_001084085.1, WP_001084086.1, WP_001084087.1, WP_001084088.1,
WP_001084089.1, WP_001084092.1, WP_001084093.1, WP_001084094.1, WP_001084095.1,
WP_001084096.1, WP_001084097.1, WP_001084098.1, WP_001084099.1, WP_001084100.1,
WP_001084101.1, WP_001084102.1, WP_001084104.1, WP_001084105.1, WP_001084106.1,
WP_001084109.1, WP_001084110.1, WP_001084111.1, WP_001084112.1, WP_001084113.1,
WP_001084115.1, WP_001084116.1, WP_001084117.1, WP_001242694.1, WP_001304057.1,
WP_001307969.1, WP_001313216.1, WP_001315810.1, WP_001317281.1, WP_001325175.1,
WP_001326095.1, WP_001331425.1, WP_001343650.1, WP_001347282.1, WP_001347764.1,
WP_001348410.1, WP_001380031.1, WP_001382398.1, WP_001383465.1, WP_001387009.1,
WP_001395991.1, WP_001416300.1, WP_001437794.1, WP_001522848.1, WP_001564555.1,
WP_002431961.1, WP_002514606.1, WP_002520770.1, WP_002546992.1, WP_002549141.1,
WP_003088905.1, WP_004074401.1, WP_004106702.1, WP_004109011.1, WP_004112666.1,
WP_004115350.1, WP_004118009.1, WP_004125152.1, WP_004127864.1, WP_004132146.1,
WP_004136185.1, WP_004138497.1, WP_004142783.1, WP_004574565.1, WP_004809665.1,
WP_004826834.1, WP_004835170.1, WP_005000855.1, WP_005154891.1, WP_006302702.1,
WP_006687055.1, WP_006733195.1, WP_006734900.1, WP_006735514.1, WP_006736346.1,
WP_008087876.1, WP_008534586.1, WP_008806236.1, WP_008864956.1, WP_009308515.1,
WP_009310573.1, WP_009344934.1, WP_009369774.1, WP_009428278.1, WP_009486039.1,
WP_009535625.1, WP_009994024.1, WP_012311912.1, WP_012602053.1, WP_012602845.1,
WP_012907164.1, WP_012914171.1, WP_012997655.1, WP_013990632.1, WP_014633160.1,

TABLE 19-continued

Type I-E cse1/casA polypeptide accession numbers
(the sequence identifier for each accession number, in the
order provided in Table 19, is SEQ ID NOs: 5235-6111).

WP_014839378.1, WP_016637266.1, WP_016838859.1, WP_019077566.1, WP_019842415.1,
WP_020759633.1, WP_020761306.1, WP_020839112.1, WP_020899160.1, WP_020973664.1,
WP_021600846.1, WP_021604023.1, WP_021604906.1, WP_021610204.1, WP_021610630.1,
WP_021613844.1, WP_021673649.1, WP_021676129.1, WP_021682641.1, WP_021868373.1,
WP_022630987.1, WP_023141767.1, WP_023147142.1, WP_023147143.1, WP_023154950.1,
WP_023156410.1, WP_023890965.1, WP_024143394.1, WP_024154924.1, WP_024156644.1,
WP_024218900.1, WP_024226281.1, WP_024229045.1, WP_024229851.1, WP_024255404.1,
WP_024258205.1, YP_003373984.1, YP_004049620.1, YP_004264312.1, YP_004367831.1,
YP_004372354.1, YP_004411729.1, YP_006059728.1, YP_006068308.1, YP_006412644.1,
YP_006449446.1, YP_006716675.1, YP_006724797.1, YP_006890377.1, YP_006972084.1,
YP_007277148.1, YP_008252271.1, YP_008253880.1, YP_008262077.1, YP_008267148.1,
YP_008307439.1, YP_008382200.1, YP_008565875.1, YP_008614581.1, and/or YP_008862373.1.

In some embodiments, Type I-E cse2/casB polypeptides include, but are not limited to, GenBank accession number as set forth in Table 20.

TABLE 20

Type I-E cse2/casB polypeptide accession numbers
(the sequence identifier for each accession number, in the
order provided in Table 20, is SEQ ID NOs: 6112-6823).

AAC75801.1, AAR34762.1, ABA88211.1, ACL06608.1, ADB14225.1, ADI84213.1, ADP38754.1,
ADR37699.1, ADY27680.1, AEB06540.1, AEB11722.1, AEB71777.1, AEC02348.1, AFH39943.1,
AFL72520.1, AFM27183.1, AFR99215.1, AFV75988.1, AGB27117.1, AGX34768.1, CCI86099.1,
CCK86080.1, CCX87058.1, EDN80089.1, EDP20980.1, EEB22225.1, EEH65616.1, EEI14201.1,
EEI27967.1, EEI78889.1, EEI86602.1, EEJ54448.1, EEP20786.1, EET77375.1, EEW16906.1,
EEW42243.1, EEW53943.1, EEX47612.1, EFA23033.1, EFB87473.1, EFB90861.1, EFD84088.1,
EFD93804.1, EFE06765.1, EFF79645.1, EFH10701.1, EFI89987.1, EFJ64186.1, EFJ75315.1,
EFJ78691.1, EFJ85027.1, EFJ97184.1, EFK01967.1, EFK08585.1, EFK13800.1, EFK21928.1,
EFK32765.1, EFK39599.1, EFK47879.1, EFK52820.1, EFK65276.1, EFK74803.1, EFL93067.1,
EFM24726.1, EFM43105.1, EFM50100.1, EFO58464.1, EFO71164.1, EFQ06780.1, EFQ22974.1,
EFQ47715.1, EFQ49115.1, EFQ52080.1, EFQ53859.1, EFS88257.1, EFT11291.1, EFT25767.1,
EFT64289.1, EFT66653.1, EFU34516.1, EFU63289.1, EFU77567.1, EFV94306.1, EFX55035.1,
EGB85503.1, EGC81860.1, EGE70489.1, EGF23575.1, EGF57390.1, EGF60538.1, EGG33809.1,
EGG50905.1, EGJ06275.1, EGL13349.1, EGL37879.1, EGR97358.1, EGS35782.1, EHI70394.1,
EHI77349.1, EHM12585.1, EHO49964.1, EHQ05137.1, EIC19434.1, EIC29372.1, EIC80106.1,
EIC97113.1, EIE98891.1, EIG78925.1, EIG93140.1, EIH01730.1, EIH21868.1, EIH32984.1, EIH43940.1,
EIH56207.1, EIH65347.1, EIH76747.1, EIH89338.1, EIH99538.1, EII13012.1, EII24837.1, EII35012.1,
EII46332.1, EII56124.1, EIJ03341.1, EIJ15160.1, EIM64764.1, EIN19762.1, EIN21472.1, EIN21899.1,
EIN36943.1, EIN38052.1, EIN40215.1, EIN52180.1, EIN55482.1, EIN58776.1, EIN69732.1, EIN73810.1,
EIN74348.1, EIN86302.1, EIN93752.1, EIN95379.1, EIN98707.1, EIO11869.1, EIO12466.1,
EIO15243.1, EIO26601.1, EIO35234.1, EIO35906.1, EIO36689.1, EIO56007.1, EIO56621.1,
EIO62658.1, EIO70785.1, EIO73007.1, EIO81613.1, EIO90645.1, EIO93917.1, EIO95544.1,
EIP08614.1, EIP08988.1, EIP12992.1, EIP22621.1, EIP26481.1, EIP31382.1, EIP38348.1, EIP43352.1,
EIP51902.1, EIP54292.1, EIP58366.1, EIP65857.1, EIP76256.1, EIP77688.1, EIV92933.1, EJF13177.1,
EJP19891.1, EKG98244.1, EKH00136.1, EKH03276.1, EKH12297.1, EKH15515.1, EKH23466.1,
EKH29554.1, EKH35393.1, EKH39835.1, EKH45718.1, EKH51233.1, EKH56805.1, EKH66296.1,
EKH68787.1, EKH74465.1, EKH82250.1, EKH86928.1, EKH99478.1, EKI05872.1, EKI36918.1,
EKI40771.1, EKI49527.1, EKI60205.1, EKI64088.1, EKI68327.1, EKI75985.1, EKI79309.1, EKI85619.1,
EKI93320.1, EKI96029.1, EKJ04228.1, EKJ08782.1, EKJ13732.1, EKJ23836.1, EKJ24258.1,
EKJ33911.1, EKJ39700.1, EKJ41366.1, EKJ50582.1, EKJ56866.1, EKJ59592.1, EKK25397.1,
EKK25898.1, EKK26847.1, EKK43172.1, EKK53358.1, EKK55961.1, EKK65124.1, EKK69920.1,
EKK73970.1, EKK84921.1, EKO32514.1, EKO79167.1, EKP14479.1, EKQ92379.1, EKQ99402.1,
EKR90051.1, EKS02270.1, EKS09451.1, EKV73579.1, EKV75705.1, EKV77179.1, EKV89036.1,
EKV91970.1, EKV95739.1, EKW07859.1, EKW08359.1, EKW11944.1, EKW25814.1, EKW26224.1,
EKW29159.1, EKW40128.1, EKW42671.1, EKW46450.1, EKW54140.1, EKW60875.1, EKW62692.1,
EKW73536.1, EKW76254.1, EKW80484.1, EKW88427.1, EKW89454.1, EKX91276.1, EKY37316.1,
EKY39008.1, ELV17237.1, ELV18607.1, ELV25662.1, ELV34157.1, ELV34681.1, ELV39484.1,
ELV48632.1, ELV51965.1, ELV54636.1, ELV67263.1, ELV67561.1, ELV69367.1, ELV79849.1,
ELV80617.1, ELV88788.1, ELV96182.1, ELV97124.1, ELW02418.1, ELW10616.1, ELW13577.1,
ELW17523.1, ELW26216.1, ELW31304.1, ELW35269.1, ELW40988.1, EMF90415.1, EMG01553.1,
EMH94921.1, EMI67328.1, EMI69776.1, EMJ47417.1, EMJ65176.1, EMJ83277.1, EMK10455.1,
EMN02648.1, EMN14473.1, EMN17149.1, EMN23273.1, EMN58106.1, EMO08717.1, EMO14814.1,
EMO23146.1, EMO33377.1, EMO44321.1, EMO48217.1, EMO56045.1, EMO62132.1, EMO69688.1,
EMO83302.1, EMO88885.1, EMP00062.1, EMP03359.1, EMP80130.1, EMQ01916.1, EMR12517.1,
EMR53801.1, EMU77116.1, EMU79862.1, EMU81924.1, EMU91999.1, EMU93517.1, EMU96752.1,
EMV05446.1, EMV10182.1, EMV20684.1, EMV20943.1, EMV31491.1, EMV37850.1, EMV40011.1,
EMV45280.1, EMV56146.1, EMV56282.1, EMV56702.1, EMV69990.1, EMV70935.1, EMV74435.1,
EMV84046.1, EMV88767.1, EMV92359.1, EMW01025.1, EMW01242.1, EMW07009.1, EMW17417.1,
EMW22259.1, EMW30605.1, EMW40791.1, EMW48038.1, EMW49824.1, EMW56696.1, EMW59912.1,
EMW66836.1, EMW73498.1, EMW77337.1, EMW78911.1, EMW94557.1, EMW98875.1, EMX07967.1,

TABLE 20-continued

Type I-E cse2/casB polypeptide accession numbers
(the sequence identifier for each accession number, in the
order provided in Table 20, is SEQ ID NOs: 6112-6823).

EMX14129.1, EMX18415.1, EMX22617.1, EMX29303.1, EMX37757.1, EMX48578.1, EMX50485.1, EMX52606.1, EMX61622.1, EMX68504.1, EMX68783.1, EMX75065.1, EMX84589.1, EMX87158.1, EMX92276.1, EMY78097.1, EMZ62958.1, EMZ66493.1, EMZ68492.1, EMZ77562.1, EMZ83214.1, EMZ91634.1, EMZ95756.1, ENA02803.1, ENA04451.1, ENA13950.1, ENA19688.1, ENA26190.1, ENA30281.1, ENA38834.1, ENA44310.1, ENA50872.1, ENA60929.1, ENA63243.1, ENA67182.1, ENA77976.1, ENA79438.1, ENA81176.1, ENA92104.1, ENA94512.1, ENA97211.1, ENB05957.1, ENB14773.1, ENB26893.1, ENB33482.1, ENB36541.1, ENB46917.1, ENB50302.1, ENB54274.1, ENB68370.1, ENB69287.1, ENB70954.1, ENB71214.1, ENB86955.1, ENB90079.1, ENB90832.1, ENC02947.1, ENC30743.1, ENC31434.1, ENC39392.1, ENC45912.1, ENC53603.1, ENC54572.1, ENC60389.1, ENC69952.1, ENC70104.1, ENC77942.1, ENC82713.1, ENC90461.1, ENC93692.1, ENC97847.1, END01583.1, END09659.1, END13720.1, END21262.1, END25412.1, END31628.1, END39635.1, END41652.1, END42390.1, END51641.1, END57070.1, END59212.1, END78711.1, END90767.1, END91686.1, END97698.1, ENE06540.1, ENE08934.1, ENE21066.1, ENE21658.1, ENE28699.1, ENE35067.1, ENE40417.1, ENE44977.1, ENE50644.1, ENE55964.1, ENE62925.1, ENE64644.1, ENE70428.1, ENE76511.1, ENE80410.1, ENE85836.1, ENE92892.1, ENE99558.1, ENF00391.1, ENF08348.1, ENF11290.1, ENF18239.1, ENF22922.1, ENF29686.1, ENF33362.1, ENF39389.1, ENF45672.1, ENF50087.1, ENF50715.1, ENF61279.1, ENF67275.1, ENF70640.1, ENF74815.1, ENF82093.1, ENF84696.1, ENF89281.1, ENF95861.1, ENG01923.1, ENG03100.1, ENG11224.1, ENG15748.1, ENG15815.1, ENG24889.1, ENG29466.1, ENG32898.1, ENG41296.1, ENG41795.1, ENG50475.1, ENG54480.1, ENG60848.1, ENG64005.1, ENG70196.1, ENG76592.1, ENG81863.1, ENG94882.1, ENG96097.1, ENH01621.1, ENH08104.1, ENH16163.1, ENH17556.1, ENH19104.1, ENH31378.1, ENH31606.1, ENH39002.1, ENH44706.1, ENH50512.1, ENH55856.1, ENO64043.1, EOY74104.1, EPA89749.1, EPE82201.1, EPG81745.1, EPI42421.1, EPI44036.1, EPI53338.1, EPI53371.1, EPI56335.1, EPI57191.1, EPI61100.1, EPI61157.1, EPI62385.1, EPI66850.1, EPI68833.1, EPI71022.1, EPI82120.1, EPI84754.1, EPI87541.1, EPI96744.1, EPJ01394.1, EPJ03483.1, EPJ11331.1, EPO19644.1, EPO86929.1, EQA60381.1, ERB70895.1, ERB72236.1, ERB73418.1, ERB82286.1, ERB89435.1, ERB96680.1, ERB96884.1, ERC04383.1, ERC12231.1, ERC16334.1, ERC19175.1, ERC27444.1, ERC33292.1, ERC38069.1, ERC42732.1, ERC50094.1, ERC55907.1, ERC58903.1, ERC64560.1, ERC68389.1, ERC77313.1, ERC81428.1, ERC84025.1, ERC93629.1, ERC97515.1, ERC97907.1, ERD08681.1, ERD13171.1, ERD13494.1, ERD25416.1, ERD27719.1, ERD31363.1, ERD40006.1, ERD43426.1, ERD48230.1, ERD57531.1, ERD59789.1, ERD62140.1, ERD70740.1, ERD75929.1, ERD79097.1, ERD86414.1, ERD91414.1, ERE02667.1, ERE13279.1, ERE16915.1, ERE25906.1, ERE27663.1, ERE32313.1, ERE40208.1, ERH14164.1, ERH14496.1, ERH20458.1, ERH21169.1, ERH32725.1, ERJ75892.1, ERJ83445.1, ERJ96447.1, ERT63128.1, ESA60138.1, ESA65715.1, ESA72995.1, ESA77457.1, ESA86350.1, ESA88076.1, ESD00139.1, ESD09711.1, ESD21950.1, ESD26437.1, ESD31841.1, ESD51510.1, ESD61896.1, ESD64309.1, ESD71330.1, ESD80443.1, ESD81867.1, ESD83159.1, ESE11367.1, ESK58509.1, ESS00990.1, ETA02742.1, ETA89352.1, ETJ98129.1, EWM59167.1, GADI7057.1, NP_417239.1, NP_952439.1, P76632.1, WP_000893379.1, WP_000893380.1, WP_000893381.1, WP_002514607.1, WP_002549205.1, WP_002887565.1, WP_003088903.1, WP_003611352.1, WP_003619871.1, WP_003711530.1, WP_004074400.1, WP_004106700.1, WP_004109007.1, WP_004112668.1, WP_004125154.1, WP_004127867.1, WP_004132148.1, WP_004136186.1, WP_004138509.1, WP_004167284.1, WP_004809666.1, WP_004826833.1, WP_004835154.1, WP_005371168.1, WP_005524431.1, WP_006002099.1, WP_006302703.1, WP_006733185.1, WP_006735505.1, WP_006736335.1, WP_006737999.1, WP_007124216.1, WP_008087921.1, WP_008462589.1, WP_008534588.1, WP_008864957.1, WP_009310572.1, WP_009344944.1, WP_009369773.1, WP_009429506.1, WP_009535624.1, WP_009560667.1, WP_009726976.1, WP_009994023.1, WP_010241931.1, WP_010942035.1, WP_011543822.1, WP_011678177.1, WP_012914172.1, WP_012997656.1, WP_013439419.1, WP_013990631.1, WP_014835009.1, WP_016637267.1, WP_016838861.1, WP_019776149.1, WP_020281497.1, WP_020484517.1, WP_020561454.1, WP_020759632.1, WP_020761305.1, WP_020973663.1, WP_021604022.1, WP_021604907.1, WP_021610631.1, WP_021613845.1, WP_021673648.1, WP_021676130.1, WP_021682642.1, WP_023269380.1, WP_023466229.1, WP_024261075.1, YP_003373985.1, YP_004049619.1, YP_004264315.1, YP_004367832.1, YP_004372355.1, YP_004411730.1, YP_006059729.1, YP_006412645.1, YP_006449447.1, YP_006716676.1, YP_006724798.1, YP_006890378.1, YP_006972085.1, and/or YP_007277147.1

In some embodiments, Type I-E cas7/casC polypeptides include, but are not limited to, GenBank accession number as set forth in Table 21.

TABLE 21

Type I-E cas7/casC polypeptide accession numbers
(the sequence identifier for each accession number, in the
order provided in Table 21, is SEQ ID NOs: 6824-7032).

AAC75800.1, ACL06610.1, ADB14459.1, ADP38755.1, ADR37698.1, AEB06541.1, AEC02350.1, AEJ53443.1, AFL73107.1, AFR99216.1, AGB27116.1, AGX34767.1, CCK86081.1, EDP20979.1, EEB22226.1, EEB34863.1, EEI14202.1, EEI27968.1, EEI64035.1, EEI78890.1, EEI86601.1, EEJ54447.1, EEP20785.1, EEW53944.1, EEW67653.1, EEX47613.1, EEZ61813.1, EFA23034.1, EFB87474.1, EFB90860.1, EFD93803.1, EFJ75316.1, EFJ78690.1, EFJ85028.1, EFJ97183.1, EFK01966.1, EFK08565.1, EFK21929.1, EFK32762.1, EFK39561.1, EFK47877.1, EFK52821.1,

TABLE 21-continued

Type I-E cas7/casC polypeptide accession numbers
(the sequence identifier for each accession number, in the
order provided in Table 21, is SEQ ID NOs: 6824-7032).

EFK65275.1, EFK66367.1, EFK74804.1, EFM24725.1, EFM43104.1, EFM49873.1, EFO58462.1,
EFQ06781.1, EFQ52086.1, EFQ53854.1, EFS88258.1, EFT11290.1, EFT25768.1, EFT64290.1,
EFT66654.1, EFU34515.1, EFU63290.1, EFU77568.1, EFX55036.1, EFY49863.1, EGB85504.1,
EGC81779.1, EGE70490.1, EGF23576.1, EGJ06276.1, EGL13344.1, EGL37416.1, EGS35793.1,
EHE85276.1, EHI77350.1, EHM12586.1, EHO49965.1, EIE98890.1, EIM64762.1, EIV92932.1,
EKX65601.1, EKX91277.1, EMH94975.1, EMR53800.1, EPI42422.1, EPI44035.1, EPI53339.1,
EPI53370.1, EPI56334.1, EPI57190.1, EPI61101.1, EPI61156.1, EPI62384.1, EPI66849.1, ERH20069.1,
ERH32726.1, ERJ75891.1, ERJ83446.1, ERJ96448.1, ESA60139.1, ESA65716.1, ESA72994.1,
ESA77458.1, ESA86351.1, ESA88075.1, ESD00138.1, ESD09710.1, ESD21949.1, ESD26438.1,
ESD31840.1, ESD51511.1, ESD61897.1, ESD64310.1, ESD64368.1, ESD71329.1, ESD80444.1,
ESD81868.1, ESD83160.1, ESE11366.1, ESK58510.1, ETA89351.1, ETE08829.1, ETE36803.1,
ETS24673.1, EWM59166.1, GAD17058.1, GAD17059.1, NP_417238.1, Q46899.1, WP_000064439.1,
WP_000064440.1, WP_000064441.1, WP_000064442.1, WP_000064443.1, WP_000064444.1,
WP_000064446.1, WP_000064447.1, WP_000064448.1, WP_000064450.1, WP_000064451.1,
WP_000210566.1, WP_000210567.1, WP_000210568.1, WP_002268123.1, WP_002438041.1,
WP_002514608.1, WP_002546993.1, WP_003088900.1, WP_004106698.1, WP_004109003.1,
WP_004112670.1, WP_004125156.1, WP_004127870.1, WP_004135188.1, WP_004136188.1,
WP_004138505.1, WP_004159615.1, WP_004167285.1, WP_004809667.1, WP_004826832.1,
WP_004835077.1, WP_005004478.1, WP_005920816.1, WP_005942576.1, WP_006002098.1,
WP_006302704.1, WP_006422698.1, WP_006591781.1, WP_006736340.1, WP_007594588.1,
WP_008087838.1, WP_008534589.1, WP_008750295.1, WP_008902366.1, WP_009314426.1,
WP_009344897.1, WP_009369771.1, WP_009429036.1, WP_009533382.1, WP_009535623.1,
WP_009663589.1, WP_009755578.1, WP_012289871.1, WP_012667164.1, WP_012914173.1,
WP_012997657.1, WP_013977922.1, WP_013990630.1, WP_014542122.1, WP_014633159.1,
WP_016637268.1, WP_016838863.1, WP_020281498.1, WP_020281499.1, WP_020759631.1,
WP_020761304.1, WP_020973662.1, WP_021600848.1, WP_021613846.1, WP_021673647.1,
WP_021676131.1, WP_021682643.1, WP_023888110.1, WP_024166819.1, YP_003373986.1,
YP_004049618.1, YP_004372356.1, YP_004411732.1, YP_006068306.1, YP_006413232.1,
YP_006724799.1, and/or YP_007277146.1

In some embodiments, Type I-E cas5/casD polypeptides include, but are not limited to, GenBank accession number as set forth in Table 22.

TABLE 22

Type I-E cas5/casD polypeptide accession numbers
(the sequence identifier for each accession number, in the
order provided in Table 22, is SEQ ID NOs: 7033-7251).

AAC75799.2, AAR34764.1, ABA88213.1, ACP32499.1, ADB14481.1, ADI66577.1, ADI84215.1,
ADP38756.1, ADR37697.1, ADY27682.1, AEB06542.1, AEB11724.1, AEB71779.1, AEC02351.1,
AFH39945.1, AFL72522.1, AFL73106.1, AFM27185.1, AFR99217.1, AFV75990.1, AGB27115.1,
AGE37472.1, AGX34766.1, CAQ05926.1, CCI86097.1, CCK86082.1, CDI66081.1, EDN80087.1,
EDP20978.1, EEB34864.1, EEH65614.1, EEI27969.1, EEI64036.1, EEI78891.1, EEI86600.1,
EEJ54446.1, EEP20784.1, EET77373.1, EEW16908.1, EEW42241.1, EEW53945.1, EEW67652.1,
EEX47614.1, EEZ61812.1, EFA23035.1, EFB87475.1, EFB90859.1, EFD84086.1, EFD93802.1,
EFE06767.1, EFF79643.1, EFH10699.1, EFI90756.1, EFJ64188.1, EFJ75317.1, EFJ78689.1,
EFJ85029.1, EFJ97182.1, EFK01965.1, EFK08634.1, EFK13798.1, EFK21930.1, EFK32759.1,
EFK39564.1, EFK47876.1, EFK52822.1, EFK66366.1, EFK74805.1, EFL93065.1, EFM24724.1,
EFM49979.1, EFO58461.1, EFQ06782.1, EFQ22977.1, EFQ47702.1, EFQ49119.1, EFQ52096.1,
EFS88259.1, EFT11289.1, EFT25769.1, EFT64291.1, EFT66655.1, EFU34514.1, EFU63291.1,
EFU77569.1, EFV94308.1, EFX55037.1, EGB85505.1, EGC81843.1, EGE70491.1, EGF23577.1,
EGF57388.1, EGF60540.1, EGG33807.1, EGG50907.1, EGJ06277.1, EGL13343.1, EGL38219.1,
EGS35926.1, EHI77351.1, EHM12587.1, EHO49966.1, EHQ05135.1, EIC19432.1, EIC29370.1,
EIE98889.1, EIM64761.1, EIV92931.1, EKW99768.1, EMH94966.1, EMR53799.1, EPI42423.1,
EPI44034.1, EPI53340.1, EPI53369.1, EPI56333.1, EPI57189.1, EPI61102.1, EPI61155.1, EPI62383.1,
EPI66848.1, EPI68831.1, EPI71020.1, EPI82118.1, EPI84752.1, EPI87539.1, EPI96742.1, EPJ01392.1,
EPJ03481.1, EPJ11329.1, ERH14162.1, ERH14498.1, ERH20070.1, ERH20456.1, ERH21171.1,
ERH32727.1, ERJ75890.1, ERJ83447.1, ERJ96449.1, ESA60140.1, ESA65717.1, ESA72993.1,
ESA77459.1, ESA86352.1, ESA88074.1, ESD00137.1, ESD09709.1, ESD21948.1, ESD26439.1,
ESD31839.1, ESD51512.1, ESD61898.1, ESD64311.1, ESD64369.1, ESD71328.1, ESD80445.1,
ESD81869.1, ESD83161.1, ESE11365.1, ESK58511.1, ETA02744.1, ETA89350.1, ETX32969.1,
GAD17060.1, NP_417237.2, NP_952441.1, Q46898.2, WP_004106696.1, WP_004109000.1,
WP_004112672.1, WP_004115346.1, WP_004125159.1, WP_004127874.1, WP_004136190.1,
WP_004138504.1, WP_005524251.1, WP_006302705.1, WP_008864959.1, WP_009429844.1,
WP_009550706.1, WP_009994022.1, WP_012914174.1, WP_016637269.1, WP_016838864.1,
WP_018637825.1, WP_020281500.1, WP_020759630.1, WP_020761303.1, WP_020973661.1,
WP_021600849.1, WP_021604020.1, WP_021604909.1, WP_021610202.1, WP_021610633.1,
WP_021613847.1, WP_021673646.1, WP_021676132.1, WP_021682644.1, WP_023140380.1,
WP_023156409.1, YP_001801360.1, YP_002834437.1, YP_003373987.1, YP_003718071.1,
YP_004049617.1, YP_004264317.1, YP_004367834.1, YP_004372357.1, YP_004411733.1,

TABLE 22-continued

Type I-E cas5/casD polypeptide accession numbers
(the sequence identifier for each accession number, in the
order provided in Table 22, is SEQ ID NOs: 7033-7251).

YP_006059731.1, YP_006412647.1, YP_006413231.1, YP_006449449.1, YP_006716678.1,
YP_006724800.1, YP_006890380.1, YP_006972087.1, YP_007277145.1, and/or YP_007417723.1

In some embodiments, Type I-E cas6e/case polypeptides include, but are not limited to, GenBank accession number as set forth in Table 23.

TABLE 23

Type I-E cas6e/case polypeptide accession numbers
(the sequence identifier for each accession number, in the
order provided in Table 23, is SEQ ID NOs: 7252-7520).

AAC75798.1, AAR34765.1, ACL06609.1, ADB14325.1, ADI66576.1, ADI84216.1, ADP38757.1,
ADR37696.1, ADY27683.1, AEB06543.1, AEB11725.1, AEB71780.1, AEC02349.1, AFH39946.1,
AFL72523.1, AFL73105.1, AFM27186.1, AFR99218.1, AFV75991.1, AGB27114.1, AGX34765.1,
CCI86096.1, CCK86083.1, CDC58447.1, CDI66082.1, EDN80086.1, EDP20977.1, EEB22228.1,
EEB34862.1, EEI14204.1, EEI27970.1, EEI64037.1, EEI77643.1, EEI78892.1, EEI86599.1,
EEJ54450.1, EEP20783.1, EET77372.1, EEW16909.1, EEW42240.1, EEW53946.1, EEW67651.1,
EEZ61811.1, EFA23036.1, EFB87476.1, EFD84085.1, EFD93801.1, EFE06768.1, EFF79642.1,
EFH10698.1, EFI90757.1, EFJ64189.1, EFJ75318.1, EFJ78688.1, EFJ85030.1, EFJ97190.1,
EFK01964.1, EFK08549.1, EFK13797.1, EFK21931.1, EFK32766.1, EFK39594.1, EFK47875.1,
EFK52823.1, EFK66365.1, EFK74806.1, EFL93064.1, EFM24723.1, EFM43102.1, EFM50285.1,
EFO58460.1, EFO71176.1, EFQ06783.1, EFQ22978.1, EFQ47730.1, EFQ49157.1, EFQ52112.1,
EFQ53869.1, EFS88260.1, EFT11288.1, EFT25770.1, EFT64292.1, EFT66656.1, EFU34513.1,
EFU63292.1, EFU77570.1, EFV94309.1, EFX55038.1, EGB85506.1, EGC81772.1, EGE70492.1,
EGF23578.1, EGF57387.1, EGF60541.1, EGG33808.1, EGG50908.1, EGJ06278.1, EGL13350.1,
EGL36080.1, EGS35882.1, EHE85271.1, EHI77352.1, EHQ05134.1, EIC19431.1, EIC29369.1,
EIE98888.1, EIM64763.1, EIV92930.1, EKX91280.1, EMH94952.1, EMR53798.1, EPI42424.1,
EPI44033.1, EPI52307.1, EPI53368.1, EPI56332.1, EPI57188.1, EPI61103.1, EPI61154.1, EPI62382.1,
EPI66847.1, EPI68830.1, EPI71019.1, EPI82117.1, EPI84751.1, EPI87538.1, EPI96741.1, EPJ01391.1,
EPJ03480.1, EPJ11328.1, EQC59007.1, EQM55565.1, ERC93626.1, ERH14161.1, ERH14499.1,
ERH20071.1, ERH20455.1, ERH21172.1, ERH32728.1, ERJ75889.1, ERJ83448.1, ERJ96450.1,
ESA60141.1, ESA65718.1, ESA72992.1, ESA77460.1, ESA86353.1, ESA88073.1, ESD00136.1,
ESD09708.1, ESD21947.1, ESD26440.1, ESD31838.1, ESD51513.1, ESD61899.1, ESD64312.1,
ESD64370.1, ESD71327.1, ESD80446.1, ESD81870.1, ESD83162.1, ESE11364.1, ESK58512.1,
ESS00993.1, ETA02745.1, ETA89349.1, ETX32968.1, EWM59164.1, NP_417236.1, NP_952442.1,
Q46897.1, WP_000275968.1, WP_000275969.1, WP_000275970.1, WP_002514610.1,
WP_002887563.1, WP_003088897.1, WP_003611355.1, WP_003619878.1, WP_003627701.1,
WP_003638535.1, WP_003680452.1, WP_003711544.1, WP_004106694.1, WP_004108997.1,
WP_004112674.1, WP_004125169.1, WP_004127877.1, WP_004132153.1, WP_004136192.1,
WP_004167288.1, WP_004271052.1, WP_004574564.1, WP_004809669.1, WP_004826830.1,
WP_004835071.1, WP_005524691.1, WP_006302706.1, WP_006499676.1, WP_006733194.1,
WP_006734894.1, WP_006735522.1, WP_006736351.1, WP_007124219.1, WP_007594585.1,
WP_008087967.1, WP_008462592.1, WP_008750297.1, WP_008753314.1, WP_008864960.1,
WP_008902364.1, WP_009344936.1, WP_009369769.1, WP_009427664.1, WP_009431210.1,
WP_009535621.1, WP_009560664.1, WP_009663637.1, WP_010241933.1, WP_010495835.1,
WP_011674074.1, WP_012391079.1, WP_012914175.1, WP_012997658.1, WP_013086434.1,
WP_013439422.1, WP_013977924.1, WP_013990628.1, WP_014082580.1, WP_014565815.1,
WP_014604239.1, WP_014633158.1, WP_014835008.1, WP_014939123.1, WP_016637270.1,
WP_016838866.1, WP_019776152.1, WP_019787555.1, WP_020758452.1, WP_020759629.1,
WP_020761302.1, WP_020973660.1, WP_021600850.1, WP_021604019.1, WP_021604910.1,
WP_021610201.1, WP_021610634.1, WP_021613848.1, WP_021673645.1, WP_021676133.1,
WP_021682645.1, WP_021816697.1, WP_022280995.1, WP_023140379.1, WP_023466234.1,
YP_003373988.1, YP_004049616.1, YP_004264318.1, YP_004367835.1, YP_004372358.1,
YP_004411731.1, YP_006059732.1, YP_006412648.1, YP_006413230.1, YP_006449450.1,
YP_006724801.1, YP_006890381.1, YP_006972088.1, and/or YP_007277144.1

In some embodiments, Type I-F cys1 polypeptides include, but are not limited to, GenBank accession number as set forth in Table 24.

TABLE 24

Type I-F cys1 polypeptide accession numbers
(the sequence identifier for each accession number, in the
order provided in Table 24, is SEQ ID NOs: 7521-8614).

AAK02389.1, AAM85292.1, AAO90474.1, AAQ59428.1, AAS62490.1, AAT03785.1, AAV89306.1,
ABA59201.1, ABE06378.1, ABG13929.1, ABG18390.1, ABJ00263.1, ABJ11602.1, ABM03215.1,
ABM25017.1, ABM40738.1, ABM57218.1, ABN73326.1, ABP40265.1, ABP60084.1, ABQ13774.1,

TABLE 24-continued

Type I-F cys1 polypeptide accession numbers
(the sequence identifier for each accession number, in the
order provided in Table 24, is SEQ ID NOs: 7521-8614).

ABS09366.1, ABS47563.1, ABS76912.2, ABS77281.1, ABX33857.1, ABX50537.1, ABX78740.1,
ABX85411.1, ABY68823.1, ACA67939.1, ACC89562.1, ACD38774.1, ACE60872.1, ACJ18399.1,
ACJ21001.1, ACJ42249.1, ACJ57095.1, ACO74062.1, ACQ92975.1, ACS84543.1, ACT05579.1,
ACV75133.1, ACX89392.1, ACY59063.1, ACY62906.1, ACZ78275.1, ADC72939.1, ADE14358.1,
ADE65025.1, ADE89458.1, ADG60301.1, ADH86222.1, ADJ29627.1, ADM99944.1, ADN71993.1,
ADR26230.1, ADT95524.1, ADU65668.1, ADV98275.1, ADX89043.1, ADX89502.1, ADZ83760.1,
ADZ92541.1, AEC02369.1, AEC18351.1, AEF92273.1, AEF99820.1, AEH62443.1, AEL09136.1,
AEL73392.1, AEO75099.1, AET15298.1, AEX04893.1, AEX51728.1, AFF23582.1, AFG36510.1,
AFH79569.1, AFH95464.1, AFI46138.1, AFI86378.1, AFI91858.1, AFJ02202.1, AFM64907.1,
AFN56495.1, AFP32551.1, AFR04904.1, AFT71809.1, AFZ95064.1, AFZ95067.1, AGA34092.1,
AGB80780.1, AGG09385.1, AGG09391.1, AGG31844.1, AGP49331.1, AGP56731.1, AGR05546.1,
AGR11302.1, AGR15392.1, AGR16666.1, AGR20776.1, AGR22558.1, AGR26149.1, AGR32635.1,
AGW13657.1, AGX88283.1, AHB09921.1, AHC77005.1, AHE63723.1, AHE99154.1, AHF01507.1,
AHH51210.1, BAH77673.1, BAL82648.1, CAE14086.1, CAG76579.1, CAH17083.1, CAH17369.1,
CAH21746.1, CAK96433.1, CAL21093.1, CAM85941.1, CAO95888.1, CAP75353.1, CAQ84811.1,
CAQ84824.1, CAR02242.1, CAR07056.1, CAS04772.1, CAX54608.1, CAY73257.1, CBA17527.1,
CBA76131.1, CBQ72655.1, CBV40988.1, CBX29755.1, CBY03554.1, CBY48580.1, CBY67065.1,
CBY69907.1, CBY72771.1, CBY75627.1, CCC73994.1, CCG18727.1, CCG19560.1, CCG88217.1,
CCH40236.1, CCI83946.1, CCJ84614.1, CCO00438.1, CCO24445.1, CCO63591.1, CCQ87260.1,
CCV12786.1, CCZ55232.1, CDD80271.1, CDF05512.1, CDG79719.1, CDH64393.1, EAL08156.1,
EAQ67604.1, EAT04042.1, EAT59333.1, EAX33530.2, EAZ67852.1, EAZ58295.1, EDM42113.1,
EDP21767.1, EDQ01683.1, EDQ48485.1, EDR35346.1, EDR37793.1, EDR45218.1, EDR48642.1,
EDR55883.1, EDU58856.1, EDV62110.1, EDZ65592.1, EEH84601.1, EEO29373.1, EEO76101.1,
EEO80178.1, EEO84410.1, EEO89852.1, EEP92231.1, EEQ03932.1, EER62392.1, EER62393.1,
EEV21941.1, EEW05501.1, EEW18398.1, EEW96609.1, EEX50304.1, EEX68259.1, EEY90281.1,
EFA49549.1, EFC58007.1, EFF94952.1, EFG00724.1, EFI23592.1, EFK42238.1, EFL78325.1,
EFL79684.1, EFM53867.1, EFM86281.1, EFM88414.1, EFM90572.1, EFM92759.1, EFM95005.1,
EFM97159.1, EFM99348.1, EFN01384.1, EFN03542.1, EFO58228.1, EFU46691.1, EFX91399.1,
EFX91400.1, EFX91401.1, EGB49277.1, EGB53896.1, EGB79047.1, EGC94951.1, EGE11094.1,
EGE12101.1, EGE14941.1, EGE19078.1, EGE19370.1, EGE21990.1, EGE24487.1, EGE25422.1,
EGE27751.1, EGF37989.1, EGJ07917.1, EGJ24489.1, EGJ59632.1, EGJ63887.1, EGM77974.1,
EGP02213.1, EGP02616.1, EGP02684.1, EGP02758.1, EGQ17530.1, EGS63957.1, EGW37653.1,
EGW90821.1, EGX68878.1, EGY35784.1, EGY36033.1, EGY38129.1, EGY39148.1, EGY39149.1,
EGY39150.1, EGY41122.1, EGY70947.1, EHG01971.1, EHJ94023.1, EHK42702.1, EHM40141.1,
EHM48029.1, EHN98428.1, EIA37119.1, EIC29311.1, EIE47040.1, EIF44409.1, EIK45283.1,
EIL54440.1, EIL76432.1, EIL89113.1, EIQ87550.1, EIQ88768.1, EIQ89495.1, EIR01144.1, EIR02488.1,
EIR05606.1, EIR16474.1, EIR17422.1, EIR19480.1, EIR30997.1, EIR32496.1, EIR33323.1, EIR45342.1,
EIR46426.1, EIR47972.1, EIR59153.1, EIR59982.1, EIR64115.1, EIR73557.1, EIR75601.1, EIR76606.1,
EIR87356.1, EIR89808.1, EIR91675.1, EIS03547.1, EIS03933.1, EIS05049.1, EIS16919.1, EIS17790.1,
EIS23399.1, EIS28664.1, EIS31268.1, EIS40840.1, EIS42738.1, EIS44211.1, EIS55614.1, EIS56044.1,
EIS60021.1, EIS66597.1, EIS73044.1, EIS76079.1, EIS78312.1, EIS86654.1, EIS90403.1, EIS94486.1,
EIS98162.1, EIT05329.1, EIT13607.1, EIT14717.1, EIT15457.1, EIT26164.1, EIT29053.1, EIT30491.1,
EIT40107.1, EIT44653.1, EIT45186.1, EIT55055.1, EIT56869.1, EIT62392.1, EJG22082.1, EJI84874.1,
EJO39737.1, EJP51268.1, EJS83105.1, EJS83187.1, EJS85444.1, EJS90168.1, EJS91482.1,
EJS92993.1, EJZ79575.1, EJZ80875.1, EJZ81232.1, EKA43936.1, EKA54579.1, EKA74315.1,
EKF84294.1, EKG52540.1, EKG57735.1, EKG62911.1, EKG63407.1, EKG52466.1, EKG59023.1,
EKK08278.1, EKK18197.1, EKK94023.1, EKL08413.1, EKL14868.1, EKL16051.1, EKL22305.1,
EKL39333.1, EKL48912.1, EKL93517.1, EKM01154.1, EKM08461.1, EKP55013.1, EKP56448.1,
EKS45299.1, EKT62227.1, EKX95270.1, ELC02438.1, ELC12192.1, ELC21170.1, ELC30642.1,
ELC31985.1, ELD54443.1, ELD92476.1, ELE13998.1, ELE25612.1, ELE34548.1, ELE51938.1,
ELE82361.1, ELE93036.1, ELF40642.1, ELF68854.1, ELF84511.1, ELF93397.1, ELF98793.1,
ELG17251.1, ELG28215.1, ELG56199.1, ELG59752.1, ELH17521.1, ELH33233.1, ELH65835.1,
ELH83714.1, ELH95193.1, ELH95740.1, ELI27976.1, ELI75034.1, ELI90641.1, ELJ31991.1,
ELJ44080.1, ELJ56850.1, ELJ58412.1, ELJ73178.1, ELT18755.1, ELY20637.1, EMI19651.1,
EMP51887.1, EMT98704.1, EMU01024.1, EMU07889.1, EMU33768.1, EMV25762.1, EMV41477.1,
EMV48349.1, EMV61751.1, EMV77001.1, EMV77660.1, EMV79454.1, EMW06845.1, EMW07144.1,
EMW11058.1, EMW22772.1, EMW28012.1, EMW63399.1, EMX55465.1, EMX95470.1, EMZ59014.1,
EMZ71046.1, ENA68768.1, ENA70831.1, ENO94850.1, ENU20823.1, ENU25384.1, ENU36865.1,
ENU64166.1, ENU64519.1, ENU68407.1, ENU79934.1, ENU84995.1, ENU90132.1,
ENU94465.1, ENV06534.1, ENV11505.1, ENV26808.1, ENV33520.1, ENV43130.1, ENV52235.1,
ENV66343.1, ENV79710.1, ENW17824.1, ENW17834.1, ENW36547.1, ENW39480.1, ENW64163.1,
ENW68335.1, ENW78806.1, ENW99800.1, ENX46545.1, ENY83744.1, ENZ96952.1, EOQ57500.1,
EOT14077.1, EOT16833.1, EOU37592.1, EOU39898.1, EOU82022.1, EOU82326.1,
EOV51400.1, EOV89558.1, EOV96440.1, EOW37719.1, EOW66748.1, EOX15982.1, EOX25496.1,
EPC00314.1, EPC10335.1, EPD43986.1, EPE65662.1, EPE66427.1, EPE67789.1, EPE69698.1,
EPE71676.1, EPE74056.1, EPE75489.1, EPP24157.1, EPP36537.1, EPP38603.1, EPR80937.1,
EPR81197.1, EPR88381.1, EPR88436.1, EPS74945.1, EQM86553.1, EQN06274.1, EQN09581.1,
EQN21673.1, EQN32966.1, EQN72751.1, EQN87317.1, EQO22615.1, EQO25947.1, EQO34067.1,
EQO52282.1, EQO63917.1, EQO87244.1, EQP27530.1, EQP52728.1, EQP62836.1, EQP80763.1,
EQQ42456.1, EQQ52930.1, EQR25824.1, EQR43473.1, EQR49983.1, EQR54852.1, EQR90841.1,
EQT05355.1, EQT30873.1, EQT84174.1, EQT86452.1, EQU02189.1, EQU15315.1, EQU15703.1,
EQU26653.1, EQU37326.1, EQU74182.1, EQU96772.1, EQV16497.1, EQV39105.1, EQV73991.1,
EQW35602.1, EQW74767.1, EQW95171.1, EQX30754.1, EQY04008.1, EQY05737.1, EQY46989.1,
EQY47415.1, EQZ21534.1, EQZ57880.1, EQZ59928.1, EQZ81916.1, ERA24939.1, ERA25706.1,
ERA94145.1, ERB37230.1, ERF78304.1, ERG16853.1, ERH80169.1, ERH80792.1, ERH82069.1,
ERH83949.1, ERH87746.1, ERL42546.1, ERO62439.1, ERO62440.1, ERO62441.1, ERP69291.1,

TABLE 24-continued

Type I-F cys1 polypeptide accession numbers
(the sequence identifier for each accession number, in the
order provided in Table 24, is SEQ ID NOs: 7521-8614).

ERP72010.1, ERP72732.1, ERP73551.1, ERP82386.1, ERT61752.1, ERU80871.1, ERU82775.1,
ERU95636.1, ERV23079.1, ERV32405.1, ERV45938.1, ERV90883.1, ERV92840.1, ERW05285.1,
ERW22632.1, ERW25389.1, ERW30733.1, ERW52654.1, ERW66576.1, ERW85641.1, ERW96792.1,
ERX11464.1, ERX57181.1, ERX57292.1, ERX68373.1, ERX76659.1, ERY56085.1, ERY93181.1,
ERY99967.1, ERZ00045.1, ERZ29314.1, ERZ42447.1, ESD40183.1, ESE13078.1, ESK35632.1,
ESK57655.1, ESM77259.1, ESM81556.1, ESN04281.1, ESN26373.1, ESN28523.1, ESN61384.1,
ESP24741.1, ESP31907.1, ESP34912.1, ESQ71810.1, EST01752.1, ETF26480.1, ETR82184.1,
ETR84943.1, ETU83908.1, ETU88442.1, ETV19934.1, ETV43751.1, ETV55561.1, ETY51218.1,
ETY53938.1, EUM12623.1, EVT85802.1, GAA37652.2, GAA60412.1, GAA79125.1, GAB03985.1,
GAC09608.1, GAC15832.1, GAC19767.1, GAC34440.1, GAC34441.1, GAE10394.1, GAF23543.1,
NP_245242.1, NP_669041.1, NP_819960.1, NP_901424.1, NP_929071.1, NP_993613.1, Q02ML9.1,
WP_000112420.1, WP_000399210.1, WP_000399211.1, WP_000415799.1, WP_000415800.1,
WP_000415801.1, WP_000415802.1, WP_000415803.1, WP_000415804.1, WP_000415805.1,
WP_000415806.1, WP_000415807.1, WP_000841017.1, WP_000841018.1, WP_000841019.1,
WP_000841020.1, WP_000841021.1, WP_000841022.1, WP_001063626.1, WP_001063627.1,
WP_001297315.1, WP_001516089.1, WP_001519631.1, WP_001546553.1, WP_001552676.1,
WP_001704454.1, WP_001706989.1, WP_001714017.1, WP_001953039.1, WP_001969798.1,
WP_001982950.1, WP_002216548.1, WP_002222491.1, WP_002225603.1, WP_002611226.1,
WP_002624011.1, WP_002802608.1, WP_002812358.1, WP_002923969.1, WP_003116911.1,
WP_003139224.1, WP_003143952.1, WP_003162917.1, WP_003464677.1, WP_003664170.1,
WP_003666003.1, WP_003667347.1, WP_003670775.1, WP_003672252.1, WP_003672780.1,
WP_003726678.1, WP_003727056.1, WP_003730930.1, WP_003738588.1, WP_004089534.1,
WP_004240705.1, WP_004279693.1, WP_004343803.1, WP_004349919.1, WP_004389634.1,
WP_004601700.1, WP_004601977.1, WP_004651370.1, WP_004652094.1, WP_004681365.1,
WP_004713756.1, WP_004728800.1, WP_004739558.1, WP_004752521.1, WP_004758712.1,
WP_004798546.1, WP_004801339.1, WP_004863337.1, WP_004895765.1, WP_004904254.1,
WP_004907049.1, WP_004918641.1, WP_004963263.1, WP_004998567.1, WP_005003488.1,
WP_005081844.1, WP_005081858.1, WP_005109633.1, WP_005163439.1, WP_005182494.1,
WP_005217654.1, WP_005346829.1, WP_005371072.1, WP_005497852.1, WP_005540027.1,
WP_005551775.1, WP_005551921.1, WP_005562569.1, WP_005562571.1, WP_005562575.1,
WP_005596018.1, WP_005600277.1, WP_005603468.1, WP_005606943.1, WP_005611354.1,
WP_005616691.1, WP_005623493.1, WP_005623497.1, WP_005623500.1, WP_005720634.1,
WP_005721278.1, WP_005725639.1, WP_005725806.1, WP_005742492.1, WP_005752986.1,
WP_005753650.1, WP_005756147.1, WP_005764761.1, WP_005769537.1, WP_005772797.1,
WP_005792703.1, WP_005792704.1, WP_005842408.1, WP_005879782.1, WP_005923785.1,
WP_005974986.1, WP_006045188.1, WP_006174403.1, WP_006331712.1, WP_006365989.1,
WP_006790330.1, WP_006912975.1, WP_007069542.1, WP_007106205.1, WP_007106206.1,
WP_007111959.1, WP_007117095.1, WP_007293313.1, WP_007620986.1, WP_007641675.1,
WP_007744292.1, WP_007749063.1, WP_007986846.1, WP_008135459.1, WP_008169482.1,
WP_008215108.1, WP_008247105.1, WP_008608781.1, WP_008698003.1, WP_008845637.1,
WP_008898789.1, WP_008911673.1, WP_009174232.1, WP_009288126.1, WP_009622501.1,
WP_009832551.1, WP_009875009.1, WP_009876497.1, WP_010106219.1, WP_010201103.1,
WP_010265207.1, WP_010279272.1, WP_010295110.1, WP_010318159.1, WP_010364313.1,
WP_010906577.1, WP_010957911.1, WP_011095181.1, WP_011135306.1, WP_011146070.1,
WP_011192626.1, WP_011212640.1, WP_011216754.1, WP_011240574.1, WP_011769775.1,
WP_011789484.1, WP_011803947.1, WP_011809225.1, WP_011927917.1, WP_011996910.1,
WP_011997338.1, WP_012016803.1, WP_012089885.1, WP_012104945.1, WP_012197494.1,
WP_012203143.1, WP_012220397.1, WP_012229482.1, WP_012303963.1, WP_012440590.1,
WP_012570060.1, WP_012570903.1, WP_012667183.1, WP_012696552.1, WP_012729574.1,
WP_012764362.1, WP_012768459.1, WP_012817199.1, WP_012886077.1, WP_012917520.1,
WP_012983811.1, WP_013032249.1, WP_013107620.1, WP_013163749.1, WP_013221692.1,
WP_013319367.1, WP_013330863.1, WP_013505553.1, WP_013657054.1, WP_013662443.1,
WP_013739764.1, WP_013747107.1, WP_013804306.1, WP_013818080.1, WP_014016721.1,
WP_014228623.1, WP_014325844.1, WP_014390883.1, WP_014424085.1, WP_014454507.1,
WP_014500608.1, WP_014509415.1, WP_014602882.1, WP_014658069.1, WP_014673057.1,
WP_014701307.1, WP_014703622.1, WP_014833996.1, WP_014848626.1, WP_014872888.1,
WP_014916577.1, WP_014995870.1, WP_015259208.1, WP_015337045.1, WP_015551640.1,
WP_015555715.1, WP_015670635.1, WP_015696920.1, WP_015731171.1, WP_015834854.1,
WP_015834867.1, WP_015862798.1, WP_016158984.1, WP_016232820.1, WP_016248534.1,
WP_016261857.1, WP_016418866.1, WP_016451883.1, WP_016504385.1, WP_016534110.1,
WP_016534296.1, WP_016534561.1, WP_016836896.1, WP_017004729.1, WP_017253215.1,
WP_017350190.1, WP_017395753.1, WP_017448229.1, WP_017466362.1, WP_017788587.1,
WP_018025761.1, WP_018076940.1, WP_018122277.1, WP_018125463.1, WP_018176610.1,
WP_018285446.1, WP_018298695.1, WP_018347332.1, WP_018414916.1, WP_018559989.1,
WP_018676856.1, WP_018719049.1, WP_019001601.1, WP_019022908.1, WP_019520403.1,
WP_019543109.1, WP_019671932.1, WP_019843462.1, WP_019935460.1, WP_019951122.1,
WP_019959484.1, WP_020161983.1, WP_020328487.1, WP_020355487.1, WP_020393891.1,
WP_020443856.1, WP_020566224.1, WP_020680648.1, WP_020870181.1, WP_021017051.1,
WP_021205340.1, WP_021325938.1, WP_021461779.1, WP_021496695.1, WP_021511678.1,
WP_021519928.1, WP_021531159.1, WP_021760540.1, WP_021986552.1, WP_022027307.1,
WP_022381641.1, WP_022498163.1, WP_022642198.1, WP_022642199.1, WP_022642200.1,
WP_022654589.1, WP_022775606.1, WP_022850861.1, WP_022852963.1, WP_023053042.1,
WP_023087478.1, WP_023091296.1, WP_023100320.1, WP_023103132.1, WP_023122499.1,
WP_023271486.1, WP_023320639.1, WP_023327012.1, WP_023337012.1, WP_023338204.1,
WP_023346464.1, WP_023593282.1, WP_023640697.1, WP_023655989.1, WP_024107197.1,
XP_001401634.1, XP_001584082.1, XP_003494537.1, XP_003665759.1, XP_004528093.1,

TABLE 24-continued

Type I-F cys1 polypeptide accession numbers
(the sequence identifier for each accession number, in the
order provided in Table 24, is SEQ ID NOs: 7521-8614).

YP_001052931.1, YP_001163238.1, YP_001176135.1, YP_001209096.1, YP_001367429.1,
YP_001400515.1, YP_001424468.1, YP_001425255.2, YP_001555797.1, YP_001562242.1,
YP_001596760.1, YP_001606220.1, YP_001651267.1, YP_001712944.1, YP_001720392.1,
YP_001873019.1, YP_001906786.1, YP_001968014.1, YP_002303544.1, YP_002306146.1,
YP_002320238.1, YP_002324895.1, YP_002347429.1, YP_002390702.1, YP_002396879.1,
YP_002555748.1, YP_002647858.1, YP_002757711.1, YP_002795071.1, YP_002892561.1,
YP_002955559.1, YP_002986365.1, YP_003003058.1, YP_003041554.1, YP_003041567.1,
YP_003225717.1, YP_003260999.1, YP_003334981.1, YP_003377521.1, YP_003461675.1,
YP_003526745.1, YP_003568287.1, YP_003626194.1, YP_003690841.1, YP_003761948.1,
YP_003884501.1, YP_003896173.1, YP_004112224.1, YP_004308958.1, YP_004314377.1,
YP_004411751.1, YP_004421248.1, YP_004490628.1, YP_004512320.1, YP_004766821.1,
YP_005019132.1, YP_005176267.1, YP_005199868.1, YP_005274576.1, YP_005362753.1,
YP_005432671.1, YP_005474217.1, YP_005505366.1, YP_005509299.1, YP_005522412.1,
YP_005620894.1, YP_005623562.1, YP_005639254.1, YP_005801628.1, YP_005975201.1,
YP_006100124.1, YP_006111505.1, YP_006119164.1, YP_006205237.1, YP_006218155.1,
YP_006239897.1, YP_006245601.1, YP_006284730.1, YP_006286210.1, YP_006292889.1,
YP_006482609.1, YP_006518017.1, YP_006559964.1, YP_006648157.1, YP_006672809.1,
YP_006675673.1, YP_006678529.1, YP_006681438.1, YP_006692986.1, YP_006754116.1,
YP_006822152.1, YP_007014582.1, YP_007217573.1, YP_007326546.1, YP_007342965.1,
YP_007506217.1, YP_007693219.1, YP_007821732.1, YP_007826786.1, YP_008163693.1,
YP_008275318.1, YP_008278180.1, YP_008282548.1, YP_008284800.1, YP_008285745.1,
YP_008289189.1, YP_008299286.1, YP_008301323.1, YP_008304316.1, YP_008570807.1,
YP_008590827.1, YP_008682386.1, YP_008685345.1, YP_008791660.1, YP_008981899.1,
YP_013608.1, YP_051769.1, YP_071020.1, YP_122343.1, YP_128164.1, YP_162417.1, YP_344731.1,
YP_539909.1, YP_647990.1, YP_651874.1, YP_790817.1, YP_851977.1, YP_942814.1, YP_963571.1,
YP_984814.1, and/or YP_996236.1

In some embodiments, Type I-F cys2 polypeptides include, but are not limited to, GenBank accession number as set forth in Table 25.

TABLE 25

Type I-F cys2 polypeptide accession numbers
(the sequence identifier for each accession number, in the
order provided in Table 25, is SEQ ID NOs: 8615-9867).

AAC65118.1, AAK02390.1, AAM85293.1, AAQ59427.1, AAS62489.1, AAV89307.2, ABA59202.1,
ABE06379.1, ABE06380.1, ABG13928.1, ABG18389.1, ABJ00264.1, ABJ11603.1, ABK50072.1,
ABM03216.1, ABM25016.1, ABM40737.1, ABM57217.1, ABN73325.1, ABO37086.1, ABP40264.1,
ABP60085.1, ABQ13203.1, ABS09365.1, ABS46484.1, ABS77509.1, ABS77769.2, ABU74104.1,
ABX33858.1, ABX50536.1, ABX84883.1, ABY68822.1, ACA67940.1, ACC89561.1, ACD38773.1,
ACD70553.1, ACE60871.1, ACH65834.1, ACJ19105.1, ACJ21002.1, ACJ27815.1, ACJ56177.1,
ACK48653.1, ACO74063.1, ACQ92976.1, ACS84542.1, ACT05580.1, ACV75132.1, ACX89391.1,
ACY59062.1, ACY62907.1, ACZ78274.1, ADC72940.1, ADE14359.1, ADE54031.1, ADE65024.1,
ADG60302.1, ADH86221.1, ADJ29628.1, ADM99943.1, ADR02760.1, ADR26231.1, ADR64330.1,
ADR64349.1, ADR64397.1, ADR64416.1, ADR64435.1, ADT68979.1, ADT95523.1, ADU65665.1,
ADV98276.1, ADX55812.1, ADX89042.1, ADX89501.1, ADZ92540.1, AEC02368.1, AEF92272.1,
AEF99821.1, AEH40082.1, AEH62442.1, AEL09137.1, AEL73393.1, AEO75098.1, AET15299.1,
AET92128.1, AEX04894.1, AEX24997.1, AEX51729.1, AEZ58314.1, AEZ59382.1, AEZ60447.1,
AFF23583.1, AFG36511.1, AFH95465.1, AFI46137.1, AFI86379.1, AFI91857.1, AFJ02201.1,
AFM64906.1, AFN56494.1, AFR04905.1, AFT71808.1, AFU66157.1, AGA34091.1, AGB12636.1,
AGB80781.1, AGG09386.1, AGG09392.1, AGK83770.1, AGN75345.1, AGN76322.1, AGQ92515.1,
AGU98412.1, AGW13658.1, AGX88282.1, AHB09920.1, AHC77004.1, AHE63724.1, AHE99153.1,
AHF01506.1, AHG62863.1, AHH51211.1, AHI99022.1, BAC62731.1, BAH15058.1, BAH77672.1,
BAL82649.1, BAM20857.1, CAE14087.1, CAG69249.1, CAG76580.1, CAH17084.1, CAH17368.1,
CAH21745.1, CAL21092.1, CAM85942.1, CAO95889.1, CAQ84810.1, CAR07057.1, CAX54609.1,
CAY73258.1, CBA17528.1, CBA76129.1, CBV40989.1, CBX29756.1, CBZ12648.1, CCC73993.1,
CCG18726.1, CCG19559.1, CCG88216.1, CCH40237.1, CCJ84615.1, CCO00437.1, CCO24444.1,
CCQ87261.1, CCZ55231.1, CDD80272.1, CDF05511.1, CDG79718.1, CDH64394.1, CDH64395.1,
EAQ67603.1, EAS64064.1, EAS76234.1, EAT04043.1, EAT33399.1, EAT59334.1, EAX33542.1,
EAZ52873.1, EAZ58296.1, EDK28162.1, EDM42114.1, EDM61554.1, EDM65937.1, EDQ01682.1,
EDR31165.1, EDR35344.1, EDR37791.1, EDR44816.1, EDR48641.1, EDR48745.1, EDR55852.1,
EDR59629.1, EDT07274.1, EDU58857.1, EDV62082.1, EDZ65397.1, EED26449.1, EEH60997.1,
EEH84600.1, EEO29372.1, EEO76100.1, EEO80177.1, EEO84409.1, EEO89851.1, EEP92232.1,
EEQ03933.1, EEV21942.1, EEW05502.1, EEW96608.1, EEX04036.1, EEX50303.1, EEX68260.1,
EEY43699.1, EEY55135.1, EEY90280.1, EFA49550.1, EFC58008.1, EFI23593.1, EFI34392.1,
EFL78324.1, EFL79685.1, EFM41492.1, EFM53866.1, EFM86280.1, EFM88413.1, EFM90571.1,
EFM92758.1, EFM95004.1, EFM97158.1, EFM99347.1, EFN01383.1, EFN03541.1, EFO35344.1,
EFO41582.1, EFO49823.1, EFO58227.1, EFO78344.1, EFU46689.1, EFU46690.1, EFV43216.2,
EFV45902.1, EFX91402.1, EFX91403.1, EGB49275.1, EGB49276.1, EGB53897.1, EGB79046.1,
EGD85262.1, EGE11095.1, EGE12102.1, EGE12619.1, EGE14942.1, EGE19077.1, EGE19369.1,
EGE21989.1, EGE24486.1, EGE25421.1, EGE27752.1, EGF40126.1, EGJ07916.1, EGJ59631.1,

TABLE 25-continued

Type I-F cys2 polypeptide accession numbers
(the sequence identifier for each accession number, in the
order provided in Table 25, is SEQ ID NOs: 8615-9867).

EGJ63888.1, EGK17297.1, EGM77973.1, EGP02214.1, EGP02617.1, EGP02827.1, EGS63958.1,
EGW44655.1, EGW90822.1, EGY35785.1, EGY38130.1, EGY39147.1, EGY41121.1, EGY70946.1,
EHG01972.1, EHG01973.1, EHJ62063.1, EHJ94022.1, EHK62470.1, EHM40142.1, EHM40143.1,
EHN98429.1, EHN98430.1, EIA37120.1, EIC20985.1, EIC29312.1, EIE47039.1, EIF30433.1,
EIF44410.1, EIK45282.1, EIL54441.1, EIL89114.1, EIQ04711.1, EIQ87532.1, EIQ88767.1, EIQ89494.1,
EIR01143.1, EIR02487.1, EIR05613.1, EIR16472.1, EIR17421.1, EIR19479.1, EIR30996.1, EIR32511.1,
EIR33322.1, EIR45359.1, EIR46447.1, EIR47971.1, EIR59136.1, EIR59981.1, EIR64114.1, EIR73558.1,
EIR75600.1, EIR76605.1, EIR87355.1, EIR89801.1, EIR91668.1, EIS03546.1, EIS03932.1, EIS05048.1,
EIS16926.1, EIS17791.1, EIS23398.1, EIS28665.1, EIS31267.1, EIS40839.1, EIS42734.1, EIS44210.1,
EIS55613.1, EIS56043.1, EIS60020.1, EIS66596.1, EIS73043.1, EIS76073.1, EIS78311.1, EIS86653.1,
EIS90404.1, EIS94485.1, EIS98161.1, EIT05328.1, EIT13606.1, EIT14716.1, EIT15455.1, EIT26170.1,
EIT29052.1, EIT30490.1, EIT40105.1, EIT44652.1, EIT45185.1, EIT55054.1, EIT56868.1, EIT62391.1,
EJG22853.1, EJH60544.1, EJI84873.1, EJJ29961.1, EJM51923.1, EJM65813.1, EJM74211.1,
EJO40234.1, EJP50675.1, EJS85445.1, EJS91481.1, EJS92992.1, EJZ16269.1, EJZ79576.1,
EJZ80876.1, EKA43935.1, EKA54578.1, EKA74427.1, EKE17716.1, EKF84295.1, EKG52541.1,
EKG57736.1, EKG62912.1, EKG63402.1, EKG72467.1, EKG93024.1, EKK08318.1, EKK18170.1,
EKK94024.1, EKL08414.1, EKL14869.1, EKL16052.1, EKL22306.1, EKL39436.1, EKL48989.1,
EKL93518.1, EKM01119.1, EKM08462.1, EKP54932.1, EKP56482.1, EKS45298.1, EKT62226.1,
EKU52245.1, EKX72657.1, EKX95269.1, ELC02439.1, ELC02440.1, ELC12193.1, ELC12194.1,
ELC21171.1, ELC30643.1, ELC31986.1, ELD54444.1, ELD92477.1, ELE13999.1, ELE14000.1,
ELE25613.1, ELE25614.1, ELE34549.1, ELE34550.1, ELE51939.1, ELE82362.1, ELE93037.1,
ELF40643.1, ELF68855.1, ELF84512.1, ELF93398.1, ELF93399.1, ELF98794.1, ELG17252.1,
ELG17253.1, ELG28216.1, ELG28217.1, ELG56200.1, ELG56201.1, ELG59753.1, ELG59754.1,
ELH17522.1, ELH33234.1, ELH65836.1, ELH83715.1, ELH95194.1, ELH95195.1, ELH95741.1,
ELH95742.1, ELI27977.1, ELI75035.1, ELI90642.1, ELJ31992.1, ELJ44081.1, ELJ44082.1, ELJ56851.1,
ELJ56852.1, ELJ58413.1, ELJ58414.1, ELJ73179.1, ELT18756.1, ELT56867.1, ELU49893.1,
ELX04694.1, ELY20636.1, EME59649.1, EMI19652.1, EMP51886.1, EMT98186.1, EMT98703.1,
EMU01025.1, EMU07890.1, EMU15105.1, EMU33767.1, EMV25763.1, EMV41478.1, EMV48350.1,
EMV61752.1, EMV77002.1, EMV77661.1, EMV79455.1, EMW06846.1, EMW07145.1, EMW11059.1,
EMW22773.1, EMW28013.1, EMW63400.1, EMX55466.1, EMX95471.1, EMZ59015.1, EMZ71020.1,
ENA68769.1, ENA70832.1, ENO94849.1, ENU20824.1, ENU25385.1, ENU26367.1, ENU36864.1,
ENU64164.1, ENU64518.1, ENU68406.1, ENU79933.1, ENU84695.1, ENU84994.1, ENU90131.1,
ENU94392.1, ENU94466.1, ENV06535.1, ENV11504.1, ENV23285.1, ENV26809.1, ENV33519.1,
ENV38701.1, ENV43129.1, ENV52234.1, ENV54186.1, ENV60435.1, ENV66342.1, ENV79711.1,
ENV88481.1, ENV99921.1, ENW17835.1, ENW36548.1, ENW39481.1, ENW64164.1, ENW68334.1,
ENW74528.1, ENW78805.1, ENW99799.1, ENX46544.1, ENZ96951.1, EOD78080.1, EOQ57499.1,
EOR06424.1, EOT14078.1, EOT16832.1, EOU37593.1, EOU37594.1, EOU39899.1, EOU39900.1,
EOU65599.1, EOU82023.1, EOU82024.1, EOU82327.1, EOV51401.1, EOV89559.1, EOV96441.1,
EOW37720.1, EOW66749.1, EOX15983.1, EOX15984.1, EOX25497.1, EPC00313.1, EPC10334.1,
EPD43985.1, EPE65661.1, EPE66428.1, EPE67790.1, EPE69699.1, EPE71677.1, EPE74057.1,
EPM42539.1, EPP24158.1, EPR80938.1, EPR81196.1, EPR88382.1, EPS74952.1, EQL85638.1,
EQL91070.1, EQM00498.1, EQM01690.1, EQM46391.1, EQM86552.1, EQN06272.1, EQN06273.1,
EQN09579.1, EQN09580.1, EQN21674.1, EQN21675.1, EQN32967.1, EQN72752.1, EQN72753.1,
EQN87316.1, EQO22616.1, EQO22617.1, EQO25948.1, EQO25949.1, EQO34068.1, EQO34069.1,
EQO52283.1, EQO63918.1, EQO63919.1, EQO87245.1, EQO87246.1, EQP27531.1, EQP27532.1,
EQP52729.1, EQP52730.1, EQP62837.1, EQP62838.1, EQP80764.1, EQP80765.1, EQQ42457.1,
EQQ42458.1, EQQ52931.1, EQQ52932.1, EQR25825.1, EQR25826.1, EQR43474.1, EQR49984.1,
EQR49985.1, EQR54853.1, EQR54854.1, EQR90839.1, EQR90840.1, EQT05353.1, EQT05354.1,
EQT30874.1, EQT30875.1, EQT84175.1, EQT84176.1, EQT86453.1, EQT86454.1, EQU02187.1,
EQU02188.1, EQU15316.1, EQU15701.1, EQU15702.1, EQU26654.1, EQU26655.1, EQU37327.1,
EQU37328.1, EQU74183.1, EQU74184.1, EQU96773.1, EQU96774.1, EQV16498.1, EQV16499.1,
EQV39103.1, EQV39104.1, EQV73992.1, EQW35603.1, EQW35604.1, EQW74766.1, EQW95169.1,
EQW95170.1, EQX30755.1, EQX30756.1, EQY04009.1, EQY04010.1, EQY05738.1, EQY05739.1,
EQY46990.1, EQY47416.1, EQZ21535.1, EQZ57878.1, EQZ57879.1, EQZ59929.1, EQZ59930.1,
EQZ81917.1, EQZ81918.1, ERA24940.1, ERA24941.1, ERA25707.1, ERA25708.1, ERA94143.1,
ERA94144.1, ERB37231.1, ERB37232.1, ERG09344.1, ERG16854.1, ERG53586.1, ERG59564.1,
ERH66546.1, ERL42547.1, ERO62442.1, ERP69292.1, ERP72009.1, ERP72731.1, ERP73550.1,
ERP82385.1, ERT12421.1, ERT61667.1, ERU80870.1, ERU82774.1, ERU95635.1, ERV23078.1,
ERV32404.1, ERV45937.1, ERV90882.1, ERV92839.1, ERW22631.1, ERW25388.1,
ERW30732.1, ERW52655.1, ERW66575.1, ERW85640.1, ERW96791.1, ERX11463.1, ERX57182.1,
ERX57291.1, ERX68374.1, ERX76658.1, ERY56084.1, ERY93180.1, ERY99966.1, ERZ00044.1,
ERZ29313.1, ERZ42446.1, ESD40182.1, ESE13076.1, ESE13077.1, ESK35633.1, ESK57656.1,
ESM77260.1, ESM81557.1, ESN04282.1, ESN26374.1, ESN52893.1, ESN61385.1, ESP24739.1,
ESP24740.1, ESP31908.1, ESP31909.1, ESP34910.1, ESP34911.1, ESQ71809.1, EST01751.1,
ESV68075.1, ESW43324.1, ETD57410.1, ETD60296.1, ETD64803.1, ETF26481.1, ETF26482.1,
ETJ46807.1, ETJ94590.1, ETQ64199.1, ETR05197.1, ETR05666.1, ETR14608.1, ETR84942.1,
ETS22726.1, ETT12868.1, ETT14317.1, ETT20303.1, ETU83909.1, ETU88441.1, ETV19933.1,
ETV55560.1, ETX25632.1, ETX50993.1, ETX59143.1, ETX78939.1, ETY51219.1, ETY51220.1,
ETY53939.1, ETY53940.1, EUC25474.1, EUC91105.1, EUC95220.1, EUD17216.1, EUL88077.1,
EUM12619.1, EUM12624.1, EVT81600.1, EVU15060.1, EWS67918.1, GAA59875.1, GAA60411.1,
GAA75156.1, GAA77962.1, GAA79126.1, GAA79127.1, GAB76061.1, GAC09609.1, GAC15831.1,
GAC19766.1, GAC34442.1, GAD77037.1, GAD89661.1, GAE10393.1, NP_218566.1, NP_245243.1,
NP_669042.1, NP_800898.1, NP_901423.1, NP_929072.1, NP_993612.1, O83163.1, Q02MM0.1,
WP_000092766.1, WP_000092767.1, WP_000092768.1, WP_000092769.1, WP_000120896.1,
WP_000120897.1, WP_000120898.1, WP_000120899.1, WP_000120900.1, WP_000120901.1,
WP_000120902.1, WP_000120903.1, WP_000120904.1, WP_000164158.1, WP_000164159.1,

TABLE 25-continued

Type I-F cys2 polypeptide accession numbers
(the sequence identifier for each accession number, in the
order provided in Table 25, is SEQ ID NOs: 8615-9867).

WP_001101620.1, WP_001101621.1, WP_001112159.1, WP_001194012.1, WP_001215683.1,
WP_001215684.1, WP_001377968.1, WP_001387630.1, WP_001516090.1, WP_001695684.1,
WP_001712676.1, WP_001982951.1, WP_002047792.1, WP_002211868.1, WP_002225497.1,
WP_002225602.1, WP_002430404.1, WP_002540931.1, WP_002802606.1, WP_002811940.1,
WP_002923967.1, WP_003116910.1, WP_003147065.1, WP_003159089.1, WP_003162918.1,
WP_003464680.1, WP_003662185.1, WP_003664172.1, WP_003673461.1, WP_003842036.1,
WP_004234138.1, WP_004279691.1, WP_004343804.1, WP_004389636.1, WP_004651372.1,
WP_004652095.1, WP_004662983.1, WP_004681363.1, WP_004713757.1, WP_004728798.1,
WP_004752519.1, WP_004758710.1, WP_004770611.1, WP_004798548.1, WP_004801338.1,
WP_004828410.1, WP_004863335.1, WP_004877063.1, WP_004895762.1, WP_004907047.1,
WP_004918642.1, WP_004928487.1, WP_004948466.1, WP_004963260.1, WP_004998564.1,
WP_005003490.1, WP_005024345.1, WP_005026491.1, WP_005048554.1, WP_005081860.1,
WP_005163437.1, WP_005217652.1, WP_005370438.1, WP_005371074.1, WP_005378542.1,
WP_005463135.1, WP_005472986.1, WP_005478157.1, WP_005497851.1, WP_005499642.1,
WP_005535624.1, WP_005540023.1, WP_005562567.1, WP_005596015.1, WP_005600276.1,
WP_005603467.1, WP_005606941.1, WP_005611344.1, WP_005614487.1, WP_005616689.1,
WP_005623503.1, WP_005623506.1, WP_005721279.1, WP_005725549.1, WP_005725807.1,
WP_005751236.1, WP_005753652.1, WP_005756148.1, WP_005764760.1, WP_005769535.1,
WP_005842409.1, WP_005879780.1, WP_005974983.1, WP_006033286.1, WP_006052519.1,
WP_006174405.1, WP_006365990.1, WP_006790331.1, WP_006790332.1, WP_007011900.1,
WP_007069541.1, WP_007106207.1, WP_007111958.1, WP_007117096.1, WP_007181148.1,
WP_007293314.1, WP_007460967.1, WP_007607346.1, WP_007620985.1, WP_007641673.1,
WP_007749065.1, WP_007815612.1, WP_007986848.1, WP_007990663.1, WP_007994009.1,
WP_008022977.1, WP_008129239.1, WP_008133919.1, WP_008135462.1, WP_008135464.1,
WP_008168509.1, WP_008169481.1, WP_008215111.1, WP_008220721.1, WP_008247106.1,
WP_008608780.1, WP_008698005.1, WP_008845636.1, WP_008869718.1, WP_008898788.1,
WP_008911672.1, WP_009095258.1, WP_009151388.1, WP_009174233.1, WP_009288125.1,
WP_009368458.1, WP_009514914.1, WP_009832550.1, WP_009875010.1, WP_009875011.1,
WP_009876498.1, WP_010106218.1, WP_010201102.1, WP_010279275.1, WP_010295112.1,
WP_010318158.1, WP_010364311.1, WP_010388189.1, WP_010554108.1, WP_010559723.1,
WP_010606800.1, WP_010631403.1, WP_010881575.1, WP_010906578.1, WP_011095182.1,
WP_011135305.1, WP_011146071.1, WP_011192625.1, WP_011212639.1, WP_011216755.1,
WP_011240575.1, WP_011525176.1, WP_011718588.1, WP_011769776.1, WP_011789483.1,
WP_011803946.1, WP_011809224.1, WP_011848336.1, WP_011927918.1, WP_011996911.1,
WP_011997339.1, WP_012016804.1, WP_012089884.1, WP_012104946.1, WP_012129694.1,
WP_012197493.1, WP_012203144.1, WP_012262739.1, WP_012303964.1, WP_012440591.1,
WP_012533314.1, WP_012570449.1, WP_012588885.1, WP_012667184.1, WP_012696553.1,
WP_012729575.1, WP_012764361.1, WP_012768460.1, WP_012817198.1, WP_012886076.1,
WP_012917521.1, WP_012983812.1, WP_013032250.1, WP_013042753.1, WP_013163748.1,
WP_013221693.1, WP_013319366.1, WP_013330864.1, WP_013465401.1, WP_013505551.1,
WP_013589020.1, WP_013662442.1, WP_013739763.1, WP_013804305.1, WP_013818081.1,
WP_013944828.1, WP_014016720.1, WP_014228624.1, WP_014234833.1, WP_014251761.1,
WP_014325845.1, WP_014342279.1, WP_014342713.1, WP_014390884.1, WP_014424086.1,
WP_014454508.1, WP_014500607.1, WP_014509416.1, WP_014658070.1, WP_014701306.1,
WP_014703621.1, WP_014848625.1, WP_014916578.1, WP_014995869.1, WP_015259207.1,
WP_015337044.1, WP_015551639.1, WP_015557714.1, WP_015670636.1, WP_015683962.1,
WP_015696921.1, WP_015731170.1, WP_015834853.1, WP_015862797.1, WP_016164443.1,
WP_016232821.1, WP_016248535.1, WP_016261858.1, WP_016360503.1, WP_016418865.1,
WP_016451882.1, WP_016504384.1, WP_016532754.1, WP_016785737.1, WP_016795643.1,
WP_017004728.1, WP_017019123.1, WP_017026497.1, WP_017031015.1, WP_017045320.1,
WP_017049067.1, WP_017064054.1, WP_017066106.1, WP_017089408.1, WP_017098522.1,
WP_017101566.1, WP_017108317.1, WP_017198528.1, WP_017216065.1, WP_017233561.1,
WP_017253164.1, WP_017395754.1, WP_017420289.1, WP_017448230.1, WP_017631032.1,
WP_017631279.1, WP_017785586.1, WP_017925083.1, WP_018025760.1, WP_018114351.1,
WP_018122276.1, WP_018125462.1, WP_018176611.1, WP_018285447.1, WP_018298696.1,
WP_018414917.1, WP_018676855.1, WP_018719048.1, WP_018838292.1, WP_018844146.1,
WP_018871531.1, WP_019001600.1, WP_019018098.1, WP_019022907.1, WP_019283232.1,
WP_019520402.1, WP_019543110.1, WP_019820373.1, WP_019843463.1, WP_019895601.1,
WP_019935461.1, WP_019951123.1, WP_019951124.1, WP_019985485.1, WP_020065396.1,
WP_020161984.1, WP_020328488.1, WP_020332815.1, WP_020393890.1, WP_020443857.1,
WP_020680649.1, WP_020841380.1, WP_020911193.1, WP_021017052.1, WP_021325939.1,
WP_021511407.1, WP_021515757.1, WP_021710780.1, WP_021760541.1, WP_022027306.1,
WP_022381642.1, WP_022498162.1, WP_022642201.1, WP_022654590.1, WP_022772662.1,
WP_022850860.1, WP_022940476.1, WP_023045107.1, WP_023052957.1, WP_023087477.1,
WP_023103131.1, WP_023116495.1, WP_023271487.1, WP_023320640.1, WP_023327013.1,
WP_023337013.1, WP_023404025.1, WP_023593281.1, WP_023640696.1, WP_023655988.1,
WP_023981414.1, WP_023982290.1, WP_023982478.1, WP_024033837.1, WP_024107196.1,
XP_001648478.1, XP_502895673.1, XP_003055745.1, XP_003239553.1, XP_003722415.1,
XP_004144180.1, XP_004528092.1, XP_004832109.1, XP_006459595.1, YP_001052930.1,
YP_001163237.1, YP_001176136.1, YP_001209097.1, YP_001367428.1, YP_001400516.1,
YP_001424469.2, YP_001425256.1, YP_001448331.1, YP_001555796.1, YP_001562243.1,
YP_001606219.1, YP_001651266.1, YP_001712945.1, YP_001720393.1, YP_001873018.1,
YP_001906787.1, YP_001933132.1, YP_001968013.1, YP_002155777.1, YP_002304250.1,
YP_002306147.1, YP_002310402.1, YP_002324896.1, YP_002347428.1, YP_002360076.1,
YP_002396880.1, YP_002647859.1, YP_002795072.1, YP_002892562.1, YP_002955558.1,
YP_002986364.1, YP_003003059.1, YP_003041553.1, YP_003225716.1, YP_003260998.1,

TABLE 25-continued

Type I-F cys2 polypeptide accession numbers
(the sequence identifier for each accession number, in the
order provided in Table 25, is SEQ ID NOs: 8615-9867).

YP_003334980.1, YP_003377522.1, YP_003461676.1, YP_003526746.1, YP_003548201.1,
YP_003568286.1, YP_003626195.1, YP_003690840.1, YP_003761949.1, YP_003884500.1,
YP_003896174.1, YP_004069130.1, YP_004112221.1, YP_004228872.1, YP_004314376.1,
YP_004411750.1, YP_004490627.1, YP_004512321.1, YP_004672873.1, YP_004766820.1,
YP_005019133.1, YP_005025972.1, YP_005043015.1, YP_005176268.1, YP_005199869.1,
YP_005222302.1, YP_005223367.1, YP_005229910.1, YP_005274575.1, YP_005362754.1,
YP_005432672.1, YP_005474218.1, YP_005505365.1, YP_005509300.1, YP_005522413.1,
YP_005620893.1, YP_005623563.1, YP_005639255.1, YP_005801629.1, YP_005975200.1,
YP_006119165.1, YP_006218156.1, YP_006239896.1, YP_006284729.1, YP_006286211.1,
YP_006292888.1, YP_006482608.1, YP_006518016.1, YP_006648158.1, YP_006822151.1,
YP_006869473.1, YP_007217572.1, YP_007301291.1, YP_007326545.1, YP_007342966.1,
YP_007821731.1, YP_007826785.1, YP_007935926.1, YP_008091000.1, YP_008118899.1,
YP_008267627.1, YP_008528750.1, YP_008570808.1, YP_008570809.1, YP_008590828.1,
YP_008682385.1, YP_008685344.1, YP_008981898.1, YP_047071.1, YP_051770.1, YP_071019.1,
YP_122342.1, YP_128165.1, YP_162418.2, YP_344732.1, YP_539910.1, YP_539911.1, YP_647989.1,
YP_651873.1, YP_790816.1, YP_851978.1, YP_871478.1, YP_942815.1, YP_963570.1, YP_984813.1,
and/or YP_996235.1

In some embodiments, Type I-F cas7/cys3 polypeptides include, but are not limited to, GenBank accession number as set forth in Table 26.

TABLE 26

Type I-F cas7/cys3 polypeptide accession numbers
(the sequene identifier for each accession number, in the
order provided in Table 26, is SEQ ID NOs: 9868-11057).

AAK02391.1, AAM85294.1, AAO89723.2, AAQ59426.1, AAS62488.1, AAV89308.1, ABA59203.1,
ABE06381.1, ABG13927.1, ABG18388.1, ABJ00265.1, ABJ11604.1, ABK50071.1, ABM03217.1,
ABM25015.1, ABM40736.1, ABM57216.1, ABN73324.1, ABP40263.1, ABP57350.1, ABP60086.1,
ABQ14256.1, ABS09364.1, ABS46029.1, ABS77636.2, ABS78227.1, ABU74105.1, ABX33859.1,
ABX50535.1, ABX78894.1, ABX85185.1, ABY68821.1, ACA67941.1, ACC89560.1, ACD38772.1,
ACE60870.1, ACH66461.1, ACJ19106.1, ACJ21003.1, ACJ27816.1, ACJ42247.1, ACJ57414.1,
ACK48652.1, ACO74064.1, ACQ92977.1, ACS84541.1, ACT05581.1, ACV75131.1, ACX89390.1,
ACY59061.1, ACY62908.1, ACZ78273.1, ADC72941.1, ADE14360.1, ADE65023.1, ADE89794.1,
ADG60303.1, ADH86220.1, ADJ29629.1, ADL13485.1, ADM99942.1, ADN71992.1, ADR26232.1,
ADT68978.1, ADT95522.1, ADU65664.1, ADV98277.1, ADX89041.1, ADX89500.1, ADZ92539.1,
AEC02367.1, AEC18349.1, AEF92271.1, AEF99822.1, AEH62441.1, AEL09138.1, AEL73394.1,
AEO64331.1, AEO75097.1, AET15300.1, AEX04895.1, AEX24996.1, AEX51730.1, AFF23584.1,
AFG36512.1, AFH95466.1, AFI46136.1, AFI86380.1, AFI91856.1, AFJ02200.1, AFM64905.1,
AFN56493.1, AFR04906.1, AFT71807.1, AGA34090.1, AGB12637.1, AGB80782.1, AGG09387.1,
AGG09393.1, AGG31841.1, AGP49333.1, AGQ92516.1, AGU98411.1, AGW13659.1, AGX88281.1,
AHB09919.1, AHC77003.1, AHE63725.1, AHE99152.1, AHF01505.1, AHI99023.1, BAC62732.1,
BAH15059.1, BAH77671.1, BAL82650.1, CAE14088.1, CAG69250.1, CAG76581.1, CAH17085.1,
CAH17367.1, CAH21744.1, CAL21091.1, CAM85943.1, CAO95890.1, CAP75355.1, CAQ84809.1,
CAR02245.1, CAR07058.1, CAX54610.1, CAY73259.1, CBA17529.1, CBA76127.1, CBV40990.1,
CBX29757.1, CBX29758.1, CCC73992.1, CCG18725.1, CCG19558.1, CCG88215.1, CCH40238.1,
CCJ84616.1, CCO00436.1, CCO24443.1, CCQ87262.1, CCZ55218.1, CDD80273.1, CDF05510.1,
CDG79717.1, CDH64396.1, EAQ67602.1, EAS64065.1, EAS76233.1, EAT04044.1, EAT59335.1,
EAX33533.1, EAZ52874.1, EAZ58297.1, EDK28163.1, EDM42115.1, EDM61485.1, EDM65938.1,
EDM65955.1, EDQ01681.1, EDR31163.1, EDR37799.1, EDR44804.1, EDR55774.1, EDR63809.1,
EDU58858.1, EDV62095.1, EDZ66531.1, EEC00793.1, EED26506.1, EEH84599.1, EEO29371.1,
EEO76099.1, EEO80176.1, EEO84408.1, EEO89850.1, EEP92233.1, EEQ03934.1, EEQ60552.1,
EEV21617.1, EEV21943.1, EEW05503.1, EEW96607.1, EEX04035.1, EEX50302.1, EEX68261.1,
EEY43700.1, EEY90279.1, EEZ00497.1, EFA49551.1, EFA49552.1, EFC58009.1, EFC99289.1,
EFI23594.1, EFI34393.1, EFL78323.1, EFL79686.1, EFM01119.1, EFM53865.1, EFM86279.1,
EFM88412.1, EFM90570.1, EFM92757.1, EFM95003.1, EFM97157.1, EFM99346.1, EFN01382.1,
EFN03540.1, EFO35311.1, EFO41813.1, EFO50039.1, EFO58226.1, EFP04516.1, EFQ88867.1,
EFU46688.1, EFV45901.1, EFX91404.1, EGB49274.1, EGB53898.1, EGB79045.1, EGC70202.1,
EGE11096.1, EGE12103.1, EGE12618.1, EGE14943.1, EGE19076.1, EGE19368.1, EGE21988.1,
EGE24485.1, EGE25420.1, EGE27753.1, EGF40127.1, EGH81486.1, EGJ07915.1, EGJ59630.1,
EGJ63889.1, EGM77972.1, EGP02204.1, EGP02205.1, EGP02206.1, EGP02209.1, EGP02618.1,
EGS63959.1, EGW44656.1, EGW90823.1, EGY35786.1, EGY38131.1, EGY39145.1, EGY39146.1,
EGY41120.1, EGY70945.1, EHF03401.1, EHG01974.1, EHJ94021.1, EHK62471.1, EHL67983.1,
EHM40144.1, EHM48027.1, EHN98431.1, EHO30911.1, EIA37121.1, EIC20986.1, EIC29313.1,
EIE47038.1, EIF44411.1, EIK45281.1, EIL54442.1, EIL76431.1, EIL89115.1, EIQ87530.1, EIQ88766.1,
EIQ89493.1, EIR01142.1, EIR02486.1, EIR05624.1, EIR16494.1, EIR17420.1, EIR19478.1, EIR31005.1,
EIR32504.1, EIR33321.1, EIR45350.1, EIR46431.1, EIR47970.1, EIR59144.1, EIR59980.1, EIR64113.1,
EIR73545.1, EIR75599.1, EIR76604.1, EIR87354.1, EIR89807.1, EIR91674.1, EIS03545.1, EIS03931.1,
EIS05047.1, EIS16929.1, EIS17794.1, EIS23397.1, EIS28671.1, EIS31266.1, EIS40838.1, EIS42728.1,
EIS44209.1, EIS55612.1, EIS56042.1, EIS60019.1, EIS66595.1, EIS73042.1, EIS76074.1, EIS78310.1,
EIS86652.1, EIS90396.1, EIS94484.1, EIS98160.1, EIT05327.1, EIT13605.1, EIT14715.1, EIT15446.1,

TABLE 26-continued

Type I-F cas7/cys3 polypeptide accession numbers
(the sequene identifier for each accession number, in the
order provided in Table 26, is SEQ ID NOs: 9868-11057).

EIT26175.1, EIT29051.1, EIT30489.1, EIT44651.1, EIT45184.1, EIT55053.1, EIT56867.1, EIT62390.1,
EIY36378.1, EJG24061.1, EJH60545.1, EJI84872.1, EJO38756.1, EJP50279.1, EJS85446.1,
EJS90160.1, EJS91479.1, EJS91480.1, EJS92991.1, EJZ79577.1, EJZ80877.1, EKA43934.1,
EKA54577.1, EKA74310.1, EKA81282.1, EKA84798.1, EKA91161.1, EKF84296.1, EKG52542.1,
EKG57737.1, EKG62913.1, EKG63403.1, EKG72468.1, EKG93025.1, EKK08296.1, EKK18171.1,
EKK94025.1, EKL08415.1, EKL14870.1, EKL16053.1, EKL22307.1, EKL39311.1, EKL48987.1,
EKL93519.1, EKM01141.1, EKM08463.1, EKP50107.1, EKP55006.1, EKP56619.1, EKS45297.1,
EKT62225.1, EKU52223.1, EKX95268.1, ELC02441.1, ELC12195.1, ELC21172.1, ELC30644.1,
ELC31987.1, ELD54445.1, ELD92478.1, ELE14001.1, ELE25615.1, ELE34551.1, ELE51940.1,
ELE82363.1, ELE93038.1, ELF40644.1, ELF68856.1, ELF84513.1, ELF93400.1, ELF98795.1,
ELG17254.1, ELG28218.1, ELG56202.1, ELG59755.1, ELH17523.1, ELH33235.1, ELH65837.1,
ELH83716.1, ELH95196.1, ELH95743.1, ELI27978.1, ELI75036.1, ELI90643.1, ELJ31993.1,
ELJ44083.1, ELJ56853.1, ELJ58415.1, ELJ73180.1, ELQ35557.1, ELQ65711.1, ELT18757.1,
ELT56868.1, ELU49892.1, ELX04705.1, ELY22222.1, EME59648.1, EMI19653.1, EMP51885.1,
EMT98185.1, EMT98702.1, EMU01026.1, EMU03117.1, EMU03919.1, EMU06894.1, EMU15104.1,
EMU33766.1, EMV25764.1, EMV41479.1, EMV48351.1, EMV61753.1, EMV77003.1, EMV77662.1,
EMV79456.1, EMW06847.1, EMW07146.1, EMW11060.1, EMW22774.1, EMW28014.1, EMW63401.1,
EMX55467.1, EMX95472.1, EMZ59016.1, EMZ70953.1, ENA68770.1, ENA70833.1, ENO94848.1,
ENU20825.1, ENU25386.1, ENU26368.1, ENU30660.1, ENU36863.1, ENU64163.1, ENU64517.1,
ENU68405.1, ENU79932.1, ENU84694.1, ENU84993.1, ENU90130.1, ENU94393.1, ENU94467.1,
ENV06536.1, ENV11503.1, ENV23284.1, ENV26810.1, ENV33518.1, ENV38702.1, ENV43128.1,
ENV52233.1, ENV54187.1, ENV60436.1, ENV66341.1, ENV79712.1, ENV88482.1, ENV99922.1,
ENW17836.1, ENW36549.1, ENW39482.1, ENW64165.1, ENW68333.1, ENW74529.1, ENW78804.1,
ENW99798.1, ENX46543.1, ENZ96950.1, EOD78079.1, EOQ57498.1, EOR06425.1, EOT14079.1,
EOT16831.1, EOU37595.1, EOU39901.1, EOU65600.1, EOU82025.1, EOU82328.1, EOV51402.1,
EOV89560.1, EOV96442.1, EOW37721.1, EOW66750.1, EOX15985.1, EOX25498.1, EPC00312.1,
EPC10333.1, EPD43984.1, EPE63816.1, EPE65660.1, EPE66429.1, EPE67791.1, EPE69700.1,
EPE71678.1, EPE74058.1, EPH62428.1, EPH95380.1, EPM42540.1, EPP24159.1, EPR80939.1,
EPR81195.1, EPR88383.1, EPS74966.1, EQL85637.1, EQL89639.1, EQL91069.1, EQM00497.1,
EQM01689.1, EQM08160.1, EQM16133.1, EQM46390.1, EQM86551.1, EQN06271.1, EQN09578.1,
EQN21676.1, EQN32968.1, EQN72754.1, EQN87315.1, EQO22618.1, EQO25950.1, EQO34070.1,
EQO52284.1, EQO63920.1, EQO87247.1, EQP27533.1, EQP52731.1, EQP62839.1, EQP80766.1,
EQP80767.1, EQQ42459.1, EQQ52933.1, EQR25827.1, EQR43475.1, EQR49986.1, EQR54855.1,
EQR90838.1, EQT05352.1, EQT30876.1, EQT84177.1, EQT86455.1, EQU02186.1, EQU15317.1,
EQU15700.1, EQU26656.1, EQU37329.1, EQU74185.1, EQU96775.1, EQV16500.1, EQV39102.1,
EQV73993.1, EQW35605.1, EQW74765.1, EQW95167.1, EQW95168.1, EQX30757.1, EQX30758.1,
EQY04011.1, EQY05740.1, EQY46991.1, EQY47417.1, EQZ21536.1, EQZ57877.1, EQZ59931.1,
EQZ81919.1, ERA24942.1, ERA25709.1, ERA94142.1, ERB37233.1, ERF78262.1, ERG09343.1,
ERG16855.1, ERG53585.1, ERG59563.1, ERH66545.1, ERL42548.1, ERO62444.1, ERP69293.1,
ERP72008.1, ERP72730.1, ERP73549.1, ERP82384.1, ERT12422.1, ERT61725.1, ERU80869.1,
ERU82773.1, ERU95634.1, ERV23077.1, ERV32403.1, ERV45936.1, ERV90881.1, ERV92838.1,
ERW05283.1, ERW22630.1, ERW25387.1, ERW30731.1, ERW52656.1, ERW66574.1, ERW85639.1,
ERW96790.1, ERX11462.1, ERX57183.1, ERX57290.1, ERX68375.1, ERX76657.1, ERY56083.1,
ERY93179.1, ERY99965.1, ERZ00043.1, ERZ29312.1, ERZ42445.1, ESD40181.1, ESE13075.1,
ESK35634.1, ESK57657.1, ESM77261.1, ESM81558.1, ESN04283.1, ESN26375.1, ESN28525.1,
ESN61386.1, ESP24738.1, ESP31910.1, ESP34909.1, ESQ71760.1, ESQ71808.1, EST01750.1,
ESV68076.1, ESW43323.1, ETD57409.1, ETF26483.1, ETJ46808.1, ETJ93022.1, ETQ64188.1,
ETR05217.1, ETR05670.1, ETR14605.1, ETR82058.1, ETR84941.1, ETS22725.1, ETT12869.1,
ETT14316.1, ETT20302.1, ETU83910.1, ETU88440.1, ETV19932.1, ETV43749.1, ETV55559.1,
ETX25633.1, ETX51000.1, ETX59131.1, ETX79026.1, ETY36823.1, ETY51221.1, ERY93941.1,
EUC25473.1, EUD17217.1, EUM12625.1, EVT81599.1, EVT85801.1, EVU15055.1, EWM39345.1,
EWS67917.1, GAA59874.1, GAA60409.1, GAA60410.1, GAA75157.1, GAA77963.1, GAA79128.1,
GAB76060.1, GAC09610.1, GAC15830.1, GAC19765.1, GAC34443.1, GAD77038.1, GAE10392.1,
NP_245244.1, NP_669043.1, NP_800899.1, NP_819209.2, NP_901422.1, NP_929073.1, NP_993611.1,
Q02MM1.1, WP_000151791.1, WP_000151792.1, WP_000151793.1, WP_000151794.1,
WP_000151795.1, WP_000417845.1, WP_000417846.1, WP_000417847.1, WP_000772598.1,
WP_000775488.1, WP_001029748.1, WP_001029749.1, WP_001029750.1, WP_001029751.1,
WP_001029752.1, WP_001029753.1, WP_001029754.1, WP_001029755.1, WP_001029756.1,
WP_001097003.1, WP_001097004.1, WP_001097005.1, WP_001107519.1, WP_001107520.1,
WP_001516091.1, WP_001707909.1, WP_001713253.1, WP_001714018.1, WP_001765856.1,
WP_002009837.1, WP_002126253.1, WP_002211867.1, WP_002232603.1, WP_002232605.1,
WP_002540929.1, WP_002802604.1, WP_002814020.1, WP_002923965.1, WP_003116112.1,
WP_003116909.1, WP_003124164.1, WP_003139222.1, WP_003143949.1, WP_003147063.1,
WP_003162919.1, WP_003170696.1, WP_003205164.1, WP_003219312.1, WP_003464683.1,
WP_003662184.1, WP_003664175.1, WP_003666005.1, WP_004089530.1, WP_004240703.1,
WP_004279690.1, WP_004343805.1, WP_004349920.1, WP_004389637.1, WP_004461135.1,
WP_004651373.1, WP_004652096.1, WP_004662984.1, WP_004670427.1, WP_004681362.1,
WP_004713758.1, WP_004728796.1, WP_004736107.1, WP_004752517.1, WP_004758707.1,
WP_004770612.1, WP_004798550.1, WP_004801336.1, WP_004828408.1, WP_004863333.1,
WP_004877064.1, WP_004895761.1, WP_004907044.1, WP_004918643.1, WP_004928488.1,
WP_004948469.1, WP_004963257.1, WP_004998562.1, WP_005003494.1, WP_005024344.1,
WP_005026493.1, WP_005048557.1, WP_005081863.1, WP_005163430.1, WP_005217651.1,
WP_005233404.1, WP_005370440.1, WP_005371075.1, WP_005378541.1, WP_005463133.1,
WP_005473079.1, WP_005478111.1, WP_005497848.1, WP_005499650.1, WP_005535622.1,
WP_005540021.1, WP_005562563.1, WP_005562565.1, WP_005596014.1, WP_005603465.1,
WP_005614485.1, WP_005616687.1, WP_005623509.1, WP_005721281.1, WP_005721282.1,

TABLE 26-continued

Type I-F cas7/cys3 polypeptide accession numbers
(the sequene identifier for each accession number, in the
order provided in Table 26, is SEQ ID NOs: 9868-11057).

WP_005721283.1, WP_005721285.1, WP_005725809.1, WP_005741648.1, WP_005751237.1,
WP_005753654.1, WP_005756149.1, WP_005764758.1, WP_005769532.1, WP_005807198.1,
WP_005815993.1, WP_005842410.1, WP_005879777.1, WP_005974981.1, WP_006033287.1,
WP_006033304.1, WP_006174407.1, WP_006187497.1, WP_006365991.1, WP_006773009.1,
WP_006790333.1, WP_006950320.1, WP_007069540.1, WP_007106208.1, WP_007111957.1,
WP_007117097.1, WP_007293315.1, WP_007620983.1, WP_007641670.1, WP_007749069.1,
WP_007986850.1, WP_008129242.1, WP_008133921.1, WP_008135466.1, WP_008168508.1,
WP_008169477.1, WP_008169478.1, WP_008215112.1, WP_008220723.1, WP_008247107.1,
WP_008608779.1, WP_008698007.1, WP_008723395.1, WP_008816754.1, WP_008845635.1,
WP_008869719.1, WP_008898787.1, WP_008911671.1, WP_009095260.1, WP_009151389.1,
WP_009174234.1, WP_009286532.1, WP_009368459.1, WP_009514887.1, WP_009832549.1,
WP_009875012.1, WP_009876499.1, WP_010106217.1, WP_010201100.1, WP_010279277.1,
WP_010295115.1, WP_010318157.1, WP_010364308.1, WP_010388192.1, WP_010554119.1,
WP_010559724.1, WP_010606801.1, WP_010906579.1, WP_010957412.1, WP_011095183.1,
WP_011135304.1, WP_011146072.1, WP_011192624.1, WP_011212638.1, WP_011216756.1,
WP_011240576.1, WP_011718587.1, WP_011769777.1, WP_011789482.1, WP_011803945.1,
WP_011809223.1, WP_011927919.1, WP_011996912.1, WP_011997340.1, WP_012016805.1,
WP_012089883.1, WP_012129695.1, WP_012197492.1, WP_012203145.1, WP_012220114.1,
WP_012262738.1, WP_012440592.1, WP_012533744.1, WP_012570450.1, WP_012570904.1,
WP_012588884.1, WP_012667185.1, WP_012696554.1, WP_012729576.1, WP_012764360.1,
WP_012768461.1, WP_012886075.1, WP_012917522.1, WP_012983813.1, WP_013032251.1,
WP_013107621.1, WP_013163747.1, WP_013221694.1, WP_013278930.1, WP_013319365.1,
WP_013330865.1, WP_013465400.1, WP_013505550.1, WP_013662441.1, WP_013739762.1,
WP_013747105.1, WP_013804304.1, WP_013818082.1, WP_014016719.1, WP_014228625.1,
WP_014234832.1, WP_014325846.1, WP_014390885.1, WP_014424087.1, WP_014454509.1,
WP_014500606.1, WP_014509417.1, WP_014701305.1, WP_014703620.1, WP_014848624.1,
WP_014916579.1, WP_014995868.1, WP_015259206.1, WP_015337043.1, WP_015422842.1,
WP_015551638.1, WP_015555713.1, WP_015670637.1, WP_015696922.1, WP_015731169.1,
WP_015834852.1, WP_015862796.1, WP_016158983.1, WP_016164444.1, WP_016237814.1,
WP_016242618.1, WP_016248536.1, WP_016380980.1, WP_016418864.1, WP_016451881.1,
WP_016533252.1, WP_016533500.1, WP_016534562.1, WP_016583645.1, WP_016584211.1,
WP_016620011.1, WP_016785736.1, WP_016795644.1, WP_017004727.1, WP_017019124.1,
WP_017026498.1, WP_017031014.1, WP_017045321.1, WP_017049066.1, WP_017058954.1,
WP_017064053.1, WP_017066107.1, WP_017089407.1, WP_017098523.1, WP_017101567.1,
WP_017108318.1, WP_017216064.1, WP_017253163.1, WP_017395755.1, WP_017448231.1,
WP_017631278.1, WP_017788585.1, WP_017791148.1, WP_018025759.1, WP_018122275.1,
WP_018125461.1, WP_018176612.1, WP_018298697.1, WP_018346686.1, WP_018347334.1,
WP_018414918.1, WP_018676854.1, WP_018719047.1, WP_018871530.1, WP_019001599.1,
WP_019018099.1, WP_019022906.1, WP_019251101.1, WP_019283233.1, WP_019520401.1,
WP_019543111.1, WP_019671930.1, WP_019820371.1, WP_019843464.1, WP_019895600.1,
WP_019935462.1, WP_019951125.1, WP_019959486.1, WP_020161985.1, WP_020328489.1,
WP_020332816.1, WP_020389180.1, WP_020393389.1, WP_020443858.1, WP_020527196.1,
WP_020680650.1, WP_020841381.1, WP_020911194.1, WP_021017053.1, WP_021325940.1,
WP_021461781.1, WP_021511406.1, WP_021525891.1, WP_021525892.1, WP_021531160.1,
WP_021575785.1, WP_021710781.1, WP_021760542.1, WP_022027305.1, WP_022381643.1,
WP_022498161.1, WP_022642203.1, WP_022654591.1, WP_022761971.1, WP_022775599.1,
WP_022850859.1, WP_022940477.1, WP_023000930.1, WP_023045108.1, WP_023053015.1,
WP_023116494.1, WP_023122498.1, WP_023131487.1, WP_023271488.1, WP_023320641.1,
WP_023327014.1, WP_023337014.1, WP_023593280.1, WP_023640695.1, WP_023655987.1,
WP_023982477.1, WP_024033838.1, WP_024107195.1, XP_001007303.1, XP_002402345.1,
XP_003087158.1, XP_003303032.1, XP_003494537.1, XP_003650667.1, XP_004404055.1,
XP_004528091.1, XP_005602236.1, XP_005602237.1, XP_005637873.1, XP_720614.1, XP_720742.1,
YP_001052929.1, YP_001163236.1, YP_001176137.1, YP_001209098.1, YP_001367427.1,
YP_001400517.1, YP_001424470.1, YP_001425257.2, YP_001448332.1, YP_001555795.1,
YP_001562244.1, YP_001596128.1, YP_001606218.1, YP_001651265.1, YP_001712946.1,
YP_001720394.1, YP_001873017.1, YP_001906788.1, YP_001968012.1, YP_002155776.1,
YP_002304251.1, YP_002306148.1, YP_002310403.1, YP_002320236.1, YP_002324897.1,
YP_002347427.1, YP_002360075.1, YP_002390703.1, YP_002396881.1, YP_002555750.1,
YP_002647860.1, YP_002795073.1, YP_002892563.1, YP_002955557.1, YP_002986363.1,
YP_003003060.1, YP_003041552.1, YP_003225715.1, YP_003260997.1, YP_003334979.1,
YP_003377523.1, YP_003461677.1, YP_003526747.1, YP_003568285.1, YP_003626196.1,
YP_003690839.1, YP_003761950.1, YP_003828550.1, YP_003884499.1, YP_003896175.1,
YP_004069129.1, YP_004112220.1, YP_004314375.1, YP_004411749.1, YP_004421246.1,
YP_004490626.1, YP_004512322.1, YP_004766819.1, YP_005019134.1, YP_005025971.1,
YP_005176269.1, YP_005199870.1, YP_005274574.1, YP_005362755.1, YP_005432673.1,
YP_005474219.1, YP_005505364.1, YP_005509301.1, YP_005522414.1, YP_005620892.1,
YP_005623564.1, YP_005639256.1, YP_005801630.1, YP_005975199.1, YP_006100125.1,
YP_006111504.1, YP_006119166.1, YP_006218157.1, YP_006239895.1, YP_006284728.1,
YP_006286212.1, YP_006292887.1, YP_006482607.1, YP_006518015.1, YP_006648159.1,
YP_006822150.1, YP_007217571.1, YP_007301292.1, YP_007326544.1, YP_007342967.1,
YP_007506214.1, YP_007821730.1, YP_007826784.1, YP_008163695.1, YP_008267628.1,
YP_008528749.1, YP_008570810.1, YP_008590829.1, YP_008682384.1, YP_008685343.1,
YP_008981897.1, YP_047072.1, YP_051771.1, YP_071018.1, YP_122341.1, YP_128166.1,
YP_162419.1, YP_344733.1, YP_539912.1, YP_647988.1, YP_651872.1, YP_790815.1, YP_851979.1,
YP_871477.1, YP_942816.1, YP_963569.1, YP_984812.1, and/or YP_996234.1

In some embodiments, Type I-F cas6f/cys4 polypeptides include, but are not limited to, GenBank accession number as set forth in Table 27.

TABLE 27

Type I-F cas6f/cys4 polypeptide accession numbers
(the sequene identifier for each accession number, in the
order provided in Table 27, is SEQ ID NOs: 11058-11528).

AAV89309.2, ABA59204.1, ABG13926.1, ABG18387.1, ABK50070.1, ABM03218.1, ABM25014.1,
ABM40735.1, ABM57215.1, ABP40262.1, ABP60087.1, ABP75546.1, ABQ13095.1, ABR71599.1,
ABS09363.1, ABS47360.1, ABX33860.1, ABX50534.1, ABX78249.1, ABX85582.1, ACA67942.1,
ACC89559.1, ACH66931.1, ACJ42246.1, ACJ58934.1, ACO74066.1, ACQ92978.1, ACS84540.1,
ACT05582.1, ACV75130.1, ACX89389.1, ACZ78272.1, ADC72942.1, ADE14361.1, ADE90298.1,
ADG60304.1, ADH86219.1, ADJ29630.1, ADT95521.1, ADU65663.1, ADV54188.1, ADV54624.1,
ADZ92538.1, AEC02366.1, AEF92270.1, AEF99823.1, AEL09139.1, AET15301.1, AEX51731.1,
AFF23585.1, AFG36513.1, AFH95467.1, AFI85399.1, AFI86381.1, AFI91855.1, AFJ02199.1,
AFN56492.1, AGA34089.1, AGB80783.1, AGG09388.1, AGG09394.1, AGG31840.1, AGQ92517.1,
AGW13660.1, AGX88280.1, AHB09918.1, AHC77002.1, AHE63726.1, AHE99151.1, AHF01504.1,
BAL82651.1, CAX54611.1, CAY73260.1, CBA17530.1, CCG88214.1, CCZ55217.1, CDD80274.1,
CDF05509.1, CDK64174.1, EAX33519.1, EDR31157.1, EDR35337.1, EDR37855.1, EDR44978.1,
EDR48741.1, EDR55755.1, EDR59630.1, EDR63807.1, EDU58859.1, EDV62090.1, EDZ65577.1,
EED26517.1, EEH84598.1, EEO29370.1, EEO29468.1, EEP92234.1, EEQ03935.1, EEQ19215.1,
EEV21944.1, EEW05504.1, EEW96606.1, EEX04034.1, EEX50301.1, EEX68262.1, EEY90278.1,
EFA49553.1, EFC58010.1, EFI23595.1, EFI34394.1, EFM86278.1, EFM88411.1, EFM90569.1,
EFM92756.1, EFM95002.1, EFM97156.1, EFM99345.1, EFN01381.1, EFN03539.1, EFO35488.1,
EFO42030.1, EFO49970.1, EFO58225.1, EFU46687.1, EGB79044.1, EGE11097.1, EGE12104.1,
EGE12617.1, EGE14944.1, EGE19075.1, EGE19367.1, EGE21987.1, EGE24484.1, EGE25419.1,
EGE27754.1, EGJ07914.1, EGJ59629.1, EGJ63890.1, EGM77971.1, EGS63960.1, EGY35787.1,
EGY38132.1, EGY39144.1, EGY41119.1, EGY70944.1, EHC04317.1, EHK62472.1, EHM40145.1,
EHM48026.1, EHN98432.1, EIC20987.1, EIC29314.1, EIF44412.1, EIK45280.1, EIL89116.1,
EJS92990.1, EKD42112.1, EKE17714.1, EKF84297.1, EKG52543.1, EKG57738.1, EKG62914.1,
EKG63404.1, EKG72469.1, EKG93026.1, EKT62224.1, EKX95267.1, ELT18758.1, ELY20635.1,
ELY22223.1, EMP51884.1, ENO94847.1, ENZ96949.1, EPC10332.1, EPE63815.1, EPE65659.1,
EPE67792.1, EPE71679.1, EPP24160.1, EPR80940.1, EPR81194.1, EPR88384.1, EQM86550.1,
ERG09342.1, ERG16856.1, ERG53584.1, ERG59562.1, ERH66544.1, ERP69294.1, ERP72007.1,
ERP72729.1, ERP73548.1, ERP82383.1, ESD40180.1, ESE13074.1, ESN61387.1, ESQ71759.1,
EST01749.1, ETJ46809.1, EVT85800.1, GAA75158.1, GAA77964.1, GAB76059.1, GAC09611.1,
GAC15829.1, GAC19764.1, GAC34444.1, NP_819208.1, Q02MM2.2, Q1RE32.1, WP_000083148.1,
WP_000083149.1, WP_000339854.1, WP_000340321.1, WP_000340322.1, WP_000350178.1,
WP_000350179.1, WP_000350182.1, WP_000350183.1, WP_000350184.1, WP_000378966.1,
WP_001104789.1, WP_001104791.1, WP_001110391.1, WP_001909069.1, WP_001982952.1,
WP_001986296.1, WP_002211866.1, WP_002802602.1, WP_002812325.1, WP_002923958.1,
WP_003116908.1, WP_003139220.1, WP_003143948.1, WP_003162920.1, WP_003464685.1,
WP_003662182.1, WP_003664177.1, WP_003666007.1, WP_003667345.1, WP_003670070.1,
WP_003670773.1, WP_003672250.1, WP_004089527.1, WP_004240702.1, WP_004279689.1,
WP_004343806.1, WP_004349921.1, WP_004389638.1, WP_004395176.1, WP_004681361.1,
WP_004713760.1, WP_004904259.1, WP_004918644.1, WP_004928490.1, WP_005026497.1,
WP_005186672.1, WP_005378540.1, WP_005473100.1, WP_005478386.1, WP_005497846.1,
WP_005499652.1, WP_005511272.1, WP_005540019.1, WP_005562562.1, WP_005565379.1,
WP_005596012.1, WP_005600275.1, WP_005606939.1, WP_005611343.1, WP_005614481.1,
WP_005616685.1, WP_005725810.1, WP_005728799.1, WP_005753657.1, WP_005764757.1,
WP_005769530.1, WP_005842411.1, WP_005974979.1, WP_006087140.1, WP_006174409.1,
WP_006790334.1, WP_007069539.1, WP_007106209.1, WP_007117098.1, WP_007293316.1,
WP_007620981.1, WP_007641668.1, WP_007986852.1, WP_008129244.1, WP_008133922.1,
WP_008135468.1, WP_008169475.1, WP_008215113.1, WP_008247108.1, WP_008608778.1,
WP_008845634.1, WP_008869720.1, WP_008898786.1, WP_008911670.1, WP_009095262.1,
WP_009174235.1, WP_009286533.1, WP_009288124.1, WP_009355633.1, WP_009832548.1,
WP_009838678.1, WP_009875013.1, WP_009876500.1, WP_010106216.1, WP_010279279.1,
WP_010295117.1, WP_010318156.1, WP_010364306.1, WP_010554110.1, WP_010559725.1,
WP_010588736.1, WP_010606802.1, WP_010906580.1, WP_011095184.1, WP_011146073.1,
WP_011212637.1, WP_011216757.1, WP_011221971.1, WP_011240577.1, WP_011703507.1,
WP_011718586.1, WP_011769778.1, WP_011789481.1, WP_011803944.1, WP_011809222.1,
WP_011919227.1, WP_011997341.1, WP_012016806.1, WP_012070375.1, WP_012089882.1,
WP_012197491.1, WP_012203146.1, WP_012220113.1, WP_012262737.1, WP_012440593.1,
WP_012534077.1, WP_012570451.1, WP_012601378.1, WP_012667186.1, WP_012696556.1,
WP_012729577.1, WP_012764359.1, WP_012768462.1, WP_012817197.1, WP_012886074.1,
WP_012917523.1, WP_012983814.1, WP_013032252.1, WP_013101298.1, WP_013107622.1,
WP_013163746.1, WP_013221695.1, WP_013319364.1, WP_013505549.1, WP_013622440.1,
WP_013739761.1, WP_013804303.1, WP_013818083.1, WP_014228626.1, WP_014325847.1,
WP_014390886.1, WP_014424088.1, WP_014509418.1, WP_014610405.1, WP_014701304.1,
WP_014703619.1, WP_014707760.1, WP_014848623.1, WP_014916580.1, WP_014995867.1,
WP_015259205.1, WP_015670638.1, WP_015696923.1, WP_015834851.1, WP_016504383.1,
WP_016785735.1, WP_017045322.1, WP_017066108.1, WP_017098524.1, WP_017108319.1,
WP_017216063.1, WP_017395756.1, WP_017448232.1, WP_017631031.1, WP_017791147.1,
WP_017926913.1, WP_019820369.1, WP_019843465.1, WP_020328490.1, WP_020841382.1,
WP_021017054.1, WP_021760543.1, WP_022027304.1, WP_022381644.1, WP_022498160.1,
WP_022654592.1, WP_022775596.1, WP_022940478.1, WP_022943263.1, WP_023593279.1,
WP_023640694.1, WP_023655986.1, WP_024107194.1, YP_001176138.1, YP_001183345.1,
YP_001209099.1, YP_001341534.1, YP_001367426.1, YP_001400518.1, YP_001555794.1,

TABLE 27-continued

Type I-F cas6f/cys4 polypeptide accession numbers
(the sequene identifier for each accession number, in the
order provided in Table 27, is SEQ ID NOs: 11058-11528).

YP_001562245.1, YP_001596127.1, YP_001720395.1, YP_001873016.1, YP_002155775.1,
YP_002320235.1, YP_002324898.1, YP_002647861.1, YP_002795075.1, YP_002892564.1,
YP_002986362.1, YP_003003061.1, YP_003225714.1, YP_003260996.1, YP_003334978.1,
YP_003377524.1, YP_003461678.1, YP_003526748.1, YP_003626197.1, YP_003690838.1,
YP_003761951.1, YP_004112219.1, YP_004314374.1, YP_004411748.1, YP_004490625.1,
YP_004512323.1, YP_005176270.1, YP_005199871.1, YP_005274573.1, YP_005362756.1,
YP_005432674.1, YP_005474220.1, YP_005639257.1, YP_005801631.1, YP_006009654.1,
YP_006010090.1, YP_006100126.1, YP_006218158.1, YP_006284727.1, YP_006286213.1,
YP_006292886.1, YP_006297044.1, YP_006518014.1, YP_007217570.1, YP_007342968.1,
YP_007506213.1, YP_008267629.1, YP_008590830.1, YP_008682383.1, YP_008981896.1,
YP_162420.2, YP_871476.1, YP_942817.1, YP_963568.1, YP_984811.1, and/or YP_996233.1

In some embodiments, Cas3 polypeptides include, but are not limited to, GenBank accession number as set forth in Table 28.

TABLE 28

Cas3 polypeptide accession numbers
(the sequene identifier for each accession number, in the
order provided in Table 28, is SEQ ID NOs: 11529-15493).

A82872, AAB89382.1, AAB91160.1, AAB98365.1, AAB98371.1, AAF30996.1, AAK41637.1,
AAK41673.1, AAK42189.1, AAL62539.1, AAL62627.1, AAL80764.1, AAM25779.1, AAM38679.1,
AAM72368.1, AAM73189.1, AAN50388.1, AAO35720.1, AAO36022.1, AAO58899.1, AAO66983.1,
AAR38876.1, AAS69549.1, AAS82462.1, AAS94335.1, AAU37598.1, AAU92783.1, AAV44424.1,
AAW74126.1, AAZ55629.1, AAZ72010.1, ABB14293.1, ABB24155.1, ABB31304.1, ABC18828.1,
ABC21145.1, ABC21629.1, ABC29591.1, ABC56823.1, ABC57331.1, ABD09411.1, ABD12698.1,
ABE48871.1, ABE96084.1, ABF44063.1, ABF44542.1, ABF89301.1, ABF91789.1, ABI67810.1,
ABI69806.1, ABJ76899.1, ABJ78235.1, ABK14431.1, ABK62334.1, ABL65464.1, ABL78751.1,
ABM29989.1, ABM34513.1, ABM80911.1, ABN07021.1, ABN53501.1, ABN54399.1, ABN69437.1,
ABO35078.1, ABO49083.1, ABO49537.1, ABP50708.1, ABP65963.1, ABP67974.2, ABP81368.1,
ABP86511.1, ABP95302.1, ABQ31016.1, ABQ47098.1, ABQ86071.1, ABQ90257.1, ABQ92673.1,
ABR47839.1, ABR48352.1, ABR54142.1, ABR56647.1, ABR74644.1, ABS22296.1, ABS51173.1,
ABS60790.1, ABU57118.1, ABU59352.1, ABU82314.1, ABV32773.1, ABV97856.1, ABW02349.1,
ABW28853.1, ABX07707.1, ABX27539.1, ABX32566.1, ABY33324.1, ABY36148.1, ABY93583.1,
ABY93798.1, ABZ82800.1, ABZ83124.1, ACA32869.1, ACA59801.1, ACA99760.1, ACB07189.1,
ACB33430.1, ACB39929.1, ACB40064.1, ACB59634.1, ACD60965.1, ACD66307.1, ACD96194.1,
ACE05063.1, ACF14187.1, ACF46440.1, ACG72014.1, ACH93761.1, ACH95048.1, ACI18894.1,
ACI19282.1, ACI20256.1, ACI20900.1, ACI50224.1, ACI51404.1, ACJ33147.1, ACJ76379.1,
ACK41909.1, ACK54968.1, ACL06606.1, ACL08914.1, ACL16920.1, ACL21948.1, ACL23508.1,
ACL24095.1, ACL48829.1, ACL62641.1, ACL64132.1, ACL75830.1, ACM04933.1, ACM51518.1,
ACM54572.1, ACM59283.1, ACN13666.1, ACN98177.1, ACN98263.1, ACO31905.1, ACO79326.1,
ACP34798.1, ACP37661.1, ACP37698.1, ACP45052.1, ACP49134.1, ACP54857.1, ACP54894.1,
ACQ71889.1, ACR11665.1, ACR41524.1, ACR76228.1, ACS24734.1, ACS33796.1, ACS39432.1,
ACS90541.1, ACS96757.1, ACT04375.1, ACT05791.1, ACT17308.1, ACU96431.1, ACV03335.1,
ACV25237.1, ACV25244.1, ACV35540.1, ACV36635.1, ACV38704.1, ACV48941.1, ACV50950.1,
ACV55943.1, ACV64361.1, ACV64476.1, ACV64955.1, ACV76424.1, ACX52110.1, ACX82534.1,
ACX92460.1, ACX95672.1, ACY48525.1, ACY96527.1, ACY97073.1, ACY98231.1, ACZ11932.1,
ACZ43323.1, ADB10235.1, ADB41980.1, ADB47144.1, ADB86651.1, ADC46647.1, ADC66005.1,
ADC69847.1, ADC69854.1, ADC74615.1, ADC88654.1, ADE02249.1, ADE15049.1, ADE56275.1,
ADE85052.1, ADG07363.1, ADG07374.1, ADG13847.1, ADG24312.1, ADG71322.1, ADG82739.1,
ADG83328.1, ADG88252.1, ADG91073.1, ADG94443.1, ADH59811.1, ADH61862.1, ADH65197.1,
ADH65311.1, ADH89239.1, ADH93443.1, ADI02109.1, ADI02511.1, ADI14777.1, ADI26432.1,
ADI36187.1, ADJ47561.1, ADJ54311.1, ADK80202.1, ADL06865.1, ADL41489.1, ADL43516.1,
ADL50598.1, ADL52044.1, ADL70071.1, ADL70152.1, ADM08199.1, ADM09596.1, ADM11310.1,
ADN01349.1, ADN51064.1, ADN55919.1, ADO45627.1, ADP38751.1, ADP70484.1, ADP74265.1,
ADP76108.1, ADP88371.1, ADQ02874.1, ADQ03682.1, ADQ08185.1, ADQ14921.1, ADQ41855.1,
ADQ42007.1, ADQ47252.1, ADR19820.1, ADT83449.1, ADU21654.1, ADU26222.1, ADU44690.1,
ADU51671.1, ADU75950.1, ADU97576.1, ADU98901.1, ADV45015.1, ADV46309.1, ADV65299.1,
ADV78762.1, ADW17641.1, ADW21871.1, ADX47759.1, ADX69768.1, ADX81772.1, ADX84850.1,
ADX89044.1, ADX89503.1, ADY01597.1, ADY32337.1, ADY55692.1, ADY61452.1, ADY61693.1,
ADZ26351.1, AEA46789.1, AEB06538.1, AEB07990.1, AEB12793.1, AEB34825.1, AEB44344.1,
AEB69536.1, AEB69628.1, AEB77509.1, AEB95258.1, AEC00931.1, AEC52733.1, AEE12856.1,
AEE14451.1, AEE48387.1, AEE91060.1, AEE94620.1, AEE97375.1, AEF18279.1, AEF19063.1,
AEF19552.1, AEF26533.1, AEF93426.1, AEF93615.1, AEG01409.1, AEG14217.1, AEG16477.1,
AEG34481.1, AEG34527.1, AEG46352.1, AEG46840.1, AEG61210.1, AEG68384.1, AEG94652.1,
AEH24643.1, AEH24650.1, AEH25129.1, AEH44114.1, AEH47545.1, AEH49389.1, AEH51233.1,
AEH51743.1, AEH52710.1, AEH61401.1, AEI14612.1, AEI37912.1, AEI38603.1, AEI51284.1,
AEJ20059.1, AEJ40708.1, AEJ53446.1, AEK19970.1, AEK44435.1, AEK72626.1, AEM38304.1,
AEM38377.1, AEM38562.1, AEM58839.1, AEM74972.1, AEM79946.1, AEN73078.1, AEN78296.1,
AEN97654.1, AEO02605.1, AEO46815.1, AEO47324.1, AEP01120.1, AEP13345.1, AER03344.1,
AER57691.1, AER59752.1, AER66006.1, AET32404.1, AET42231.1, AET91880.1, AEV15287.1,

TABLE 28-continued

Cas3 polypeptide accession numbers
(the sequene identifier for each accession number, in the
order provided in Table 28, is SEQ ID NOs: 11529-15493).

AEV69184.1, AEW01075.1, AEW06745.1, AEW20272.1, AEX45154.1, AEX75344.1, AEX84728.1,
AEY65498.1, AEY94191.1, AFA39172.1, AFA49665.1, AFC23727.1, AFD27466.1, AFD28167.1,
AFH39982.1, AFH42054.1, AFI31622.1, AFI85402.1, AFI86062.1, AFI87829.1, AFK07284.1,
AFK07934.1, AFK21440.1, AFK22398.1, AFK56999.1, AFK85420.1, AFK85609.1, AFL66342.1,
AFL66903.1, AFL68258.1, AFL73110.1, AFL81871.1, AFL94590.1, AFL96007.1, AFM22197.1,
AFM40488.1, AFN03429.1, AFN35324.1, AFN74053.1, AFN83063.1, AFO79272.1, AFR21613.1,
AFS77696.1, AFU15849.1, AFU57332.1, AFU72004.1, AFU72533.1, AFV12618.1, AFV22011.1,
AFV99699.1, AFY60377.1, AFY70022.1, AFY88490.1, AFY93139.1, AFY97157.1, AFZ31566.1,
AFZ36228.1, AFZ48716.1, AFZ54740.1, AFZ72876.1, AFZ74578.1, AGA24811.1, AGA56396.1,
AGA59188.1, AGA59290.1, AGB01360.1, AGB03157.1, AGB03722.1, AGB05366.1, AGB20225.1,
AGB28829.1, AGB40918.1, AGC48889.1, AGC49201.1, AGC68637.1, AGC68871.1, AGE29602.1,
AGF58565.1, AGF68345.1, AGF87287.1, AGG07000.1, AGG09390.1, AGG14996.1, AGG15486.1,
AGH38685.1, AGH40903.1, AGH74517.1, AGH79297.1, AGH93293.1, AGH93786.1, AGI10360.1,
AGI32657.1, AGI35539.1, AGI39649.1, AGI39869.1, AGJ61862.1, AGK02814.1, AGK16439.1,
AGK21126.1, AGK54740.1, AGK61245.1, AGK71297.1, AGL00361.1, AGL03423.1, AGM22631.1,
AGN16029.1, AGN26280.1, AGN82557.1, AGO11300.1, AGO59985.1, AGO61200.1, AGQ24924.1,
AGQ37973.1, AGQ40489.1, AGR15964.1, AGR27583.1, AGR75973.1, AGT86400.1, AGX42979.1,
AGX43469.1, AGX94067.1, AGY75622.1, AHB67949.1, AHB88121.1, AHC14004.1, AHC19698.1,
AHC35948.1, AHC52232.1, AHF04639.1, AHG05448.1, AHG75938.1, AHG77946.1, AHG79310.1,
AHG81514.1, AHG83785.1, AHG86048.1, AHG86669.1, AHH03843.1, AHH06893.1, AHH98593.1,
AHI12341.1, AHJ12410.1, AHJ17863.1, AHJ19775.1, AHJ21576.1, AHJ25216.1, B4JT42.1,
BAA30013.1, BAD39294.1, BAD39649.1, BAD49297.1, BAD59279.1, BAD72026.1, BAD84639.1,
BAD84710.1, BAE67553.1, BAF39967.1, BAF60097.1, BAF60175.1, BAG02901.1, BAG34482.1,
BAH74926.1, BAI69701.1, BAI80031.1, BAI81692.1, BAJ48042.1, BAJ48053.1, BAJ50842.1,
BAJ63262.1, BAJ64869.1, BAK19888.1, BAK22115.1, BAK63461.1, BAK54126.1, BAK54840.1,
BAK56461.1, BAK66413.1, BAK73770.1, BAK79790.1, BAK81137.1, BAK95333.1, BAL57693.1,
BAL59377.1, BAL61648.1, BAL99623.1, BAM47258.1, BAM55624.1, BAM59636.1, BAM70228.1,
BAN13318.1, CAB49887.1, CAB49933.1, CAC82713.1, CAE50741.1, CAG20009.1, CAG23839.1,
CAG85921.1, CAI07978.1, CAI36811.1, CAI54792.1, CAI83546.1, CAJ69338.2, CAJ69872.1,
CAJ73675.1, CAJ74859.1, CAO81147.1, CAP54009.1, CAP56153.1, CAT71365.1, CAZ87333.1,
CBA17362.1, CBA64403.1, CBA65389.1, CBA65917.1, CBE05592.1, CBE06410.1, CBE06725.1,
CBG02711.1, CBJ42356.1, CBK91605.1, CBK92834.1, CBK99507.1, CBL01823.1, CBL28678.1,
CBL34416.1, CBL44341.1, CBL92314.1, CBN58992.1, CBN86967.1, CBV16231.1, CBX22851.1,
CBY03039.1, CBY13641.1, CBY24163.1, CBY35617.1, CBY48113.1, CBY97120.1, CCA82578.1,
CCA92395.1, CCB93365.1, CCC40226.1, CCC74213.1, CCC80913.1, CCC81888.1, CCE23035.1,
CCE70385.1, CCE70431.1, CCF16786.1, CCF67639.1, CCF98722.1, CCG39874.1, CCG47211.1,
CCH29336.1, CCH39302.1, CCH56578.1, CCH91971.1, CCI01093.1, CCI24645.1, CCI36963.1,
CCI87322.1, CCJ00347.1, CCJ04669.1, CCJ32924.1, CCJ34804.1, CCJ37384.1, CCJ95684.1,
CCJ97150.1, CCK60669.1, CCK64991.1, CCK79125.1, CCK81116.1, CCK83452.1, CCK86078.1,
CCK87446.1, CCK87791.1, CCK88322.1, CCK90900.1, CCK91257.1, CCK91757.1, CCK94929.1,
CCK95460.1, CCK96293.1, CCK98528.1, CCK98869.1, CCK99453.1, CCL02781.1, CCL07489.1,
CCL08294.1, CCL08499.1, CCL10368.1, CCL11549.1, CCL12261.1, CCL14832.1, CCL15412.1,
CCL18865.1, CCL19411.1, CCL22787.1, CCL23334.1, CCL30688.1, CCL32494.1, CCL34646.1,
CCL35212.1, CCL38535.1, CCL39059.1, CCL39262.1, CCL42750.1, CCL43258.1, CCL46772.1,
CCL47271.1, CCL49882.1, CCL50401.1, CCL53862.1, CCL54351.1, CCL57969.1, CCL61501.1,
CCL65498.1, CCL66039.1, CCL69457.1, CCL69961.1, CCL73147.1, CCL73646.1, CCL76804.1,
CCL77342.1, CCL80652.1, CCL81171.1, CCL84106.1, CCL84681.1, CCL84887.1, CCL88298.1,
CCL88856.1, CCL91963.1, CCL92529.1, CCL96069.1, CCO07752.1, CCP41951.1, CCQ64199.1,
CCQ74032.1, CCQ92532.1, CCQ93021.1, CCQ94190.1, CCQ94850.1, CCU61100.1, CCU72642.1,
CCU78369.1, CCU84801.1, CCX34714.1, CCX48507.1, CCX71696.1, CCY33510.1, CCY40554.1,
CCY42904.1, CCY59069.1, CCY75833.1, CCZ06019.1, CCZ32688.1, CCZ61767.1, CCZ62158.1,
CCZ77974.1, CCZ80189.1, CCZ85780.1, CDA07279.1, CDA09427.1, CDA10107.1, CDA45399.1,
CDA52081.1, CDA64490.1, CDA72497.1, CDA89886.1, CDB08502.1, CDB14570.1, CDB26321.1,
CDB26705.1, CDB93765.1, CDB98421.1, CDC01245.1, CDC12998.1, CDC19292.1, CDC28488.1,
CDC34385.1, CDC38721.1, CDC44659.1, CDC50440.1, CDC66729.1, CDC79980.1, CDC92392.1,
CDC93210.1, CDD36453.1, CDD54038.1, CDD57366.1, CDD59787.1, CDD73516.1, CDD90196.1,
CDD98973.1, CDE06404.1, CDE35767.1, CDE46263.1, CDE52108.1, CDE80449.1, CDE83596.1,
CDE90309.1, CDE94634.1, CDF00453.1, CDF05500.1, CDF10538.1, CDF13246.1, CDG01443.1,
CDG36819.1, CDG37686.1, CDG64475.1, CDH12429.1, CDH15937.1, CDH34486.1, CDI40530.1,
CDI43447.1, CDI49495.1, CDI64713.1, CDM19083.1, CDM39372.1, CDM67380.1, EAA21639.1,
EAL07806.1, EAQ01271.1, EAQ10652.1, EAQ36305.1, EAR27413.1, EAS32118.2, EAS33820.2,
EAT98291.1, EAX48300.1, EAY05909.1, EAY25591.1, EAY30150.1, EBA01538.1, EDL53718.1,
EDM24313.1, EDN73318.1, EDN76108.1, EDN80092.1, EDN84726.1, EDO58925.1, EDP75025.1,
EDP14353.1, EDP20982.1, EDP25153.1, EDP75372.1, EDP75968.1, EDR99201.1, EDS00204.1,
EDS06801.1, EDS74682.1, EDS76093.1, EDS77863.1, EDT14747.1, EDT45689.1, EDT49006.1,
EDT87976.1, EDU19429.1, EDU38642.1, EDU50692.1, EDV94932.1, EDW71200.1, EDX73017.1,
EDY32901.1, EDY34617.1, EDY50238.1, EEA82746.1, EEB22223.1, EEB34859.1, EED10539.1,
EEF14674.1, EEF65985.1, EEG30527.1, EEG33497.1, EEG35953.1, EEG37133.1, EEG56414.1,
EEG71149.1, EEG75124.1, EEI14199.1, EEI20245.1, EEI64038.1, EEI86604.1, EEK17370.1,
EEK86602.1, EEL37865.1, EEL73902.1, EEM24968.1, EEN82622.1, EEN82842.1, EEO29471.1,
EEO43828.2, EEP20788.1, EEP61026.1, EEP68245.1, EEQ57501.1, EER08657.1, EER55916.1,
EES53465.1, EES63310.1, EES76422.2, EES90489.1, EET44429.1, EEI62040.1, EEI78542.1,
EEU01236.1, EEV20769.1, EEV89022.1, EEW19884.1, EEW20709.1, EEW64900.1, EEW67152.1,
EEW94247.2, EEX23201.1, EEX36423.1, EEX49288.1, EEX75936.1, EEY11077.1, EEY13112.1,
EEY17555.1, EEZ28139.1, EEZ61816.1, EEZ75906.1, EFA85676.1, EFA89358.1, EFB31591.1,
EFB38093.1, EFB38350.1, EFB90864.1, EFB90879.1, EFC51249.1, EFC81107.1, EFC87158.1,

TABLE 28-continued

Cas3 polypeptide accession numbers
(the sequene identifier for each accession number, in the
order provided in Table 28, is SEQ ID NOs: 11529-15493).

EFC90517.1, EFD10034.1, EFD25242.1, EFD93806.1, EFE72199.1, EFF22494.1, EFF35101.1,
EFF66132.1, EFF79647.1, EFF97458.1, EFG33109.2, EFG83860.1, EFH05802.1, EFH07555.1,
EFH07718.1, EFH10703.1, EFH15420.1, EFH16151.1, EFH17186.1, EFH21869.1, EFH93275.1,
EFH99030.1, EFI35150.1, EFI47367.1, EFI68559.1, EFK09596.1, EFK39565.1, EFK41205.1,
EFK85685.1, EFL31934.1, EFL84472.1, EFM09026.1, EFM24728.1, EFP59913.1, EFQ06778.1,
EFQ52067.1, EFR34556.1, EFR88682.1, EFS01190.1, EFS20744.1, EFS21648.1, EFS26649.1,
EFS28322.1, EFT83494.1, EFU63287.1, EFV01201.1, EFV16751.1, EFV21400.1, EFV34594.1,
EFV81297.1, EFV94303.1, EFW09840.1, EFW38350.1, EFW90578.1, EFX55033.1, EFX91371.1,
EFY07104.1, EGA93917.1, EGB16321.1, EGB18209.1, EGB62267.1, EGB94715.1, EGC00354.1,
EGC03297.1, EGC18027.1, EGC19799.1, EGC74255.1, EGC88910.1, EGD11110.1, EGD49240.1,
EGD50530.1, EGE48063.1, EGF23573.1, EGF30315.1, EGG91968.1, EGG92690.1, EGH09961.1,
EGH15666.1, EGH44318.1, EGH46858.1, EGH58454.1, EGH72941.1, EGH79509.1, EGJ10203.1,
EGL83972.1, EGL83995.1, EGM53069.1, EGN31536.1, EGN35868.1, EGN46218.1, EGN57519.1,
EGN64311.1, EGQ14151.1, EGQ77220.1, EGR34669.1, EGS63956.1, EGT75759.1, EGT79807.1,
EGV09281.1, EGV32622.1, EGV37148.1, EGV37208.1, EGV49999.1, EGV50073.1, EGW49960.1,
EGW53127.1, EGX28858.1, EGX58186.1, EGX72596.1, EGX99506.1, EGY17212.1, EGY31348.1,
EGY32749.1, EGY34065.1, EGY35530.1, EGY37213.1, EGY39664.1, EGY39881.1, EGY41441.1,
EGY42393.1, EGY45570.1, EGY46700.1, EGY53769.1, EGY61569.1, EGY70642.1, EGY70872.1,
EGY75560.1, EGY80085.1, EGZ43695.1, EGZ44573.1, EGZ49811.1, EHA63801.1, EHB48930.1,
EHB62321.1, EHB89135.1, EHC33898.1, EHC75648.1, EHD00339.1, EHE98233.1, EHF03247.1,
EHG19002.1, EHG23348.1, EHG32767.1, EHI57520.1, EHI68706.1, EHI70385.1, EHI77347.1,
EHJ01147.1, EHJ13335.1, EHJ25273.1, EHJ27822.1, EHJ35718.1, EHJ36415.1, EHJ47331.1,
EHK89929.1, EHL03894.1, EHL13043.1, EHL17679.1, EHL19479.1, EHL21081.1, EHL24440.1,
EHL64636.1, EHL70092.1, EHL79448.1, EHL85839.1, EHL92940.1, EHM10681.1, EHM13741.1,
EHM32926.1, EHM50506.1, EHM87976.1, EHO16226.1, EHO40938.1, EHO49962.1, EHO68883.1,
EHO77291.1, EHO85748.1, EHO85976.1, EHP69911.1, EHP86554.1, EHP88828.1, EHQ05140.1,
EHQ30580.1, EHQ52969.1, EHQ62727.1, EHR37292.1, EHR79727.1, EHS84825.1, EHV69086.1,
EHY79335.1, EIA21828.1, EIA26373.1, EIA26754.1, EIA28594.1, EIA30741.1, EIC02346.1, EIC03818.1,
EIC11167.1, EIC21115.1, EIC80038.1, EID14936.1, EID43006.1, EIF93150.1, EIG30378.1, EIG54633.1,
EII12409.1, EIJ71523.1, EIJ72206.1, EIM00774.1, EIM57400.1, EIM63784.1, EIM64766.1, EIM74523.1,
EIQ00065.1, EIT84250.1, EIT88138.1, EIW00129.1, EIW91734.1, EIY59735.1, EJF40839.1,
EJF52125.1, EJG07256.1, EJG08369.1, EJL46317.1, EJN45241.1, EJN52402.1, EJN54262.1,
EJO68220.1, EJO71294.1, EJO77844.1, EJP02505.1, EJP04930.1, EJP15618.1, EJP17851.1,
EJP19875.1, EJP23267.1, EJP29626.1, EJP85708.1, EJR93712.1, EJS10963.1, EJS45098.1,
EJU06234.1, EJU16838.1, EJU19961.1, EJU22340.1, EJU25588.1, EJU32127.1, EJV73278.1,
EJW09517.1, EJW17214.1, EJW82196.1, EJZ69664.1, EJZ85814.1, EKA01293.1, EKA13056.1,
EKA91355.1, EKB47818.1, EKD25942.1, EKD55710.1, EKE30556.1, EKE43332.1, EKG52539.1,
EKG57734.1, EKG62910.1, EKG63400.1, EKG72465.1, EKG93022.1, EKI36920.1, EKK94022.1,
EKL08412.1, EKL14867.1, EKL16050.1, EKL22304.1, EKL93516.1, EKM01145.1, EKM08460.1,
EKM99101.1, EKN16816.1, EKN22397.1, EKN28556.1, EKN67977.1, EKN86875.1, EKN88349.1,
EKN96987.1, EKO04942.1, EKO14466.1, EKO24574.1, EKO26697.1, EKO32500.1, EKO52371.1,
EKO52653.1, EKO59403.1, EKO61592.1, EKO69587.1, EKO70653.1, EKO77440.1, EKO79148.1,
EKO94703.1, EKO96202.1, EKP03649.1, EKP04460.1, EKP14641.1, EKP22570.1, EKP76315.1,
EKP83838.1, EKP95533.1, EKQ37062.1, EKQ39127.1, EKQ46592.1, EKQ47948.1, EKQ76725.1,
EKQ84991.1, EKQ85289.1, EKQ92341.1, EKQ99808.1, EKR06850.1, EKR08167.1, EKR15339.1,
EKR25310.1, EKR27775.1, EKR36474.1, EKR46947.1, EKR57319.1, EKR63579.1, EKR74663.1,
EKR81630.1, EKR84713.1, EKR90045.1, EKS02024.1, EKS09343.1, EKS09475.1, EKT85826.1,
EKU24261.1, EKU43640.1, EKU78427.1, EKU91951.1, EKU95518.1, EKX88305.1, EKX94127.1,
EKX95309.1, EKY02928.1, ELA07948.1, ELH35798.1, ELH49225.1, ELI28693.1, ELK21783.1,
ELK22578.1, ELQ17188.1, ELR65959.1, ELR72966.1, ELS04216.1, ELT18754.1,
ELT51926.1, ELT53860.1, ELT59291.1, ELV09153.1, ELW71756.1, ELY32095.1, ELY41479.1,
ELY64892.1, ELY69634.1, ELY72598.1, ELY84664.1, ELZ04990.1, ELZ06192.1, ELZ40748.1,
ELZ59540.1, ELZ60429.1, ELZ68875.1, ELZ71861.1, ELZ72260.1, ELZ84576.1, ELZ89349.1,
ELZ93661.1, ELZ97243.1, ELZ99742.1, EMA05599.1, EMA08152.1, EMA18800.1, EMA25144.1,
EMA34112.1, EMA56846.1, EMA69346.1, EMB14050.1, EMD31853.1, EMD37413.1, EME03974.1,
EME83389.1, EMF30787.1, EMF35383.1, EMF41746.1, EMF56342.1, EMF70591.1, EMF80240.1,
EMF90484.1, EMG01549.1, EMG09248.1, EMG31014.1, EMH94950.1, EMI10503.1, EMI28180.1,
EMI57446.1, EMI63031.1, EMI66058.1, EMI67349.1, EMI69780.1, EMI71641.1, EMJ34611.1,
EMJ36108.1, EMJ45623.1, EMJ47435.1, EMJ52875.1, EMJ54316.1, EMJ55098.1, EMJ58565.1,
EMJ63194.1, EMJ65258.1, EMJ68919.1, EMJ69812.1, EMJ72474.1, EMJ74248.1, EMJ80477.1,
EMJ80648.1, EMJ83296.1, EMJ85541.1, EMJ91110.1, EMJ92590.1, EMK02765.1, EMK06056.1,
EMK07522.1, EMK08549.1, EMK10539.1, EMK14171.1, EMK16101.1, EMK18454.1, EMK23383.1,
EMK24843.1, EMK26080.1, EMM72348.1, EMM76998.1, EMM84368.1, EMM85990.1,
EMM88565.1, EMM92118.1, EMM95757.1, EMM98808.1, EMN02654.1, EMN05708.1, EMN06831.1,
EMN08538.1, EMN23280.1, EMN26929.1, EMN27444.1, EMN30500.1, EMN35886.1, EMN37001.1,
EMN38877.1, EMN40237.1, EMN46520.1, EMN50253.1, EMN52157.1, EMN53645.1, EMN58263.1,
EMN64601.1, EMN69109.1, EMN71256.1, EMN72171.1, EMN74279.1, EMN77340.1, EMN81816.1,
EMN82468.1, EMN85327.1, EMN89990.1, EMN94815.1, EMN96888.1, EMN97741.1, EMN98295.1,
EMO07500.1, EMO08696.1, EMO14454.1, EMO14780.1, EMO16223.1, EMO21355.1, EMO23320.1,
EMO29540.1, EMO30696.1, EMO33387.1, EMO36352.1, EMO42416.1, EMO44418.1, EMO48161.1,
EMO51803.1, EMO56069.1, EMO60007.1, EMO65721.1, EMO68743.1, EMO69635.1, EMO73270.1,
EMO74239.1, EMO77649.1, EMO78641.1, EMO79140.1, EMO83150.1, EMO83521.1, EMO88906.1,
EMO89073.1, EMO94054.1, EMO95195.1, EMO96578.1, EMP00001.1, EMP03296.1, EMP04911.1,
EMP80131.1, EMR04142.1, EMR53804.1, EMS78532.1, EMS83942.1, EMS85264.1, EMT39598.1,
EMT47060.1, EMT51171.1, EMT52265.1, EMV20686.1, EMV40013.1, EMW18023.1, EMW94559.1,
EMX92278.1, EMY03896.1, EMY05816.1, EMY12534.1, EMY23097.1, EMY26723.1, EMY55509.1,

TABLE 28-continued

Cas3 polypeptide accession numbers
(the sequene identifier for each accession number, in the
order provided in Table 28, is SEQ ID NOs: 11529-15493).

EMY78151.1, EMY79390.1, EMZ33825.1, EMZ36272.1, ENA30283.1, ENA77979.1, ENA79233.1,
ENB26895.1, ENB33487.1, END57072.1, ENF74818.1, ENH55858.1, ENO18092.1, ENO64014.1,
ENO70114.1, ENO72462.1, ENO77315.1, ENO81517.1, ENO88272.1, ENO94488.1, ENV75859.1,
ENX62341.1, ENY72536.1, ENY88093.1, ENY95896.1, ENZ05665.1, ENZ10231.1, ENZ13876.1,
ENZ16946.1, ENZ26111.1, ENZ26403.1, ENZ39044.1, ENZ43233.1, ENZ45621.1, ENZ47415.1,
ENZ54160.1, ENZ65663.1, ENZ69351.1, ENZ72154.1, EOA48846.1, EOA55010.1, EOD01823.1,
EOH73740.1, EOH98200.1, EOK98747.1, EOQ36054.1, EOR26383.1, EOR71324.1, EOR85350.1,
EOS34141.1, EOS50043.1, EOS52985.1, EOS54124.1, EOS60749.1, EOS64689.1, EOS73777.1,
EOS81386.1, EOT28172.1, EOT59713.1, EOT81526.1, EOT82464.1, EOZ98894.1, EPC07706.1,
EPD26791.1, EPD37768.1, EPD73804.1, EPD77061.1, EPE60581.1, EPE61218.1, EPE82200.1,
EPE83106.1, EPG48147.1, EPG50248.1, EPG59032.1, EPG81685.1, EPI61098.1, EPI66853.1,
EPL64360.1, EPM81961.1, EPP16777.1, EPP17870.1, EPR34127.1, EPR39928.1, EPR43455.1,
EPS25302.1, EPT33668.1, EPX80546.1, EPY00200.1, EPZ01041.1, EPZ01870.1, EPZ27877.1,
EPZ29483.1, EPZ29863.1, EPZ39767.1, EQA36843.1, EQA44025.1, EQA60409.1, EQA71142.1,
EQA80741.1, EQE08411.1, EQE09392.1, EQE22719.1, EQE23424.1, EQE38501.1, EQE39192.1,
EQE41871.1, EQE43063.1, EQE47806.1, EQE53151.1, EQE68292.1, EQE68942.1, EQE74684.1,
EQE90184.1, EQE92082.1, EQF02570.1, EQF05751.1, EQF10567.1, EQF14265.1, EQF18484.1,
EQF26960.1, EQF31380.1, EQF36043.1, EQF38900.1, EQF50395.1, EQF51992.1, EQF52847.1,
EQF60174.1, EQF60779.1, EQF66130.1, EQF67397.1, EQF74261.1, EQF75116.1, EQF79634.1,
EQF80477.1, EQF94905.1, EQF98043.1, EQG00969.1, EQG02089.1, EQG09649.1, EQG18536.1,
EQG25400.1, EQG32966.1, EQG33557.1, EQG34473.1, EQG40556.1, EQG45069.1, EQG51715.1,
EQG59858.1, EQG65544.1, EQG69423.1, EQG77053.1, EQG78886.1, EQG81962.1, EQG83633.1,
EQG94071.1, EQG94500.1, EQH12985.1, EQH17954.1, EQH34295.1, EQH35108.1, EQH35210.1,
EQH37869.1, EQH51122.1, EQH59205.1, EQH63460.1, EQH66791.1, EQH67918.1, EQH70277.1,
EQH70390.1, EQH74803.1, EQH75580.1, EQH80103.1, EQH82323.1, EQH88065.1, EQH93750.1,
EQH96575.1, EQH97199.1, EQI02705.1, EQI10736.1, EQI22141.1, EQI33687.1, EQI38169.1,
EQI45906.1, EQI54641.1, EQI55928.1, EQI72787.1, EQI78469.1, EQI79463.1, EQI85815.1,
EQI90985.1, EQI99102.1, EQJ06189.1, EQJ09400.1, EQJ29787.1, EQJ34932.1, EQJ38317.1,
EQJ39103.1, EQJ49186.1, EQJ51305.1, EQJ55005.1, EQJ67541.1, EQJ77202.1, EQJ77539.1,
EQJ78490.1, EQJ94680.1, EQK00624.1, EQK02220.1, EQK05298.1, EQK11680.1, EQK17629.1,
EQK21844.1, EQK30840.1, EQK38720.1, EQK69061.1, EQK70288.1, EQK74204.1, EQK74849.1,
EQK75067.1, EQK76493.1, EQK85633.1, EQK86103.1, EQK87001.1, EQL06443.1, EQL07764.1,
EQM72183.1, EQQ19466.1, ERF59736.1, ERF73398.1, ERF77710.1, ERG84986.1, ERG92582.1,
ERH14166.1, ERH21167.1, ERH28582.1, ERH28848.1, ERI04811.1, ERI06128.1, ERI07857.1,
ERI68079.1, ERI74755.1, ERI93851.1, ERJ00270.1, ERJ18000.1, ERJ23348.1, ERJ27563.1,
ERJ28377.1, ERJ30380.1, ERJ63858.1, ERJ64712.1, ERJ67424.1, ERJ69592.1, ERJ75894.1,
ERJ81455.1, ERJ83443.1, ERJ84271.1, ERJ89571.1, ERJ91347.1, ERJ93150.1, ERK01555.1,
ERK03431.1, ERK56582.1, ERK64507.1, ERK89865.1, ERL64692.1, ERM25313.1, ERM29350.1,
ERM37468.1, ERM45585.1, ERM83477.1, ERM91448.1, ERN17773.1, ERP31667.1, ERP69290.1,
ERS40012.1, ERS57091.1, ERS64303.1, ERS74209.1, ERS80389.1, ERT07692.1, ERT32147.1,
ERT38008.1, ERT39869.1, ERT63105.1, ERV42110.1, ERV60146.1, ERY77981.1, ESH23406.1,
ESP86782.1, ESQ74771.1, EST01179.1, EST90151.1, ETA02740.1, ETA67349.1, ETA80091.1,
ETC74838.1, ETC88558.1, ETD02077.1, ETD17843.1, ETD20916.1, ETD77751.1, ETD86668.1,
ETE54109.1, ETI80953.1, ETI96854.1, ETK36602.1, ETO39378.1, ETO39674.1, ETZ17788.1,
ETZ19045.1, ETZ24058.1, EUB26789.1, EUB36157.1, EUC57952.1, EUJ23989.1, EUJ32652.1,
EUJ37074.1, EUJ38058.1, EUJ39374.1, EUJ40151.1, EUJ45450.1, EUJ57889.1, EWC94823.1,
EWM59169.1, G4RJZ3.1, GAA95795.1, GAB61209.1, GAB63519.1, GAC40773.1, GAC87195.1,
GAC90884.1, GAD05081.1, GAD07317.1, GAD27285.1, GAE14529.1, GAE18299.1, GAE82156.1,
NP_068912.1, NP_070699.1, NP_078421.1, NP_126656.1, NP_126702.1, NP_142841.1, NP_247350.1,
NP_247357.1, NP_342847.1, NP_342883.1, NP_343399.1, NP_375874.1, NP_378652.1, NP_558357.1,
NP_558445.1, NP_578369.1, NP_J88050.1, NP_624175.1, NP_644143.1, NP_662026.1, NP_662847.1,
NP_689391.1, NP_713370.1, NP_775649.1, NP_781783.1, NP_782085.1, NP_900894.1, NP_906084.1,
NP_940521.1, NP_963315.1, NP_982339.1, O94536.1, Q1CW46.1, Q57821.2, Q57828.1, Q6BV94.1,
WP_000038360.1, WP_000038361.1, WP_000038362.1, WP_000038364.1, WP_000236442.1,
WP_000343809.1, WP_000389287.1, WP_000506550.1, WP_000533899.1, WP_000601693.1,
WP_000601694.1, WP_000601695.1, WP_000601696.1, WP_000601698.1, WP_000601699.1,
WP_000601700.1, WP_000601701.1, WP_000601702.1, WP_000601703.1, WP_000601704.1,
WP_000601705.1, WP_000601706.1, WP_000601707.1, WP_000601708.1, WP_000601709.1,
WP_000601711.1, WP_000601712.1, WP_000637358.1, WP_000718775.1, WP_000827889.1,
WP_000827890.1, WP_000827892.1, WP_000827893.1, WP_000827896.1, WP_000827897.1,
WP_000827903.1, WP_000827904.1, WP_000827905.1, WP_000827907.1, WP_000827908.1,
WP_000827910.1, WP_000989806.1, WP_000989808.1, WP_001111734.1, WP_001233948.1,
WP_001394698.1, WP_001397702.1, WP_001416758.1, WP_001423115.1, WP_001537536.1,
WP_001613696.1, WP_001616387.1, WP_001636574.1, WP_001670744.1, WP_001696768.1,
WP_001718761.1, WP_001744249.1, WP_001971951.1, WP_001976831.1, WP_001982406.1,
WP_002025055.1, WP_002090052.1, WP_002097183.1, WP_002101799.1, WP_002102561.1,
WP_002106407.1, WP_002120618.1, WP_002129431.1, WP_002134050.1, WP_002138873.1,
WP_002145812.1, WP_002149052.1, WP_002180514.1, WP_002184099.1, WP_002187916.1,
WP_002189459.1, WP_002193570.1, WP_002198318.1, WP_002204285.1, WP_002296585.1,
WP_002299427.1, WP_002317880.1, WP_002323590.1, WP_002325837.1, WP_002330771.1,
WP_002338495.1, WP_002346439.1, WP_002568440.1, WP_002570354.1, WP_002571312.1,
WP_002577346.1, WP_002585642.1, WP_002589367.1, WP_002594033.1, WP_002595864.1,
WP_002606243.1, WP_002631668.1, WP_002633777.1, WP_002634037.1, WP_002656855.1,
WP_002695764.1, WP_002697310.1, WP_002702610.1, WP_002703150.1, WP_002725655.1,
WP_002734241.1, WP_002744093.1, WP_002748765.1, WP_002749879.1, WP_002760324.1,
WP_002765497.1, WP_002766210.1, WP_002769499.1, WP_002793659.1, WP_002822258.1,

TABLE 28-continued

Cas3 polypeptide accession numbers
(the sequene identifier for each accession number, in the
order provided in Table 28, is SEQ ID NOs: 11529-15493).

WP_002835740.1, WP_002849088.1, WP_002924830.1, WP_002938503.1, WP_002944230.1,
WP_002950094.1, WP_002951339.1, WP_002995136.1, WP_003001266.1, WP_003019324.1,
WP_003045456.1, WP_003116912.1, WP_003253162.1, WP_003272375.1, WP_003285127.1,
WP_003298383.1, WP_003330674.1, WP_003345771.1, WP_003352577.1, WP_003364902.1,
WP_003377379.1, WP_003388335.1, WP_003389993.1, WP_003393817.1, WP_003405054.1,
WP_003411614.1, WP_003416597.1, WP_003417576.1, WP_003422616.1, WP_003424502.1,
WP_003426159.1, WP_003430915.1, WP_003439784.1, WP_003464176.1, WP_003465424.1,
WP_003480734.1, WP_003480771.1, WP_003488962.1, WP_003500204.1, WP_003509199.1,
WP_003511802.1, WP_003513457.1, WP_003518145.1, WP_003557944.1, WP_003620497.1,
WP_003627154.1, WP_003680285.1, WP_003680674.1, WP_003685530.1, WP_003693855.1,
WP_003708649.1, WP_003714211.1, WP_003721308.1, WP_003744754.1, WP_003745656.1,
WP_003746225.1, WP_003754488.1, WP_003758684.1, WP_003762750.1, WP_003777787.1,
WP_003781704.1, WP_003790983.1, WP_003797752.1, WP_003811036.1, WP_003827015.1,
WP_003833376.1, WP_003834169.1, WP_003839261.1, WP_003871403.1, WP_003887835.1,
WP_003955762.1, WP_003990046.1, WP_004038948.1, WP_004040746.1, WP_004043129.1,
WP_004046325.1, WP_004053328.1, WP_004060809.1, WP_004062467.1, WP_004064675.1,
WP_004066422.1, WP_004068712.1, WP_004073070.1, WP_004074442.1, WP_004140340.1,
WP_004174175.1, WP_004220823.1, WP_004228693.1, WP_004260229.1, WP_004269026.1,
WP_004274589.1, WP_004278456.1, WP_004284063.1, WP_004299435.1, WP_004311070.1,
WP_004331265.1, WP_004333836.1, WP_004333879.1, WP_004373509.1, WP_004378890.1,
WP_004397036.1, WP_004399634.1, WP_004417293.1, WP_004420696.1, WP_004424736.1,
WP_004426862.1, WP_004433165.1, WP_004435928.1, WP_004446305.1, WP_004448860.1,
WP_004450054.1, WP_004453436.1, WP_004454738.1, WP_004456150.1, WP_004460803.1,
WP_004461820.1, WP_004465593.1, WP_004467844.1, WP_004469627.1, WP_004470803.1,
WP_004473238.1, WP_004475261.1, WP_004477311.1, WP_004477346.1, WP_004478346.1,
WP_004480114.1, WP_004480905.1, WP_004481897.1, WP_004483223.1, WP_004484155.1,
WP_004486391.1, WP_004486948.1, WP_004488659.1, WP_004489502.1, WP_004489563.1,
WP_004492043.1, WP_004492122.1, WP_004493161.1, WP_004494548.1, WP_004497010.1,
WP_004500122.1, WP_004501114.1, WP_004503356.1, WP_004508369.1, WP_004513240.1,
WP_004517274.1, WP_004520758.1, WP_004565442.1, WP_004603532.1, WP_004604885.1,
WP_004608922.1, WP_004609979.1, WP_004612298.1, WP_004617476.1, WP_004628994.1,
WP_004651369.1, WP_004751134.1, WP_004755739.1, WP_004756542.1, WP_004757818.1,
WP_004762441.1, WP_004762642.1, WP_004766473.1, WP_004767907.1, WP_004769089.1,
WP_004770101.1, WP_004778144.1, WP_004778274.1, WP_004778982.1, WP_004779839.1,
WP_004782375.1, WP_004783205.1, WP_004807169.1, WP_004820509.1, WP_004826232.1,
WP_004826835.1, WP_004853847.1, WP_004884713.1, WP_004889381.1, WP_004890807.1,
WP_004966756.1, WP_004971287.1, WP_004990091.1, WP_004993637.1, WP_005278168.1,
WP_005323014.1, WP_005345380.1, WP_005348716.1, WP_005351106.1, WP_005352686.1,
WP_005392862.1, WP_005487696.1, WP_005533723.1, WP_005540315.1, WP_005540831.1,
WP_005545917.1, WP_005547684.1, WP_005552076.1, WP_005553119.1, WP_005555124.1,
WP_005557278.1, WP_005562352.1, WP_005565160.1, WP_005565929.1, WP_005567425.1,
WP_005575141.1, WP_005576671.1, WP_005578469.1, WP_005578603.1, WP_005582026.1,
WP_005582665.1, WP_005583993.1, WP_005584761.1, WP_005587231.1, WP_005588971.1,
WP_005594953.1, WP_005610775.1, WP_005618939.1, WP_005623551.1, WP_005626998.1,
WP_005635200.1, WP_005641496.1, WP_005651105.1, WP_005659290.1, WP_005674862.1,
WP_005702609.1, WP_005703620.1, WP_005738157.1, WP_005759097.1, WP_005806403.1,
WP_005806453.1, WP_005817557.1, WP_005846115.1, WP_005856776.1, WP_005874865.1,
WP_005879976.1, WP_005910161.1, WP_005920822.1, WP_005927109.1, WP_005931444.1,
WP_005939911.1, WP_005942565.1, WP_005948318.1, WP_005957092.1, WP_005963237.1,
WP_005965994.1, WP_005966192.1, WP_005977423.1, WP_005986309.1, WP_005988922.1,
WP_006000240.1, WP_006003774.1, WP_006040012.1, WP_006060988.1, WP_006071458.1,
WP_006103819.1, WP_006114887.1, WP_006116158.1, WP_006165225.1, WP_006165798.1,
WP_006188476.1, WP_006194034.1, WP_006248102.1, WP_006250667.1, WP_006252733.1,
WP_006283988.1, WP_006288912.1, WP_006290255.1, WP_006291904.1, WP_006302701.1,
WP_006305876.1, WP_006320565.1, WP_006344761.1, WP_006354666.1, WP_006361705.1,
WP_006421768.1, WP_006432253.1, WP_006442421.1, WP_006475676.1, WP_006489322.1,
WP_006504184.1, WP_006508676.1, WP_006521013.1, WP_006521531.1, WP_006529642.1,
WP_006543631.1, WP_006555931.1, WP_006565553.1, WP_006569795.1, WP_006584176.1,
WP_006591777.1, WP_006599004.1, WP_006673620.1, WP_006676313.1, WP_006689762.1,
WP_006693575.1, WP_006695541.1, WP_006697087.1, WP_006736328.1, WP_006782617.1,
WP_006786408.1, WP_006788404.1, WP_006852984.1, WP_006860501.1, WP_006903554.1,
WP_006915304.1, WP_006928015.1, WP_006966952.1, WP_006986815.1, WP_007000523.1,
WP_007002118.1, WP_007039822.1, WP_007043771.1, WP_007131592.1, WP_007132951.1,
WP_007188930.1, WP_007203218.1, WP_007220334.1, WP_007222606.1, WP_007249159.1,
WP_007282373.1, WP_007285548.1, WP_007310315.1, WP_007348310.1, WP_007358163.1,
WP_007363022.1, WP_007364801.1, WP_007366427.1, WP_007427676.1, WP_007441153.1,
WP_007465277.1, WP_007473122.1, WP_007481209.1, WP_007497428.1, WP_007502660.1,
WP_007502707.1, WP_007525095.1, WP_007546053.1, WP_007575137.1, WP_007594600.1,
WP_007653600.1, WP_007708670.1, WP_007736479.1, WP_007742639.1, WP_007778800.1,
WP_007781428.1, WP_007791481.1, WP_007863421.1, WP_007982332.1, WP_008086256.1,
WP_008087910.1, WP_008090744.1, WP_008094402.1, WP_008164960.1, WP_008210195.1,
WP_008248777.1, WP_008274385.1, WP_008286675.1, WP_008286998.1, WP_008314377.1,
WP_008320683.1, WP_008324575.1, WP_008336138.1, WP_008354169.1, WP_008391432.1,
WP_008395459.1, WP_008398606.1, WP_008401180.1, WP_008410781.1, WP_008437586.1,
WP_008444866.1, WP_008462586.1, WP_008473514.1, WP_008494660.1, WP_008512434.1,
WP_008519405.1, WP_008523303.1, WP_008534584.1, WP_008538510.1, WP_008565746.1,

TABLE 28-continued

Cas3 polypeptide accession numbers
(the sequene identifier for each accession number, in the
order provided in Table 28, is SEQ ID NOs: 11529-15493).

WP_008572450.1, WP_008576910.1, WP_008592329.1, WP_008661066.1, WP_008664693.1,
WP_008675258.1, WP_008686022.1, WP_008687425.1, WP_008694963.1, WP_008709256.1,
WP_008712394.1, WP_008718030.1, WP_008768971.1, WP_008800823.1, WP_008801717.1,
WP_008847070.1, WP_008870464.1, WP_008902369.1, WP_008903299.1, WP_008906511.1,
WP_008908199.1, WP_008910043.1, WP_008932536.1, WP_008976787.1, WP_009002347.1,
WP_009035931.1, WP_009052108.1, WP_009054238.1, WP_009056605.1, WP_009056651.1,
WP_009062292.1, WP_009070156.1, WP_009078987.1, WP_009109521.1, WP_009117239.1,
WP_009117695.1, WP_009128505.1, WP_009143226.1, WP_009151518.1, WP_009164672.1,
WP_009164687.1, WP_009171794.1, WP_009180735.1, WP_009186590.1, WP_009194073.1,
WP_009200364.1, WP_009219478.1, WP_009220014.1, WP_009245305.1, WP_009247872.1,
WP_009255684.1, WP_009264823.1, WP_009274449.1, WP_009285143.1, WP_009290821.1,
WP_009299152.1, WP_009303809.1, WP_009304156.1, WP_009308516.1, WP_009311469.1,
WP_009317888.1, WP_009344901.1, WP_009361657.1, WP_009369775.1, WP_009371073.1,
WP_009427624.1, WP_009432992.1, WP_009441729.1, WP_009449141.1, WP_009495564.1,
WP_009501852.1, WP_009524580.1, WP_009528184.1, WP_009528498.1, WP_009531650.1,
WP_009533379.1, WP_009557947.1, WP_009578428.1, WP_009605938.1, WP_009643690.1,
WP_009646961.1, WP_009663617.1, WP_009667967.1, WP_009681865.1, WP_009742518.1,
WP_009743820.1, WP_009752219.1, WP_009755575.1, WP_009796703.1, WP_009804182.1,
WP_009832552.1, WP_009838675.1, WP_009856768.1, WP_009886020.1, WP_009887252.1,
WP_009891526.1, WP_009893604.1, WP_009893752.1, WP_009894922.1, WP_009897635.1,
WP_009898075.1, WP_009899276.1, WP_009903197.1, WP_009903367.1, WP_009905915.1,
WP_009925356.1, WP_009984824.1, WP_009985561.1, WP_009988399.1, WP_009991629.1,
WP_009996237.1, WP_010033566.1, WP_010064751.1, WP_010075382.1, WP_010076567.1,
WP_010109762.1, WP_010129883.1, WP_010174191.1, WP_010175117.1, WP_010197096.1,
WP_010214280.1, WP_010236953.1, WP_010255759.1, WP_010258238.1, WP_010260000.1,
WP_010289123.1, WP_010310345.1, WP_010346271.1, WP_010372421.1, WP_010381913.1,
WP_010413199.1, WP_010472238.1, WP_010479715.1, WP_010502804.1, WP_010528948.1,
WP_010543174.1, WP_010543771.1, WP_010571031.1, WP_010588738.1, WP_010600771.1,
WP_010619184.1, WP_010621280.1, WP_010626366.1, WP_010636398.1, WP_010679155.1,
WP_010680295.1, WP_010747303.1, WP_010761587.1, WP_010766148.1, WP_010794551.1,
WP_010868096.1, WP_010868140.1, WP_010869875.1, WP_010869882.1, WP_010877585.1,
WP_010879367.1, WP_010885008.1, WP_010923377.1, WP_010923405.1, WP_010923716.1,
WP_010932807.1, WP_010933627.1, WP_010935668.1, WP_010956474.1, WP_010959999.1,
WP_010960245.1, WP_010977965.1, WP_010980735.1, WP_011007011.1, WP_011007099.1,
WP_011011760.1, WP_011026652.1, WP_011099382.1, WP_011099682.1, WP_011134779.1,
WP_011153018.1, WP_011174432.1, WP_011176706.1, WP_011194444.1, WP_011194797.1,
WP_011200168.1, WP_011202915.1, WP_011210963.1, WP_011218326.1, WP_011221974.1,
WP_011222269.1, WP_011229077.1, WP_011237673.1, WP_011249405.1, WP_011249476.1,
WP_011257747.1, WP_011273277.1, WP_011309890.1, WP_011345041.1, WP_011358027.1,
WP_011388093.1, WP_011388583.1, WP_011392035.1, WP_011396660.1, WP_011406530.1,
WP_011407656.1, WP_011437724.1, WP_011460583.1, WP_011478968.1, WP_011525937.1,
WP_011529388.1, WP_011556939.1, WP_011557183.1, WP_011606664.1, WP_011639918.1,
WP_011641886.1, WP_011669569.1, WP_011671997.1, WP_011695828.1, WP_011722694.1,
WP_011743511.1, WP_011745280.1, WP_011753016.1, WP_011787402.1, WP_011797000.1,
WP_011822229.1, WP_011833222.1, WP_011838628.1, WP_011861556.1, WP_011861769.1,
WP_011868532.1, WP_011876920.1, WP_011877366.1, WP_011900615.1, WP_011914753.1,
WP_011915923.1, WP_011917896.1, WP_011942508.1, WP_011943626.1, WP_011955426.1,
WP_011956604.1, WP_011959010.1, WP_011972045.1, WP_011973779.1, WP_011994105.1,
WP_012002254.1, WP_012019694.1, WP_012021089.1, WP_012033072.1, WP_012033150.1,
WP_012062877.1, WP_012063328.1, WP_012073021.1, WP_012076828.1, WP_012094489.1,
WP_012108277.1, WP_012119548.1, WP_012121776.1, WP_012123278.1, WP_012139909.1,
WP_012164219.1, WP_012182158.1, WP_012186568.1, WP_012192596.1, WP_012209663.1,
WP_012212137.1, WP_012222313.1, WP_012226058.1, WP_012241780.1, WP_012255980.1,
WP_012258801.1, WP_012266054.1, WP_012268883.1, WP_012281431.1, WP_012281751.1,
WP_012302386.1, WP_012307383.1, WP_012309086.1, WP_012346192.1, WP_012350349.1,
WP_012350483.1, WP_012369059.1, WP_012446056.1, WP_012458647.1, WP_012459384.1,
WP_012470527.1, WP_012475527.1, WP_012500271.1, WP_012505973.1, WP_012524841.1,
WP_012538566.1, WP_012539200.1, WP_012544994.1, WP_012545630.1, WP_012547526.1,
WP_012547914.1, WP_012553115.1, WP_012574446.1, WP_012580505.1, WP_012582994.1,
WP_012585432.1, WP_012613089.1, WP_012615874.1, WP_012616459.1, WP_012618239.1,
WP_012624554.1, WP_012632151.1, WP_012641435.1, WP_012660064.1, WP_012662915.1,
WP_012673502.1, WP_012673588.1, WP_012701710.1, WP_012710929.1, WP_012710965.1,
WP_012713195.1, WP_012715850.1, WP_012717741.1, WP_012718681.1, WP_012735794.1,
WP_012743321.1, WP_012752544.1, WP_012768670.1, WP_012771277.1, WP_012796572.1,
WP_012808608.1, WP_012817716.1, WP_012823708.1, WP_012844136.1, WP_012851311.1,
WP_012851857.1, WP_012853015.1, WP_012856696.1, WP_012876354.1, WP_012902380.1,
WP_012917355.1, WP_012930468.1, WP_012938133.1, WP_012952594.1, WP_012955598.1,
WP_012963881.1, WP_012966344.1, WP_012980756.1, WP_012980763.1, WP_012984526.1,
WP_012991061.1, WP_013007279.1, WP_013008929.1, WP_013032915.1, WP_013047541.1,
WP_013067031.1, WP_013076646.1, WP_013076657.1, WP_013100592.1, WP_013101295.1,
WP_013104703.1, WP_013113745.1, WP_013120749.1, WP_013121322.1, WP_013129466.1,
WP_013131785.1, WP_013136588.1, WP_013144992.1, WP_013149497.1, WP_013150995.1,
WP_013159711.1, WP_013159789.1, WP_013166743.1, WP_013170929.1, WP_013175511.1,
WP_013175713.1, WP_013178145.1, WP_013179915.1, WP_013205427.1, WP_013227616.1,
WP_013231969.1, WP_013253666.1, WP_013260842.1, WP_013274917.1, WP_013289496.1,
WP_013291510.1, WP_013291735.1, WP_013299027.1, WP_013299107.1, WP_013299173.1,

TABLE 28-continued

Cas3 polypeptide accession numbers
(the sequene identifier for each accession number, in the
order provided in Table 28, is SEQ ID NOs: 11529-15493).

WP_013300570.1, WP_013313190.1, WP_013336789.1, WP_013399553.1, WP_013400578.1,
WP_013401698.1, WP_013404323.1, WP_013405999.1, WP_013410714.1, WP_013411097.1,
WP_013418888.1, WP_013431320.1, WP_013433570.1, WP_013433717.1, WP_013448697.1,
WP_013452029.1, WP_013466747.1, WP_013484592.1, WP_013495974.1, WP_013497831.1,
WP_013502807.1, WP_013518021.1, WP_013538361.1, WP_013548602.1, WP_013554002.1,
WP_013559650.1, WP_013561214.1, WP_013562521.1, WP_013596235.1, WP_013604759.1,
WP_013611555.1, WP_013624562.1, WP_013630169.1, WP_013647395.1, WP_013683461.1,
WP_013704838.1, WP_013705103.1, WP_013708281.1, WP_013720551.1, WP_013720640.1,
WP_013726790.1, WP_013733004.1, WP_013737756.1, WP_013749283.1, WP_013756176.1,
WP_013760345.1, WP_013762951.1, WP_013774551.1, WP_013776535.1, WP_013777983.1,
WP_013781802.1, WP_013789005.1, WP_013809679.1, WP_013809811.1, WP_013815296.1,
WP_013819638.1, WP_013821732.1, WP_013823987.1, WP_013832760.1, WP_013842962.1,
WP_013858608.1, WP_013876766.1, WP_013877551.1, WP_013877756.1, WP_013898837.1,
WP_013902813.1, WP_013905700.1, WP_013905707.1, WP_013906185.1, WP_013906861.1,
WP_013930568.1, WP_013932452.1, WP_013932951.1, WP_013934307.1, WP_013945611.1,
WP_013969349.1, WP_013987426.1, WP_013990633.1, WP_013999400.1, WP_014012310.1,
WP_014016934.1, WP_014025981.1, WP_014026054.1, WP_014026239.1, WP_014030715.1,
WP_014043410.1, WP_014066765.1, WP_014073498.1, WP_014076064.1, WP_014080660.1,
WP_014094597.1, WP_014097199.1, WP_014101083.1, WP_014125373.1, WP_014126170.1,
WP_014127143.1, WP_014147831.1, WP_014161864.1, WP_014162429.1, WP_014220987.1,
WP_014225626.1, WP_014251514.1, WP_014255746.1, WP_014288232.1, WP_014295800.1,
WP_014302523.1, WP_014323745.1, WP_014346689.1, WP_014415275.1, WP_014432862.1,
WP_014474603.1, WP_014484101.1, WP_014511104.1, WP_014511145.1, WP_014511986.1,
WP_014513746.1, WP_014514653.1, WP_014524690.1, WP_014555906.1, WP_014557203.1,
WP_014563206.1, WP_014616405.1, WP_014630466.1, WP_014686562.1, WP_014695809.1,
WP_014696638.1, WP_014702220.1, WP_014702541.1, WP_014707763.1, WP_014731183.1,
WP_014731689.1, WP_014733924.1, WP_014747988.1, WP_014757341.1, WP_014757523.1,
WP_014767243.1, WP_014767799.1, WP_014769137.1, WP_014777595.1, WP_014783120.1,
WP_014788231.1, WP_014789638.1, WP_014807422.1, WP_014826495.1, WP_014840100.1,
WP_014855489.1, WP_014956475.1, WP_014958325.1, WP_014966833.1, WP_015001116.1,
WP_015017879.1, WP_015022440.1, WP_015051480.1, WP_015072146.1, WP_015099449.1,
WP_015123921.1, WP_015155037.1, WP_015159303.1, WP_015164988.1, WP_015189436.1,
WP_015193896.1, WP_015220463.1, WP_015224029.1, WP_015233838.1, WP_015243996.1,
WP_015253163.1, WP_015255923.1, WP_015256022.1, WP_015283989.1, WP_015284324.1,
WP_015286120.1, WP_015286684.1, WP_015290768.1, WP_015293951.1, WP_015312650.1,
WP_015326643.1, WP_015329041.1, WP_015353142.1, WP_015353454.1, WP_015359321.1,
WP_015359551.1, WP_015370998.1, WP_015394874.1, WP_015407304.1, WP_015419282.1,
WP_015419759.1, WP_015425005.1, WP_015432823.1, WP_015439068.1, WP_015450163.1,
WP_015462030.1, WP_015487360.1, WP_015537471.1, WP_015556825.1, WP_015565149.1,
WP_015567040.1, WP_015580742.1, WP_015590843.1, WP_015594792.1, WP_015605258.1,
WP_015691376.1, WP_015717148.1, WP_015724182.1, WP_015738987.1, WP_015759048.1,
WP_015759160.1, WP_015759625.1, WP_015760876.1, WP_015763783.1, WP_015766731.1,
WP_015767810.1, WP_015769052.1, WP_015785746.1, WP_015791970.1, WP_015791977.1,
WP_015817777.1, WP_015836560.1, WP_015847311.1, WP_015849758.1, WP_015858908.1,
WP_015860136.1, WP_015864168.1, WP_015881448.1, WP_015895954.1, WP_015906762.1,
WP_015924972.1, WP_015934178.1, WP_015944883.1, WP_015949643.1, WP_016148217.1,
WP_016175473.1, WP_016188721.1, WP_016207023.1, WP_016217544.1, WP_016264725.1,
WP_016280410.1, WP_016299058.1, WP_016314141.1, WP_016314948.1, WP_016319071.1,
WP_016339464.1, WP_016357732.1, WP_016361153.1, WP_016442351.1, WP_016453852.1,
WP_016460509.1, WP_016478059.1, WP_016487078.1, WP_016510117.1, WP_016510766.1,
WP_016519079.1, WP_016519968.1, WP_016560536.1, WP_016564035.1, WP_016568441.1,
WP_016647301.1, WP_016668942.1, WP_016687507.1, WP_016696748.1, WP_016731280.1,
WP_016731501.1, WP_016731712.1, WP_016732168.1, WP_016732176.1, WP_016732427.1,
WP_016737727.1, WP_016750258.1, WP_016751556.1, WP_016751644.1, WP_016752742.1,
WP_016753856.1, WP_016756796.1, WP_016758536.1, WP_016838858.1, WP_016851257.1,
WP_016915812.1, WP_016922099.1, WP_016994002.1, WP_017116854.1, WP_017119022.1,
WP_017135671.1, WP_017172610.1, WP_017215443.1, WP_017303317.1, WP_017306224.1,
WP_017318860.1, WP_017320064.1, WP_017364196.1, WP_017407429.1, WP_017427970.1,
WP_017429509.1, WP_017448228.1, WP_017463411.1, WP_017470764.1, WP_017539384.1,
WP_017540929.1, WP_017552094.1, WP_017552735.1, WP_017558277.1, WP_017559346.1,
WP_017572806.1, WP_017587082.1, WP_017602138.1, WP_017615956.1, WP_017619212.1,
WP_017622955.1, WP_017637954.1, WP_017690353.1, WP_017717455.1, WP_017740138.1,
WP_017748679.1, WP_017751166.1, WP_017754499.1, WP_017778774.1, WP_017826608.1,
WP_017838894.1, WP_017839476.1, WP_017841804.1, WP_017851557.1, WP_017854157.1,
WP_017854286.1, WP_017857943.1, WP_017860276.1, WP_017861029.1, WP_017863290.1,
WP_017869337.1, WP_017870393.1, WP_017873804.1, WP_017890208.1, WP_017907374.1,
WP_017938168.1, WP_017948473.1, WP_017950340.1, WP_017973756.1, WP_017980956.1,
WP_018033621.1, WP_018034885.1, WP_018060812.1, WP_018086140.1, WP_018106361.1,
WP_018119873.1, WP_018130450.1, WP_018153316.1, WP_018154664.1, WP_018186243.1,
WP_018192946.1, WP_018193691.1, WP_018206664.1, WP_018215904.1, WP_018220085.1,
WP_018223837.1, WP_018230088.1, WP_018252767.1, WP_018255307.1, WP_018258158.1,
WP_018289398.1, WP_018346676.1, WP_018358703.1, WP_018360773.1, WP_018367987.1,
WP_018383064.1, WP_018402825.1, WP_018409882.1, WP_018449896.1, WP_018466793.1,
WP_018466925.1, WP_018490087.1, WP_018493896.1, WP_018501141.1, WP_018508656.1,
WP_018540248.1, WP_018556241.1, WP_018559300.1, WP_018571692.1, WP_018574520.1,
WP_018575259.1, WP_018590885.1, WP_018596860.1, WP_018621542.1, WP_018649506.1,

TABLE 28-continued

Cas3 polypeptide accession numbers
(the sequene identifier for each accession number, in the
order provided in Table 28, is SEQ ID NOs: 11529-15493).

WP_018652887.1, WP_018710328.1, WP_018713225.1, WP_018719629.1, WP_018724540.1,
WP_018732470.1, WP_018734992.1, WP_018737826.1, WP_018740929.1, WP_018758583.1,
WP_018790942.1, WP_018799110.1, WP_018815209.1, WP_018821755.1, WP_018829239.1,
WP_018862901.1, WP_018887429.1, WP_018887587.1, WP_018908951.1, WP_018916771.1,
WP_018920531.1, WP_018963744.1, WP_018964769.1, WP_018969391.1, WP_018979029.1,
WP_018988391.1, WP_018990863.1, WP_018999161.1, WP_019000931.1, WP_019007706.1,
WP_019033984.1, WP_019064969.1, WP_019108546.1, WP_019153453.1, WP_019165691.1,
WP_019184218.1, WP_019273183.1, WP_019338273.1, WP_019358609.1, WP_019397356.1,
WP_019403922.1, WP_019415299.1, WP_019419611.1, WP_019426617.1, WP_019462123.1,
WP_019463219.1, WP_019497303.1, WP_019500469.1, WP_019532635.1, WP_019538393.1,
WP_019540684.1, WP_019543035.1, WP_019551463.1, WP_019555031.1, WP_019586913.1,
WP_019595929.1, WP_019610388.1, WP_019636670.1, WP_019659222.1, WP_019680702.1,
WP_019703285.1, WP_019726858.1, WP_019776147.1, WP_019807552.1, WP_019855133.1,
WP_019910873.1, WP_019912989.1, WP_019950949.1, WP_019960729.1, WP_019968532.1,
WP_019977116.1, WP_019989964.1, WP_019991492.1, WP_020005377.1, WP_020039660.1,
WP_020074382.1, WP_020074665.1, WP_020087242.1, WP_020220936.1, WP_020250593.1,
WP_020253683.1, WP_020265457.1, WP_020305675.1, WP_020305858.1, WP_020310784.1,
WP_020312615.1, WP_020314570.1, WP_020314718.1, WP_020326061.1, WP_020340121.1,
WP_020373620.1, WP_020373820.1, WP_020380337.1, WP_020383873.1, WP_020410295.1,
WP_020448805.1, WP_020493800.1, WP_020506072.1, WP_020530991.1, WP_020537508.1,
WP_020560769.1, WP_020587139.1, WP_020599886.1, WP_020602099.1, WP_020608603.1,
WP_020612862.1, WP_020651075.1, WP_020678825.1, WP_020750859.1, WP_020762501.1,
WP_020765669.1, WP_020765987.1, WP_020774517.1, WP_020779218.1, WP_020779678.1,
WP_020780952.1, WP_020781866.1, WP_020783925.1, WP_020784106.1, WP_020784342.1,
WP_020784475.1, WP_020864067.1, WP_020877258.1, WP_020880186.1, WP_020886855.1,
WP_020985351.1, WP_020993579.1, WP_021022952.1, WP_021052092.1, WP_021085882.1,
WP_021088056.1, WP_021089598.1, WP_021093589.1, WP_021093748.1, WP_021133737.1,
WP_021210211.1, WP_021279370.1, WP_021311726.1, WP_021329089.1, WP_021329905.1,
WP_021331295.1, WP_021359473.1, WP_021359715.1, WP_021360801.1, WP_021361002.1,
WP_021362774.1, WP_021362907.1, WP_021362978.1, WP_021363718.1, WP_021363850.1,
WP_021363926.1, WP_021364750.1, WP_021365607.1, WP_021365749.1, WP_021367003.1,
WP_021367925.1, WP_021369762.1, WP_021371378.1, WP_021371446.1, WP_021372124.1,
WP_021372533.1, WP_021373543.1, WP_021373587.1, WP_021376023.1, WP_021376270.1,
WP_021378270.1, WP_021380017.1, WP_021380654.1, WP_021385911.1, WP_021385995.1,
WP_021388087.1, WP_021390231.1, WP_021394445.1, WP_021394986.1, WP_021397103.1,
WP_021398090.1, WP_021398788.1, WP_021401430.1, WP_021401940.1, WP_021402633.1,
WP_021406024.1, WP_021408552.1, WP_021408663.1, WP_021411254.1, WP_021412323.1,
WP_021414455.1, WP_021415812.1, WP_021416873.1, WP_021417289.1, WP_021419388.1,
WP_021421656.1, WP_021422491.1, WP_021422633.1, WP_021422666.1, WP_021422973.1,
WP_021422994.1, WP_021423805.1, WP_021424005.1, WP_021424306.1, WP_021424823.1,
WP_021425615.1, WP_021426566.1, WP_021426790.1, WP_021427109.1, WP_021462178.1,
WP_021604024.1, WP_021610629.1, WP_021615272.1, WP_021615580.1, WP_021623242.1,
WP_021625637.1, WP_021637099.1, WP_021640897.1, WP_021654353.1, WP_021659783.1,
WP_021662697.1, WP_021663530.1, WP_021665805.1, WP_021666375.1, WP_021673650.1,
WP_021676128.1, WP_021677807.1, WP_021679319.1, WP_021685843.1, WP_021687361.1,
WP_021751292.1, WP_021761190.1, WP_021816692.1, WP_021823925.1, WP_021825208.1,
WP_021836920.1, WP_021856107.1, WP_021869885.1, WP_021875389.1, WP_021932608.1,
WP_021958974.1, WP_021988549.1, WP_022009882.1, WP_022033205.1, WP_022033510.1,
WP_022046300.1, WP_022048651.1, WP_022051789.1, WP_022051847.1, WP_022069845.1,
WP_022070969.1, WP_022071459.1, WP_022103208.1, WP_022108012.1, WP_022119726.1,
WP_022127775.1, WP_022143367.1, WP_022161369.1, WP_022169014.1, WP_022176830.1,
WP_022177040.1, WP_022228625.1, WP_022228951.1, WP_022232568.1, WP_022240071.1,
WP_022248003.1, WP_022257409.1, WP_022264212.1, WP_022271469.1, WP_022272153.1,
WP_022282399.1, WP_022286809.1, WP_022298984.1, WP_022302638.1, WP_022343366.1,
WP_022356881.1, WP_022361840.1, WP_022363354.1, WP_022377859.1, WP_022400167.1,
WP_022402823.1, WP_022410980.1, WP_022424424.1, WP_022431366.1, WP_022444764.1,
WP_022445689.1, WP_022475431.1, WP_022477155.1, WP_022484701.1, WP_022486952.1,
WP_022494224.1, WP_022498152.1, WP_022502228.1, WP_022507269.1, WP_022530081.1,
WP_022588386.1, WP_022636790.1, WP_022654262.1, WP_022656789.1, WP_022659414.1,
WP_022660216.1, WP_022681043.1, WP_022742456.1, WP_022745994.1, WP_022746617.1,
WP_022748670.1, WP_022786162.1, WP_022799399.1, WP_022803626.1, WP_022803642.1,
WP_022805381.1, WP_022816096.1, WP_022819292.1, WP_022835069.1, WP_022835510.1,
WP_022838084.1, WP_022846699.1, WP_022854085.1, WP_022855921.1, WP_022856085.1,
WP_022856207.1, WP_022861871.1, WP_022926574.1, WP_022937467.1, WP_022947926.1,
WP_022949623.1, WP_023018586.1, WP_023023280.1, WP_023039492.1, WP_023039732.1,
WP_023042241.1, WP_023059996.1, WP_023062929.1, WP_023066170.1, WP_023103416.1,
WP_023104938.1, WP_023233924.1, WP_023389230.1, WP_023396043.1, WP_023438292.1,
WP_023450090.1, WP_023485929.1, WP_023606049.1, WP_023796429.1, WP_023844485.1,
WP_023903632.1, WP_023911235.1, WP_023921142.1, WP_023922811.1, WP_023937046.1,
WP_023945257.1, WP_023988271.1, WP_023991511.1, WP_024025745.1, WP_024075605.1,
WP_024084607.1, WP_024105345.1, WP_024107004.1, WP_024124530.1, WP_024174209.1,
WP_024176794.1, WP_024194483.1, WP_024262709.1, XP_001318132.1, XP_001436424.1,
XP_001606022.2, XP_001938105.1, XP_001945184.2, XP_001994196.1, XP_002059142.1,
XP_002365536.1, XP_002776841.1, XP_003005711.1, XP_003072670.1, XP_003426140.1,
XP_003522431.1, XP_003526886.1, XP_004039973.1, XP_006449459.1, XP_006814937.1,
XP_006815053.1, XP_006817051.1, XP_006856306.1, XP_457875.1, XP_730074.1, YP_000912.1,

TABLE 28-continued

Cas3 polypeptide accession numbers
(the sequene identifier for each accession number, in the
order provided in Table 28, is SEQ ID NOs: 11529-15493).

YP_001030288.1, YP_001038694.1, YP_001039592.1, YP_001040345.1, YP_001088965.2,
YP_001089496.1, YP_001097293.1, YP_001111908.1, YP_001112362.1, YP_001153360.1,
YP_001174210.1, YP_001179154.1, YP_001181165.2, YP_001189243.1, YP_001191226.1,
YP_001212466.1, YP_001212544.1, YP_001234935.1, YP_001244674.1, YP_001275021.1,
YP_001276207.1, YP_001278623.1, YP_001319498.1, YP_001320011.1, YP_001322754.1,
YP_001325259.1, YP_001344579.1, YP_001375291.1, YP_001405995.1, YP_001410447.1,
YP_001431136.1, YP_001433370.1, YP_001435721.1, YP_001466976.1, YP_001469837.1,
YP_001518170.1, YP_001536847.1, YP_001541339.1, YP_001547835.1, YP_001568889.1,
YP_001577840.1, YP_001600362.1, YP_001602455.1, YP_001619825.1, YP_001633713.1,
YP_001636537.1, YP_001658093.1, YP_001663919.1, YP_001664134.1, YP_001678811.1,
YP_001679135.1, YP_001717433.1, YP_001735016.1, YP_001736872.1, YP_001741353.1,
YP_001752667.1, YP_001790195.1, YP_001794375.1, YP_001794510.1, YP_001812651.1,
YP_001915497.1, YP_001930079.1, YP_001930861.1, YP_001952714.1, YP_001960544.1,
YP_001974440.1, YP_001996634.1, YP_002016087.1, YP_002133143.1, YP_002222467.1,
YP_002223269.1, YP_002248912.1, YP_002249826.1, YP_002249951.1, YP_002250045.1,
YP_002274839.1, YP_002276019.1, YP_002315132.1, YP_002335720.1, YP_002352523.1,
YP_002355864.1, YP_002434074.1, YP_002436382.1, YP_002460384.1, YP_002461944.1,
YP_002462531.1, YP_002466643.1, YP_002479507.1, YP_002491198.1, YP_002495133.1,
YP_002505810.1, YP_002521277.1, YP_002567843.1, YP_002570898.1, YP_002572056.1,
YP_002601830.1, YP_002728806.1, YP_002728847.1, YP_002753899.1, YP_002800301.1,
YP_002828959.1, YP_002828996.1, YP_002831443.1, YP_002836974.1, YP_002841056.1,
YP_002842902.1, YP_002842939.1, YP_002887334.1, YP_002914192.1, YP_002938362.1,
YP_002950000.1, YP_002952812.1, YP_002959660.1, YP_002962709.1, YP_002994890.1,
YP_003003270.1, YP_003006844.1, YP_003014461.1, YP_003021066.1, YP_003074490.1,
YP_003128737.1, YP_003128744.1, YP_003133258.1, YP_003135792.1, YP_003163695.1,
YP_003167469.1, YP_003168564.1, YP_003178648.1, YP_003179541.1, YP_003182332.1,
YP_003192984.1, YP_003193099.1, YP_003193578.1, YP_003215317.1, YP_003215784.1,
YP_003215962.1, YP_003218826.1, YP_003219291.1, YP_003219469.1, YP_003227008.1,
YP_003238960.1, YP_003255753.1, YP_003262719.1, YP_003290913.1, YP_003298565.1,
YP_003299111.1, YP_003300269.1, YP_003303967.1, YP_003324145.1, YP_003361059.1,
YP_003377356.1, YP_003390779.1, YP_003398459.1, YP_003419021.1, YP_003423539.1,
YP_003432902.1, YP_003436280.1, YP_003458583.1, YP_003458590.1, YP_003463071.1,
YP_003472781.1, YP_003495787.1, YP_003497448.1, YP_003527436.1, YP_003533667.1,
YP_003552999.1, YP_003577459.1, YP_003590507.1, YP_003590518.1, YP_003616811.1,
YP_003618264.1, YP_003623186.1, YP_003633521.1, YP_003640640.1, YP_003641229.1,
YP_003650025.1, YP_003652145.1, YP_003656950.1, YP_003671009.1, YP_003675822.1,
YP_003677873.1, YP_003686705.1, YP_003686819.1, YP_003693858.1, YP_003698062.1,
YP_003702674.1, YP_003702876.1, YP_003705320.1, YP_003707160.1, YP_003744986.1,
YP_003767963.1, YP_003773133.1, YP_003802796.1, YP_003810000.1, YP_003824488.1,
YP_003839475.1, YP_003841502.1, YP_003842362.1, YP_003843808.1, YP_003853155.1,
YP_003853236.1, YP_003853340.1, YP_003854738.1, YP_003873622.1, YP_003902115.1,
YP_003905210.1, YP_003985774.1, YP_003988876.1, YP_003990719.1, YP_003993554.1,
YP_003995275.1, YP_004001414.1, YP_004001482.1, YP_004011583.1, YP_004025071.1,
YP_004027468.1, YP_004027620.1, YP_004048353.1, YP_004051983.1, YP_004070672.1,
YP_004090953.1, YP_004102398.1, YP_004104288.1, YP_004109423.1, YP_004125789.1,
YP_004152217.1, YP_004162601.1, YP_004168058.1, YP_004173862.1, YP_004175469.1,
YP_004176781.1, YP_004185145.1, YP_004194932.1, YP_004202420.1, YP_004236326.1,
YP_004245099.1, YP_004252517.1, YP_004265693.1, YP_004271474.1, YP_004271715.1,
YP_004294513.1, YP_004341504.1, YP_004368903.1, YP_004369171.1, YP_004372353.1,
YP_004385354.1, YP_004385446.1, YP_004397285.1, YP_004440944.1, YP_004409742.1,
YP_004414390.1, YP_004424737.1, YP_004437582.1, YP_004442024.1, YP_004445260.1,
YP_004456924.1, YP_004458918.1, YP_004460367.1, YP_004464197.1, YP_004471951.1,
YP_004496338.1, YP_004496527.1, YP_004509027.1, YP_004513908.1, YP_004516018.1,
YP_004518278.1, YP_004534213.1, YP_004546496.1, YP_004568096.1, YP_004587626.1,
YP_004589470.1, YP_004603180.1, YP_004616620.1, YP_004620601.1, YP_004623915.1,
YP_004623922.1, YP_004624401.1, YP_004625078.1, YP_004658416.1, YP_004660329.1,
YP_004660839.1, YP_004662202.1, YP_004673776.1, YP_004698567.1, YP_004720451.1,
YP_004727889.1, YP_004742713.1, YP_004762303.1, YP_004767040.1, YP_004771203.1,
YP_004780556.1, YP_004780629.1, YP_004780814.1, YP_004785823.1, YP_004799949.1,
YP_004821230.1, YP_004824915.1, YP_004832232.1, YP_004834870.1, YP_004839586.1,
YP_004857063.1, YP_004859900.1, YP_004863862.1, YP_004887497.1, YP_004891993.1,
YP_004892966.1, YP_004916629.1, YP_004931732.1, YP_004932103.1, YP_004934107.1,
YP_004957573.1, YP_005010478.1, YP_005015167.1, YP_005042767.1, YP_005071108.1,
YP_005084656.1, YP_005096026.1, YP_005126356.1, YP_005136892.1, YP_005147303.1,
YP_005169124.1, YP_005258417.1, YP_005259779.1, YP_005321311.1, YP_005441521.1,
YP_005511920.1, YP_005533892.1, YP_005554087.1, YP_005583248.1, YP_005641608.1,
YP_005641654.1, YP_005644061.1, YP_005644986.1, YP_005648064.1, YP_005653361.1,
YP_005668366.1, YP_005689401.1, YP_005704009.1, YP_005839933.1, YP_005841506.1,
YP_005849755.1, YP_005964505.1, YP_005989327.1, YP_006028920.1, YP_006046612.1,
YP_006047121.1, YP_006059768.1, YP_006068309.1, YP_006115.1, YP_006196970.1,
YP_006199527.1, YP_006199998.1, YP_006200194.1, YP_006250064.1, YP_006262541.1,
YP_006271827.1, YP_006272774.1, YP_006285894.1, YP_006287661.1, YP_006297047.1,
YP_006346527.1, YP_006347177.1, YP_006351427.1, YP_006354473.1, YP_006373981.1,
YP_006391019.1, YP_006391208.1, YP_006401917.1, YP_006402478.1, YP_006403833.1,
YP_006413235.1, YP_006418886.1, YP_006424384.1, YP_006425801.1, YP_006444522.1,
YP_006465820.1, YP_006491721.1, YP_006501931.1, YP_006527066.1, YP_006552217.1,

TABLE 28-continued

Cas3 polypeptide accession numbers
(the sequene identifier for each accession number, in the
order provided in Table 28, is SEQ ID NOs: 11529-15493).

YP_006655417.1, YP_006680971.1, YP_006692471.1, YP_006720032.1, YP_006759829.1,
YP_006761820.1, YP_006787543.1, YP_006831248.1, YP_006845020.1, YP_006860989.1,
YP_006865570.1, YP_006887325.1, YP_006921117.1, YP_006930948.1, YP_006982631.1,
YP_007036209.1, YP_007060920.1, YP_007092359.1, YP_007096666.1, YP_007102450.1,
YP_007128726.1, YP_007133194.1, YP_007162784.1, YP_007166365.1, YP_007177325.1,
YP_007179027.1, YP_007200506.1, YP_007211394.1, YP_007214186.1, YP_007214288.1,
YP_007247532.1, YP_007247867.1, YP_007249664.1, YP_007250229.1, YP_007265296.1,
YP_007269509.1, YP_007296335.1, YP_007299922.1, YP_007315011.1, YP_007318532.1,
YP_007364573.1, YP_007364885.1, YP_007373247.1, YP_007373481.1, YP_007393663.1,
YP_007457819.1, YP_007484342.1, YP_007500039.1, YP_007500529.1, YP_007548476.1,
YP_007555209.1, YP_007593343.1, YP_007629877.1, YP_007638256.1, YP_007647093.1,
YP_007647586.1, YP_007652558.1, YP_007666165.1, YP_007669047.1, YP_007679667.1,
YP_007679887.1, YP_007682879.1, YP_007688876.1, YP_007773719.1, YP_007800216.1,
YP_007827924.1, YP_007837791.1, YP_007839945.1, YP_007841644.1, YP_007864862.1,
YP_007872240.1, YP_007884170.1, YP_007894111.1, YP_007899160.1, YP_007907238.1,
YP_007923449.1, YP_007944037.1, YP_007947099.1, YP_008018527.1, YP_008071635.1,
YP_008074473.1, YP_008095151.1, YP_008140886.1, YP_008142101.1, YP_008219478.1,
YP_008221977.1, YP_008233404.1, YP_008282084.1, YP_008299750.1, YP_008339180.1,
YP_008428006.1, YP_008462068.1, YP_008618774.1, YP_008675016.1, YP_008675506.1,
YP_008698878.1, YP_008773532.1, YP_008797472.1, YP_008874109.1, YP_008899634.1,
YP_008911631.1, YP_008915221.1, YP_008932958.1, YP_009169.1, YP_074138.1,
YP_074493.1, YP_088183.1, YP_099831.1, YP_113419.1, YP_120643.1, YP_129811.1, YP_133639.1,
YP_134130.1, YP_145469.1, YP_158879.1, YP_182863.1, YP_182934.1, YP_199511.1, YP_250429.1,
YP_289652.1, YP_306590.1, YP_308462.1, YP_375198.1, YP_395104.1, YP_425432.1, YP_425916.1,
YP_429371.1, YP_434016.1, YP_447466.1, YP_447974.1, YP_449827.1, YP_479140.1, YP_482427.1,
YP_518999.1, YP_544712.1, YP_594137.1, YP_603711.1, YP_635133.1, YP_635377.1, YP_715739.1,
YP_745202.1, YP_753181.1, YP_755177.1, YP_797168.1, YP_801657.1, YP_843071.1, YP_878706.1,
YP_910049.1, YP_911888.1, YP_920754.1, YP_961177.1, and/or YP_972287.1

Thus, in some embodiments, a recombinant nucleic acid molecule of this invention comprising a nucleotide sequence encoding a subset of CRISPR-Cas polypeptides, or functional fragments thereof, from a type I CRISPR-Cas system can comprise, consist essentially of, or consist of a nucleotide sequence encoding three or more polypeptides having the GenBank accession numbers set forth above, or any other type I CRISPR-Cas polypeptide.

In another aspect, the present invention provides a recombinant CRISPR array comprising, consisting essentially of, or consisting of two or more repeat nucleotide sequences, or portion thereof, and one or more spacer nucleotide sequence(s), wherein each spacer nucleotide sequence in said CRISPR array is linked at its 5' end and at its 3' end to a repeat nucleotide sequence. Accordingly, the repeat nucleotide sequences and spacer nucleotide sequences of the CRISPR array alternate with each other, e.g., 5' to 3', repeat, spacer, repeat, and the like.

A recombinant CRISPR array of the invention can be of any length and comprise any number of spacer nucleotide sequences alternating with repeat nucleotide sequences, as described above, necessary to achieve the desired level of repression of expression (e.g., repression of transcription) of one or more target genes. In some embodiments, a CRISPR array can comprise, consist essentially of, or consist of 1 to about 100 spacer nucleotide sequences, each linked on its 5' end and its 3' end to a repeat nucleotide sequence. Thus, in some embodiments, a recombinant CRISPR array of the invention can comprise, consist essentially of, or consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more, spacer nucleotide sequences.

A repeat nucleotide sequence of a CRISPR array of the invention can comprise, consist essentially of, or consist of a nucleotide sequence of any known repeat nucleotide sequence of a type-I CRISPR cas system. As described herein, a repeat nucleotide sequence can also be of a synthetic design comprising the secondary structure of a native repeat from a type-I CRISPR cas system (e.g., an internal hairpin). In some embodiments, a repeat nucleotide sequence of the recombinant CRISPR array of the invention can comprise, consist essentially of, or consist of a nucleotide sequence of SEQ ID NOs:59-249.

In some embodiments, the at least one spacer nucleotide sequence can be linked at its 3' end to a repeat sequence and linked at its 5' end to about 1 to about 8, about 1 to about 10, about 1 to about 15 nucleotides from the 3' end of a repeat nucleotide sequence (e.g., a portion of a repeat nucleotide sequence). In other embodiments, the at least one spacer nucleotide sequence can be linked at its 5' end to about 2 to about 6, or about 2 to about 4 nucleotides from the 3' end of a repeat nucleotide sequence.

In representative embodiments, the recombinant CRISPER array comprises two or more (e.g., 2, 3, 4, 5, 6, 7, 8, 9, 10, or more, as described herein) spacer nucleotide sequences, each spacer nucleotide sequence flanked on its 3' and its 5' end by a repeat nucleotide sequence, and the at least two of the two or more spacer nucleotide sequences of said recombinant CRISPR array can each comprise a nucleotide sequence that is complementary to a different target nucleotide sequence from a single target gene (e.g., a different region of the same target gene). By targeting at least two different regions of a single target gene, a CRISPR array can be used to modify repression (e.g., increase or decrease the level of repression) of the expression of said target gene. More specifically, a CRISPR array having multiple spacer nucleotide sequences each of which are complementary to a different non-overlapping target nucleotide sequence from a single gene, can provide stronger/ increased repression of expression of that target gene as compared with a CRISPR array having comparatively fewer spacer nucleotide sequences each of which are complementary to different target nucleotide sequences from a single target gene. The level of transcription repression can be further modified by designing a CRISPR array having spacer nucleotide sequences that are complementary to overlapping target nucleotide sequences within the same target gene. Overlapping spacer nucleotide sequences that are complementary to overlapping target nucleotide sequences within the same target gene can result in reduced repression of expression of that target gene as compared to a CRISPR array in which the spacer nucleotide sequences are complementary to different target nucleotide sequences within the same target gene but which said target nucleotide sequences do not overlap. That is, such overlapping spacer sequences have a reduced effect on repression of expression than spacer sequences that do not overlap. Without wishing to be bound to any particular theory it is believed that the overlapping sequences compete with one another, thereby reducing the level of repression as compared with non-overlapping sequences In addition to targeting different locations/regions on a single gene to modulate the repression of that gene, the length of the spacer or its complementarity to the target nucleotide sequence can be altered to modulate repression. Thus, for example, shorter spacers or a spacer with less complementarity to a target nucleotide sequence will typically result in reduced repression as compared a longer spacer and/or a spacer with greater complementarity to a target nucleotide sequence, respectively.

Accordingly, in some embodiments, repression by a spacer can be increased by adding one or more nucleotides to the length of said spacer, said spacer resulting in increased repression when used with the recombinant nucleic acids of the invention as compared with the same spacer but without the additional nucleotides. In some embodiments, the length of the spacer can be increased by one to about 100 nucleotides, and/or any range or value therein (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more). In representative embodiments, the length of the spacer can be increased by about 1 to about 40, about 5 to about 30, 10 to about 30, about 20 to about 30 nucleotides. In other embodiments, the length of the spacer can be increased by about 6 nucleotides, about 8 nucleotides, about 10 nucleotides, about 12 nucleotides, about 18 nucleotides, about 24 nucleotides, and the like.

In further embodiments, repression by a spacer can be decreased by reducing the length of said spacer by one or more nucleotides, said spacer resulting in decreased repression when used with the recombinant nucleic acids of the invention as compared with the same spacer but without a reduced number of nucleotides. Accordingly, in some embodiments, repression by a spacer can be decreased by decreasing the length of the spacer by 1 to about 100 nucleotides, and any range or value therein. In representative embodiments, the length of the spacer can be decreased by about 1 to about 40, about 5 to about 30, 10 to about 30, about 20 to about 30 nucleotides. In other embodiments, the length of the spacer can be decreased by about 6 nucleotides, about 8 nucleotides, about 10 nucleotides, about 12 nucleotides, about 18 nucleotides, about 24 nucleotides, and the like.

In further aspects, a spacer sequence of a CRISPR array of the invention can be complementary to a target nucleotide sequence that is from a coding strand or a plus (top) strand and/or from a non-coding strand or a minus (bottom) strand of a double stranded target gene. As demonstrated herein, designing a recombinant CRISPR array to include spacers targeting a coding/plus strand rather than a non-coding/minus strand, and vice versa, provides further modulation of repression with targeting of coding/plus strands providing increased or greater repression as compared to targeting of non-coding/minus strands of the same target gene.

These variations of a spacer nucleotide sequence of a CRISPR array construct as described herein and other variations are possible and can be used to repress or modify repression of expression of a target gene. Any combination of the types of spacers described herein as well as other types of spacers can be used alone or in any combination for repressing expression or modulating the repression of expression of a target gene.

Thus, as is clear, the above described and other variations in CRISPR array design can be used to achieve a desired level of repression of expression of a target gene.

In other embodiments, a recombinant CRISPR array can be designed to comprise, consist essentially of, consist of at least two spacer nucleotide sequences each of which comprise a nucleotide sequence that is complementary to a different target nucleotide sequence from a different target gene, thereby achieving repression of expression of different target genes using a single CRISPR array. Alternatively, different genes can be targeted for repression of expression using two or more recombinant CRISPR arrays.

As would be readily understood, various recombinant CRISPR array designs can be constructed and introduced into a cell or an organism in single or in multiple recombinant CRISPR array constructs for use in repressing and/or modulating the expression of one or more target genes in said cell or organism. Thus, for example, various combinations of different types of spacer nucleotide sequences, as described herein, can be introduced on a single recombinant CRISPR array such that expression of one or more target genes can be repressed and/or modulated. Alternatively, in other embodiments, various spacer nucleotide sequences can be introduced on two or more recombinant CRISPR arrays for repressing or modulating expression of one or more target genes.

In some embodiments, a spacer nucleotide sequence of the recombinant CRISPR array of the invention can be fully identical to or substantially identical to a target nucleotide sequence, or complement thereof, from a target gene. In particular embodiments, the one or more spacer nucleotide sequence(s) can have at least about 50% identity to a target nucleotide sequence, or complement thereof. In other embodiments, the one or more spacer nucleotide sequence(s) can have at least about 70% identity to a target nucleotide sequence, or complement thereof. In further embodiments, the one or more spacer nucleotide sequence(s) can have at least about 80% identity to a target nucleotide sequence, or complement thereof. In still further embodiments, the one or more spacer nucleotide sequence(s) can have at least about 85%, 90%, 95%, 96%, 97%, 98%, 99% or 100% identity to a target nucleotide sequence, or complement thereof.

In other aspects of the invention, the target nucleotide sequence and/or the target gene is from a genome, a plasmid, or a plastid of a target organism.

In some embodiments, a target organism can be a eukaryote, a prokaryote or a virus. In other embodiments, a prokaryote includes, but is not limited to, a bacterium or an archaeon. In still other embodiments, a eukaryote includes, but is not limited to, an animal, a mammal, an insect, a plant, a fungus, an insect, a bird, a fish, an amphibian, a reptile, or a cnidarian. In additional embodiments, a mammal can include, but is not limited to, a rodent, a horse, a dog a cat, a human, a non-human primate (e.g., monkeys, baboons, and chimpanzees), a goat, a pig, a cow (e.g., cattle), a sheep, laboratory animals (e.g., rats, mice, gerbils, hamsters, and the like) and the like. Non-limiting examples of birds useful with this invention include chickens, ducks, turkeys, geese, quails and birds kept as pets (e.g., parakeets, parrots, macaws, and the like). Additional embodiments can include, for example, mammalian and insect cell lines. Non-limiting examples of mammalian and insect cell lines include HEK293 cells, HeLa cells, CHO cells, MEF cells, 3T3 cells, Hi-5 cells, and Sf21 cells.

Suitable target organism can include both males and females and subjects of all ages including embryonic (e.g., in utero or in ovo), infant, juvenile, adolescent, adult and geriatric subjects. In embodiments of the invention, the target organism is not a human embryonic subject.

Thus, for example, any bacterium, archaeon, plant, or fungus can be employed in practicing the present invention. In representative embodiments, non-limiting examples of bacteria useful with this invention include *Escherichia* spp., *Salmonella* spp., *Bacillus* spp., *Corynebacterium Clostridium* spp., *Clostridium* spp., *Pseudomonas* spp., *Clostridium* spp., *Lactococcus* spp. *Acinetobacter* spp., *Mycobacterium* spp., *Myxococcus* spp., *Staphylococcus* spp., *Streptococcus* spp., or cyanobacteria. In further embodiments, non-limiting examples of bacteria useful with this invention include *Escherichia coli, Salmonella enterica, Bacillus subtilis, Clostridium acetobutylicum, Clostridium ljungdahlii, Clostridium difficile, Acinetobacter baumannii, Mycobacterium tuberculosis, Myxococcus xanthus, Staphylococcus aureus, Streptococcus pyogenes*, or cyanobacteria. Further non-limiting examples of bacteria useful with this invention include lactic acid bacteria including but not limited to *Lactobacillus* spp. and *Bifidobacterium* spp.; electrofuel bacterial strains including but not limited to *Geobacter* spp., *Clostridium* spp., or *Ralstonia eutropha*; or bacteria pathogenic on, for example, plants and mammals. In particular embodiments, the bacterium can be *Escherichia coli*.

Non-limiting examples of such archaea include *Pyrococcus furiosus, Thermus aquaticus, Sulfolobus sulfataricus*, or haloarchaea including but not limited to *Haladaptatus* (e.g., *Haladaptatus paucihalophilus*), *Halalkalicoccus* (e.g., *Halalkalicoccus tibetensis*), *Halobaculum* (e.g., *Halobaculum gomorrense*), *Halobellus* (e.g., *Halobellus clavatus*), *Halomicrobium* (e.g., *Halomicrobium mukohataei*), *Natrialba* (e.g., *Natrialba asiatica*), *Natrinema* (e.g., *Natrinema pellirubrum*), *Natronorubrum* (e.g., *Natronorubrum bangense*), *Salarchaeum* (e.g., *Salarchaeum japonicum*)

In some embodiments of this invention, a plant and/or plant cell useful with this invention can include, but not is not limited to, *Camelina, Glycine, Sorghum, Brassica, Allium, Armoracia, Poa, Agrostis, Lolium, Festuca, Calamogrostis, Deschampsia, Spinacia, Beta, Pisum, Chenopodium, Helianthus, Pastinaca, Daucus, Retroselium, Populus, Prunus, Castanea, Eucalyptus, Acer, Quercus, Salix, Juglans, Picea, Pinus, Abies, Lemna, Wolffia, Spirodela, Oryza, Zea* or *Gossypium*. In other embodiments, the plant and/or plant cell can include, but is not limited to, *Camelina alyssum* (Mill.) Thell., *Camelina microcarpa* Andrz. ex DC., *Camelina rumelica* Velen., *Camelina sativa* (L.) Crantz, *Sorghum bicolor* (e.g., *Sorghum bicolor* L. Moench), *Gossypium hirsutum, Glycine max, Zea mays, Brassica oleracea, Brassica rapa, Brassica napus, Raphanus sativus, Armoracia rusticana, Allium sative, Allium cepa, Populus grandidentata, Populus tremula, Populus tremuloides, Prunus serotina, Prunus pensylvanica, Castanea dentate, Populus balsamifer, Populus deltoids, Acer Saccharum, Acer nigrum, Acer negundo, Acer rubrum, Acer saccharinum, Acer pseudoplatanus* or *Oryza sativa*. In additional embodiments, a plant and/or plant cell can be, but is not limited to, wheat, barley, oats, turfgrass (bluegrass, bentgrass, ryegrass, fescue), feather reed grass, tufted hair grass, spinach, beets, chard, quinoa, sugar beets, lettuce, sunflower (*Helianthus annuus*), peas (*Pisum sativum*), parsnips (*Pastinaca sativa*), carrots (*Daucus carota*), parsley (*Petroselinum crispum*), duckweed, pine, spruce, fir, *eucalyptus*, oak, walnut, or willow. In particular embodiments, the plant and/or plant cell can be *Arabidopsis thaliana*. In some representative embodiments, the plant and/or plant cell can be *camelina*, wheat, rice, corn, rape, canola, soybean, sorghum, tomato, bamboo, or cotton.

In further embodiments, a plant and/or plant cell can be an algae or algae cell including, but not limited to, a Bacillariophyceae (diatoms), Haptophyceae, Phaeophyceae (brown algae), Rhodophyceae (red algae) or Glaucophyceae (red algae). In still other embodiments, non-limiting examples of an algae or algae cell can be *Achnanthidium, Actinella, Nitzschia, Nupela, Geissleria, Gomphonema, Planothidlum, Halamphora, Psammothidium, Navicula, Eunotia, Stauroneis, Chlamydomonas, Dunaliella, Nannochloris, Nannochloropsis, Scenedesmus, Chlorella, Cyclotella, Amphora, Thalassiosira, Phaeodadylum, Chrysochromulina, Prymnesium, Thalassiosira, Phaeodactylum, Glaucocysts, Cyanophora, Galdieria*, or *Porphyridium*.

Non-limiting examples of fungi useful with this invention include *Candida* spp., *Fusarium* spp., *Aspergillus* spp., *Cryptococcus* spp., *Coccidioides* spp., *Tinea* spp., *Sporothrix* spp., *Blastomyces* spp., *Histoplasma* spp., *Pneumocystis* spp, *Saccharomyces* spp., *Saccharomycodes* spp., *Kluyveromyces* spp., *Pichia* spp., *Candida* spp., *Zygosaccharomyces* spp. or *Hanseniaspora* spp. In representative embodiments, the fungus can include, but is not limited to, *Saccharomyces cerevisiae, S. uvarum (carlsbergensis), S. diastaticus, Saccharomycodes ludwigii, Kluyveromyces marxianus, Pichia pastoris, Candida stellata, C. pulcherrima, Zygosaccharomyces fermentati, Hanseniaspora uvarum, Aspergillus fumigatus, Aspergillus flavus, Aspergillus niger, Aspergillus terreus, Aspergillus nidulans, Candida albicans, Coccidioides immitis, Cryptococcus neoformans, Fusarium solani, Fusarium culmorum, Tinea unguium, Tinea corporis, Tinea cruris, Sporothrix schenckii, Blastomyces dermatitidis, Histoplasma capsulatum, Pneumocystis carinii*, or *Histoplasma duboisii*.

The target gene can be any gene of interest for which there is a desire to repress expression or modulate the repression of expression. Thus, in some embodiments, non-limiting examples of a target gene can include a gene encoding a transcriptional regulator, a translational regulator, a polymerase gene, a metabolic enzyme, a transporter, an RNase, a protease, a DNA replication enzyme, a DNA modifying or degrading enzyme, a regulatory RNA, a transfer RNA, or a ribosomal RNA. A target gene can also be a gene that, for example, is involved in cell-division, cell structure, metabolism, motility, pathogenicity or virulence. In other embodiments, a target gene useful with this invention can also include a hypothetical gene whose function is not yet characterized (see, e.g., Kolker et al. *Nucleic Acids Research* 32(8): 2353-2363 (2004)).

In representative embodiments, a target nucleotide sequence can comprise, consist essentially of or consist of all or a part of a nucleotide sequence encoding a promoter, or a complement thereof, of a target gene. The present inventors have discovered that spacer nucleotide sequences that are complementary to a promoter, or a part thereof, of a target gene achieve substantial gene repression when used as disclosed herein. In particular, it was discovered that substantial gene repression can be achieved with such spacers, regardless of which strand was targeted.

In further aspects, recombinant nucleic acid molecules, recombinant CRISPR arrays, and/or the nucleotide sequences of this invention can be introduced into a cell of a host organism. Any cell/host organism for which this invention is useful with can be used. Exemplary host organisms include, but are not limited to, a plant, bacterium, archaeon, fungus, animal, mammal, insect, bird, fish, amphibian, cnidarian, human, or non-human primate. In further embodiments, a cell useful with this invention can be, but is not limited to a stem cell, somatic cell, germ cell, plant cell, animal cell, bacterial cell, archaeon cell, fungal cell, mammalian cell, insect cell, bird cell, fish cell, amphibian cell, cnidarian cell, human cell, or non-human primate cell. Thus, in some embodiments, a recombinant nucleic acid molecule, recombinant CRISPR array, or a nucleotide sequence of this invention can be introduced into a cell of an organism for which repression of expression or modulation of repression of expression is desirable for target genes in said cell/organism Accordingly, further provided are methods for using the recombinant nucleic acid molecules and CRISPR arrays of this disclosure. Thus, in some embodiments, a method for a repressing the expression (reducing transcription) of a target gene is provided, the method comprising: introducing of an organism (e.g., into a cell) a recombinant nucleic acid molecule of the invention and at least one recombinant CRISPR array of the invention, thereby repressing the expression (reducing the transcription) of said target gene. Varying levels of repression can be achieved according to the methods of this invention. Thus, the extent of repression (e.g., silencing) for any given target gene will depend on the design of the spacers that are targeting the gene of interest (e.g., target gene) including, but not limited to, the number of spacers used to target the gene of interest (multiplexing), the location of the target nucleotide sequence on the target gene to which the spacer has complementarity (including the number of overlapping versus non-overlapping target nucleotide sequences), the length of the spacers and/or the complementarity of each spacer to the target nucleotide sequence of the target gene.

In other embodiments, a method for a repressing the expression (reducing transcription) of a target gene is provided, the method comprising: introducing of an organism (e.g., into a cell of said organism) a recombinant nucleic acid molecule of the invention and at least one recombinant CRISPR array of the invention, wherein the at least one recombinant CRISPR array introduced into the organism comprises at least two spacer nucleotide sequences each comprising a nucleotide sequence that is complementary to a different target nucleotide sequence from a single target gene, thereby modulating the repression of said target gene relative to a recombinant CRISPR array having no spacers directed to said target gene or a CRISPR array that has more or fewer of such spacer nucleotide sequences each comprising a nucleotide sequence that is complementary to a different target nucleotide sequence from a single target gene.

In other embodiments, a CRISPR array having fewer spacer nucleotide sequences that are complementary to a different target nucleotide sequence derived from a single target gene when introduced into an organism or cell can result in reduced or decreased repression as compared to a CRISPR array having more spacer nucleotide sequences that are complementary to a different target nucleotide sequence derived from the same target gene.

In further embodiments, a spacer nucleotide sequence that is less complementary to a target nucleotide sequence derived from a single target gene when introduced into an organism or cell can result in reduced or decreased repression as compared to a spacer nucleotide sequence that has a greater degree of complementarity to the same target nucleotide sequence derived from the same target gene. In still further embodiments, a longer spacer nucleotide sequence complementary to a target nucleotide sequence derived from a single target gene when introduced into an organism or cell can result in increased repression as compared to a shorter spacer nucleotide sequence that is complementary to the same target nucleotide sequence derived from the same target gene.

As the skilled artisan would readily understand, the various spacer nucleotide sequence and CRISPR array designs can be used, alone or in combination with each other and in single or multiple CRISPR arrays, to provide significant flexibility in the amount or level of repression achieved in a single or in multiple target genes. Thus, for example, the total number of spacers, as well as the length of each spacer, location in the target gene, and/or the degree of complementarity can be used, alone or in combination, along with any other spacer/CRISPR array designs to provide a desired level of repression of a target gene.

In still other embodiments, a method for repressing the expression (reducing transcription) of at least two genes in an organism is provided, the method comprising: introducing into an organism a recombinant nucleic acid molecule of the invention and at least one recombinant CRISPR array of the invention, wherein the at least one recombinant CRISPR array comprises at least two spacer nucleotide sequences each comprising a nucleotide sequence that is complementary to a different target nucleotide sequence from a different target gene, thereby repressing the expression of at least two genes in said organism. As would be readily understood by the skilled artisan, any combination of spacer and CRISPR array design described herein and variations thereof can be used to repress the expression and/or modulate the repression of expression of said two genes.

In some embodiments, to design a spacer nucleotide sequence for targeting a genomic sequence, one first identifies a region of the gene of interest (e.g., the target nucleotide sequence) that is adjacent to a set of nucleotide sequences called a protospacer adjacent motif (PAM). This motif is thus found in the target gene next to the region to which a spacer sequence binds as a result of being complementary to that region and identifies the point at which base pairing with the spacer nucleotide sequence begins. For type I systems, the PAM is located immediately 5' to the sequence that matches the spacer, and thus is 3' to the sequence that base pairs with the spacer nucleotide sequence. Non-limiting examples of PAMs include CCA, CCT, CCG, CCT, CCA, TTC, AAG, AGG, ATG, GAG, and/or CC.

In some embodiments, the polypeptides encoded by a recombinant nucleic acid molecule as disclosed herein can be introduced as protein complex. Accordingly, in some embodiments, a protein complex can comprise, consist essentially of, or consist of any subset of a group of polypeptides from a type-I Cascade. In other embodiments, a protein complex can comprise, consist essentially of, or consist of (a) a Cas6b polypeptide, a Cas8b (Csh1) polypeptide, a Cas7 (Csh2) polypeptide and a Cas5d polypeptide (Type I-B); (b) a Cas5 polypeptide, a Cas8c (Csd1) polypeptide, and a Cas7 (Csd2) polypeptide (Type I-C); (c) a Cse1 (CasA) polypeptide, a Cse2 (CasB) polypeptide, a Cas7 (CasC) polypeptide, a Cas5 (CasD) polypeptide and a Cas6e (CasE) polypeptide (Type I-E); (d) a Cys1 polypeptide, a Cys2 polypeptide, a Cas7 (Cys3) polypeptide and a Cas6f polypeptide (Type I-F); (e) a Cas7 (Csa2) polypeptide, a Cas8a1 (Csx13) polypeptide or a Cas8a2 (Csx9) polypeptide, a Cas5 polypeptide, a Csa5 polypeptide, a Cas6a polypeptide, a Cas3' polypeptide, and a Cas3" polypeptide having no nuclease activity (Type I-A); or (f) a Cas10d (Csc3) polypeptide, a Csc2 polypeptide, a Csc1 polypeptide, and a Cas6d polypeptide (Type I-D). Thus, in some embodiments, a protein complex and a CRISPR array are introduced into a cell free system, a cell and/or an organism. In some embodiments, said protein complex and CRISPR array are introduced separately or together as a ribonucleoprotein.

Thus, in further embodiments, a ribonucleoprotein complex comprising, consisting essentially of, or consisting of the protein complex and a CRISPR array of the invention can be introduced into a cell free system, a cell and/or an organism. In some embodiments, the protein complex/ribonucleoprotein complex can be delivered to transiently repress genes, thereby providing further advantageous methods for achieving desired levels of target gene repression.

Accordingly, in still further embodiments, the polypeptide encoded by a recombinant nucleic acid molecule can be delivered as a protein complex, DNA, RNA (e.g., mRNA) or a ribonucleoprotein complex. In some embodiments, the CRISPR array can be delivered as a DNA or an RNA.

In additional aspects, the present invention provides a method of repressing the expression of a bacterium or archaeon target gene, comprising: disrupting an endogenous cas3 nucleotide sequence in a bacterium or archaeon, wherein the disrupted endogenous cas3 nucleotide sequence is not present, or is present but not expressed and/or is expressed but non-functional; and introducing into said bacterium or archaeon at least one recombinant CRISPR array of the invention or an expression cassette or vector comprising at least one recombinant CRISPR array of the invention, thereby repressing the expression of said bacterium or target gene.

In still further aspects, the present invention provides a method of modulating the repression of expression of a bacterium or archaeon target gene, comprising: disrupting an endogenous cas3 nucleotide sequence in a bacterium or archaeon, wherein the disrupted endogenous cas3 nucleotide sequence is not present, or is present but not expressed and/or is expressed but non-functional; and introducing into said bacterium or archaeon at least one recombinant CRISPR array of the invention or an expression cassette or vector comprising at least one recombinant CRISPR array of the invention, wherein the at least one recombinant CRISPR array comprises at least two spacer nucleotide sequences each comprising a nucleotide sequence that is complementary to a different target nucleotide sequence from a single target gene, thereby modulating the repression of said bacterium or archaeon target gene relative to a the same target gene in a bacterium or archaeon that comprises a CRISPR array having no spacers directed to said target gene or a CRISPR array having more or fewer of such spacer nucleotide sequences each comprising a nucleotide sequence that is complementary to a different target nucleotide sequence from a single target gene.

In additional embodiments, the present invention provides a method of repressing the expression of at least two genes of a bacterium or archaeon target gene, comprising: disrupting an endogenous cas3 nucleotide sequence in a bacterium or archaeon, wherein the disrupted endogenous cas3 nucleotide sequence is not present, or is present but not expressed and/or is expressed but non-functional; and introducing into said bacterium or archaeon at least one recombinant CRISPR array of the invention or an expression cassette or vector comprising at least one recombinant CRISPR array of the invention, wherein the at least one recombinant CRISPR array comprises at least two spacer nucleotide sequences each comprising a nucleotide sequence that is complementary to a different target nucleotide sequence from a different target gene, thereby repressing the expression of at least two target genes of said bacterium or archaeon.

In some embodiments, the at least one recombinant CRISPR array of the invention or an expression cassette or vector comprising at least one recombinant CRISPR array of the invention can be introduced into said bacterium or archaeon at the same time as the disrupting of said endogenous cas3 nucleotide sequence. In other embodiments, the at least one recombinant CRISPR array of the invention or an expression cassette or vector comprising at least one recombinant CRISPR array of the invention can be introduced into said bacterium or archaeon after the endogenous cas3 nucleotide sequence is disrupted. In some embodiments, said bacterium or archaeon comprises an endogenous Cascade. In further embodiments, at least one heterologous promoter is introduced into the bacterium or archaeon and operably linked to said endogenous Cascade. In representative embodiments, said heterologous promoter(s) is introduced at the same time as the disrupting of the endogenous cas3 via, for example, homologous recombination.

As used herein, "disrupt", "disrupted," or "disrupting" and/or other grammatical variations, means that the cas3 nucleotide sequence is mutated or otherwise altered such that either the nucleotide sequence encoding the Cas3 protein is absent, or the nucleotide sequence encoding the Cas3 protein is present, but the Cas3 protein is not produced or is produced and is non-functional.

Disruption of the cas3 nucleotide sequence can be accomplished by any method known to those of ordinary skill in the art for altering or mutating a nucleotide sequence. Such methods include, but are not limited to, generating point mutations (e.g., missense, or nonsense, or insertions or deletions of single base pairs that result in frame shifts), insertions, deletions, and/or truncations.

In some embodiments, disruption results in the removal or deletion of the entire cas3 nucleotide sequence, or a portion thereof (e.g., 1% to 99%, or any value or range therein). In representative embodiments, the entire nucleotide sequence encoding the cas3 gene is deleted by, for example, homologous recombination. In particular embodiments, the disruptions can result in premature translational termination, premature transcriptional termination, disruption endonuclease catalytic sites, or mutations that destabilize or prevent proper folding of the protein, wherein no cas3 polypeptide is produced or a non-functional cas3 polypeptide is produced. Methods for mutating or otherwise altering an endogenous gene are well known in the art and can be readily used with the methods of this invention to produce a bacterium or archaeon having no endogenous cas3 polypeptide or a non-functional cas3 polypeptide.

"A non-functional Cas3 polypeptide" as used herein is a Cas3 polypeptide having little or no nuclease activity. Having "little or no nuclease activity" means that the disrupted cas3 polypeptide exhibits about 10% or less activity (e.g., about 10%, 9%, 8%, 7%, 6%, 5%, 4%, 3%, 2%, 1%, or 0%, or any value or range therein) as compared to the wild-type/non-disrupted Cas3 polypeptide. Further, as used herein, a non-functional Cas3 polypeptide has little or no nuclease activity over a wide range of temperatures including from about 10° C. to about 125° C., or any value or range therein. Therefore, a non-functional Cas3 polypeptide as defined herein is a Cas3 polypeptide having little to no activity at a temperature of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, and/or 125° C. Accordingly, as one example, a disrupted Cas3 polypeptide of the invention includes a cas3 polypeptide that is active at 30° C. but inactive at 42° C.

A further aspect of the invention relates to kits for use in the methods of the invention. The kit can comprise the recombinant nucleic acid constructs, CRISPR arrays, nucleotide sequences and/or vectors/expression cassettes of the invention in a form suitable for introduction into a cell and/or administration to a subject. The kit can further comprise other therapeutic agents, carriers, buffers, containers, devices for administration, and the like. The kit can further comprise labels and/or instructions for repression of expression a target gene and/or modulation of repression of expression of a target gene. Such labeling and/or instructions can include, for example, information concerning the amount, frequency and method of introduction and/or administration of the recombinant nucleic acid constructs, CRISPR arrays, nucleotide sequences and/or vectors/expression cassettes.

Accordingly, in one aspect, a kit for repressing the expression of at least one target nucleotide sequence is provided, said kit comprising, consisting essentially of, consisting of a recombinant nucleic acid molecule of the invention, a recombinant CRISPR array of the invention and/or an expression cassette or vector comprising said recombinant nucleic acid molecule of the invention and/or a recombinant CRISPR array of the invention.

In some embodiments, a kit is provided for modulating the repression of at least one target gene, the kit comprising, consisting essentially of, consisting of a recombinant nucleic acid molecule of the invention, a recombinant CRISPR array of the invention and/or an expression cassette or vector comprising said recombinant nucleic acid molecule of the invention and/or a recombinant CRISPR array of the invention, wherein the recombinant CRISPR array comprises, consists essentially of, consists of at least two spacer nucleotide sequences each comprising a nucleotide sequence that is complementary to a different target nucleotide sequence from a single target gene.

In additional embodiments, a kit is provided for modulating the repression of at least two target genes, the kit comprising, consisting essentially of, consisting of a recombinant nucleic acid molecule of the invention, a recombinant CRISPR array of the invention and/or an expression cassette or vector comprising said recombinant nucleic acid molecule of the invention and/or a recombinant CRISPR array of the invention, wherein the recombinant CRISPR array comprises, consists essentially of, consists of at least two spacer nucleotide sequences each comprising a nucleotide sequence that is complementary to a different target nucleotide sequence from a different target gene.

In some embodiments, the recombinant nucleic acid molecule and the recombinant CRISPR array of said kits are comprised on a single vector or expression cassette or on separate vectors or expression cassettes. In further embodiments, the kits comprise instructions for use.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1. Methods

Using homologous recombination and P1 transduction, the cas3 gene knocked out of the genome of *E. coli* BW25113 as well as the genome of *E. coli* MG1655 and a constitutive promoter placed upstream of the casABCDE operon. This ensured that the Cas3 protein would be completely absent while the Cascade complex (comprised of the five Cas proteins CasA, CasB, CasC, CasD, and CasE) would be constitutively expressed.

Spacers were designed to target a fluorescent reporter plasmid, pUA66lacZ. This plasmid expresses the fluorescent GFP protein under the control of the lacZ promoter. Spacers were designed by locating the PAM (protospacer-adjacent motif) sequence—either AGG or AAG—and selecting the adjacent 30 nucleotides on the 3' end. Spacers were selected to cover different locations of interest, including the promoter, untranslated region, and coding region. Both the coding and non-coding strands of DNA were targeted.

Each spacer was cloned into the expression vector pCRISPR. This vector contains a minimal CRISPR array: a promoter, a single repeat, and a terminator. The vector allows for sequential introduction of spacers so that multiple spacers can be expressed from a single CRISPR array. With a working spacer, Cascade (e.g., the recombinant nucleic acid molecule) was directed to bind to the DNA of pUA66lacZ and reduce the expression level of GFP, thus reducing fluorescence. The plasmids pUA66lacZ and pCRISPR were co-transformed into BW25113Δcas3. Cells harboring a pCRISPR plasmid with the indicated spacer were grown in M9 minimal medium supplemented with 0.4% glycerol and 0.2% casamino acids, back-diluted into the same medium, and grown for 6 hours to mid-log phase. Fluorescence was then measured on an Accuri C6 flow cytometer.

Using flow cytometry, the levels of transcriptional repression were quantified by measuring a reduction in fluorescence. In the absence of any repression, pUA66lacZ yields strong fluorescence.

Spacers were further designed to target the promoters of three endogenous operons responsible for the catabolism of L-arabinose (araBAD), D-xylose (xylAB), and lactose (lacZYA). The transduced MG1655 cells harboring the pCRISPR or the spacer-encoding plasmids were grown for 24 hours in M9 medium supplemented with glycerol, back-diluted to $ABS_{600}$ of 0.001 in M9 medium supplemented with the indicated carbon source, and cultured at 37° C. for 22 hours. The final $ABS_{600}$ value of each culture was then measured using a Nanodrop 2000c spectrophotometer.

Example 2. Data

Shown in FIG. 1 is the region of interest in the plasmid pUA66lacZ that encodes fluorescent GFP polypeptide under control of the lacZ promoter. The long green arrow indicates the coding region of gfp. The thin black arrow indicates the start of transcription with the −35 and −10 elements of the promoter outlined in black. Each spacer on the top matches the top strand or the coding strand (and therefore, binds the bottom strand or non-coding strand). Similarly each spacer on the bottom matches the bottom strand or the non-coding strand (and therefore, binds the top strand). The established PAM AAG or AGG is located at the 5' end of each protospacer.

Figure 2:
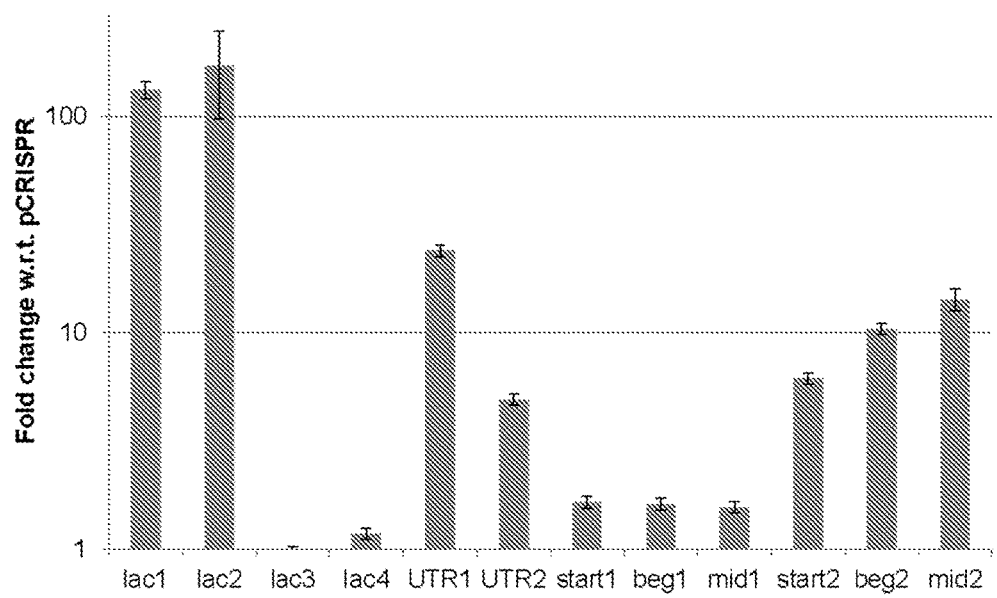
FIG. 2 provides a graph showing transcriptional repression of fluorescent GFP protein in *Escherichia coli* K-12 substrain MG1655 harboring the plasmid pUA66lacZ using methods of the invention as described herein. Cells harboring a pCRISPR plasmid with the indicated spacer were grown in M9 minimal medium supplemented with 0.4% glycerol and 0.2% casamino acids, back-diluted into the same medium, and grown for 6 hours to mid-log phase. Fluorescence was then measured on an Accuri C6 flow cytometer. Fold Change w.r.t. pCRISPR means fold change with respect to pCRISPR. pCRISPR is the same plasmid but does not encode spacers targeting the GFP gene.

FIG. 2 provides a graph showing transcriptional repression of fluorescent GFP protein in transduced MG1655 cells harboring the plasmid pUA66lacZ. Fold Change w.r.t. pCRISPR means fold change with respect to pCRISPR lacking any spacers. The flow cytometry experiments were conducted in triplicate. To compute fold-repression, the median fluorescence for each spacer was averaged and background autofluorescence was removed. Next, the fluorescence was compared against the original pCRISPR that does not any encode any spacers. For example, the pCRISPR control recorded 7332 AU and lac1 recorded 56 AU; this corresponds to a 131-fold change.

Figure 3:
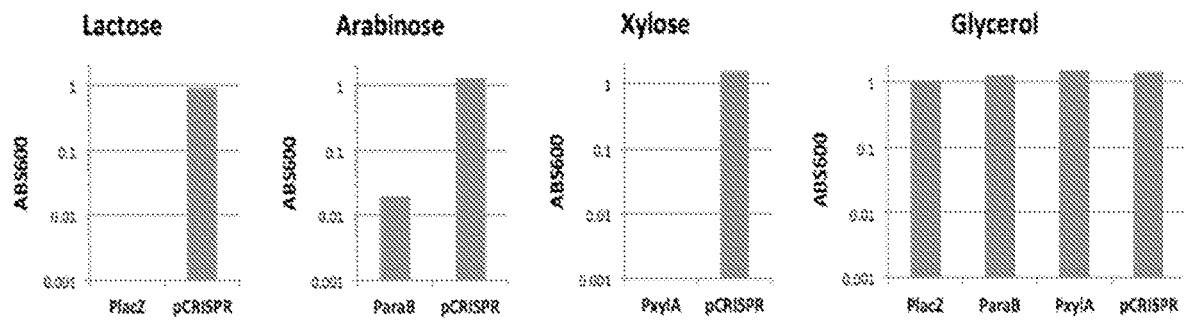
FIG. 3 provides a bar chart of the optical densities ($ABS_{600}$) of cultures of transduced MG1655 cells harboring plasmids with spacers targeting different endogenous sugar-utilization operons, and shows the resulting impact on the growth of the culture on the indicated sugar. Cells were transformed with the pCRISPR plasmid (pCRISPR) or the same plasmid harboring a spacer against the promoter of utilization genes of the associated sugar (ParaB, the araB promoter for L-arabinose; PlacZ, the lacZ promoter for lactose; and PxylA, the xylA promoter for D-xylose). Cells were grown for 24 hours in M9 medium supplemented with glycerol, back-diluted to $ABS_{600}$ of 0.001 in M9 medium supplemented with the indicated carbon source, and cultured for 22 hours. The bar graphs report the final $ABS_{600}$ value as measured using a Nanodrop 2000c spectrophotometer.

FIG. 3 provides a bar chart of the optical densities of cultures of transduced MG1655 cells harboring plasmids with spacers targeting different endogenous sugar-utilization operons, and the resulting impact on the growth of the culture on the indicated sugar. Glycerol was used as a negative control whose catabolism should not be impacted by any of the spacers. A single experiment was conducted for the growth assays, which report the measured $ABS_{600}$ value.

Example 3. Results and Conclusions

The data confirm that this invention works as expected; in the absence of Cas3, Cascade binds to DNA and elicits variable levels of transcriptional repression. In addition to the conceptual proof-of-principle, we also found that (1) targeting the promoter in the −35/−10 region (lac1/lac2) elicits the strongest repression and (2) within the transcribed region, spacers that bind the coding DNA strand show stronger silencing than spacers that bind the non-coding DNA strand. It was further found that targeting endogenous sugar utilization genes leads to negligible growth on the associated sugar. These data demonstrate that the invention can also repress the expression of endogenous genes, leading to expected phenotypes.

Example 4. Modulating Repression Via Spacer Length

Figure 12A:
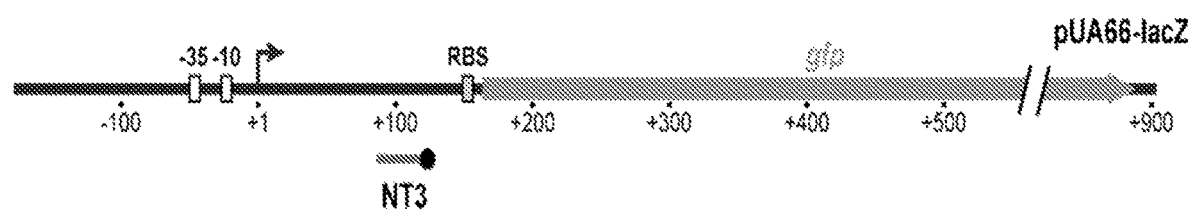
FIGS. 12A-12B shows the affect on repression of changing the length of the spacer in the recombinant constructs of the invention.
Figure 12B:
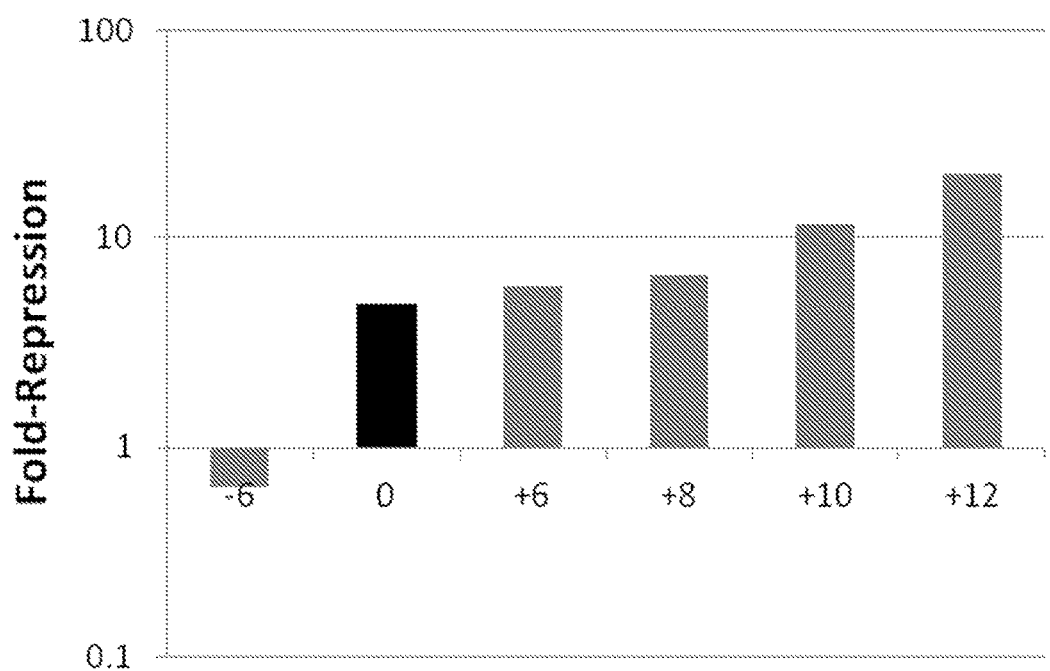

The length of an E. coli spacer was varied and the impact of the changes in length on the degree of repression was measured. The original spacer had a length of 32 nucleotides. In this study, the spacer length was increased by 6, 8, 10 or 12 nucleotides or decreased by 6 nucleotides. The construct is shown in FIG. 12A. The results are shown in FIG. 12B, wherein increased length resulted in increased repression while decreased length abolished repression.

Example 5. Modulated Gene Silencing by Altering Spacer Length and Degree of Complementarity Using the two reported spacers targeting the promoter of pUA66lacZ, we will vary the length of the spacer between 15 nts and 40 nts. We also will vary the degree of complementarity for these spacers between 50% and 100% across the entire 32-nt spacer as well as within the first 8 nts (starting at the 5' end). Each spacer will be flanked on both sides by the same repeat sequence (GAGTTCCCCGCGCCAGCGGGGATAAACCG, SEQ ID NO:250) within the pCRISPR plasmid. It will be demonstrated that reducing the length and extent of complementarity reduces the extent of GFP expression.

Example 6. Gene Silencing Through Heterologous Expression

The casABCDE operon from E. coli MG1655 will be expressed off of the pCDF-1b plasmid in an E. coli BL21 (DE3) strain in which the entire native CRISPR-Cas system will be deleted by homologous recombination. The strain will also harbor the pUA66lacZ plasmid and the pCRISPR plasmid either with no spacer or a lacZ-targeting spacer. We then will measure GFP expression in each strain, where we expect that the strain expressing the casABCDE operon and the lacZ-targeting spacer will show reduced expression in comparison to a strain not expressing the operon or the lacZ-targeting spacer. This will demonstrate gene silencing through heterologous expression of the genes from a Type I-E system.

Example 7. Multiplexed Targeting of the Same or Different Genes

Two to four spacers already shown to reduce expression from pUA66lacZ will be combined into a single array (e.g. repeat-spacer1-repeat-spacer2-repeat-spacer3-repeat for three spacers) in the pCRISPR plasmid. Additionally, we will integrate and test a spacer with a target overlapping one of the other spacers. We then will measure GFP expression for each strain. We expect GFP expression to decrease with the addition of a non-overlapping spacer, and to increase with the addition of an overlapping spacer. In addition, we will combine the three spacers targeting the sugar utilization operons (araBAD, lacZYA, xylAB) into a single array in the pCRISPR plasmid. The transduced E. coli MG1655 strains harboring this plasmid or the original pCRISPR plasmid will be grown in M9 minimal medium on each associated sugar (L-arabinose, lactose, D-xylose) or on glucose. Our expectation is that the pCRISPR plasmid with the three spacers will reduce growth on L-arabinose, lactose, and D-xylose but not on glucose. Silencing will be confirmed by qRT-PCR. These experiments will demonstrate the use of multiple spacers in a single array for modulated silencing or the silencing of multiple genes.

Example 8. Catalytically Dead Cas3

Point mutations in the cas3 gene of E. coli MG1655 will be introduced that inactivate the Cas3 catalytic activity. These point mutations, D75A and D229A, are located in the active sites of Cas3. The resulting gene will be encoded on the pCDF-1b plasmid. An E. coli BL21(DE3) strain with the native CRISPR-Cas system deleted and harboring this plasmid along with pUA66lacZ and a pCRISPR plasmid encoding one of the validated lacZ-targeting spacers. We then will measure GFP expression by flow cytometry analysis for this strain along with a strain with the original pCDF1-b plasmid. Our expectation is that the strains with an inactive Cas3 or no Cas3 will yield similar levels of GFP.

Example 9. Spacer Location within CRISPR Array

To test whether the location of a spacer within the array affects its repression efficacy, we will encode 4-spacer arrays with three non-targeting spacers and one validated lacZ-targeting spacer within the pCRISPR plasmid. Each array will contain the lacZ-targeting spacer in a different location within the array. The transduced E. coli MG1655 strain harboring pUA66lacZ and each pCRISPR plasmid will be tested by quantifying GFP expression by flow cytometry. By comparing levels of repression, we can compare which locations within the CRISPR array elicit the strongest repression or whether the location is irrelevant.

Example 10. Other Type I Systems

The present approach using the Type I-E CRISPR-Cas system in E. coli will be generalized to other Type I systems. The reasoning is that cas3 is the signature gene associated with all Type I systems (I-A, I-B, I-C, I-D, I-E, I-F) with the conserved function of cleaving and degrading DNA bound by Cascade. To further explore the propensity of other Type I systems to achieve transcriptional repression, we will investigate the Type I-C system in *Streptococcus pyogenes*, the Type I-F system in *Pectobacterium atrosepticum*, the Type I-B system in *Aeropyrum pernix*, and the Type I-D system in *Methanospirillum hungatei*. We will encode the genes that comprise Cascade from each system as operons in the pCDF-1b and pRSF-1b expression vectors. E. coli BL21(DE3) cells will then be transformed with plasmids encoding each system and the original pCRISPR plasmid or a pCRISPR plasmid encoding a spacer flanked by repeats from the native system. The spacer will be designed to target the xylA promoter using a PAM derived from the native system. We then will evaluate growth and xylAB expression (by qRT-PCR). We expect cells encoding each system and targeting the xylA promoter will grow poorly on xylose and showed reduced xylAB expression.

Example 11. Archaea

Transcriptional silencing with Type I systems in archaea will also be investigated using *Pyrococcus furiosus* COM1. First, we will delete the native cas3 gene (PFC_04820) associated with the Type I-B system by homologous recombination of the $P_{gdh}$-pyrF gene and selection on defined medium with uracil followed by removal of the pyrF gene by growth on 5'FOA. The cas3' (PFC_02330) and the cas3" (PFC_02335) genes associated with the Type I-A system will also be deleted using the same approach. We will then encode a 30-nt spacer flanked on both sides by the native repeat sequence (GTTACAATAAGACTAAAATAGAATT-GAAAG, SEQ ID NO:251) targeting the promoter of the gdh gene (PFC_00670) or the 2-hydroacid dehydrogenase gene (PFC_00915). Spacers with a protospacer with a 5' CCN PAM will be tested. Each construct will be driven by the S-layer protein (slp) promoter and integrated with pyrF into the genome. We will then measure mRNA levels of each target gene by qRT-PCR for the targeting spacer and a non-targeting spacer. We expected to substantially reduce mRNA levels for either gene in the COM1 strain lacking cas3 as well as the strain lacking cas3, cas3', and cas3".

Example 12. Eukaryotic Organisms

Transcriptional silencing in eukaryotic organisms will be investigated using Baker's yeast and Hela cells as exemplary hosts. A synthetic CRISPR array and the Cascade genes from the Type I-E system in E. coli (casA, casB, casC, casD, casE) will be encoded in standard expression vectors for each host, where each gene will be individually expressed from a separate promoter and terminator (e.g. CMV promoter and SV40 polyA tail for each gene). We also will encode multiple genes in two transcripts using intervening IRES sequences and self-cleaving peptide sequences to simplify the expression constructs. The constructs will be transformed into cell lines stably expressing GFP. The array will encode one, two, or three 32-nt spacers designed to target the heterologous GFP promoter as well as the coding region. Flow cytometry analysis will be used to measure the extent of repression. It is expected that GFP fluorescence will decrease in cell lines expressing the CRISPR array and Cascade genes.

Example 13

Strains and Plasmid Construction.

Table 1, below, provides the list of the E. coli strains used.

TABLE 1

| E. coli strains | | | |
|---|---|---|---|
| Strains | Genotype | Source | Stock # |
| BW25113 | *Escherichia coli* K12 F− DE(araD-araB)567 lacZ4787(del)(::rrnB-3) λ− rph-1 DE(rhaD-rhaB)568 hsdR514 | CGSC[a] #7636 | pCB294 |
| BW25113 Δcas3::cat | BW25113 [Δcas3 $P_{cse1}$::[cat $P_{J23119}$] | This study | pCB385 |
| BW25113 Δcas3 | BW25113 [Δcas3 $P_{cse1}$::[$P_{J23119}$] | This study | pCB400 |
| BW25113 ΔCRISPR-Cas | BW25113 [Δcas3-cse1-cse2-cas7-cas5-cas6e-CRISPR1]::cat | This study | pCB401 |
| NM500 cas3+ | NM500 [ΔP$_{cse1}$]::[cat P$_{J23119}$] | This study | pCB402 |
| MG1655 | *Escherichia coli* K12 F− λ− ilvG− rfb-50 rph-1 | Storz lab (NIH) | pCB1 |
| MG1655 Δcas3::cat | MG1655 [Δcas3 $P_{cse1}$::[cat $P_{J23119}$] | This study | pCB386 |

[a]CGSC: Coli Genetic Stock Center (cgsc.biology.yale.edu).

To generate BW25113 Δcas3::cat and MG1655 Δcas3::cat, the cat resistance cassette was PCR-amplified from the pKD3 plasmid (Datsenko et al. (2000) *Proc. Natl. Acad. Sci. U.S.A.*, 97, 6640-6645) using oligonucleotides that append the synthetic constitutive promoter J23119 (BBa_J23119 in the registry for standard biological parts, partsregistry.org) (J23119-pKD3.for, J23119-pKD3.rev). Following a second PCR amplification to introduce homology arms (HR-cas3.for, HR-cas3.rev), the resulting PCR product was recombineered into NM500 by mini-λ-mediated recombination (Court et al. (2003) *Gene*, 315, 63-69). The insertion replaced the native cas3 gene and the native promoter for the Cascade operon with the cat cassette and the J23119 promoter. Successful recombination was verified by sequencing. P1 transduction was then used to transfer the cat cassette and the synthetic promoter into BW25113 and MG1655. Successful transduction was verified by PCR. To generate BW25113 Δcas3, the cat cassette from BW25113 Δcas3::cat was excised using the pCP20 plasmid as described previously (Cherepanov, et al. (1995) *Gene*, 158, 9-14). To generate NM500 cas3+, the cat resistance cassette was PCR-amplified from the pKD3 plasmid using oligonucleotides that append the constitutive promoter J23119 (J23119-pKD3.for, HR-casA.rev). Following a second PCR amplification to introduce homology arms (HR-cas3.for, HR-casA.rev), the resulting PCR product was recombined into NM500. This NM500 cas3+ strain replaces the native promoter for the Cascade operon with a constitutive promoter while retaining the native cas3 gene. To generate BW25113 ΔCRISPR-Cas::cat, the cat resistance cassette was PCR-amplified from the pKD3 plasmid (HR-CRISPR-.for, HR-cas3.rev), and recombineered into NM500, followed by P1 transduction into BW25113. This BW25113 ΔCRISPR-Cas eliminates the entire CRISPR locus as well as cas3, the Cascade operon, and the CRISPR1 locus.

See Table 2, below, for a list of all plasmids used in this work.

TABLE 2

Plasmids

| Plasmid | Description | Resistance marker | Source | Stock # |
|---|---|---|---|---|
| pUA66-lacZ | lacZ promoter upstream of GFP | Kanamycin | OpenBiosystems | pCB338 |
| pUA66-araB | araB promoter upstream of GFP | Kanamycin | OpenBiosystems | pCB208 |
| pUA66-xylA | xylA promoter upstream of GFP | Kanamycin | Ref. (3) | pCB289 |
| pUA66-rhaB | rhaB promoter upstream of GFP | Kanamycin | Ref. (3) | pCB292 |
| pBAD18 | L-arabinose-inducible plasmid with araC regulator | Ampicillin | Ref. (3) | pCB284 |
| pcrRNA.ind | pBAD18 with single repeat | Ampicillin | This study | pCB359 |
| pcrRNA.ind-T1 | pcrRNA.ind with spacer T1 | Ampicillin | This study | pCB360 |
| pcrRNA.ind-T2 | pcrRNA.ind with spacer T2 | Ampicillin | This study | pCB361 |
| pcrRNA.ind-T3 | pcrRNA.ind with spacer T3 | Ampicillin | This study | pCB362 |
| pcrRNA.ind-T4 | pcrRNA.ind with spacer T4 | Ampicillin | This study | pCB363 |
| pcrRNA.ind-T5 | pcrRNA.ind with spacer T5 | Ampicillin | This study | pCB364 |
| pcrRNA.ind-T6 | pcrRNA.ind with spacer T6 | Ampicillin | This study | pCB365 |
| pcrRNa.ind-NT1 | pcrRNA.ind with spacer NT1 | Ampicillin | This study | pCB366 |
| pcrRNA.ind-NT2 | pcrRNA.ind with spacer NT2 | Ampicillin | This study | pCB367 |
| pcrRNA.ind-NT3 | pcrRNA.ind with spacer NT3 | Ampicillin | This study | pCB368 |
| pcrRNA.ind-NT4 | pcrRNA.ind with spacer NT4 | Ampicillin | This study | pCB369 |
| pcrRNA.ind-NT5 | pcrRNA.ind with spacer NT5 | Ampicillin | This study | pCB370 |
| pcrRNA.ind-NT6 | pcrRNA.ind with spacer NT6 | Ampicillin | This study | pCB371 |
| pcrRNA.ind-LM | pcrRNA.ind with spacers T2-mviM | Ampicillin | This study | pCB372 |
| pcrRNA.ind-LMM | pcrRNA.ind with spacers T2-mviM-mviM | Ampicillin | This study | pCB373 |
| pcrRNA.ind-LMMM | pcrRNA.ind with spacers T2-mviM-mviM-mviM | Ampicillin | This study | pCB374 |
| pcrRNA.ind-MLMM | pcrRNA.ind with spacers mviM-T2-mviM-mviM | Ampicillin | This study | pCB375 |
| pcrRNA.ind-MMLM | pcrRNA.ind with spacers mviM-mviM-T2-mviM | Ampicillin | This study | pCB376 |
| pcrRNA.ind-MMML | pcrRNA.ind with spacers mviM-mviM-mviM-T2 | Ampicillin | This study | pCB377 |
| pcrRNA.ind-MMMM | pcrRNA.ind with spacers mviM-mviM-mviM-mviM | Ampicillin | This study | pCB378 |
| pcrRNA.con | pcrRNA.con with synthetic constitutive promoter | Ampicillin | This study | pCB379 |
| pcrRNA.con-lacZ | pcrRNA.con with spacer T2 | Ampicillin | This study | pCB380 |
| pcrRNA.con-araB | pcrRNA.con with spacer araB | Ampicillin | This study | pCB381 |
| pcrRNA.con-xylA | pcrRNA.con with spacer xylA | Ampicillin | This study | pCB382 |
| pcrRNA.con-rhaB | pcrRNA.con with spacer rhaB | Ampicillin | This study | pCB383 |
| pcrRNA.con-araB/rhaB/xylA/T2 | pcrRNA.con with spacers araB-rhaB-xylA-T2 | Ampicillin | This study | pCB384 |

The GFP reporter plasmids were based on the pUA66 plasmid (low-copy sc101 origin-of-replication) (Zaslaver at al. (2006) *Nat. Methods*, 3, 623-628) and reported in previous work (Afroz et al. (in press) Bacterial sugar utilization gives rise to distinct single-cell behaviors. *Mol. Microbiol.*). To construct the arabinose-inducible pcrRNA.ind plasmid (medium-copy pBR322 origin-of-replication), oligonucleotides were designed to encode a single repeat and a synthetic rho-independent terminator (BBa_B1006 in the registry for standard biological parts) (pcrRNA.ind.for, pcrRNA.ind.rev). These oligonucleotides were annealed, 5' phosphorylated using polynucleotide kinase (PNK), and ligated into the pBAD18 plasmid digested with KpnI-HF and HindIII-HF. To construct the constitutively expressed pcrRNA.con plasmid, oligonucleotides encoding the synthetic constitutive promoter J23119 (pcrRNA.con.for, pcrRNcon.rev) were annealed, 5' phosphorylated with polynucleotide kinase (PNK), and ligated into the pcrRNA.ind plasmid digested with NsiI and NheI. The insertion replaced the araC gene and P$_{araB}$a promoter with the synthetic constitutive promoter. To insert new repeat-spacer pairs into pcrRNA.con or pcrRNA.ind, oligonucleotides encoding the palindromic repeat and crRNA spacers were annealed, 5' phosphorylated with PNK, and ligated into either plasmid digested with KpnI and XhoI. See FIG. 6 for an illustration of the cloning scheme.

All plasmid cloning was verified by sequencing. See Table 3, below, for a list of oligonucleotides used in this work. The oligonucleotides were chemically synthesized by IDT. All enzymes were purchased from NEB.

TABLE 3

| Oligonucleotides | |
|---|---|
| Name | Sequence |
| J23119-pKD3.for | GCTAGCATTATACCTAGGACTGAGCTAGCTGTCAATCCATATGAA<br>TATCCTCCTTAG<br>SEQ ID NO: 252 |
| J23119-pKD3.rev | TGTAGGCTGGAGCTGCTT<br>SEQ ID NO: 253 |
| HR-cas3.for | TACAATTAACCTATACATATATTAAGATGTGTTGAATTGTGCTAG<br>CATTATACCTAGGAC<br>SEQ ID NO: 254 |
| HR-cas3.rev | TGATATCATCGATAATACTAAAAAAACAGGGAGGCTATTATGTAG<br>GCTGGAGCTGCTT<br>SEQ ID NO: 255 |
| HR-CRISPR.rev | ACCGCAGAGGCGGGGGAACTCCAAGTGATATCCATCATTCCATAT<br>GAATATCCTCCTTAG<br>SEQ ID NO: 256 |
| perRNA.ind.for | CCACCTCGAGTTCCCCGCGCCAGCGGGGATAAACCGAAAAAAAA<br>ACCCCGCCCCTGACAGGGCGGGGTTTTTTTA<br>SEQ ID NO: 257 |
| perRNA.ind.rev | AAGCTTAAAAAAAACCCCGCCCTGTCAGGGGCGGGGTTTTTTTT<br>CGGTTTATCCCCGCTGGCGCGGGGAACTCGAGGTGGTACC<br>SEQ ID NO: 258 |
| perRNA.con.for | TTTGACAGCTAGCTCAGTCCTAGGTATAATGCTAGCG<br>SEQ ID NO: 259 |
| perRNA.con.rev | CTAGCGCTAGCATTATACCTAGGACTGAGCTAGCTGTCAAATGCA<br>SEQ ID NO: 260 |
| T2.for | CACCTCGAGTTCCCCGCGCCAGCGGGGATAAACCGCTTTACACTT<br>TATGCTTCCGGCTCGTATGT<br>SEQ ID NO: 261 |
| T2.rev | TCGAACATACGAGCCGGAAGCATAAAGTGTAAAGCGGTTTATCC<br>CCGCTGGCGCGGGGAACTCGAGGTGGTAC<br>SEQ ID NO: 262 |
| NT2.for | CACCTCGAGTTCCCCGCGCCAGCGGGGATAAACCGCATAAAGTGT<br>AAAGCCTGGGGTGCCTAATG<br>SEQ ID NO: 263 |
| NT2.rev | TCGACATTAGGCACCCCAGGCTTTACACTTTATGCGGTTTATCCCC<br>GCTGGCGCGGGGAACTCGAGGTGGTAC<br>SEQ ID NO: 264 |
| T3.for | CACCTCGAGTTCCCCGCGCCAGCGGGGATAAACCGAAACAGCTA<br>TGACCATGATTACGGATTCAC<br>SEQ ID NO: 265 |
| T3.rev | TCGAGTGAATCCGTAATCATGGTCATAGCTGTTTCGGTTTATCCCC<br>GCTGGCGCGGGGAACTCGAGGTGGTAC<br>SEQ ID NO: 266 |
| NT3.for | CACCTCGAGTTCCCCGCGCCAGCGGGGATAAACCGGCGATTAAGT<br>TGGGTAACGCCAGGGTTTTC<br>SEQ ID NO: 267 |
| NT3.rev | TCGAGAAAACCCTGGCGTTACCCAACTTAATCGCCGGTTTATCCC<br>CGCTGGCGCGGGGAACTCGAGGTGGTAC<br>SEQ ID NO: 268 |

TABLE 3-continued

Oligonucleotides

| Name | Sequence |
|---|---|
| T1.for | CACCTCGAGTTCCCCGCGCCAGCGGGGATAAACCGCCCTTTCGTC<br>TTCACACTCGAGCACGACAG<br>SEQ ID NO: 269 |
| T1.rev | TCGACTGTCGTGCTCGAGTGTGAAGACGAAAGGGCGGTTTATCCC<br>CGCTGGCGCGGGGAACTCGAGGTGGTAC<br>SEQ ID NO: 270 |
| T4.for | CACCTCGAGTTCCCCGCGCCAGCGGGGATAAACCGAGATATACA<br>TATGAGTAAAGGAGAAGAACT<br>SEQ ID NO: 271 |
| T4.rev | TCGAAGTTCTTCTCCTTTACTCATATGTATATCTCGGTTTATCCCC<br>GCTGGCGCGGGGAACTCGAGGTGGTAC<br>SEQ ID NO: 272 |
| T5.for | CACCTCGAGTTCCCCGCGCCAGCGGGGATAAACCGTGATGCAAC<br>ATACGGAAAACTTACCCTTAA<br>SEQ ID NO: 273 |
| T5.rev | TCGATTAAGGGTAAGTTTTCCGTATGTTGCATCACGGTTTATCCCC<br>GCTGGCGCGGGGAACTCGAGGTGGTAC<br>SEQ ID NO: 274 |
| T6.for | CACCTCGAGTTCCCCGCGCCAGCGGGGATAAACCGTGATACCCTT<br>GTTAATAGAATCGAGTTAAA<br>SEQ ID NO: 275 |
| T6.rev | TCGATTTAACTCGATTCTATTAACAAGGGTATCACGGTTTATCCCC<br>GCTGGCGCGGGGAACTCGAGGTGGTAC<br>SEQ ID NO: 276 |
| NT1.for | CACCTCGAGTTCCCCGCGCCAGCGGGGATAAACCGACGAAAGGG<br>CCTCGTGATACGCCTATTTTT<br>SEQ ID NO: 277 |
| NT1.rev | TCGAAAAAATAGGCGTATCACGAGGCCCTTTCGTCGGTTTATCCC<br>CGCTGGCGCGGGGAACTCGAGGTGGTAC<br>SEQ ID NO: 278 |
| NT4.for | CACCTCGAGTTCCCCGCGCCAGCGGGGATAAACCGTTCTTCTCCT<br>TTACTCATATGTATATCTCC<br>SEQ ID NO: 279 |
| NT4.rev | TCGAGGAGATATACATATGAGTAAAGGAGAAGAACGGTTTATCC<br>CCGCTGGCGCGGGGAACTCGAGGTGGTAC<br>SEQ ID NO: 280 |
| NT5.for | CACCTCGAGTTCCCCGCGCCAGCGGGGATAAACCGGTAAGTTTTC<br>CGTATGTTGCATCACCTTCA<br>SEQ ID NO: 281 |
| NT5.rev | TCGATGAAGGTGATGCAACATACGGAAAACTTACCGGTTTATCCC<br>CGCTGGCGCGGGGAACTCGAGGTGGTAC<br>SEQ ID NO: 282 |
| NT6.for | CACCTCGAGTTCCCCGCGCCAGCGGGGATAAACCGGTATCACCTT<br>CAAACTTGACTTCAGCACGT<br>SEQ ID NO: 283 |
| NT6.rev | TCGAACGTGCTGAAGTCAAGTTTGAAGGTGATACCGGTTTATCCC<br>CGCTGGCGCGGGGAACTCGAGGTGGTAC<br>SEQ ID NO: 284 |
| araB.for | CACCTCGAGTTCCCCGCGCCAGCGGGGATAAACCGATTAGCGGA<br>TCCTACCTGACGCTTTTTATC<br>SEQ ID NO: 285 |
| araB.rev | TCGAGATAAAAAGCGTCAGGTAGGATCCGCTAATCGGTTTATCCC<br>CGCTGGCGCGGGGAACTCGAGGTGGTAC<br>SEQ ID NO: 286 |
| xylA.for | CACCTCGAGTTCCCCGCGCCAGCGGGGATAAACCGGAGTGCCCA<br>ATATTACGACATCATCCATCA<br>SEQ ID NO: 287 |

TABLE 3-continued

Oligonucleotides

| Name | Sequence |
|---|---|
| xylArev | TCGATGATGGATGATGTCGTAATATTGGGCACTCCGGTTTATCCC CGCTGGCGCGGGGAACTCGAGGTGGTAC SEQ ID NO: 288 |
| rhaB.for | CACCTCGAGTTCCCCGCGCCAGCGGGGATAAACCGGTCGCGAATT CAGGCGCTTTTTAGACTGGT SEQ ID NO: 289 |
| rhaB.rev | TCGAACCAGTCTAAAAAGCGCCTGAATTCGCGACCGGTTTATCCC CGCTGGCGCGGGGAACTCGAGGTGGTAC SEQ ID NO: 290 |
| mviM.for | CACCTCGAGTTCCCCGCGCCAGCGGGGATAAACCGAGCGCGGGC AGGGTATTCTCATCAAACCCA SEQ ID NO: 291 |
| mviM.rev | TCGATGGGTTTGATGAGAATACCCTGCCCGCGCTCGGTTTATCCC CGCTGGCGCGGGGAACTCGAGGTGGTAC SEQ ID NO: 292 |
| lacZ-qPCR.fwd | CGGCGTATCGCCAAAATCAC SEQ ID NO: 293 |
| lacZ-qPCR.rev | ATGGGTAACAGTCTTGGCGG SEQ ID NO: 294 |
| araB-qPCR.fwd | TACCAGTGCGTTAGGCTGTG SEQ ID NO: 295 |
| araB-qPCR.rev | CTGGACCCGATCCTCAATCG SEQ ID NO: 296 |
| xylA-qPCR.fwd | CGCCCCACAGGACATAGTTT SEQ ID NO: 297 |
| xylA-qPCR.rev | GGAACGGCCAACTGCTTTAC SEQ ID NO: 298 |
| rhaB-qPCR.fwd | TCACTTTCCGGGATCGGTTG SEQ ID NO: 299 |
| rhaB-qPCR.rev | TTCAGCGAGTGCTTCAGGAG SEQ ID NO: 300 |

Growth Conditions

All strains were cultured in 14 ml round-bottom polypropylene tubes at 37° C. and 250 RPM in up to 5 ml of LB medium (10 g/L tryptone, 5 g/L yeast extract, 10 g/L NaCl) or M9 minimal medium (1×M9 salts, 2 mM $MgSO_4$, 0.1 mM $CaCl_2$, 10 µg/ml thiamine) containing some combination of 0.4% glycerol, 0.2% indicated sugar, and 0.2% casamino acids. All strains were plated on LB agar (LB medium with 1.2% agar) in 100×15 mm polystyrene petri dishes. To maintain any plasmids, cells were cultured in liquid medium or on agar plates containing appropriate antibiotics at the following concentration: 50 µg/ml of ampicillin, 34 µg/ml of chloramphenicol, 50 µg/ml of kanamycin.

Spacer Design

See Table 4, below, for a list of protospacers targeted in this work.

TABLE 4

Protospacers

| Spacer name | Target strand[a] | Distance from TSS[b] | Protospacer sequence[c] |
|---|---|---|---|
| T1 | T | −141 | AGGCCCTTTCGTCTTCACaCTCGAGCACGACAG SEQ ID NO: 301 |
| T2/lacZ | T | −37 | AGGCTTTACACTTTATGCTTCCGGCTCGTATGT SEQ ID NO: 302 |
| T3 | T | +27 | AGGAAACAGCTATGACCATGATTACGGATTCAC SEQ ID NO: 303 |
| T4 | T | +149 | ACGAGATATACATATGAGTAAAGGAGAAGAACT SEQ ID NO: 304 |

TABLE 4-continued

Protospacers

| Spacer name | Target strand[a] | Distance from TSS[b] | Protospacer sequence[c] |
|---|---|---|---|
| T5 | T | +263 | AGGTGATGCAACATACGGAAAACTTACCCTTAA SEQ ID NO: 305 |
| T6 | T | +506 | AGGTGATACCCTTGTTAATAGAATCGAGTTAAA SEQ ID NO: 306 |
| NT1 | N | −129 | AAGACGAAAGGGCCTCGTGATACGCCTATTTTT SEQ ID NO: 307 |
| NT2 | N | −20 | AAGCATAAAGTGTAAAGCCTGGGGTGCCTAATG SEQ ID NO: 308 |
| NT3 | N | +119 | AAGGCGATTAAGTTGGGTAACGCCAGGGTTTTC SEQ ID NO: 309 |
| NT4 | N | +180 | AAGTTCTTCTCCTTTACTCATATGTATATCTCC SEQ ID NO: 310 |
| NT5 | N | +290 | AGGGTAAGTTTTCCGTATGTTGCATCACCTTCA SEQ ID NO: 311 |
| NT6 | N | +515 | AGGGTATCACCTTCAAACTTGACTTCAGCACGT SEQ ID NO: 312 |
| araB | T | −53 | AAGATTAGCGGATCCTACCTGACGCTTTTTATC SEQ ID NO: 313 |
| xylA | T | −19 | AGGGAGTGCCCAATATTACGACATCATCCATCA SEQ ID NO: 314 |
| rhaB | T | −33 | AAGGTCGCGAATTCAGGCGCTTTTTAGACTGGT SEQ ID NO: 315 |
| mviM[d] | N/A | N/A | AAGAGCGCGGGCAGGGTATTCTCATCAAACCCA SEQ ID NO: 316 |

[a]Characteristics of the target strand, which is complementary to the spacer: T, template strand of gene; N, non-template strand of the gene.
[b]Distance from the transcriptional start site (TSS) to the closest end of the PAM. Negative and positive values are upstream and downstream of the TSS, respectively.
[c]PAMs are in bold red lettering (first three nucleotides of each sequence). CRISPR spacers were designed to match the protospacer sequence.
[d]Targets a protospacer in Salmonella typhimurium LT2 and has been shown to be non-targeting in E. coli(4).

Protospacers were selected by identifying a PAM (CTT, CCT, CAT, CTC located at the 3' end of the target sequence) for the Type I-E system in E. coli (Westra et al. (2012) Mol. Cell, 46, 595-605). Note that only CTT and CCT were used in this work based on our previous experience with these PAM sequences (Gomaa et al. (2014) mBio, 5, e00928-00913). The 32 nucleotides immediately downstream of the PAM were then used as the spacer. The cloning scheme required changing the final two nucleotides of the spacer to TC (FIG. 6), which is not expected to impact crRNA activity (Semenova et al. (2011) Proc. Natl. Acad. Sci. U.S.A., 108, 10098-10103).

Transformation Assays

The transformation assay was conducted similar to previous work (Gomaa et al. (2014) mBio, 5, e00928-00913). Briefly, E. coli BW25113 Δcas3::cat or NM500 cas3* cells were cultured overnight in LB medium. Cultures were back-diluted 1:25 into 25 ml of LB medium in 125 ml Erlenmeyer flasks and grown to an $ABS_{600}$ of 0.6-0.8, which was quantified using a Nanodrop 2000c spectrophotometer (Thermo Scientific). The cells were then washed in ice-cold 10% glycerol and concentrated by a factor of 100. A total of 50 μl of the concentrated cells were transformed with 50 ng of plasmid DNA using a MicroPulser electroporator (Bio-Rad). Transformed cells were recovered in 500 μl SOC medium for 1 hr at 37° C. After the recovery period, the cells were diluted by factors of $10^4$-$10^6$ and 250 μl of the dilution were plated on LB agar with appropriate antibiotics and inducers.

Flow Cytometry Analysis

Cells grown overnight in M9 minimal medium containing 0.2% casamino acids and 0.4% glycerol were back-diluted to an $ABS_{600}$ of 0.01 into M9 minimal medium with the specified combination of 0.1 mM IPTG and 0.2% of the indicated inducing sugar. Upon reaching an $ABS_{600}$ of about 0.2 after about 3-4 hours of growth, the cultures were diluted 1:100 in 1×PBS and run on an Accuri C6 Flow Cytometer (Becton Dickinson) equipped with CFlow plate sampler, a 488 nm laser, and a 530±15 nm bandpass filter. Events reflecting cells were gated based on forward scatter (FSC-H) and side scatter (SSC-H) with respective lower cutoffs of 11,500 and 600 to reduce the measurement of particulates. The gate was set using E. coli cells stained with the DRAQ5 dye (Thermo Scientific). The fluorescence of the gated cells was then measured in FL1-H. At least 30,000 events were analyzed for each sample.

For the reversibility experiments, cells were grown overnight in M9 minimal medium containing 0.2% casamino acids, 0.4% glycerol, and 0.1 mM IPTG, with or without 0.2% L-arabinose. Overnight cultures were pelleted and resuspended twice in M9 minimal media with 0.2% casamino acids, 0.4% glycerol, and 0.1 mM IPTG to remove residual L-arabinose. The washed cultures were then back-diluted to an $ABS_{600}$ of ~0.001 in 30 ml of the same medium without or with 0.2% L-arabinose, respectively. Every hour, 800 µl of culture was withdrawn for flow cytometry analysis and measurement of the $ABS_{600}$.

Doubling-Time Measurements

Cells were grown overnight in M9 minimal medium with 0.4% glycerol. The overnight cultures were pelleted and resuspended twice in M9 minimal medium with no carbon source. The washed cultures were then back-diluted to an $ABS_{600}$ of ~0.001 into 25 ml of M9 minimal medium containing 0.2% of the indicated sugar in 125 ml Erlenmeyer flasks. Every 30 minutes, 800 µl of culture was withdrawn for measurement of the $ABS_{600}$.

Quantitative Real-Time PCR

Cells were grown overnight in M9 minimal medium containing 0.2% casamino acids and 0.4% glycerol. Overnight cultures were back-diluted 1:250 in M9 minimal medium containing 0.2% casamino acids, 0.4% glycerol, and 0.2% of the indicated sugar. Once cultures reached an $ABS_{600}$ of about 0.4, total RNA was isolated as reported previously (Stead, et al. (2012) *Nucleic Acids Res.*, 40, e156) followed by treatment with DNase I. cDNAs were generated from 2 µg of the resulting RNA using random primers and SuperScript III reverse-transcriptase (Invitrogen) followed by treatment with RNase H. Quantitative PCR was conducted on cDNA samples using the gene specific primers (X-qPCR.fwd/rev, where X is the target gene) provided in Table 3 and SYBR Green (Bio-Rad). cDNAs were run on a Mastercycler ep realplex² real-time PCR system (Eppendorf) according to the manufacturer's instructions. For the PCR runs, each cDNA was heated to 95° C. for 2 minutes followed by 50 cycles of a 15-second denaturing step at 95° C., a 15-second annealing step at 55° C., and a 30-second extension step at 72° C. At the end of the run a melt curve was generated to ensure the absence of non-specific products. Relative quantitation of gene expression was calculated using the $2^{\Delta Ct}$ method.

Growth Assays

Cells were inoculated into M9 minimal medium containing 0.4% glycerol and grown overnight. After 24 hours, cells were pelleted and resuspended in 2 ml of M9 minimal medium with no carbon source two times to remove glycerol as a possible source of growth. The washed cultures were then back-diluted to an $ABS_{600}$ of 0.001 into 2 ml of M9 minimal medium containing 0.2% of the indicated sugar(s). Finally, the cultures were grown for 24 hours until the $ABS_{600}$ was measured.

Example 14. Results

Targeted Gene Repression Following Deletion of Cas3

Figure 4A:
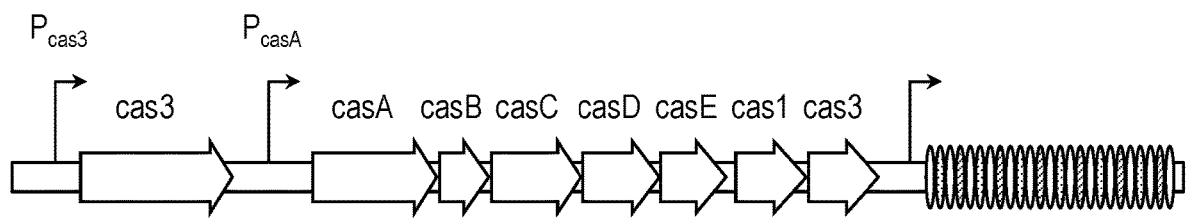
FIGS. 4A-4B show the Type I-E CRISPR-Cas system in E. coli K-12.
Figure 4B:
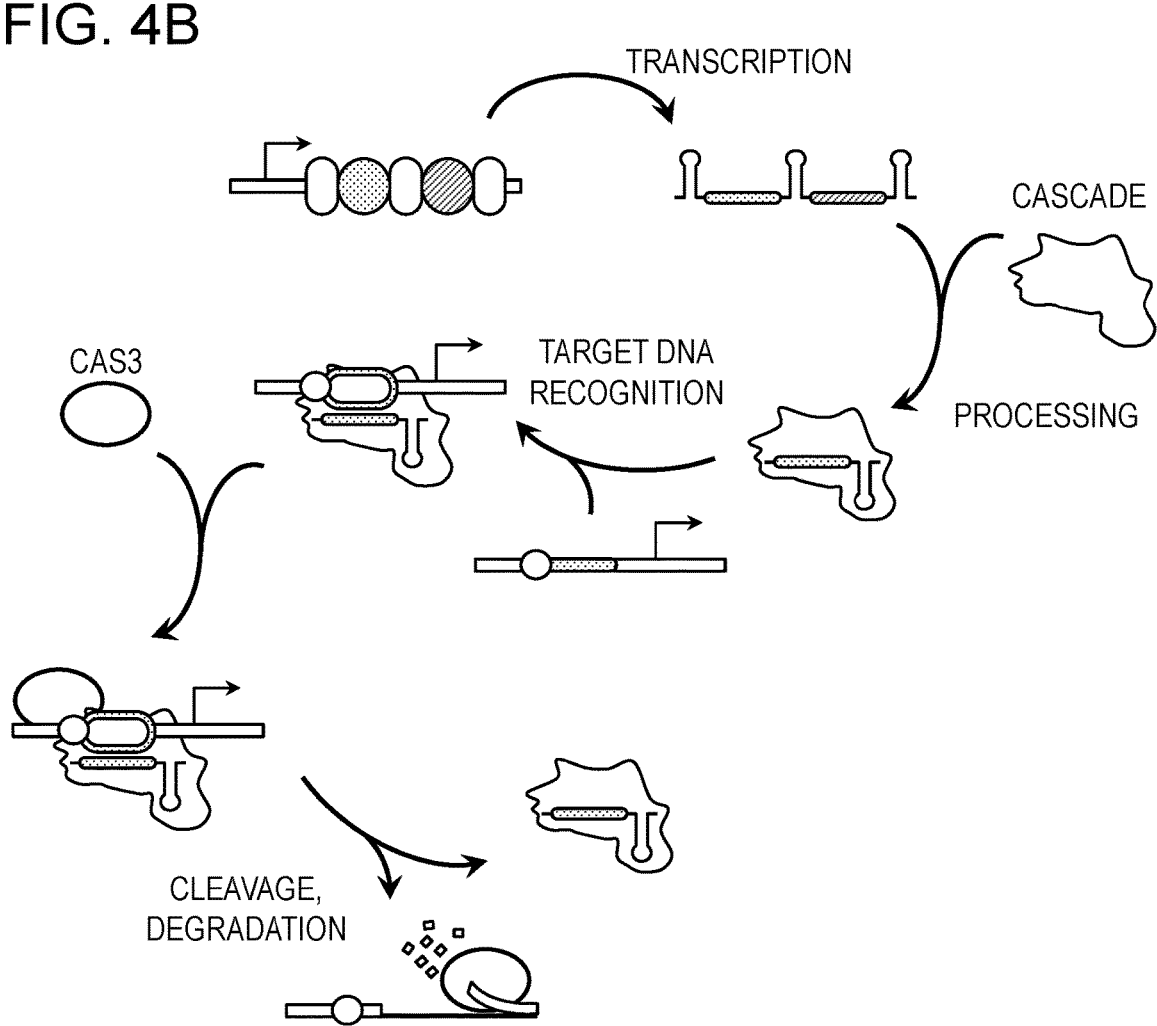
Figure 5A:
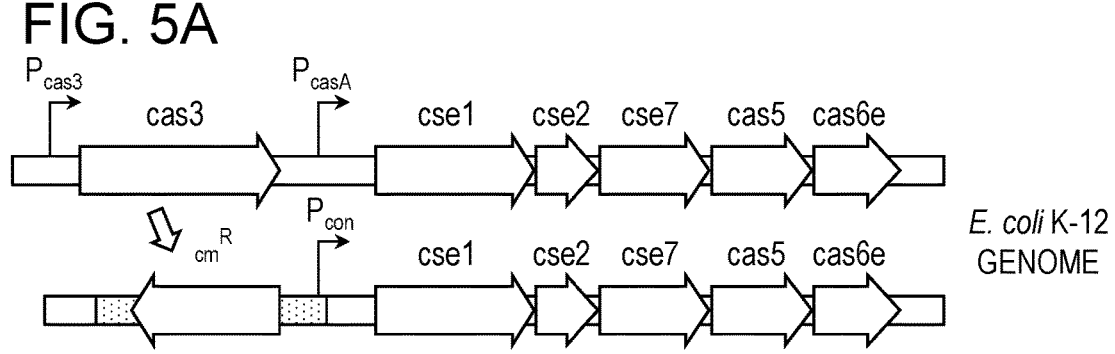
FIGS. 5A-5B show repurposing of the Type I-E CRISPR-Cas system in E. coli K-12 for programmable gene repression.
Figure 5B:
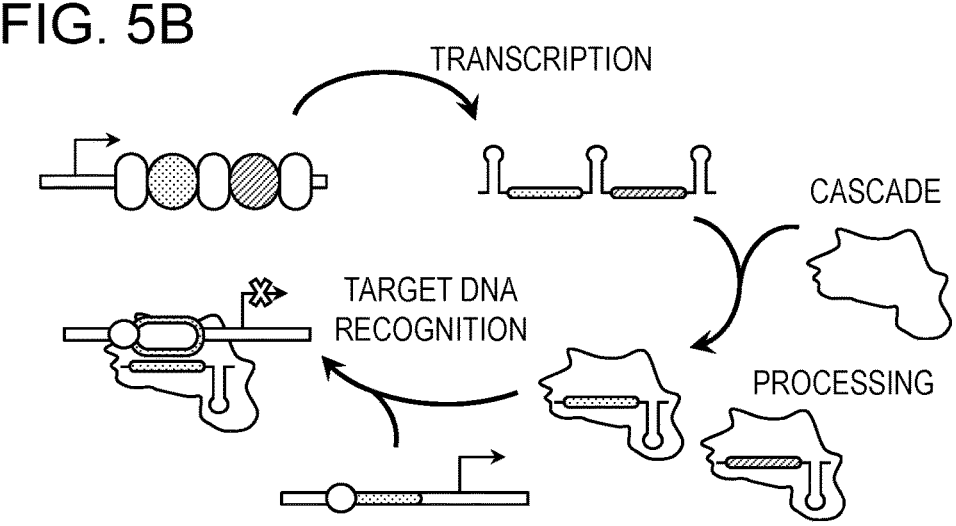
Figure 6:
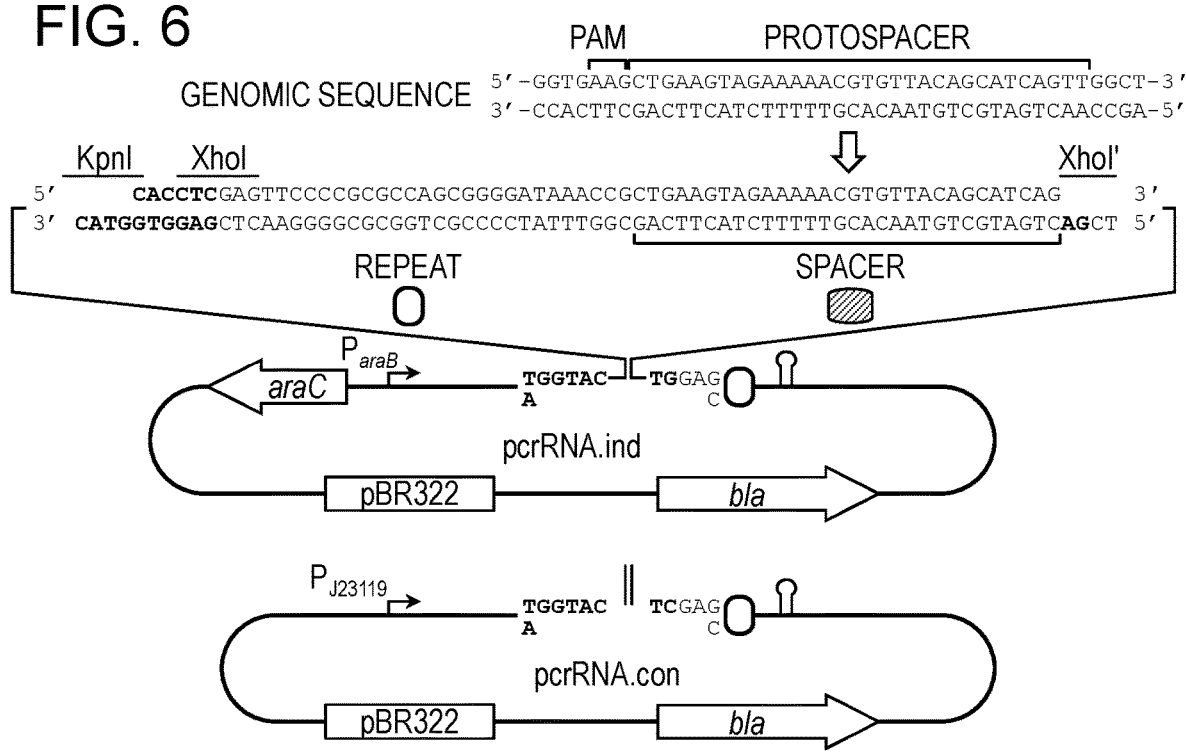
FIG. 6 provides a cloning scheme for the synthetic Type I-E CRISPR arrays. Following identification of a PAM in the target sequence (upper dsDNA, SEQ ID NO:321 (top strand), SEQ ID NO:322 (bottom strand)), the downstream 32 base pairs serve as the protospacer. All but the last two base pairs are copied into two annealed oligonucleotides that, when annealed, form a repeat-spacer pair. The spacer-repeat pair contains the overhangs for a cleaved KpnI restriction site (left) and cleaved XhoI restriction site (right) along with an internal XhoI restriction site. As long as the $30^{th}$ base in the protospacer is not a C, ligation of the annealed oligonucleotides (lower dsDNA, SEQ ID NO:323 (top strand), SEQ ID NO:324 (bottom strand)) into either plasmid digested with KpnI/XhoI disrupts the original XhoI restriction site. Consequently, additional repeat-spacer pairs can be sequentially inserted into the KpnI/XhoI restriction sites.
Figure 7A:
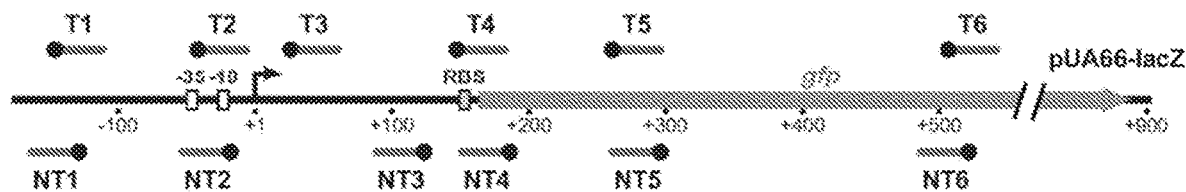
FIGS. 7A-7C show RNA-mediated transcriptional repression with the repurposed Type I-E CRISPR-Cas system in E. coli K-12.

To explore the capacity of Type I systems for gene regulation, we employed the Type I-E CRISPR-Cas system in *Escherichia coli* K-12 (FIG. 4). Because the casABCDE operon encoding Cascade (cse1-cse2-cas7-cas5-cas6e) is strongly repressed under normal growth conditions (Pul, et al. (2010) *Mol. Microbiol.*, 75, 1495-1512; Westra, et al. (2010) *Mol. Microbiol.*, 77, 1380-1393), we replaced cas3 and the native cse1 promoter with a constitutive promoter in one round of homologous recombination (FIG. 5). The resulting strain (BW25113 Δcas3::cat) was transformed with a medium-copy plasmid encoding L-arabinose-inducible single-spacer arrays (FIG. 6) and a low-copy reporter plasmid encoding the green fluorescent protein (gfp) gene downstream of the lacZ promoter (pUA66-lacZ, Table 5). The spacers were designed to target ten locations in the promoter and gfp coding region as well as two locations far upstream of the promoter (FIG. 7A, Table 4). Using flow cytometry analysis, the fluorescence of individual cells was then measured following induction of GFP and crRNA expression.

TABLE 5

Promoter sequences

| Promoter | Sequence[a] |
|---|---|
| lacZ | CTTTCGTCTTCACACTCGAGCACGACAGGTTTCCCGACTGGAAAGCGGGCAGTGAGCGC |
|  | AACGCAATTAATGTGAGTTAGCTCACTCATTAGGCACCCCAGGCTTTACACTTTATGCTTCC |
|  | GGCTCGTATGTTGTGTGG<u>A</u>ATTGTGAGCGGATAACAATTTCACACAGGAAACAGCTATGAC |
|  | CATGATTACGGATTCACTGGCCGTCGTTTTACAACGTCGTGACTGGGAAAACCCTGGCGTT |
|  | ACCCAACTTAATCGCCTTGCAGCACAGGATCCTCTAGATTTAAGAA SEQ ID NO: 317 |
| araB | CCTGTCTCTTGATCAGATCTGGCCTCAATCGGCGTTAAACCCGCCACCAGATGGGCGTTA |
|  | AACGAGTATCCCGGCAGCAGGGGATCATTTTGCGCTTCAGCCATACTTTTCATACTCCCACC |
|  | ATTCAGAGAAGAAACCAATTGTCCATATTGCATCAGACATTGCCGTCACTGCGTCTTTTACT |
|  | GGCTCTTCTCGCTAACCCAACCGGTAACCCCGCTTATTAAAAGCATTCTGTAACAAAGCGG |
|  | GACCAAAGCCATGACAAAAACGCGTAACAAAAGTGTCTATAATCACGGCAGAAAAGTCCA |
|  | CATTGATTATTTGCACGGCGTCACACTTTGCTATGCCATAGCATTTTTATCCATAAGATTAG |
|  | CGGATCCTACCTGACGCTTTTTATCGCAACTCTCTACTGTTTCTCCAT<u>A</u>CCCGTTTTTTGGA |
|  | TGGAGTGAAACGATGGCGATTGCAATTGGCCTCGATTTTGGCAGTGATTCTGTGCGAGCTT |
|  | TGGCGGTGGACTGCGCTACCGGTGAAGCTCGAGGGGATCCTCTAGA SEQ ID NO: 318 |

TABLE 5-continued

Promoter sequences

| Promoter | Sequence[a] |
|---|---|
| xylA | CGAGGCCCTTTCGTCTTCACGGTGTAGGGCCTTCTGTAGTTAGAGGACAGTTTTAATAAG |
| | TAACAATCACCGCGATAAACGTAACCAATTTTTAGCAACTAAACAGGGGAAAACAATTAC |
| | AGATTTTTATCTTTCGATTACGATTTTTGGTTTATTTCTTGATTTATGACCGAGATCTTACTT |
| | TTGTTGCGCAATTGTACTTATTGCATTTTTCTCTTCGAGGAATTACCCAGTTTCATCATTCCA |
| | TTTTATTTTGCGAGCGAGCGCACACTTGTGAATTATCTCAATAGCAGTGTGAAATAACATA |
| | ATTGAGCAACTGAAAGGGAGTGCCCAATATTACGACATCATCCATCACCCGCGGCATTACC |
| | TGATTATGGAGTTCAATATGCAAGCCTATTTTGACCAGCTCGATCGCGTTCGTTATGAAGGC |
| | TCAAAATCCTCAAACCCGTTAGCATTCCGTCACTACAATCCCGACGAACTGGTGTTGGGTA |
| | AGCGTATGTAATCTAGATTTAAGAAGGAGAT SEQ ID NO: 319 |
| rhaB | CCTGTCTCTTGATCAGATCTGTTCTATCGCCACGGACGCGTTACCAGACGGAAAAAAATC |
| | CACACTATGTAATACGGTCATACTGGCCTCCTGATGTCGTCAACACGGCGAAATAGTAATC |
| | ACGAGGTCAGGTTCTTACCTTAAATTTTCGACGGAAAACCACGTAAAAAACGTCGATTTTT |
| | CAAGATACAGCGTGAATTTTCAGGAAATGCGGTGAGCATCACATCACCACAATTCAGCAAA |
| | TTGTGAACATCATCACGTTCATCTTTCCCTGGTTGCCAATGGCCCATTTTCCTGTCAGTAAC |
| | GAGAAGGTCGCGAATTCAGGCGCTTTTTAGACTGGTCGTAATGAAATTCAGCAGGATCACA |
| | TTATGACCTTTCGCAATTGTGTCGCCGTCGATCTCGGCGCATCCAGTGGGCGCGTGATGCTG |
| | GCGCGTTACGAGCGTGAATGGGATCCTCTAGATTTAAGAA SEQ ID NO: 320 |

[a]Sequences in bold are from pUA66, indicating where each promoter was inserted into the plasmid. The underlined and bolded base is the previously mapped transcriptional start site.

Figure 7B:
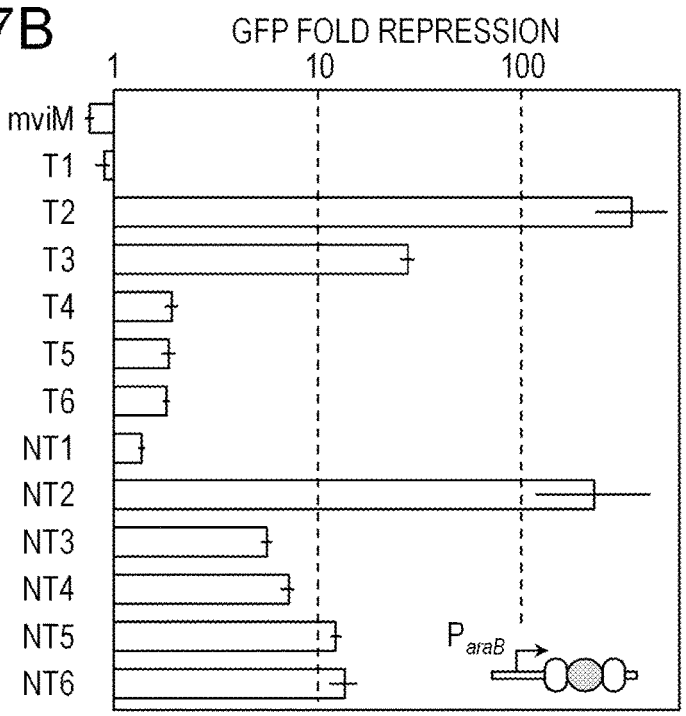
Figure 7C:
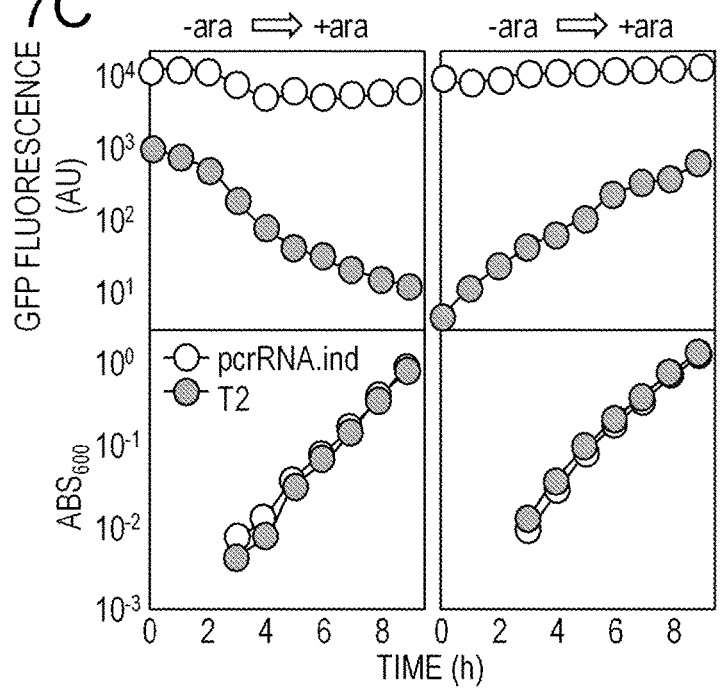

In comparison to the spacer-free plasmid (pCRISPR.ind, FIG. 6), we observed ranging extents of repression that depended on which region of pUA66-lacZ was targeted (FIG. 7B). Targeting either strand of the promoter region strongly reduced GFP fluorescence (~200-fold). Targeting the transcribed region moderately reduced GFP fluorescence, but only when targeting anywhere along the non-template strand or in the vicinity of the RNA polymerase footprint on the template strand (Kovacic, R. T. (1987) *J. Biol. Chem.*, 262, 13654-13661). Interestingly, the strand bias observed when targeting the template versus non-template strand mirrors that observed for dCas9 in bacteria (Qi et al. (2013) *Cell*, 152, 1173-1183; Bikard et al. (2013) *Nucleic Acids Res.*, 41, 7429-37). As expected, targeting upstream of the promoter region negligibly reduced fluorescence. In all cases, the extent of gene silencing was uniform across the entire bacterial population. Importantly, GFP levels were similar for the no-spacer plasmid and a plasmid encoding a spacer targeting the mviM gene in *Salmonella enterica* (FIG. 7B), ruling out potential differences due to the assembly of Cascade. We also found that GFP silencing was reversible based on the change in fluorescence following addition or removal of L-arabinose (FIG. 7C). The associated dynamics can be attributed to the stability of GFP similar to previous work (Bikard et al. (2013) *F1000prime Rep.*, 5, 47).

Figure 8A:
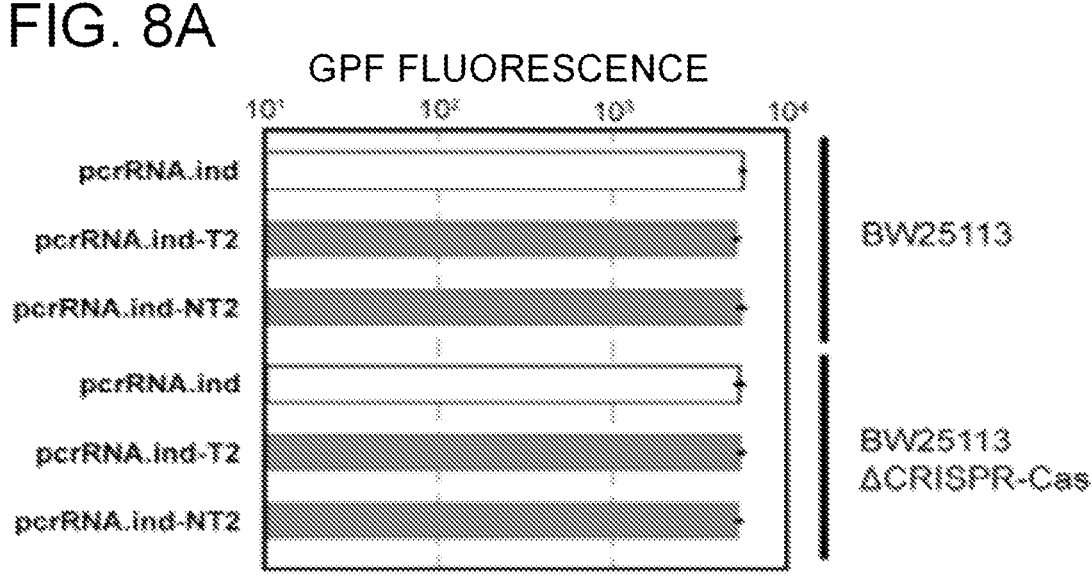
FIGS. 8A-8C show GFP expression and DNA transformation in variants of the parent strain BW25113 and NM500.
Figure 8B:
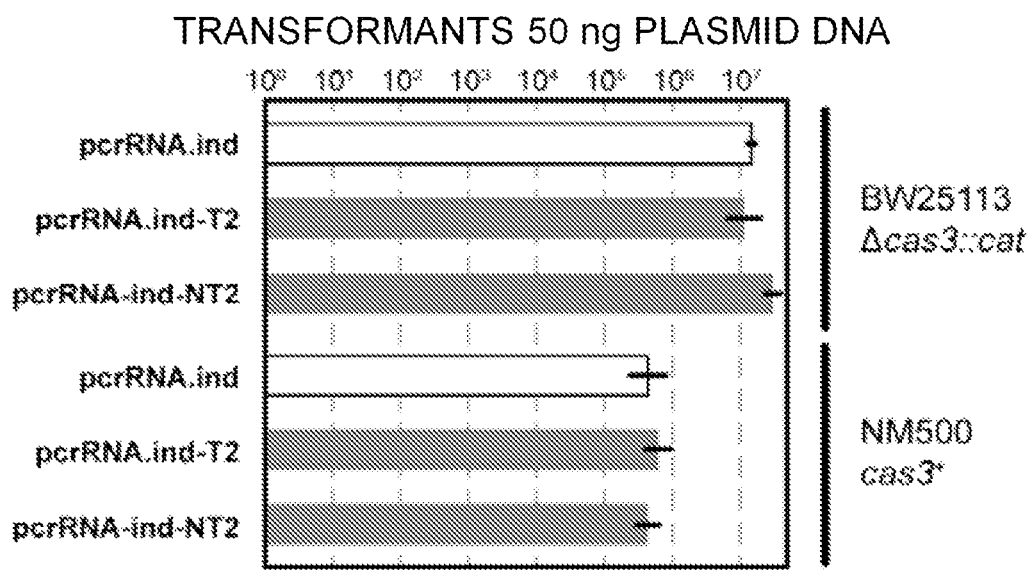
Figure 8C:
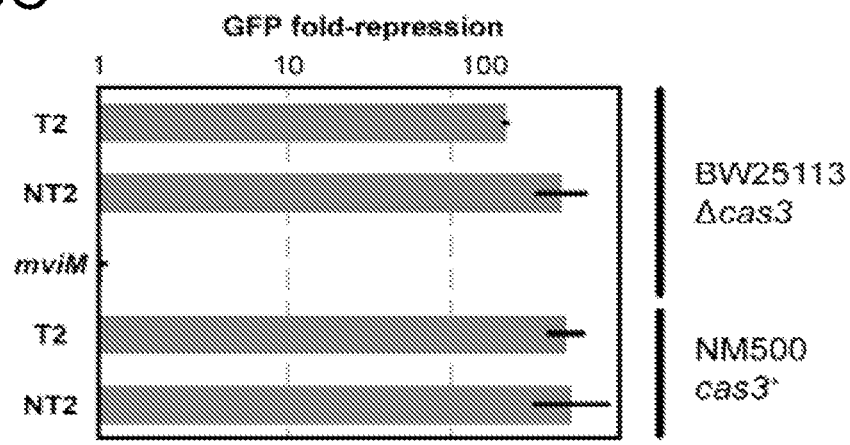

We next performed a series of control experiments to assess the impact of deleting cas3 and constitutively expressing Cascade operon. We first measured GFP fluorescence in the original wild type strain in which the Cascade operon was tightly repressed and cas3 was still present (BW25113) and in a strain in which cas3 and the Cascade operon were both deleted (BW25113 ΔCRISPR-Cas::cat). The fluorescence levels were similar regardless of whether a targeting spacer was used (FIG. 8A), indicating that Cascade must be present and Cas3 must be absent for gene silencing. Next, to assess the impact on DNA integrity, we measured the transformation efficiencies for targeting and non-targeting plasmids in strains with Cascade constitutively expressed and cas3 present (NM500 cas3$^+$) or absent (BW25113 Δcas3::cat). Surprisingly, we observed similar transformation efficiencies for the targeting and non-targeting plasmids even when cas3 was present (FIG. 8B), suggesting that Cas3 is poorly expressed or inactive in this strain. As further support, the strain with cas3 present could still strongly silence GFP (FIG. 8C). Finally, to gauge the impact of the resistance cassette, we excised the cassette used to delete cas3 to produce BW25113 Δcas3-cat strain and measured gene silencing. The resulting strain (BW25113 Δcas3) and the original strain (BW25113 Δcas3:: cat) exhibited similar silencing efficiencies (Supplementary Figure S4C), indicating a negligible impact of the resistance cassette.

Impact of Array Length and Spacer Position

Figure 9:
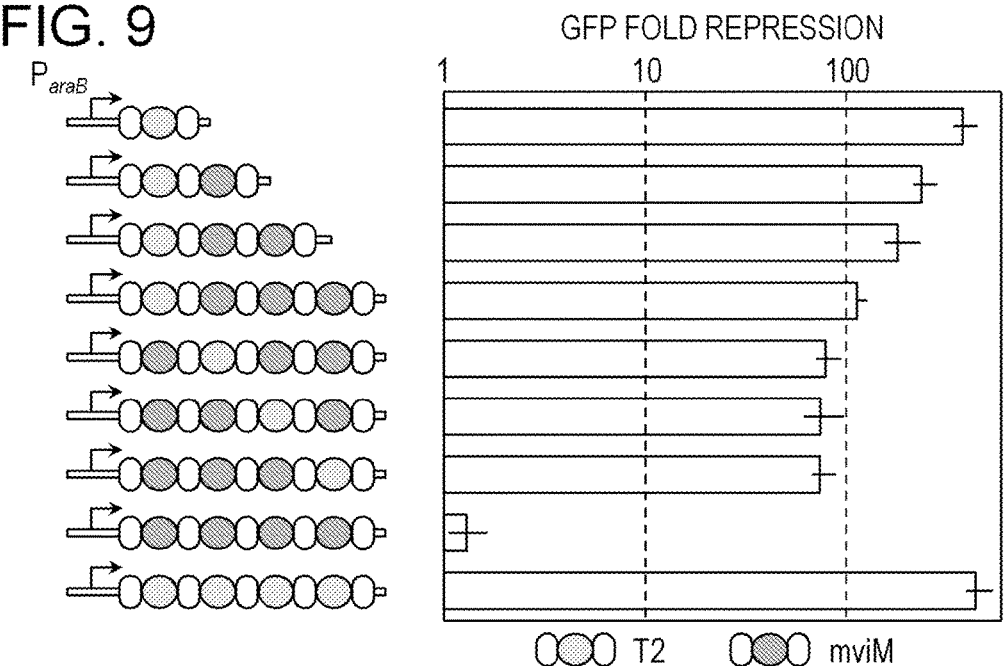
FIG. 9 shows the impact of array length and spacer location on silencing efficiency. BW25113 Δcas3::cat cells harboring pUA66-lacZ and the indicated inducible CRISPR array plasmid were subjected to flow cytometry analysis following induction with IPTG and L-arabinose. Repression is calculated as the ratio of the autofluorescence-subtracted fluorescence for the inducible no-spacer plasmid (pcrRNA.ind) and each multi-spacer plasmid. Repeats, white ovals; T2 spacers, dotted circles; non-targeting spacers matching the Salmonella enterica mviM gene, hashmark circles. Values represent geometric mean and S.E.M. from independent experiments staring with three separate colonies.

One beneficial feature of Cascade is that it can process multiple crRNAs from a single spacer array. However, little is known about how the composition of natural or synthetic multi-spacer arrays quantitatively impacts individual targets. To evaluate the impact of array length, we generated arrays with one promoter-targeting spacer (T2) followed by zero to three non-targeting spacers (mviM) (FIG. 9). Flow cytometry analysis revealed a gradual decrease in silencing efficiency with each additional spacer. We speculate that this decrease may be due to non-targeting spacers diluting available Cascade complexes for targeting crRNAs, as observed with other RNA-based systems (Hussein, R. and Lim, H. N. (2011) *Proc. Natl. Acad. Sci. U.S.A.,* 108, 1110-1115). In support of this assertion, the single-spacer array and an array of four targeting spacers exhibited statistically indistinguishable extents of silencing (two-tailed t-test, t(4)=1.05, p=0.35) (FIG. 9). To evaluate the impact of spacer position, we generated arrays with different permutations of one targeting and three non-targeting spacers (FIG. 9). With the exception of a targeting spacer in the first position of the four-spacer array, the extent of gfp silencing was similar regardless of spacer position (one-way ANOVA, F(2,6) =0.15, p=0.86). These results suggest that longer arrays can reduce the potency of individual spacers, whereas the exact location of a spacer within an array has a lesser contribution to the potency of silencing.

Multiplexed Repression of Endogenous Genes

As a complement to targeting heterologous genes such as gfp, we explored the ability of spacers to regulate endogenous targets. We focused on operons involved in the catabolism of the sugars L-arabinose (araBAD), L-rhamnose (rhaBAD), D-xylose (xylAB), and D-lactose (lacZYA) (FIG. 10, panel A) because these operons are well characterized and are required for growth on their cognate sugar (Gross, J. and Englesberg, E. (1959) *Virology,* 9, 314-331; Power, J. (1967) *Genetics,* 55, 557-568; Lawlis, et al. (1984) *Appl. Environ. Microbiol.,* 47, 15-21; Beckwith, J. R. (1967) *Science,* 156, 597-604). Because the araBAD, rhaBAD, and lacZYA operons are disrupted in BW25113, we imported the cas3 deletion and synthetic promoter into another strain of *E. coli* K-12 (MG1655 Δcas3::cat). We also placed each single-spacer array under the control of the strong constitutive promoter to circumvent the need for L-arabinose as an inducer (FIG. 6).

Figure 10:
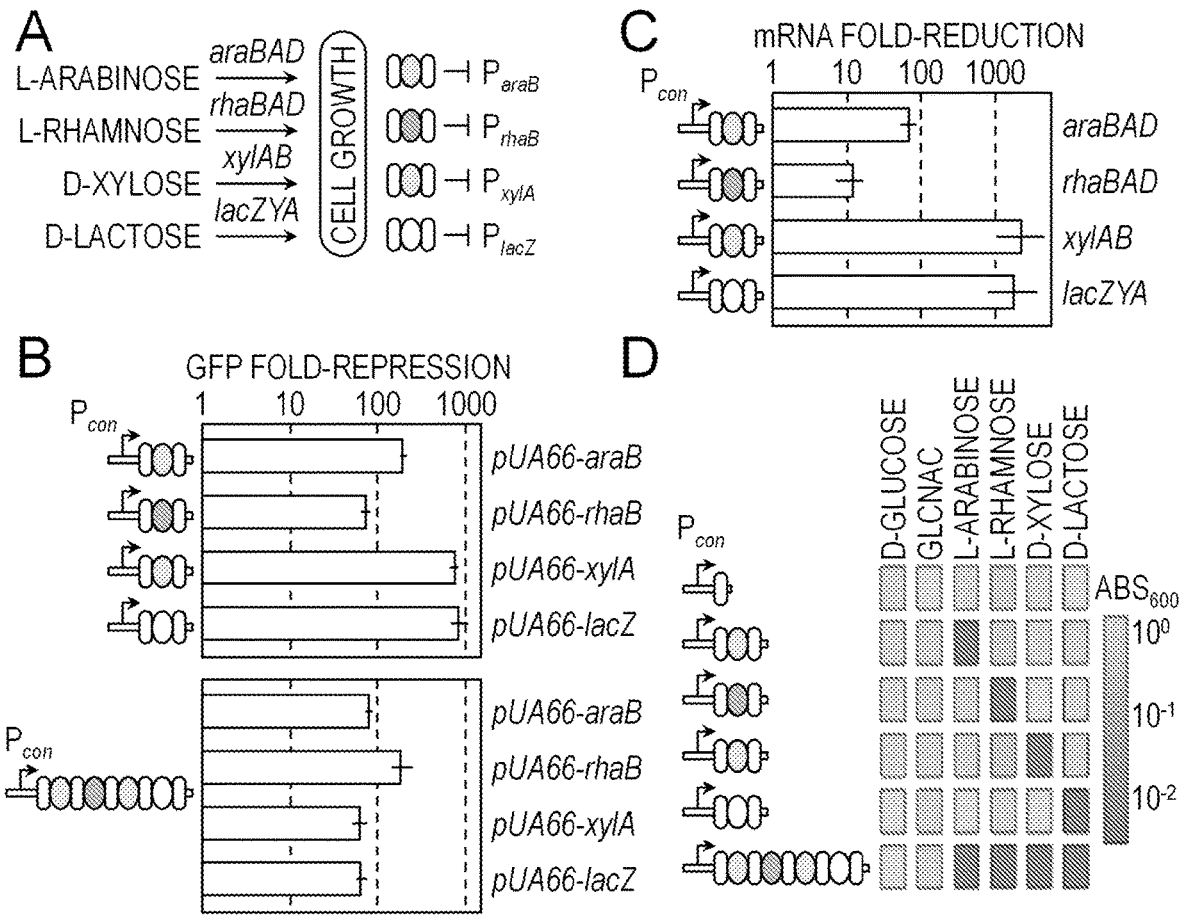
FIG. 10, panels A-D show targeted repression of endogenous genes and pathways.

To assess silencing of promoter activity, we cloned the promoter of each operon upstream of gfp in the pUA66 plasmid (Table 5, below). The resulting plasmids were placed in MG1655 Δcas3 cells harboring the corresponding single-spacer plasmid (top) or multi-spacer plasmid (bottom) and then tested for the ability to repress their respective target promoter by flow cytometry analysis following promoter induction with the cognate sugar (FIG. 10, panel B). In comparison to the spacer-free plasmid (pCRISPRcon, FIG. 6), each targeting plasmid greatly reduced fluorescence (about 80-fold to about 900-fold). As expected, combining the spacers into one array strongly reduced fluorescence for all four promoters when tested individually (FIG. 10, panel B), although the degree of silencing was generally less than that observed for the individual spacers (FIG. 9).

To evaluate silencing of the endogenous genes, we measured mRNA levels of each operon for cells with each single-spacer plasmid. In comparison to the no-spacer plasmid, the single-spacer plasmids greatly reduced mRNA levels (about 11-fold to about 2,200-fold) of the target operons (FIG. 10, panel C), paralleling that observed for the GFP reporters (FIG. 10, panel B). This wide range in repression matches the variability in gene silencing observed with dCas9 (Qi et al. (2013) *Cell,* 152, 1173-1183; Bikard et al. (2013) *Nucleic Acids Res.,* 41, 7429-37)

Figure 11A:
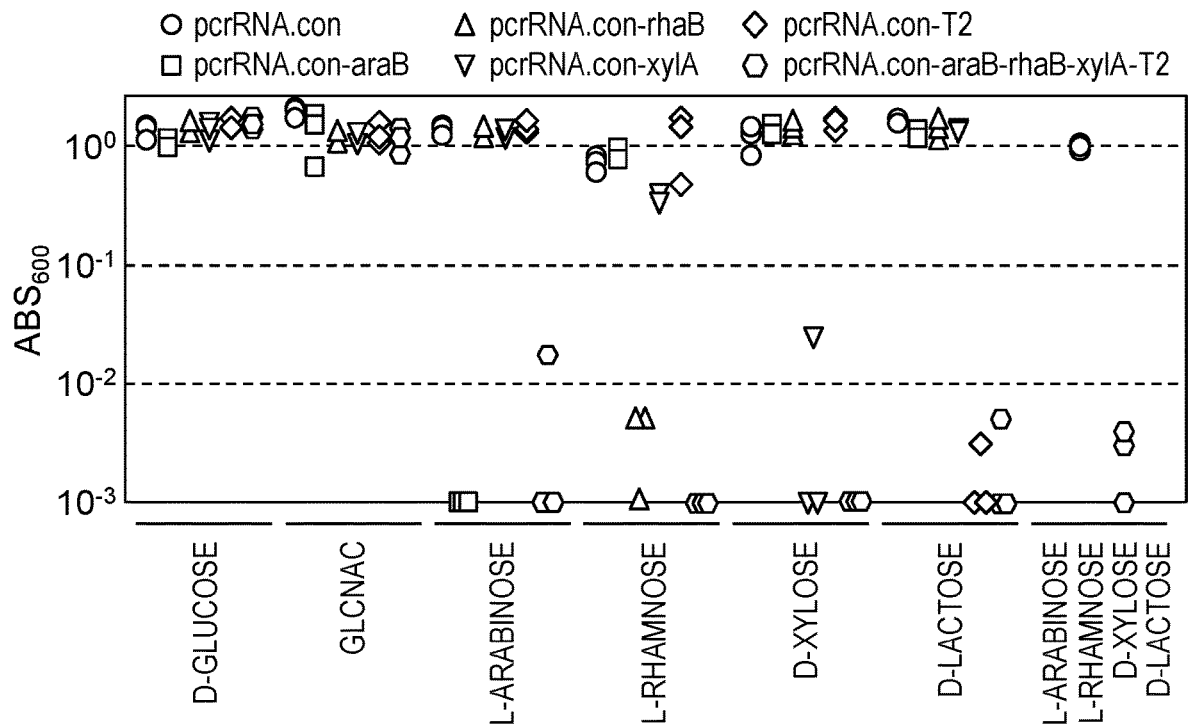
FIGS. 11A-11B show extended information for the growth assays.
Figure 11B:
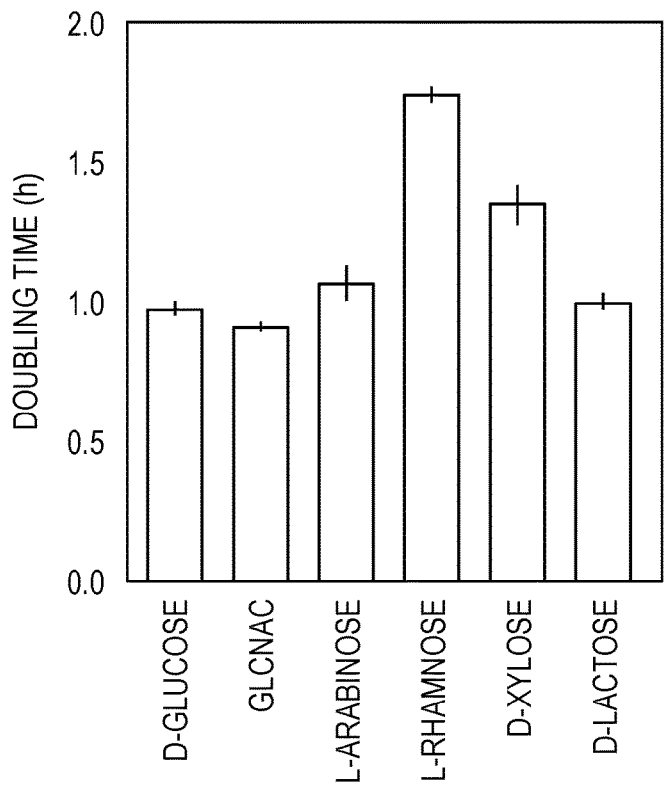

Finally, we explored whether targeting endogenous genes could generate defined phenotypes. Because each operon is required for the catabolism of its cognate sugar, we measured growth on each sugar as well as on two non-targeted sugars D-glucose and N-acetyl-D-glucosamine (GlcNAc). We cultured MG1655 Δcas3::cat expressing a single-spacer or four-spacer array with the different sugars as sole carbon sources and measured the turbidity of the culture after 24 hours of growth (FIG. 10, panel D; FIG. 11A). We found that targeting each operon limited growth on the cognate sugar, whether using a single-spacer array or the four-spacer array. The four-spacer array silenced all target operons in individual cells, as this array limited growth in medium containing all four targeted sugars (FIG. 11A). Growth was unhampered for all non-targeted sugars, supporting the specificity of targeting. The final turbidity was generally lower for all cultures grown in L-rhamnose (FIG. 10, panel D, FIG. 11A), which we attribute to L-rhamnose being a poor carbon source (FIG. 11B). We thus conclude that the Type I-E system deprived of Cas3 in *E. coli* can be programmed to silence multiple endogenous genes and generate complex phenotypes.

Example 15. Discussion

As shown herein, the Type I-E CRISPR-Cas system in *E. coli* can be repurposed for programmable gene repression through the deletion of cas3 and constitutive expression of the Cascade operon. Structural and phylogenetic data suggest that this same phenomenon would apply readily to Type I-B, I-C, and I-F systems based on the stability of Cascade in the absence of Cas3 and the ability of this complex to process transcribed CRISPR arrays (Makarova et al. (2011) 9, 467-477; Nam et al. (2012) *Struct. Lond. Engl.* 1993, 20, 1574-1584; Brendel et al. (2014) *J. Biol. Chem.,* 289, 7164-7177; Wiedenheft et al. (2011) *Proc. Natl. Acad. Sci. U.S.A.,* 108, 10092-10097). Type I-A and I-B systems appear to be exceptions, as two distinct Cas3 proteins (Cas3' and Cas3") are required for stabilization of the Type I-A Cascade and the uncharacterized Type I-B Cascade is most closely related to Type I-A systems (Sorek et al. (2013) *Annu. Rev. Biochem.,* 82, 237-266; Plagens et al. (2014) *Nucleic Acids Res.,* 42, 5125-5138). However, these cas3 genes could be catalytically inactivated (Hochstrasser et al. (2014) *Proc. Natl. Acad. Sci. U.S.A.,* 111, 6618-6623) as performed with Cas9 (Jinek et al. (2012) *Science,* 337, 816-821), albeit with point mutations that are harder to introduce using rudimentary genetic tools.

With this demonstration, another question is whether Type I systems or Type II systems should be employed for transcriptional regulation. Type II systems in the form of dCas9 are highly attractive because they offer a compact heterologous system that can be imported into diverse organisms. However, exploiting endogenous Type I systems does offer some potential advantages. For instance, once cas3 is deleted, only the CRISPR array totaling at most a few hundred bases must be introduced. Another potential advantage is that the native Type I system would be well suited for thermophilic and hyperthermophilic microorganisms that thrive in environmental conditions that would prevent proper folding of common Cas9 proteins. Type I systems also offer PAMs that are distinct from those associated with known Type II systems, including a different orientation and a bias toward T/C-rich sequences (Sorek et al. (2013) *Annu. Rev. Biochem.,* 82, 237-266; Westra et al. (2012) *Mol. Cell,* 46, 595-605; Esvelt et al. (2013) *Nat. Methods,* 10, 1116-21). Finally, Type I systems are naturally found in diverse industrially and medically relevant strains, including *Escherichia coli, Streptococcus thermophilus, Clostridium autoethanogenum,* and *Acinetobacter baumannii* (Grissa et al. (2007) *BMC Bioinformatics,* 8, 172). A possible drawback to this strategy is that the strains may lose immunity against some invading pathogens. Overexpression of Cascade in the absence of Cas3 may also inadvertently impact the transcriptional landscape, although this remains to be explored even for dCas9.

One interesting parallel observed for transcriptional regulation with Type I and Type II systems is the strand bias when targeting transcribed regions (FIG. 7B) (Qi et al. (2013) Cell, 152, 1173-1183; Bikard et al. (2013) Nucleic Acids Res., 41, 7429-37). Previous work with dCas9 demonstrated that targeting the non-template strand but not the template strand strongly interfered with RNA polymerase extension. We observed the same trend with the Type I-E Cascade (FIG. 7B) despite structural differences and opposing PAM locations in comparison to dCas9 (Jore et al. (2011) Nat. Struct. Mol. Biol., 18, 529-536; Westra et al. (2012) Mol. Cell, 46, 595-605; Jiang et al. (2013) Nat. Biotechnol., 31, 233-239; Nishimasu et al. (2014) Cell, 156, 935-949).

In summary, the present invention offers novel strategies for exploiting Type I CRISPR-Cas system for transcriptional regulation. Moreover, our findings provide a framework to identify natural Type I systems that naturally regulate gene expression, potentially expanding the list of known systems that coordinate cellular processes (Sampson et al. (2014) Proc. Natl. Acad. Sci. U.S.A., 111, 11163-8; Sampson et al. (2013) Nature, 497, 254-257).

Example 16. Spacer Length

Figure 13:
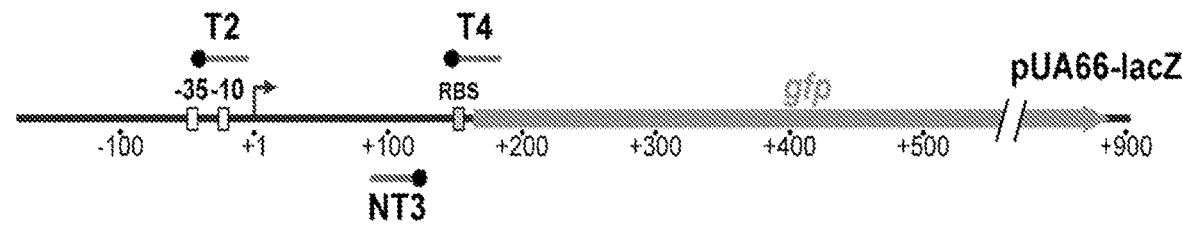
FIG. 13 shows a schematic of different locations targeted for the spacer length variants. T2 targets the template strand in the promoter region, T4 targets the template strand in the coding region, an NT3 targets the non-template strand in the untranslated region.
Figure 14:
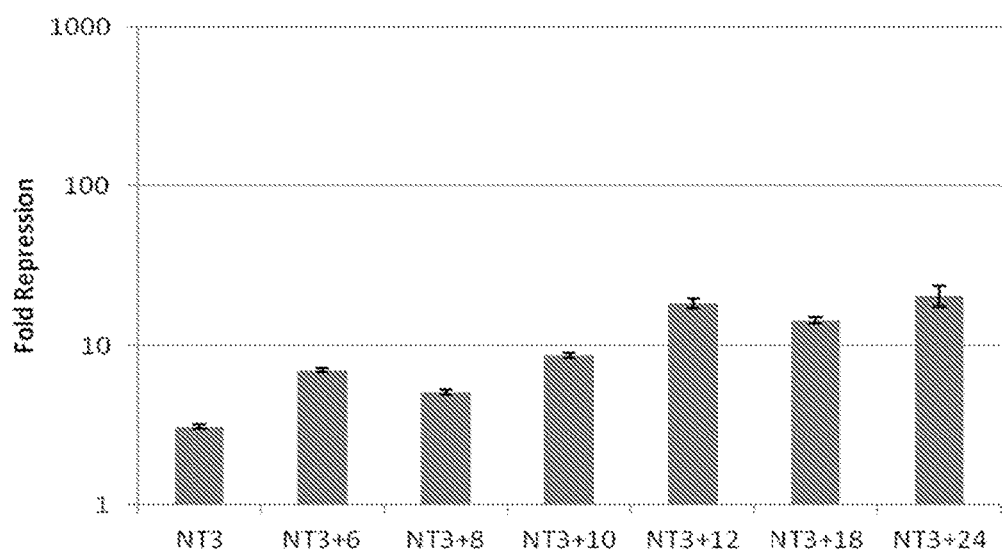
FIG. 14 shows average fold-repression of NT3 increasing spacer length variants. The designated length is in addition to the standard 30 nucleotides. For instance, NT3+12 encodes a spacer of 42 nucleotides.
Figure 15:
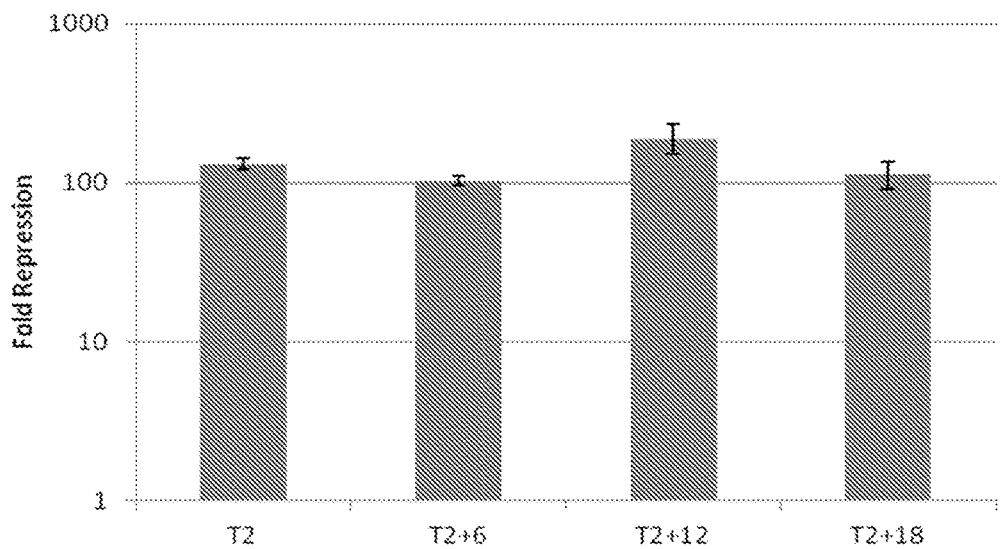
FIG. 15 shows average fold-repression of T2 spacer length variants. See FIG. 14 for more information about the spacer length.
Figure 16:
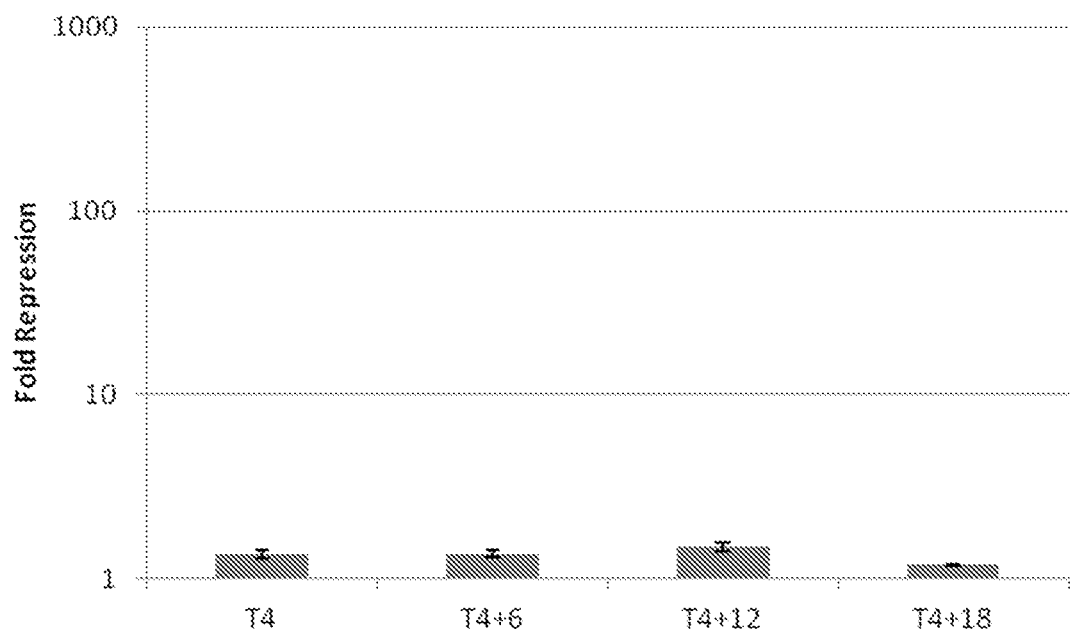
FIG. 16 shows average fold-repression of T4 spacer length variants. See FIG. 14 for more information about the spacer length.

The effect of spacer length and other characteristics of the Type 1 CRISPR-Cas system was studied. The spacer was extended from its 3' end, which preserves the location of the PAM. FIG. 13 shows a schematic of different locations that were targeted. FIG. 14 goes up to a +24 nucleotide to NT3 spacer and shows that increasing spacer length improves silencing efficiency, though the trend is non-monotonic. FIG. 15 shows that increasing spacer length does not appear to improve silencing efficiency with the T2 spacer as the "normal" spacer length has already reduced fluorescence to near-background levels, leaving little room for possible silencing improvement. FIG. 16 shows that increasing spacer length does not appear to improve silencing efficiency with the T4 spacer.

Figure 17:
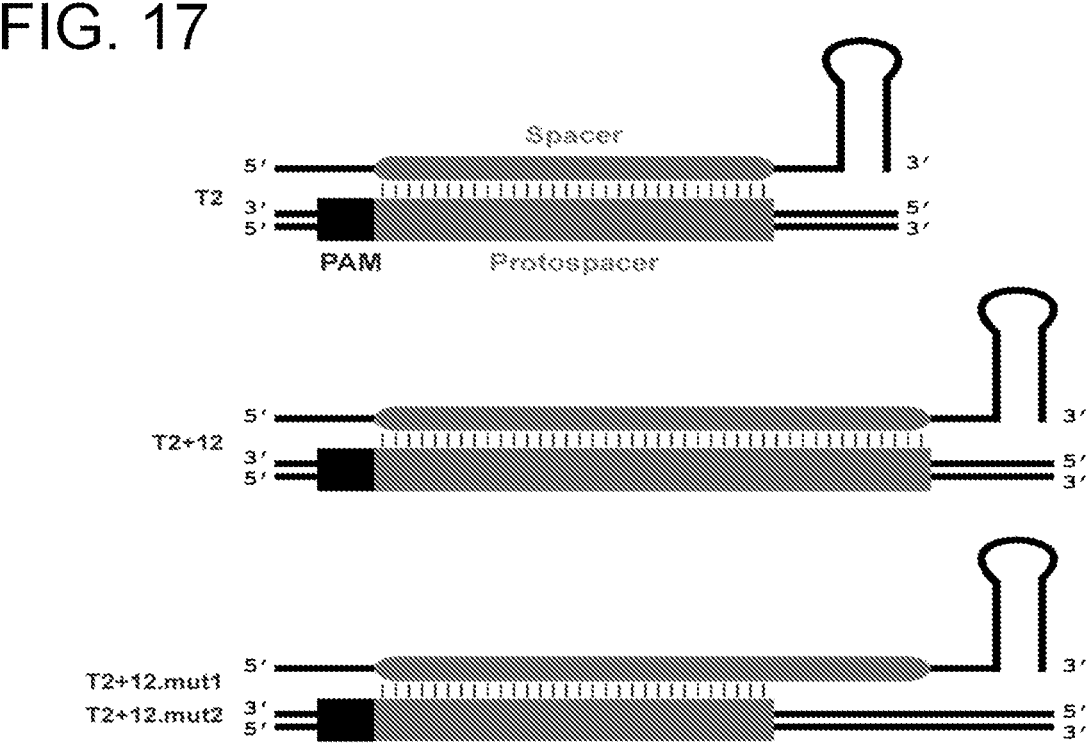
FIG. 17 shows a schematic of disrupting base-pairing interactions between the longer spacer and the target. The bottom image depicts the T2+12 mutants where the extra 12 nucleotides distal to the 5' handle of the crRNA were designed not to base-pair to the target. Base-pairing is maintained between the first 30 nucleotides of the spacer to the target.
Figure 18:
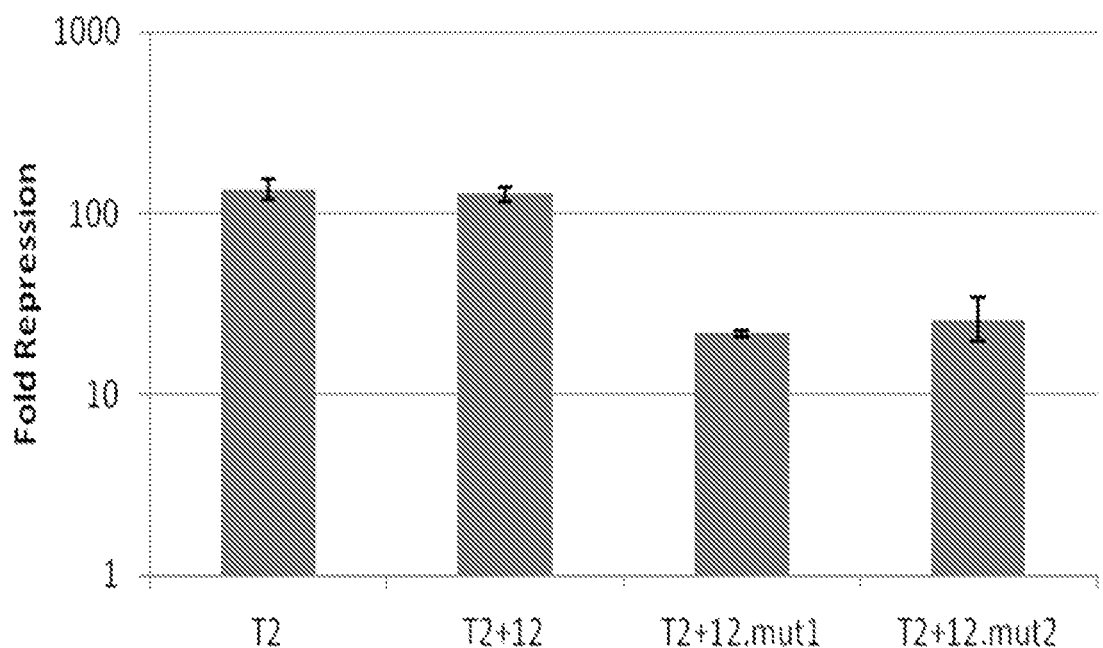
FIG. 18 shows average fold-repression of the T2 mutant spacers.
Figure 19:
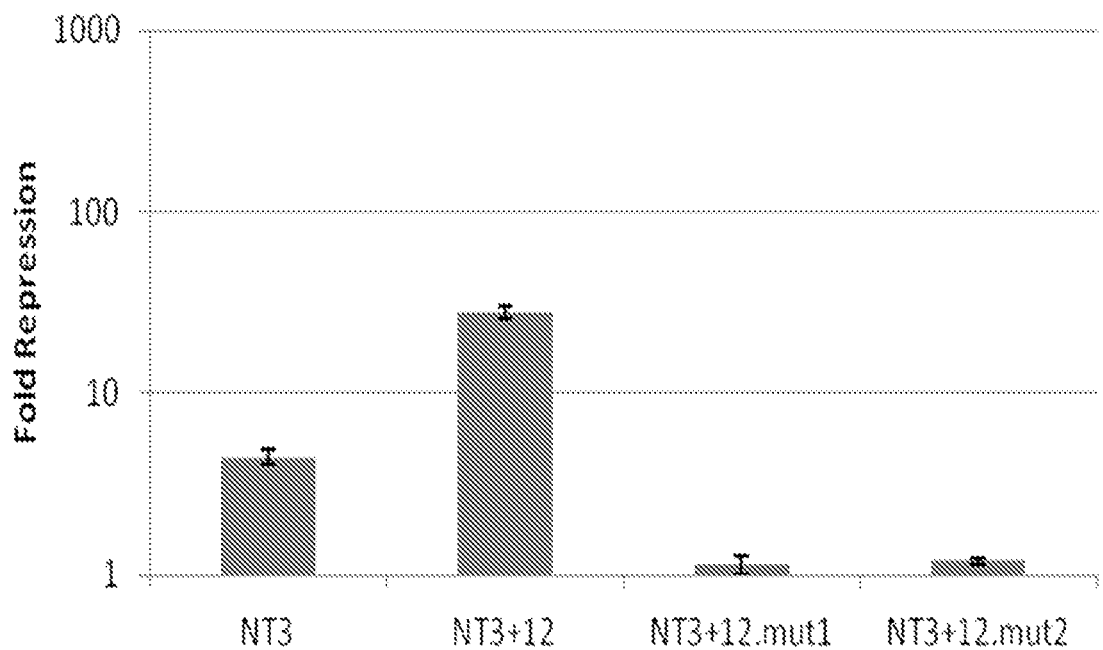
FIG. 19 shows average fold-repression of NT3 mutant spacers.

FIGS. 17, 18, and 19 show how the amount of complementarity affects the effect of silencing with the longer spacers. FIG. 17 shows a schematic of disrupting base-pairing interactions between the longer spacer and the target. FIGS. 18 and 19 show the disruption of base-pairing with the extra nucleotides reduced the silencing efficiency by about 10-fold. Overall, the data show that the silencing efficiency can be altered by varying the length of the spacer and extended base pairing must be maintained to preserve silencing activity.

Example 17. Targeted Gene Repression with Cascade from the Bacillus halodurans Type I-C Crispr-Cas System The three genes associated with the I-C Cascade complex (cas5c, cas8c, and cas7) were expressed from a constitutive plasmid in Escherichia coli. The E. coli cells also harbored a plasmid encoding the green fluorescent protein (gfp) gene controlled by the lac promoter and another plasmid encoding the B. halodurans repeat (spacer −) or a repeat-spacer-repeat (spacer+). The integrated spacer was designed to target a sequence within the lac promoter with a flanking CTC or TTC PAM. Both PAM's were predicted for Type I-C systems. Cells harboring the three plasmids were grown overnight in LB with appropriate antibiotics, back-diluted into the same medium, and cultured until reaching mid-log phase. The cultures were then analyzed by flow cytometry analysis. The reported values are the mean fluorescence of the unimodal histogram minus the fluorescence of GFP-negative cells.

Figure 20A:
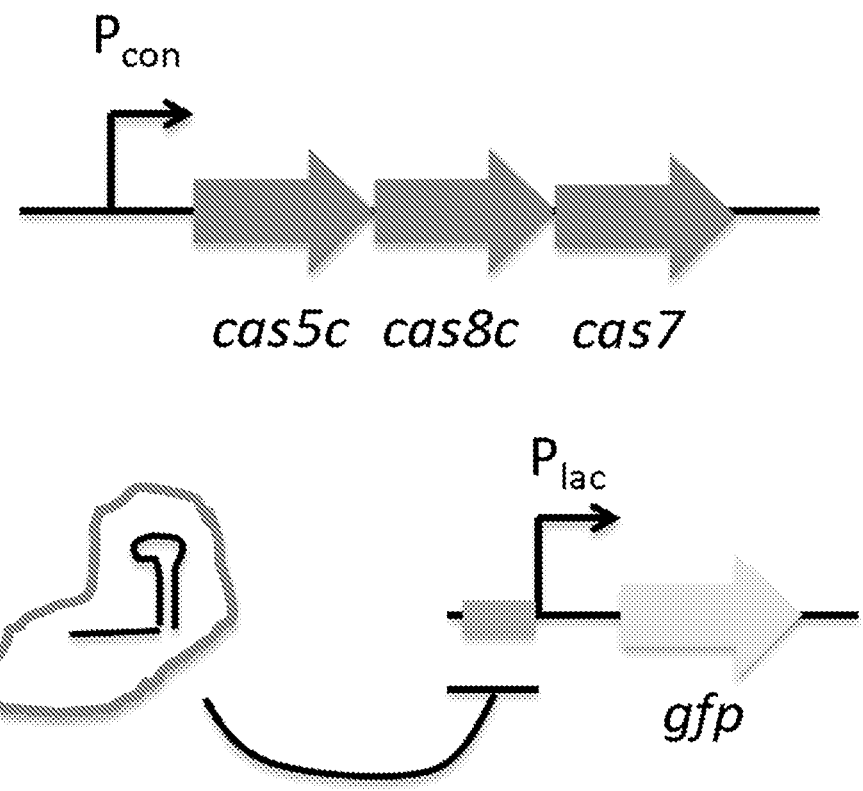
FIGS. 20A-20B shows targeted gene repression with Cascade from the *Bacillus halodurans* Type I-C CRISPR-Cas system.
Figure 20B:
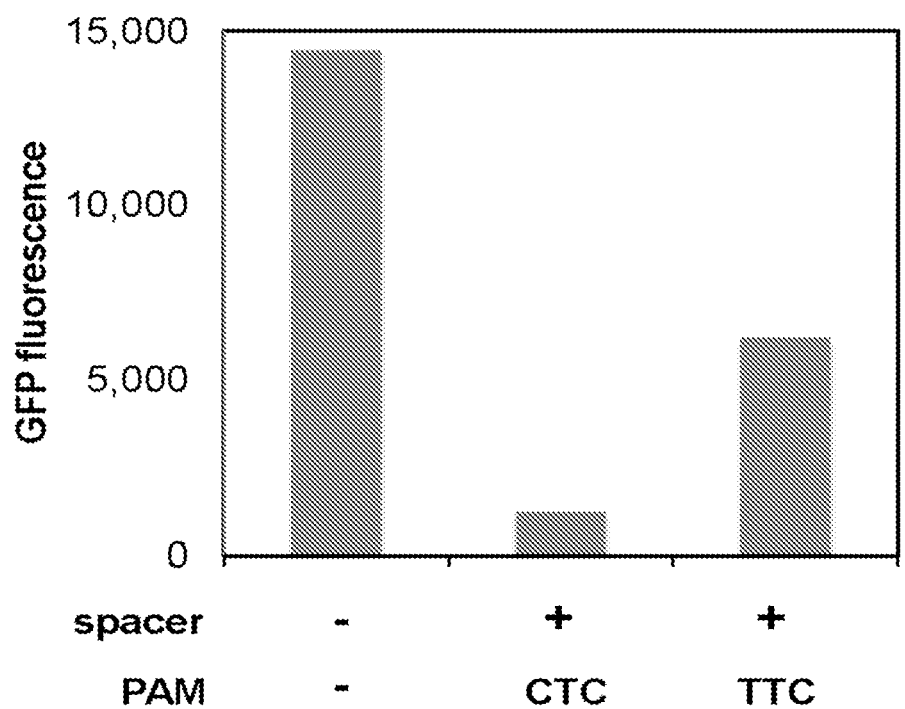

FIG. 20A shows B. halodurans Type I-C Cascade operon under the control of a constitutive promoter. As depicted below, the CRISPR RNA guides Cascade to bind the lac promoter controlling GFP expression; FIG. 20B shows analysis of cultures by flow cytometry analysis. The data demonstrate repression by the I-C Cascade from B. halodurans, where the extent of repression varied between the two different PAM's. These data demonstrate our ability to enact targeted gene silencing using heterologously expressed Cascade and the applicability of our general approach beyond the Type I-E system.

The foregoing is illustrative of the invention, and is not to be construed as limiting thereof. The invention is defined by the following claims, with equivalents of the claims to be included therein.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11439712B2). An electronic copy of the "Sequence Listing" will also be available from the USPTO upon request and payment of the fee set forth in 37 CFR 1.19(b)(3).

That which is claimed is:

1. A method for repressing expression of a first target gene in a bacterium or an archaeon, the method comprising introducing into the bacterium or the archaeon:

(a) a first nucleic acid sequence encoding at least three polypeptides of a Type I CASCADE, wherein the Type I CASCADE is a Type I-B CASCADE, a Type I-C CASCADE, a Type I-E CASCADE, a Type I-F CASCADE, a Type I-A CASCADE or a Type I-D CASCADE; and (b) a second nucleic acid sequence encoding at least one CRISPR array comprising two or more repeat sequences and at least one spacer sequence that is complementary to a first target sequence from the first target gene, wherein the at least one spacer sequence is increased in length by about 1 to about 100 nucleotides when compared to a normal spacer length, wherein:

the Type I-B CASCADE comprises a Cas6b polypeptide having at least 95% sequence identity to any one of the sequences of SEQ ID NOs:18-20 or 335-340, a Cas8b (Csh1) polypeptide having at least 95% sequence identity to any one of the sequence of SEQ ID NOs:21, 22, or 1043-1158, a Cas7 (Csh2) polypeptide having at least 95% sequence identity to any one of the sequences of SEQ ID NOs:23, 24, or 1159-1209, and a Cas5 polypeptide having at least 95% sequence identity to any one of the sequences of SEQ ID NOs:25, 26, or 1210-2372, the Type I-C CASCADE comprises a Cas5d polypeptide having at least 95% sequence identity to any one of the sequences of SEQ ID NOs:27, 28, or 2373-2973, a Cas8c (Csd1) polypeptide having at least 95% sequence identity to any one of the sequences of SEQ ID NOs:29, 30, or 2974-3847, and a Cas7 (Csd2) polypeptide having at least 95% sequence identity to any one of the sequences of SEQ ID NOs:31, 32, or 3848-4371, the Type I-E CASCADE comprises a Cse1 (CasA) polypeptide having at least 95% sequence identity to any one of the sequences of SEQ ID NOs:41, 42, or 5235-6111, a Cse2 (CasB) polypeptide having at least 95% sequence identity to any one of the sequences of SEQ ID NOs:43, 44, or 6112-6823, a Cas7 (CasC) polypeptide having at least 95% sequence identity to any one of the sequences of SEQ ID NOs:45, 46, or 6824-7032, a Cas5 (CasD) polypeptide having at least 95% sequence identity to any one of the sequences of SEQ ID NOs:47, 48, or 7033-7251, and a Cas6e (CasE) polypeptide having at least 95% sequence identity to any one of the sequences of SEQ ID NOs:49, 50, or 7252-7520, the Type I-F CASCADE comprises a Cys1 polypeptide having at least 95% sequence identity to any one of the sequences of SEQ ID NOs:51, 52, or 7521-8614, a Cys2 polypeptide having at least 95% sequence identity to any one of the sequences of SEQ ID NOs:53, 54, or 8614-9867, a Cas7 (Cys3) polypeptide having at least 95% sequence identity to any one of the sequences of SEQ ID NOs:55, 56, or 9868-11057, and a Cas6f polypeptide having at least 95% sequence identity to any one of the sequences of SEQ ID NOs:57, 58, or 11058-11528, the Type I-A CASCADE comprises a Cas7 (Csa2) polypeptide having at least 95% sequence identity to any one of the sequences of SEQ ID NOs:1-3, a Cas8a1 (Csx13) polypeptide having at least 95% sequence identity to any one of the sequences of SEQ ID NOs:4, or 341-640 or a Cas8a2 (Csx9) polypeptide having at least 95% sequence identity to any one of the sequences of SEQ ID NOs:5, 6, or 641-666, a Cas5 polypeptide having at least 95% sequence identity to any one of the sequences of SEQ ID NOs:7-9, or 667-871, a Csa5 polypeptide having at least 95% sequence identity to any one of the sequences of SEQ ID NOs:872-1042, a Cas6a polypeptide having at least 95% sequence identity to any one of the sequences of SEQ ID NOs:10, 11, or 325-328, a Cas3' polypeptide having at least 95% sequence identity to any one of the sequences of SEQ ID NOs:12-14, or 329-331, and a Cas3" polypeptide having no nuclease activity and having at least 95% sequence identity to any one of the sequences of SEQ ID NOs:15-17, or 332-334, said polypeptides having at least 95% sequence identity to one of the sequences of SEQ ID NOs:1-17, 325-334, or 341-1042, and the Type I-D CASCADE comprises a Cas10d (Csc3) polypeptide having at least 95% sequence identity to any one of the sequences of SEQ ID NOs:33, 34, or 4372-4678, a Csc2 polypeptide having at least 95% sequence identity to any one of the sequences of SEQ ID NOs:35, 36, or 4679-4985, Csc1 polypeptide having at least 95% sequence identity to any one of the sequences of SEQ ID NOs:37, 38, or 4986-5234, a Cas6d polypeptide having at least 95% sequence identity to any one of the sequences of SEQ ID NOs:39 or 40, thereby repressing expression of the first target gene in the bacterium or archaeon.

2. The method of claim 1, wherein repressing expression of the target gene comprises an increase in repression of the target gene.

3. The method of claim 1, wherein the CRISPR array is operably linked to a promoter and/or a terminator.

4. The method of claim 1, wherein the first nucleic acid sequence is operably linked to a promoter, regulatory element, or any combination thereof.

5. The method of claim 1, wherein the at least one CRISPR array comprises at least two spacer sequences, a first spacer sequence and a second spacer sequence, the first spacer sequence being complementary to a first target site in the first target gene and the second spacer sequence being complementary to a second target site in the first target gene, thereby modulating expression of the first target gene.

6. The method of claim 1, wherein the at least one CRISPR array comprises at least two spacer sequences, a first spacer sequence and a second spacer sequence, the first spacer sequence being complementary to the first target gene and the second spacer being complementary to a second target sequence in a second target gene, thereby modulating expression of at least two genes in the bacterium or the archaeon.

7. The method of claim 1, wherein the first target sequence comprises all or a part of a promoter sequence.

8. The method of claim 1, wherein the first target sequence is located on a coding strand of a transcribed region of the target gene.

9. The method of claim 6, wherein the second target sequence comprises all or a part of a promoter sequence.

10. The method of claim 6, wherein the second target sequence is located on a coding strand of a transcribed region of the target gene.

11. The method of claim 1, wherein the first nucleic acid sequence and the second nucleic acid sequence are on the same or a different expression cassettes or vectors.

12. The method of claim 1, wherein the first nucleic acid sequence and the second nucleic acid sequence are operably linked together on the same expression cassette or vector.

13. The method of claim 1, wherein the first nucleic acid sequence and the second nucleic acid sequence are transiently or stably incorporated into the bacterium or the archaeon.

14. The method of claim 1, wherein the two or more repeat sequences comprise a first repeat sequence and a second repeat sequence and the first repeat sequence is linked to the 5' end of the spacer sequence and the second repeat sequence is linked to the 3' end of the spacer sequence and the first repeat sequence or the second repeat sequence comprises a portion of a wild type repeat sequence having at least three contiguous nucleotides of a wild type repeat sequence.

15. The method of claim 1, wherein the bacterium is pathogenic.

16. The method of claim 1, wherein the at least one spacer sequence comprises a length of about 32 nucleotides to about 100 nucleotides.

17. The method of claim 1, wherein the at least one spacer sequence is increased in length by 6, 12, 18, 24, 30 or 36 nucleotides when compared to a normal spacer length.

* * * * *

UNITED STATES PATENT AND TRADEMARK OFFICE
CERTIFICATE OF CORRECTION

PATENT NO. : 11,439,712 B2
APPLICATION NO. : 15/302655
DATED : September 13, 2022
INVENTOR(S) : Beisel et al.

It is certified that error appears in the above-identified patent and that said Letters Patent is hereby corrected as shown below:

On the Title Page

Item (56) References Cited; OTHER PUBLICATIONS, Page 4, Column 2, Line 18: Please correct "Internatianal" to read --International--

In the Specification

Column 6, Line 36: Please correct "NM500 cas3'" to read --NM500 cas3$^+$--

Column 6, Line 44: Please correct "NM500 cas3$_+$" to read --NM500 cas3$^+$--

Column 9, Line 34: Please correct "5'-A-G-T-3′″" to read to read --"5'-A-G-T-3'"--

Column 18, Line 4: Please correct "0.1 SM" to read --0.1 5M--

Column 21, Line 55: Please correct "T3lac" to read --T3-lac--

Column 23, Line 49: Please correct "(Prm)" to read --(Prrn)--

Column 30, Line 47: Please correct "BAB84980.2" to read --BAB64980.2--

Column 30, Line 48: Please correct "YP_005844988.1" to read --YP_005644988.1--

Column 30, Line 49: Please correct "YP_005848062" to read --YP_005648062--

Column 123, Line 6: Please correct "$P_{araB}$a promoter" to read --$P_{araB}$ promoter--

Column 127, Table 3, SEQ ID NO: 288 Name: Please correct "xylArev" to read --xylA.rev--

Column 129, Line 59: Please correct "cas3*" to read --cas3$^+$--

Signed and Sealed this
Twenty-fourth Day of January, 2023

Katherine Kelly Vidal
*Director of the United States Patent and Trademark Office*

Column 132, Line 5: Please correct "$2^{\Delta Ct}$" to read --$2^{-\Delta Ct}$--

In the Claims

Column 139, Line 7, Claim 1: Please correct "sequence" to read --sequences--